(12) United States Patent
De Geus et al.

(10) Patent No.: US 8,445,752 B2
(45) Date of Patent: May 21, 2013

(54) BRASSICA OLERACEA PLANTS WITH A RESISTANCE TO ALBUGO CANDIDA

(75) Inventors: Jan De Geus, Oudkarspel (NL); Albertus Johannes Maria Schrijver, Warmenhuizen (NL); Johannes Gerardus Maria Hoogland, Hoorn (NL); Adriana Dorien Postma-Haarsma, Middenmeer (NL)

(73) Assignee: Bejo Zaden B.V., Warmenhuizen (NL)

( * ) Notice: Subject to any disclaimer, the term of this patent is extended or adjusted under 35 U.S.C. 154(b) by 569 days.

(21) Appl. No.: 12/450,727

(22) PCT Filed: Apr. 22, 2008

(86) PCT No.: PCT/NL2008/050232
§ 371 (c)(1),
(2), (4) Date: Oct. 9, 2009

(87) PCT Pub. No.: WO2008/133503
PCT Pub. Date: Nov. 6, 2008

(65) Prior Publication Data
US 2011/0030085 A1 Feb. 3, 2011

(30) Foreign Application Priority Data
May 1, 2007 (NL) .................................... 2000622

(51) Int. Cl.
*A01H 1/00* (2006.01)
*A01H 1/02* (2006.01)
*A01H 5/00* (2006.01)
*C12Q 1/68* (2006.01)
*C12N 15/00* (2006.01)

(52) U.S. Cl.
USPC ........... 800/306; 800/265; 800/266; 800/267; 800/279; 800/298; 435/6.1

(58) Field of Classification Search
None
See application file for complete search history.

(56) References Cited

FOREIGN PATENT DOCUMENTS
WO  WO 00/08189  2/2000

OTHER PUBLICATIONS

Bernier, Can. Plant Dis. Surv. 52: 108, 1972.
Fan et al., Can. J. Genet. Cytol. 25: 420-424, 1983.
Harper and Pittman, Phytopathology 64: 408-410. 1974.
Varshney et al., Theoretical and Applied Genetics 109: 153-159, 2004.
Ebrahimi et al., Proc. Am. Phytopathol. Soc. 3: 273, 1976.
Delwiche and Williams, Proc. Am. Phytopathol. Soc. 1: 66, 1974.
Tiwari et al., Can. J. of Plant Science 68: 297-300, 1988.
Kole et al., Genome 45: 22-27, 2002.
Tanhuanpää, Theoretical and Applied Genetics 108: 1039-1046, 2004.
International Preliminary Report on Patentability; 2008.
M.R. Santos et al., "Evaluation of a core collection of *Brassica oleracea* accessions for resistance to white rust of crucifers (*Albugo candida*) at the cotyledon stage", Genetic Resources and Crop Evolution, Kluwer Academic Publishers,, vol. 51, No. 7, Nov. 1, 2004, pp. 713-722.
A.W. May et al., "Linkage Studies in Brassica-Oleracea of Morphologic and Isozymic Markers and Disease Resistance" Phytopathology, vol. 77, No. 12, 1987, p. 1772.
W.Y. Cheung et al., Identification of RFLP markers linked to the white rust resistance gene (*Acr*) in mustard (*Brassica juncea* (L.) Czern. and Coss.), Genome, vol. 41, No. 4, Aug. 1998, pp. 626-628.
Mohammad H. Borhan et al., "White rust (*Albugo candida*) resistance loci on three Arabidopsis chromosomes are closely linked to downy mildew (*Peronospora parasitica*) resistance loci" Molecular Plant Pathology, vol. 2, No. 2, Mar. 2001, pp. 87-95.
International Search Report, 2008.

*Primary Examiner* — Medina A Ibrahim
(74) *Attorney, Agent, or Firm* — Harness, Dickey & Pierce, P.L.C.

(57) ABSTRACT

At least one embodiment of the present invention relates to *Brassica oleracea* plants with a resistance gene to *Albugo candida*, the cause of white blister. At least one embodiment of the invention also relates to a method for providing a *Brassica oleracea* plant with a resistance to *Albugo candida*, the at least one embodiment including a) providing a first *B. oleracea* plant which comprises a resistance gene to *A. candida*; (b) crossing the resistant plant with a susceptible second *B. oleracea* plant; (c) isolating genomic DNA from the progeny for detecting the presence of an introgression with the resistance gene using one or more specific DNA markers linked to the resistance gene; and (d) selecting from the progeny a *B. oleracea* plant in which the presence of the introgression with the resistance gene has been demonstrated in step (c).

21 Claims, No Drawings

BRASSICA OLERACEA PLANTS WITH A RESISTANCE TO ALBUGO CANDIDA

CROSS REFERENCE TO RELATED APPLICATIONS

This application is the national phase under 35 U.S.C. §371 of PCT International Application No. PCT/NL2008/050232 which has an International filing date of 22 Apr. 2008, which designated the United States of America and which claims priority on Netherlands Application No. 2000622, the entire contents of each of which are hereby incorporated herein by reference.

REFERENCE TO A SEQUENCE LISTING

The material in the ASCII text file entitled 1470765_1.txt is hereby incorporated herein by reference in its entirety. The ASCII text file entitled 1470765_1.txt was created on 16 May 2012 and the size is 222 KB.

FIELD

The present invention relates to *Brassica oleracea* plants which are resistant to *Albugo candida*, the cause of white blister. The invention also relates to the seeds, fruits and/or other plant parts from these resistant plants. The present invention further relates to a method for providing *B. oleracea* plants which are resistant to *A. candida*. The invention also relates to the use of specific DNA markers which are linked to the *A. candida* resistance gene for the purpose of identifying resistant *B. oleracea* plants.

BACKGROUND

White blister (*A. candida*; synonyms: *A. cruciferum*, *A. cruciferatum*, white rust, staghead) is a plant disease which causes many problems in vegetables crops of cabbage, but also in related species such as rape, mustard and radish. The disease can in principle occur on all cruciferae, so also on wild species such as shepherd's purse (*Capsella bursa-pastoris*) and wild mustard (charlock mustard, *Sinapis arvensis*). Contrary to what the name suggests, this is not a rust fungus but an oomycete closely related to downy mildew (*Peronospora parasitica*) and *Phytophtora*. Oomycetes are not fungi and, although they also grow in threads, they are more related to algae.

The oomycete causes blisters with spores (sori, pustules) on the leaves, stems and ovaries (siliques) of Brassica plants. Distortions in the form of spots/are also often present. Systemic infection of plants results in abnormal growth, deformations and sometimes sterility of the flowers or inflorescence. The oomycete thrives best at temperatures between and 20° C. and in moist conditions. A leaf wetness period of 2.5 hours is sufficient to result in infection, at which there is an incubation period of 10 to 14 days. Moist weather conditions with moderate temperatures are therefore ideal for infection and spreading of the oomycete.

When spores of *A. candida* land on a cabbage leaf, they form a germ tube with which they penetrate the leaf. In here, the mycelium grows intercellularly and absorbs nutrients via haustoria. The vegetative spore formation takes place in the zoosporangium which develops under the epidermis. Created herein are the asexual zoospores which, when there is sufficient moisture, are released from the zoosporangia and can then cause new infections. The spores have two whiplash tails (flagellae), one for forward movement and one for the swimming direction.

*A. candida* can overwinter in the ground in sexual form with thick-walled oospores, which may or may not be on infected plant remnants, or in asexual form (mycelium) on winter-hardened host plants. During mild winters the oomycete does not really go to rest but remains active at a lower level. New plants can be infected in the spring. Plant material can also be already infected on the plant bed without symptoms becoming visible. Spread of the oomycete takes place through sporangia being carried away by air movements, hard rainfall, watering, machines, farm workers and insects, whereby other plants are infected.

Host specialization in *A. candida* is known and different physiological species and formae specialis are distinguished on the basis of the species or the line which is infected and the aggressiveness of the isolate on the line.

*Brassica* is a plant genus in the family Brassicaceae (formerly referred to as Cruciferae). The members of this genus are referred to as cabbage or mustard. The genus *Brassica* comprises a number of important agricultural and horticultural crops, including rape, cauliflower, red cabbage, savoy cabbage, white cabbage, oxheart cabbage, curly cale cabbage, broccoli, Brussels sprouts, Chinese cabbage, turnip cabbage and Portuguese cabbage (tronchuda). Almost all parts of the plants are used as food, such as the roots (turnip), stalks (turnip cabbage), leaves (white cabbage), axillary buds (sprouts), flowers (cauliflower, broccoli) and seeds (rape). Rape and rape seed are also used for oil, both for consumption and for fuel. Some species with white or purple flowers or distinct colour or shape of the leaves are cultivated for ornamental purposes. The *Brassica* family occurs worldwide and consists of annuals, biennials and perennials. The family also comprises a large number of wild species.

At the moment few agents are known which can be used to control white blister in Brassica. An increasing number of countries in Europe moreover have a policy aimed at reducing the use of crop protection agents. If the use of control agents is no longer allowed at all, this can result in major problems in the cultivation of Brassica species. In crops such as for instance *Brassica rapa* (syn. *campestris*) (turnip rape), *Brassica juncea* (mustard) and *Brassica napus* (rapeseed) white blister can cause huge losses in yield (Bernier, Can. Plant Dis. Surv. 52: 108, 1972; Fan et al., Can. J. Genet. Cytol. 25: 420-424, 1983); Harper and Pittman, Phytopathology 64: 408-410, 1974; Varshney et al., Theoretical and Applied Genetics 109: 153-159, 2004). In vegetable crops the quality aspect is particularly important. Vegetables such as sprouts, headed cabbage and curly cale cabbage infected by white blister are no longer sellable because of the cosmetic damage. There is therefore a great need for Brassica vegetable crops which are resistant to white blister.

Resistance to white blister is described in diverse Brassica species such as *B. rapa, B. napus* and *B. juncea* (Ebrahimi et al., Proc. Am. Phytopathol. Soc. 3: 273, 1976; Delwiche and Williams, Proc. Am. Phytopathol. Soc. 1: 66, 1974; Tiwari et al., Can. J. Of Plant Science 68: 297-300, 1988; Kole et al., Genome 45: 22-27, 2002; Varshney et al., Theoretical and Applied Genetics 109: 153-159, 2004; Tanhuanpad, Theoretical and Applied Genetics 108: 1039-1046, 2004). In addition, partial resistance has been demonstrated in *B. oleracea* lines (Santos and Dias, Genetic Resources and Crop Evolution 51: 713-722, 2004). Full resistance to white blister in *B. oleracea* vegetable crops has however not as yet been described.

SUMMARY

An object of the present invention is to provide a *B. oleracea* plant with a resistance to *A. candida*, the cause of white blister.

The invention provides to this end a *B. oleracea* plant comprising a resistance gene to *A. candida*.

DETAILED DESCRIPTION

The resistance gene according to the invention provides a monogenic and dominant resistance to *A. candida*. The resistance gene is preferably present in heterozygous form, and more preferably the resistance gene is present in homozygous form.

According to the invention the resistance gene to *A. candida* preferably comes from the *B. oleracea* plant, the seeds of which were deposited in the American Type Culture Collection (ATCC, Patent Depository, 10801 University Boulevard, Manassas, Va. 20110, United States of America) on 1 Mar. 2006 under number PTA 74-12. Surprisingly, it has been found that with the resistance gene according to the invention a dominant resistance is provided to *A. candida*.

In order to obtain a full resistance to *A. candida* in *B. oleracea* the transmission is described in this invention of a dominant, monogenic resistance to *A. candida* from a first *B. oleracea* source to different other *B. oleracea* types such as white cabbage, Brussels sprouts, cauliflower and turnip cabbage.

Using a disease test for white blister resistance *B. oleracea* lines were screened and a white blister resistance source was identified. The resistance was then transmitted from the source to existing quality lines by means of repeated backcrossing, in some cases as many as four to six times, followed by multiple generations of self-pollination. A disease test was performed here each time in order to select the resistant plants for the continuation of the backcrossing program. In the evaluation of these disease tests, plants were grouped into the classes resistant (no visible reaction or necrotic spots), susceptible (many sporulating blisters) and intermediate (necrotic spots and several sporulating blisters). It was found from the segregation ratios found during the backcrossing program that the resistance was a monogenic dominant trait. A lack of resistant plants was however found in many genetic backgrounds and, in addition, a great variation in numbers in the intermediate class (from several plants to half the population). The penetration of this gene was thus very incomplete in these genetic backgrounds and the breeding program was greatly hampered as a result.

In a further preferred embodiment of the invention the resistance gene is linked to one or more specific DNA markers. So as to be better able to monitor the resistance and transmit it more quickly, DNA markers have been developed according to the present invention which are closely linked to the introgression having thereon the disease-resistance gene against white blister. These markers have been developed by means of a BSA (Bulked Segregant Analysis). For this purpose individuals from a correct (1:1) segregating BC population were divided on the basis of the disease test into a resistant and a susceptible class. DNA was then isolated from all plants, and the resistant plants were bulked to form a resistant pool, and the susceptible plants to form a susceptible pool. Marker analyses were then performed on these pools by means of the RAMP technique and markers were identified which were closely linked to the resistance. By means of an analysis with the closely linked markers the plants were selected with certainty which contained the resistance gene in populations where the disease test does not give an unambiguous picture (many intermediary reactions, not a good segregation ratio). In addition, the homozygous resistant plants are directly differentiated from the heterozygous resistant plants during inbreeding. This results in an accelerated breeding program.

In a preferred embodiment of the invention the presence of the introgression with the resistance gene to *A. candida* can be demonstrated using at least two, preferably at least three, more preferably at least four, more preferably at least five, six, seven or eight, most preferably nine DNA markers linked to the resistance gene, wherein the DNA markers enclose the resistance gene. Enclose in the present application is understood to mean that the DNA markers are located on the genome on both sides of the resistance gene, i.e. "upstream" as well as "downstream" of the resistance gene. Demonstrating the presence of a plurality of DNA markers, which are linked to the resistance gene, and moreover enclosing the resistance gene ensure that the introgression with the resistance gene is actually present.

The DNA markers according to the invention are preferably chosen from table 1, wherein the presence of the DNA markers in the genome of the plant is demonstrated using the primer sequences chosen from the group consisting of SEQ ID NO: 1 up to and including SEQ ID NO: 10 (table 2).

In the research which has led to the present invention it has been demonstrated that the relevant DNA markers are characteristic for the introgression of the resistance to *A. candida*. The DNA markers according to the invention are DNA fragments which are linked to the relevant resistance gene, have a determined size (bp) as indicated in table 1, and can be demonstrated by using specific primer combinations.

The plant according to the invention is preferably chosen from the group consisting of *B. oleracea* convar. *botrytis* var. *botrytis* (cauliflower, romanesco), *B. oleracea* convar. *botrytis* var. *cymosa* (broccoli), *B. oleracea* convar. *botrytis* var. *asparagoides* (sprouting broccoli), *B. oleracea* convar. *oleracea* var. *gemnifera* (Brussels sprouts), *B. oleracea* convar. *capitata* var. *alba* (white cabbage, oxheart cabbage), *B. oleracea* convar. *capitata* var. *rubra* (red cabbage), *B. oleracea* convar. *capitata* var. *sabauda* (savoy cabbage), *B. oleracea* convar. *acephela* var. *sabellica* (curly cale cabbage), *B. oleracea* convar. *acephela* var. *gongyloides* (turnip cabbage) and *B. oleracea* var. *tronchuda* syn. *costata* (Portuguese cabbage).

The invention also relates to the seeds, fruits and/or other plant parts from the above described plants. Plant parts are here understood to mean, among others, the edible parts of the plant, such as for instance axillary buds (sprouts).

The invention also relates to a method for obtaining a *B. oleracea* plant with a resistance to *A. candida*, which method comprises at least the following steps of:

(a) providing a first *B. oleracea* plant, which plant comprises a resistance gene to *A. candida*;

(b) crossing the resistant plant with a susceptible second *B. oleracea* plant;

(c) isolating genomic DNA from the progeny for detecting the presence of an introgression with the resistance gene using one or more specific DNA markers linked to the resistance gene; and (d) selecting from the progeny a *B. oleracea* plant in which the presence of the introgression with the resistance gene has been demonstrated in step (c).

With the method according to the invention resistant *B. oleracea* plants can be provided in rapid and simple manner by making use of DNA markers which are specific to the introgression with the resistance gene according to the invention.

Using the method according to the present invention and the use of the specific DNA markers linked to a resistance gene it is possible to determine in simple manner wether a plant contains the resistance gene. Performing the disease test is a very time-consuming procedure. Selection of resistant plants by utilizing the specific DNA markers linked to a resistance gene is much more efficient. Larger numbers of plants can hereby be tested more easily. The introgression with the resistance gene can also be more readily mapped, whereby plants with the smallest possible introgression can be selected. Furthermore, distinction can be made between homozygous and heterozygous resistant plants.

The plants selected in step (d) of the method according to the invention can optionally be subjected to additional steps, such as back-crossing or self-pollination of the plant obtained in step (d) one or more times with a susceptible B. oleracea plant and subsequently selecting once again from the progeny a resistant B. oleracea plant using the specific DNA markers. The plants obtained in step (d) can for instance also be made homozygous by means of techniques known to the skilled person such as anther and/or microspore culture.

In a preferred embodiment of the method the presence of the introgression with the resistance gene in the selected plants is confirmed by means of a disease test. The presence and effect of the resistance gene can be definitively confirmed by performing a disease test.

The first B. oleracea plant preferably comprises a resistance gene which gives a monogenic and dominant resistance to A. candida. In a preferred embodiment of the invention the resistance gene is present in heterozygous form, preferably in a homozygous form.

In a preferred embodiment the first B. oleracea plant comprises a resistance gene from the B. oleracea plant, the seeds of which were deposited in the American Type Culture Collection (ATCC, Patent Depository, 10801 University Boulevard, Manassas, Va. 20110, United States of America) on 1 Mar. 2006 under number PTA 74-12.

In a further preferred embodiment of the method according to the invention the selection of the resistant B. oleracea plant in step (d) comprises of selecting a B. oleracea plant which comprises at least two, preferably at least three, more preferably at least four, more preferably at least five, six, seven or eight, and most preferably nine DNA markers linked to the resistance gene, wherein the DNA markers enclose the resistance gene. It is hereby possible to determine with certainty that the plant actually possesses the introgression with the resistance gene.

The DNA markers according to the invention are preferably chosen from table 1, wherein the presence of the DNA markers in the genome of the plant is demonstrated using the primer sequences chosen from the group consisting of SEQ ID NO: 1 up to and including SEQ ID NO: 10 (table 2).

In a particular embodiment according to the invention the first B. oleracea plant comprises a resistance gene to A. candida originating from the B. oleracea plant, the seeds of which were deposited in the American Type Culture Collection (ATCC, Patent Depository, 10801 University Boulevard, Manassas, Va. 20110, United States of America) on 1 Mar. 2006 under number PTA 74-12.)

The susceptible B. oleracea plant into which the resistance gene is inserted is preferably chosen from the group consisting of B. oleracea convar. botrytis var. botrytis (cauliflower, romanesco), B. oleracea convar. botrytis var. cymosa (broccoli), B. oleracea convar. botrytis var. asparagoides (sprouting broccoli), B. oleracea convar. oleracea var. gemnifera (Brussels sprouts), B. oleracea convar. capitata var. alba (white cabbage, oxheart cabbage), B. oleracea convar. capitata var. rubra (red cabbage), B. oleracea convar. capitata var. sabauda (savoy cabbage) B. oleracea convar. acephela var. sabellica (curly cale cabbage), B. oleracea convar. acephela var. gongyloides (turnip cabbage) and B. oleracea var. tronchuda syn. costata (Portuguese cabbage).

The invention further relates to the B. oleracea plants obtainable with the above described method, and to the seeds and/or plant parts thereof.

The invention also relates to the use of at least one DNA marker linked to a resistance gene to A. candida for identifying a B. oleracea plant which is resistant to A. candida, wherein the DNA marker is chosen from the DNA markers of table 1 and wherein the DNA marker is demonstrated with the primer sequences chosen from the group consisting of SEQ ID NO: 1 up to and including SEQ ID NO: 10 (table 2).

The resistance gene preferably originates from the B. oleracea plant of which the seeds were deposited in the American Type Culture Collection (ATCC, Patent Depository, 10801 University Boulevard, Manassas, Va. 20110, United States of America) on 1 Mar. 2006 under number PTA 74-12.

EXAMPLES

The invention is further elucidated on the basis of the following examples.

Example 1

Populations and Disease Test

The white blister resistance source originates from the parent line 9002757 of Bejo Zaden BV, seeds of which were deposited at the (ATCC, Patent Depository, 10801 University Boulevard, Manassas, Va. 20110, United States of America) on 1 Mar. 2006 under number PTA 74-12. Using this source crossings were made with different B. oleracea species (curly cale cabbage, turnip cabbage, broccoli, sprouting broccoli, white cabbage, oxheart cabbage, red cabbage, savoy cabbage, tronchuda, Brussels sprouts and cauliflower). BC1 populations were obtained after backcrossing with susceptible parent lines. Use was made of a disease test in order to select the resistant plants from these populations.

In order to preserve A. candida isolates which are used for the disease test, zoosporangia from susceptible B. oleracea plants from the field were isolated. After germination in water the spores were used to inoculate susceptible plants. After development of the blisters, these zoosporangia were harvested and stored in liquid nitrogen until use. The eventual disease test took place in the glasshouse on seedlings of the BC1 population, the seed leaves of which had developed 24 to 48 hours before. The plants were inoculated with a fresh zoospore suspension ($5 \times 10^4$ zoospores per ml) which was prepared by washing zoosporangia from susceptible plants and allowing them to germinate in water. Several drops of zoospore suspension were pipetted onto the seed leaves. After the pipetting the plants were further grown under a plastic tunnel in order to ensure optimum conditions for infection. Two weeks after inoculation the plants were assessed, wherein they were grouped into the classes resistant, susceptible or intermediate (Williams, Screening crucifers for multiple disease resistance. Workshop, Sep. 2-3, 1981, J.F. Friedrick Center, University of Wisconsin, Madison, USA).

After performing of the disease test on the seedlings, the resistant plants were retained for the following step in the backcrossing program. The results of the disease test showed that the resistance was in principle a monogenic dominant trait. Plants with intermediate reactions were however also often found in addition to plants with susceptible and resistant reactions. This was found to be highly dependent upon the genetic background in which work was being done. Different populations were selected from the programme in which there was no, or hardly any, intermediate reaction and in which the expected segregation ratio (1:1 for a BC and 3:1 for a self-pollination) was also found.

Example 2

Marker Development

For the development of linked DNA markers, four populations of about 200 individuals were used (cauliflower, curly cale cabbage, tronchuda, white cabbage). DNA of all individuals was isolated from leaf punches (~0.3 cm2/leaf punch). A BSA method was used to generate closely linked DNA markers, with the aid of the RAMP technique (Random Amplified Microsatellite Polymorphisms) (Matsumoto et al., Mammalian Genome 9: 531-535, 1998; Reiter, PCR-based marker systems, in: R. L. Philips & I. K. Vasil (eds.), DNA-based markers in plants, Kluwer Academic Publishers, 2001; Weising et al., DNA fingerprinting in plants, principles, methods and application, CRC Press, 2nd ed., 21-73, 2005).

The RAMP technique, wherein an iSSR and a RAPD-primer were combined, produced band patterns having fragments therein which specifically co-segregated with the resistance, and wherein a distinction could be made between plants with and without the resistance gene. By mapping the RAMP-fragments, closely linked RAMP-markers were identified which enclose the resistance gene.

Example 3

PCR Conditions and Marker Analysis

The PCR conditions used for the RAMP reactions are as follows:
PCR mix
75 mM Tris-HCL (pH 8.8)
20 mM NH4SO4
0.01% (v/v) Tween20
2.8 mM MgCl2
0.25 mM dNTPs
0.15 µM forward primer
0.2 µM reverse primer
0.04 units/µl Red Hot® DNA Polymerase (ABgene, Epsom, UK)
~0.2 ng/µl genomic plant DNA
PCR Program:
step 1: 2 min. 93° C.
step 2: 30 sec. 93° C.
step 3: 30 sec. 35° C.
step 4: heating by 0.3°/sec to 72° C.
step 5: 1 min. 30 sec 72° C.
steps 2-5: repeat 40×
step 6: 5 min 72° C.
Polyacryl Gel Electrophoresis For analysis of the RAMP patterns use was made of "Gene ReadIR 4200 DNA analyzers" (Licor Inc.). On the basis of an optimal concentration of 6.5% acryl amide, fragments can be separated which have a difference in size of a single base.

In order to make the fragments visible on this system it is necessary to use labelled (IRDye labels) primers. For this purpose a third of the quantity of the forward primer was replaced by a labelled primer with the same sequence.

Example 4

Marker Overview

Given in tables 1 and 2 for the different RAMP markers are the sequences of the primers, the size of the informative fragment and the estimated distance from the resistance in cM based on the number of crossing-overs in the population. Analysis of the number of crossing-overs between the different markers shows that the markers enclose the resistance gene.

TABLE 1

Overview of the RAMP markers

| RAMP SEQ ID Combination | Fragment size (bp) | Position in cM relative to resistance gene |
| --- | --- | --- |
| 1 + 10-1209 | 325 | +6.1 |
| 2 + 10-1209 | 393 | +4.6 |
| 3 + 10-1209 | 508 | +4.2 |
| 4 + 10-1209 | 830 | −1.2 |
| 5 + 10-1209 | 285 | −2.0 |
| 6 + 10-1209 | 607 | −8.8 |
| 7 + 10-1209 | 875 | +0.1 |
| 8 + 10-1209 | 291 | 0.0 |
| 9 + 10-1209 | 138 | −0.1 | where + and − indicate that the markers lie on either side of the disease-resistance gene

TABLE 2

Overview of SEQ ID nos.

| SEQ ID no. | | Sequence |
| --- | --- | --- |
| 1 | iSSR | CAGGAAACAGCTATGACAAAAAGAGAGAGAG |
| 2 | iSSR | CAGGAAACAGCTATGACTACGACACACACAC |
| 3 | iSSR | CAGGAAACAGCTATGACATACATATATATATATAT |
| 4 | iSSR | CAGGAAACAGCTATGACCCAGGTGTGTGTGT |
| 5 | iSSR | CAGGAAACAGCTATGACAGTGGAGAGAGAGAG |
| 6 | iSSR | CAGGAAACAGCTATGACACTATCTCTCTCTC |
| 7 | iSSR | CAGGAAACAGCTATGACATCTTCATCATCATCA |
| 8 | iSSR | CAGGAAACAGCTATGACGTTTGAGAGAGAGA |
| 9 | iSSR | CAGGAAACAGCTATGACCCCACAACAACAACAA |
| 10 | Operon RAPD ® 10-mer kits A-01 to BH-20 | |

TABLE 3

Operon RAPD ® 10-mer kits A-01 to BH-20

| Kit Name | Primer Name | Sequence | SEQ ID NO: |
| --- | --- | --- | --- |
| KIT A | OPA-01 | CAGGCCCTTC | 10 |
| | OPA-02 | TGCCGAGCTG | 11 |
| | OPA-03 | AGTCAGCCAC | 12 |
| | OPA-04 | AATCGGGCTG | 13 |

TABLE 3-continued

Operon RAPD ® 10-mer kits A-01 to BH-20

| Kit Name | Primer Name | Sequence | SEQ ID NO: |
|---|---|---|---|
| | OPA-05 | AGGGGTCTTG | 14 |
| | OPA-06 | GGTCCCTGAC | 15 |
| | OPA-07 | GAAACGGGTG | 16 |
| | OPA-08 | GTGACGTAGG | 17 |
| | OPA-09 | GGGTAACGCC | 18 |
| | OPA-10 | GTGATCGCAG | 19 |
| | OPA-11 | CAATCGCCGT | 20 |
| | OPA-12 | TCGGCGATAG | 21 |
| | OPA-13 | CAGCACCCAC | 22 |
| | OPA-14 | TCTGTGCTGG | 23 |
| | OPA-15 | TTCCGAACCC | 24 |
| | OPA-16 | AGCCAGCGAA | 25 |
| | OPA-17 | GACCGCTTGT | 26 |
| | OPA-18 | AGGTGACCGT | 27 |
| | OPA-19 | CAAACGTCGG | 28 |
| | OPA-20 | GTTGCGATCC | 29 |
| KIT B | OPB-01 | GTTTCGCTCC | 30 |
| | OPB-02 | TGATCCCTGG | 31 |
| | OPB-03 | CATCCCCCTG | 32 |
| | OPB-04 | GGACTGGAGT | 33 |
| | OPB-05 | TGCGCCCTTC | 34 |
| | OPB-06 | TGCTCTGCCC | 35 |
| | OPB-07 | GGTGACGCAG | 36 |
| | OPB-08 | GTCCACACGG | 37 |
| | OPB-09 | TGGGGGACTC | 38 |
| | OPB-10 | CTGCTGGGAC | 39 |
| | OPB-11 | GTAGACCCGT | 40 |
| | OPB-12 | CCTTGACGCA | 41 |
| | OPB-13 | TTCCCCCGCT | 42 |
| | OPB-14 | TCCGCTCTGG | 43 |
| | OPB-15 | GGAGGGTGTT | 44 |
| | OPB-16 | TTTGCCCGGA | 45 |
| | OPB-17 | AGGGAACGAG | 46 |
| | OPB-18 | CCACAGCAGT | 47 |
| | OPB-19 | ACCCCCGAAG | 48 |
| | OPB-20 | GGACCCTTAC | 49 |
| KIT C | OPC-01 | TTCGAGCCAG | 50 |
| | OPC-02 | GTGAGGCGTC | 51 |
| | OPC-03 | GGGGGTCTTT | 52 |
| | OPC-04 | CCGCATCTAC | 53 |
| | OPC-05 | GATGACCGCC | 54 |
| | OPC-06 | GAACGGACTC | 55 |
| | OPC-07 | GTCCCGACGA | 56 |
| | OPC-08 | TGGACCGGTG | 57 |
| | OPC-09 | CTCACCGTCC | 58 |
| | OPC-10 | TGTCTGGGTG | 59 |
| | OPC-11 | AAAGCTGCGG | 60 |
| | OPC-12 | TGTCATCCCC | 61 |
| | OPC-13 | AAGCCTCGTC | 62 |
| | OPC-14 | TGCGTGCTTG | 63 |
| | OPC-15 | GACGGATCAG | 64 |
| | OPC-16 | CACACTCCAG | 65 |
| | OPC-17 | TTCCCCCCAG | 66 |
| | OPC-18 | TGAGTGGGTG | 67 |
| | OPC-19 | GTTGCCAGCC | 68 |
| | OPC-20 | ACTTCGCCAC | 69 |
| KIT D | OPD-01 | ACCGCGAAGG | 70 |
| | OPD-02 | GGACCCAACC | 71 |
| | OPD-03 | GTCGCCGTCA | 72 |
| | OPD-04 | TCTGGTGAGG | 73 |
| | OPD-05 | TGAGCGGACA | 74 |
| | OPD-06 | ACCTGAACGG | 75 |
| | OPD-07 | TTGGCACGGG | 76 |
| | OPD-08 | GTGTGCCCCA | 77 |
| | OPD-09 | CTCTGGAGAC | 78 |
| | OPD-10 | GGTCTACACC | 79 |
| | OPD-11 | AGCGCCATTG | 80 |
| | OPD-12 | CACCGTATCC | 81 |
| | OPD-13 | GGGGTGACGA | 82 |
| | OPD-14 | CTTCCCCAAG | 83 |
| | OPD-15 | CATCCGTGCT | 84 |
| | OPD-16 | AGGGCGTAAG | 85 |
| | OPD-17 | TTTCCCACGG | 86 |
| | OPD-18 | GAGAGCCAAC | 87 |

TABLE 3-continued

Operon RAPD ® 10-mer kits A-01 to BH-20

| Kit Name | Primer Name | Sequence | SEQ ID NO: |
|---|---|---|---|
|  | OPD-19 | CTGGGGACTT | 88 |
|  | OPD-20 | ACCCGGTCAC | 89 |
| KIT E | OPE-01 | CCCAAGGTCC | 90 |
|  | OPE-02 | GGTGCGGGAA | 91 |
|  | OPE-03 | CCAGATGCAC | 92 |
|  | OPE-04 | GTGACATGCC | 93 |
|  | OPE-05 | TCAGGGAGGT | 94 |
|  | OPE-06 | AAGACCCCTC | 95 |
|  | OPE-07 | AGATGCAGCC | 96 |
|  | OPE-08 | TCACCACGGT | 97 |
|  | OPE-09 | CTTCACCCGA | 98 |
|  | OPE-10 | CACCAGGTGA | 99 |
|  | OPE-11 | GAGTCTCAGG | 100 |
|  | OPE-12 | TTATCGCCCC | 101 |
|  | OPE-13 | CCCGATTCGG | 102 |
|  | OPE-14 | TGCGGCTGAG | 103 |
|  | OPE-15 | ACGCACAACC | 104 |
|  | OPE-16 | GGTGACTGTG | 105 |
|  | OPE-17 | CTACTGCCGT | 106 |
|  | OPE-18 | GGACTGCAGA | 107 |
|  | OPE-19 | ACGGCGTATG | 108 |
|  | OPE-20 | AACGGTGACC | 109 |
| KIT F | OPF-01 | ACGGATCCTG | 110 |
|  | OPF-02 | GAGGATCCCT | 111 |
|  | OPF-03 | CCTGATCACC | 112 |
|  | OPF-04 | GGTGATCAGG | 113 |
|  | OPF-05 | CCGAATTCCC | 114 |
|  | OPF-06 | GGGAATTCGG | 115 |
|  | OPF-07 | CCGATATCCC | 116 |
|  | OPF-08 | GGGATATCGG | 117 |
|  | OPF-09 | CCAAGCTTCC | 118 |
|  | OPF-10 | GGAAGCTTGG | 119 |
|  | OPF-11 | TTGGTACCCC | 120 |
|  | OPF-12 | ACGGTACCAG | 121 |
|  | OPF-13 | GGCTGCAGAA | 122 |
|  | OPF-14 | TGCTGCAGGT | 123 |
|  | OPF-15 | CCAGTACTCC | 124 |
|  | OPF-16 | GGAGTACTGG | 125 |
|  | OPF-17 | AACCCGGGAA | 126 |
|  | OPF-18 | TTCCCGGGTT | 127 |
|  | OPF-19 | CCTCTAGACC | 128 |
|  | OPF-20 | GGTCTAGAGG | 129 |
| KIT G | OPG-01 | CTACGGAGGA | 130 |
|  | OPG-02 | GGCACTGAGG | 131 |
|  | OPG-03 | GAGCCCTCCA | 132 |
|  | OPG-04 | AGCGTGTCTG | 133 |
|  | OPG-05 | CTGAGACGGA | 134 |
|  | OPG-06 | GTGCCTAACC | 135 |
|  | OPG-07 | GAACCTGCGG | 136 |
|  | OPG-08 | TCACGTCCAC | 137 |
|  | OPG-09 | CTGACGTCAC | 138 |
|  | OPG-10 | AGGGCCGTCT | 139 |
|  | OPG-11 | TGCCCGTCGT | 140 |
|  | OPG-12 | CAGCTCACGA | 141 |
|  | OPG-13 | CTCTCCGCCA | 142 |
|  | OPG-14 | GGATGAGACC | 143 |
|  | OPG-15 | ACTGGGACTC | 144 |
|  | OPG-16 | AGCGTCCTCC | 145 |
|  | OPG-17 | ACGACCGACA | 146 |
|  | OPG-18 | GGCTCATGTG | 147 |
|  | OPG-19 | GTCAGGGCAA | 148 |
|  | OPG-20 | TCTCCCTCAG | 149 |
| KIT H | OPH-01 | GGTCGGAGAA | 150 |
|  | OPH-02 | TCGGACGTGA | 151 |
|  | OPH-03 | AGACGTCCAC | 152 |
|  | OPH-04 | GGAAGTCGCC | 153 |
|  | OPH-05 | AGTCGTCCCC | 154 |
|  | OPH-06 | ACGCATCGCA | 155 |
|  | OPH-07 | CTGCATCGTG | 156 |
|  | OPH-08 | GAAACACCCC | 157 |
|  | OPH-09 | TGTAGCTGGG | 158 |
|  | OPH-10 | CCTACGTCAG | 159 |
|  | OPH-11 | CTTCCGCAGT | 160 |
|  | OPH-12 | ACGCGCATGT | 161 |
|  | OPH-13 | GACGCCACAC | 162 |

TABLE 3-continued

Operon RAPD ® 10-mer kits A-01 to BH-20

| Kit Name | Primer Name | Sequence | SEQ ID NO: |
|---|---|---|---|
| | OPH-14 | ACCAGGTTGG | 163 |
| | OPH-15 | AATGGCGCAG | 164 |
| | OPH-16 | TCTCAGCTGG | 165 |
| | OPH-17 | CACTCTCCTC | 166 |
| | OPH-18 | GAATCGGCCA | 167 |
| | OPH-19 | CTGACCAGCC | 168 |
| | OPH-20 | GGGAGACATC | 169 |
| KIT I | OPI-01 | ACCTGGACAC | 170 |
| | OPI-02 | GGAGGAGAGG | 171 |
| | OPI-03 | CAGAAGCCCA | 172 |
| | OPI-04 | CCGCCTAGTC | 173 |
| | OPI-05 | TGTTCCACGG | 174 |
| | OPI-06 | AAGGCGGCAG | 175 |
| | OPI-07 | CAGCGACAAG | 176 |
| | OPI-08 | TTTGCCCGGT | 177 |
| | OPI-09 | TGGAGAGCAG | 178 |
| | OPI-10 | ACAACGCGAG | 179 |
| | OPI-11 | ACATGCCGTG | 180 |
| | OPI-12 | AGAGGGCACA | 181 |
| | OPI-13 | CTGGGGCTGA | 182 |
| | OPI-14 | TGACGGCGGT | 183 |
| | OPI-15 | TCATCCGAGG | 184 |
| | OPI-16 | TCTCCGCCCT | 185 |
| | OPI-17 | GGTGGTGATG | 186 |
| | OPI-18 | TGCCCAGCCT | 187 |
| | OPI-19 | AATGCGGGAG | 188 |
| | OPI-20 | AAAGTGCGGG | 189 |
| KIT J | OPJ-01 | CCCGGCATAA | 190 |
| | OPJ-02 | CCCGTTGGGA | 191 |
| | OPJ-03 | TCTCCGCTTG | 192 |
| | OPJ-04 | CCGAACACGG | 193 |
| | OPJ-05 | CTCCATGGGG | 194 |
| | OPJ-06 | TCGTTCCGCA | 195 |
| | OPJ-07 | CCTCTCGACA | 196 |
| | OPJ-08 | CATACCGTGG | 197 |
| | OPJ-09 | TGAGCCTCAC | 198 |
| | OPJ-10 | AAGCCCGAGG | 199 |
| | OPJ-11 | ACTCCTGCGA | 200 |
| | OPJ-12 | GTCCCGTGGT | 201 |
| | OPJ-13 | CCACACTACC | 202 |
| | OPJ-14 | CACCCGGATG | 203 |
| | OPJ-15 | TGTAGCAGGG | 204 |
| | OPJ-16 | CTGCTTAGGG | 205 |
| | OPJ-17 | ACGCCAGTTC | 206 |
| | OPJ-18 | TGGTCGCAGA | 207 |
| | OPJ-19 | GGACACCACT | 208 |
| | OPJ-20 | AAGCGGCCTC | 209 |
| KIT K | OPK-01 | CATTCGAGCC | 210 |
| | OPK-02 | GTCTCCGCAA | 211 |
| | OPK-03 | CCAGCTTAGG | 212 |
| | OPK-04 | CCGCCCAAAC | 213 |
| | OPK-05 | TCTGTCGAGG | 214 |
| | OPK-06 | CACCTTTCCC | 215 |
| | OPK-07 | AGCGAGCAAG | 216 |
| | OPK-08 | GAACACTGGG | 217 |
| | OPK-09 | CCCTACCGAC | 218 |
| | OPK-10 | GTGCAACGTG | 219 |
| | OPK-11 | AATGCCCCAG | 220 |
| | OPK-12 | TGGCCCTCAC | 221 |
| | OPK-13 | GGTTGTACCC | 222 |
| | OPK-14 | CCCGCTACAC | 223 |
| | OPK-15 | CTCCTGCCAA | 224 |
| | OPK-16 | GAGCGTCGAA | 225 |
| | OPK-17 | CCCAGCTGTG | 226 |
| | OPK-18 | CCTAGTCGAG | 227 |
| | OPK-19 | CACAGGCGGA | 228 |
| | OPK-20 | GTGTCGCGAG | 229 |
| KIT L | OPL-01 | GGCATGACCT | 230 |
| | OPL-02 | TGGGCGTCAA | 231 |
| | OPL-03 | CCAGCAGCTT | 232 |
| | OPL-04 | GACTGCACAC | 233 |
| | OPL-05 | ACGCAGGCAC | 234 |
| | OPL-06 | GAGGGAAGAG | 235 |
| | OPL-07 | AGGCGGGAAC | 236 |
| | OPL-08 | AGCAGGTGGA | 237 |

TABLE 3-continued

Operon RAPD ® 10-mer kits A-01 to BH-20

| Kit Name | Primer Name | Sequence | SEQ ID NO: |
|---|---|---|---|
| | OPL-09 | TGCGAGAGTC | 238 |
| | OPL-10 | TGGGAGATGG | 239 |
| | OPL-11 | ACGATGAGCC | 240 |
| | OPL-12 | GGGCGGTACT | 241 |
| | OPL-13 | ACCGCCTGCT | 242 |
| | OPL-14 | GTGACAGGCT | 243 |
| | OPL-15 | AAGAGAGGGG | 244 |
| | OPL-16 | AGGTTGCAGG | 245 |
| | OPL-17 | AGCCTGAGCC | 246 |
| | OPL-18 | ACCACCCACC | 247 |
| | OPL-19 | GAGTGGTGAC | 248 |
| | OPL-20 | TGGTGGACCA | 249 |
| KIT M | OPM-01 | GTTGGTGGCT | 250 |
| | OPM-02 | ACAACGCCTC | 251 |
| | OPM-03 | GGGGGATGAG | 252 |
| | OPM-04 | GGCGGTTGTC | 253 |
| | OPM-05 | GGGAACGTGT | 254 |
| | OPM-06 | CTGGGCAACT | 255 |
| | OPM-07 | CCGTGACTCA | 256 |
| | OPM-08 | TCTGTTCCCC | 257 |
| | OPM-09 | GTCTTGCGGA | 258 |
| | OPM-10 | TCTGGCGCAC | 259 |
| | OPM-11 | GTCCACTGTG | 260 |
| | OPM-12 | GGGACGTTGG | 261 |
| | OPM-13 | GGTGGTCAAG | 262 |
| | OPM-14 | AGGGTCGTTC | 263 |
| | OPM-15 | GACCTACCAC | 264 |
| | OPM-16 | GTAACCAGCC | 265 |
| | OPM-17 | TCAGTCCGGG | 266 |
| | OPM-18 | CACCATCCGT | 267 |
| | OPM-19 | CCTTCAGGCA | 268 |
| | OPM-20 | AGGTCTTGGG | 269 |
| KIT N | OPN-01 | CTCACGTTGG | 270 |
| | OPN-02 | ACCAGGGGCA | 271 |
| | OPN-03 | GGTACTCCCC | 272 |
| | OPN-04 | GACCGACCCA | 273 |
| | OPN-05 | ACTGAACGCC | 274 |

TABLE 3-continued

Operon RAPD ® 10-mer kits A-01 to BH-20

| Kit Name | Primer Name | Sequence | SEQ ID NO: |
|---|---|---|---|
| | OPN-06 | GAGACGCACA | 275 |
| | OPN-07 | CAGCCCAGAG | 276 |
| | OPN-08 | ACCTCAGCTC | 277 |
| | OPN-09 | TGCCGGCTTG | 278 |
| | OPN-10 | ACAACTGGGG | 279 |
| | OPN-11 | TCGCCGCAAA | 280 |
| | OPN-12 | CACAGACACC | 281 |
| | OPN-13 | AGCGTCACTC | 282 |
| | OPN-14 | TCGTGCGGGT | 283 |
| | OPN-15 | CAGCGACTGT | 284 |
| | OPN-16 | AAGCGACCTG | 285 |
| | OPN-17 | CATTGGGGAG | 286 |
| | OPN-18 | GGTGAGGTCA | 287 |
| | OPN-19 | GTCCGTACTG | 288 |
| | OPN-20 | GGTGCTCCGT | 289 |
| KIT O | OPO-01 | GGCACGTAAG | 290 |
| | OPO-02 | ACGTAGCGTC | 291 |
| | OPO-03 | CTGTTGCTAC | 292 |
| | OPO-04 | AAGTCCGCTC | 293 |
| | OPO-05 | CCCAGTCACT | 294 |
| | OPO-06 | CCACGGGAAG | 295 |
| | OPO-07 | CAGCACTGAC | 296 |
| | OPO-08 | CCTCCAGTGT | 297 |
| | OPO-09 | TCCCACGCAA | 298 |
| | OPO-10 | TCAGAGCGCC | 299 |
| | OPO-11 | GACAGGAGGT | 300 |
| | OPO-12 | CAGTGCTGTG | 301 |
| | OPO-13 | GTCAGAGTCC | 302 |
| | OPO-14 | AGCATGGCTC | 303 |
| | OPO-15 | TGGCGTCCTT | 304 |
| | OPO-16 | TCGGCGGTTC | 305 |
| | OPO-17 | GGCTTATGCC | 306 |
| | OPO-18 | CTCGCTATCC | 307 |
| | OPO-19 | GGTGCACGTT | 308 |
| | OPO-20 | ACACACGCTG | 309 |
| KIT P | OPP-01 | GTAGCACTCC | 310 |
| | OPP-02 | TCGGCACGCA | 311 |
| | OPP-03 | CTGATACGCC | 312 |

TABLE 3-continued

Operon RAPD ® 10-mer kits A-01 to BH-20

| Kit Name | Primer Name | Sequence | SEQ ID NO: |
|---|---|---|---|
| | OPP-04 | GTGTCTCAGG | 313 |
| | OPP-05 | CCCCGGTAAC | 314 |
| | OPP-06 | GTGGGCTGAC | 315 |
| | OPP-07 | GTCCATGCCA | 316 |
| | OPP-08 | ACATCGCCCA | 317 |
| | OPP-09 | GTGGTCCGCA | 318 |
| | OPP-10 | TCCCGCCTAC | 319 |
| | OPP-11 | AACGCGTCGG | 320 |
| | OPP-12 | AAGGGCGAGT | 321 |
| | OPP-13 | GGAGTGCCTC | 322 |
| | OPP-14 | CCAGCCGAAC | 323 |
| | OPP-15 | GGAAGCCAAC | 324 |
| | OPP-16 | CCAAGCTGCC | 325 |
| | OPP-17 | TGACCCGCCT | 326 |
| | OPP-18 | GGCTTGGCCT | 327 |
| | OPP-19 | GGGAAGGACA | 328 |
| | OPP-20 | GACCCTAGTC | 329 |
| KIT Q | OPQ-01 | GGGACGATGG | 330 |
| | OPQ-02 | TCTGTCGGTC | 331 |
| | OPQ-03 | GGTCACCTCA | 332 |
| | OPQ-04 | AGTGCGCTGA | 333 |
| | OPQ-05 | CCGCGTCTTG | 334 |
| | OPQ-06 | GAGCGCCTTG | 335 |
| | OPQ-07 | CCCCGATGGT | 336 |
| | OPQ-08 | CTCCAGCGGA | 337 |
| | OPQ-09 | GGCTAACCGA | 338 |
| | OPQ-10 | TGTGCCCGAA | 339 |
| | OPQ-11 | TCTCCGCAAC | 340 |
| | OPQ-12 | AGTAGGGCAC | 341 |
| | OPQ-13 | GGAGTGGACA | 342 |
| | OPQ-14 | GGACGCTTCA | 343 |
| | OPQ-15 | GGGTAACGTG | 344 |
| | OPQ-16 | AGTGCAGCCA | 345 |
| | OPQ-17 | GAAGCCCTTG | 346 |
| | OPQ-18 | AGGCTGGGTG | 347 |
| | OPQ-19 | CCCCCTATCA | 348 |
| | OPQ-20 | TCGCCCAGTC | 349 |
| KIT R | OPR-01 | TGCGGGTCCT | 350 |
| | OPR-02 | CACAGCTGCC | 351 |
| | OPR-03 | ACACAGAGGG | 352 |
| | OPR-04 | CCCGTAGCAC | 353 |
| | OPR-05 | GACCTAGTGG | 354 |
| | OPR-06 | GTCTACGGCA | 355 |
| | OPR-07 | ACTGGCCTGA | 356 |
| | OPR-08 | CCCGTTGCCT | 357 |
| | OPR-09 | TGAGCACGAG | 358 |
| | OPR-10 | CCATTCCCCA | 359 |
| | OPR-11 | GTAGCCGTCT | 360 |
| | OPR-12 | ACAGGTGCGT | 361 |
| | OPR-13 | GGACGACAAG | 362 |
| | OPR-14 | CAGGATTCCC | 363 |
| | OPR-15 | GGACAACGAG | 364 |
| | OPR-16 | CTCTGCGCGT | 365 |
| | OPR-17 | CCGTACGTAG | 366 |
| | OPR-18 | GGCTTTGCCA | 367 |
| | OPR-19 | CCTCCTCATC | 368 |
| | OPR-20 | ACGGCAAGGA | 369 |
| KIT S | OPS-01 | CTACTGCGCT | 370 |
| | OPS-02 | CCTCTGACTG | 371 |
| | OPS-03 | CAGAGGTCCC | 372 |
| | OPS-04 | CACCCCTTG | 373 |
| | OPS-05 | TTTGGGCCT | 374 |
| | OPS-06 | GATACCTCGG | 375 |
| | OPS-07 | TCCGATGCTG | 376 |
| | OPS-08 | TTCAGGGTGG | 377 |
| | OPS-09 | TCCTGGTCCC | 378 |
| | OPS-10 | ACCGTTCCAG | 379 |
| | OPS-11 | AGTCGGGTGG | 380 |
| | OPS-12 | CTGGGTGAGT | 381 |
| | OPS-13 | GTCGTTCCTG | 382 |
| | OPS-14 | AAAGGGGTCC | 383 |
| | OPS-15 | CAGTTCACGG | 384 |
| | OPS-16 | AGGGGGTTCC | 385 |
| | OPS-17 | TGGGGACCAC | 386 |
| | OPS-18 | CTGGCGAACT | 387 |

TABLE 3-continued

Operon RAPD ® 10-mer kits A-01 to BH-20

| Kit Name | Primer Name | Sequence | SEQ ID NO: |
|---|---|---|---|
| | OPS-19 | GAGTCAGCAG | 388 |
| | OPS-20 | TCTGGACGGA | 389 |
| KIT T | OPT-01 | GGGCCACTCA | 390 |
| | OPT-02 | GGAGAGACTC | 391 |
| | OPT-03 | TCCACTCCTG | 392 |
| | OPT-04 | CACAGAGGGA | 393 |
| | OPT-05 | GGGTTTGGCA | 394 |
| | OPT-06 | CAAGGGCAGA | 395 |
| | OPT-07 | GGCAGGCTGT | 396 |
| | OPT-08 | AACGGCGACA | 397 |
| | OPT-09 | CACCCCTGAG | 398 |
| | OPT-10 | CCTTCGGAAG | 399 |
| | OPT-11 | TTCCCCGCGA | 400 |
| | OPT-12 | GGGTGTGTAG | 401 |
| | OPT-13 | AGGACTGCCA | 402 |
| | OPT-14 | AATGCCGCAG | 403 |
| | OPT-15 | GGATGCCACT | 404 |
| | OPT-16 | GGTGAACGCT | 405 |
| | OPT-17 | CCAACGTCGT | 406 |
| | OPT-18 | GATGCCAGAC | 407 |
| | OPT-19 | GTCCGTATGG | 408 |
| | OPT-20 | GACCAATGCC | 409 |
| KIT U | OPU-01 | ACGGACGTCA | 410 |
| | OPU-02 | CTGAGGTCTC | 411 |
| | OPU-03 | CTATGCCGAC | 412 |
| | OPU-04 | ACCTTCGGAC | 413 |
| | OPU-05 | TTGGCGGCCT | 414 |
| | OPU-06 | ACCTTTGCGG | 415 |
| | OPU-07 | CCTGCTCATC | 416 |
| | OPU-08 | GGCGAAGGTT | 417 |
| | OPU-09 | CCACATCGGT | 418 |
| | OPU-10 | ACCTCGGCAC | 419 |
| | OPU-11 | AGACCCAGAG | 420 |
| | OPU-12 | TCACCAGCCA | 421 |
| | OPU-13 | GGCTGGTTCC | 422 |
| | OPU-14 | TGGGTCCCTC | 423 |
| | OPU-15 | ACGGGCCAGT | 424 |
| | OPU-16 | CTGCGCTGGA | 425 |
| | OPU-17 | ACCTGGGGAG | 426 |
| | OPU-18 | GAGGTCCACA | 427 |
| | OPU-19 | GTCAGTGCGG | 428 |
| | OPU-20 | ACAGCCCCCA | 429 |
| KIT V | OPV-01 | TGACGCATGG | 430 |
| | OPV-02 | AGTCACTCCC | 431 |
| | OPV-03 | CTCCCTGCAA | 432 |
| | OPV-04 | CCCCTCACGA | 433 |
| | OPV-05 | TCCGAGAGGG | 434 |
| | OPV-06 | ACGCCCAGGT | 435 |
| | OPV-07 | GAAGCCAGCC | 436 |
| | OPV-08 | GGACGGCGTT | 437 |
| | OPV-09 | TGTACCCGTC | 438 |
| | OPV-10 | GGACCTGCTG | 439 |
| | OPV-11 | CTCGACAGAG | 440 |
| | OPV-12 | ACCCCCCACT | 441 |
| | OPV-13 | ACCCCCTGAA | 442 |
| | OPV-14 | AGATCCCGCC | 443 |
| | OPV-15 | CAGTGCCGGT | 444 |
| | OPV-16 | ACACCCCACA | 445 |
| | OPV-17 | ACCGGCTTGT | 446 |
| | OPV-18 | TGGTGGCGTT | 447 |
| | OPV-19 | GGGTGTGCAG | 448 |
| | OPV-20 | CAGCATGGTC | 449 |
| KIT W | OPW-01 | CTCAGTGTCC | 450 |
| | OPW-02 | ACCCCGCCAA | 451 |
| | OPW-03 | GTCCGGAGTG | 452 |
| | OPW-04 | CAGAAGCGGA | 453 |
| | OPW-05 | GGCGGATAAG | 454 |
| | OPW-06 | AGGCCCGATG | 455 |
| | OPW-07 | CTGGACGTCA | 456 |
| | OPW-08 | GACTGCCTCT | 457 |
| | OPW-09 | GTGACCGAGT | 458 |
| | OPW-10 | TCGCATCCCT | 459 |
| | OPW-11 | CTGATGCGTG | 460 |
| | OPW-12 | TGGGCAGAAG | 461 |
| | OPW-13 | CACAGCGACA | 462 |

TABLE 3-continued

Operon RAPD® 10-mer kits A-01 to BH-20

| Kit Name | Primer Name | Sequence | SEQ ID NO: |
|---|---|---|---|
| | OPW-14 | CTGCTGAGCA | 463 |
| | OPW-15 | ACACCGGAAC | 464 |
| | OPW-16 | CAGCCTACCA | 465 |
| | OPW-17 | GTCCTGGGTT | 466 |
| | OPW-18 | TTCAGGGCAC | 467 |
| | OPW-19 | CAAAGCGCTC | 468 |
| | OPW-20 | TGTGGCAGCA | 469 |
| KIT X | OPX-01 | CTGGGCACGA | 470 |
| | OPX-02 | TTCCGCCACC | 471 |
| | OPX-03 | TGGCGCAGTG | 472 |
| | OPX-04 | CCGCTACCGA | 473 |
| | OPX-05 | CCTTTCCCTC | 474 |
| | OPX-06 | ACGCCAGAGG | 475 |
| | OPX-07 | GAGCGAGGCT | 476 |
| | OPX-08 | CAGGGGTGGA | 477 |
| | OPX-09 | GGTCTGGTTG | 478 |
| | OPX-10 | CCCTAGACTG | 479 |
| | OPX-11 | GGAGCCTCAG | 480 |
| | OPX-12 | TCGCCAGCCA | 481 |
| | OPX-13 | ACGGGAGCAA | 482 |
| | OPX-14 | ACAGGTGCTG | 483 |
| | OPX-15 | CAGACAAGCC | 484 |
| | OPX-16 | CTCTGTTCGG | 485 |
| | OPX-17 | GACACGGACC | 486 |
| | OPX-18 | GACTAGGTGG | 487 |
| | OPX-19 | TGGCAAGGCA | 488 |
| | OPX-20 | CCCAGCTAGA | 489 |
| KIT Y | OPY-01 | GTGGCATCTC | 490 |
| | OPY-02 | CATCGCCGCA | 491 |
| | OPY-03 | ACAGCCTGCT | 492 |
| | OPY-04 | GGCTGCAATG | 493 |
| | OPY-05 | GGCTGCGACA | 494 |
| | OPY-06 | AAGGCTCACC | 495 |
| | OPY-07 | AGAGCCGTCA | 496 |
| | OPY-08 | AGGCAGAGCA | 497 |
| | OPY-09 | AGCAGCGCAC | 498 |
| | OPY-10 | CAAACGTGGG | 499 |
| | OPY-11 | AGACGATGGG | 500 |
| | OPY-12 | AAGCCTGCGA | 501 |
| | OPY-13 | GGGTCTCGGT | 502 |
| | OPY-14 | GGTCGATCTG | 503 |
| | OPY-15 | AGTCGCCCTT | 504 |
| | OPY-16 | GGGCCAATGT | 505 |
| | OPY-17 | GACGTGGTGA | 506 |
| | OPY-18 | GTGGAGTCAG | 507 |
| | OPY-19 | TGAGGGTCCC | 508 |
| | OPY-20 | AGCCGTGGAA | 509 |
| KIT Z | OPZ-01 | TCTGTGCCAC | 510 |
| | OPZ-02 | CCTACGGGGA | 511 |
| | OPZ-03 | CAGCACCGCA | 512 |
| | OPZ-04 | AGGCTGTGCT | 513 |
| | OPZ-05 | TCCCATGCTG | 514 |
| | OPZ-06 | GTGCCGTTCA | 515 |
| | OPZ-07 | CCAGGAGGAC | 516 |
| | OPZ-08 | GGGTGGGTAA | 517 |
| | OPZ-09 | CACCCCAGTC | 518 |
| | OPZ-10 | CCGACAAACC | 519 |
| | OPZ-11 | CTCAGTCGCA | 520 |
| | OPZ-12 | TCAACGGGAC | 521 |
| | OPZ-13 | GACTAAGCCC | 522 |
| | OPZ-14 | TCGGAGGTTC | 523 |
| | OPZ-15 | CAGGGCTTTC | 524 |
| | OPZ-16 | TCCCCATCAC | 525 |
| | OPZ-17 | CCTTCCCACT | 526 |
| | OPZ-18 | AGGGTCTGTG | 527 |
| | OPZ-19 | GTGCGAGCAA | 528 |
| | OPZ-20 | ACTTTGGCGG | 529 |
| KIT AA | OPAA-01 | AGACGGCTCC | 530 |
| | OPAA-02 | GAGACCAGAC | 531 |
| | OPAA-03 | TTAGCGCCCC | 532 |
| | OPAA-04 | AGGACTGCTC | 533 |
| | OPAA-05 | GGCTTTAGCC | 534 |
| | OPAA-06 | GTGGGTGCCA | 535 |
| | OPAA-07 | CTACGCTCAC | 536 |
| | OPAA-08 | TCCGCAGTAG | 537 |

TABLE 3-continued

Operon RAPD® 10-mer kits A-01 to BH-20

| Kit Name | Primer Name | Sequence | SEQ ID NO: |
|---|---|---|---|
| | OPAA-09 | AGATGGGCAG | 538 |
| | OPAA-10 | TGGTCGGGTG | 539 |
| | OPAA-11 | ACCCGACCTG | 540 |
| | OPAA-12 | GGACCTCTTG | 541 |
| | OPAA-13 | GAGCGTCGCT | 542 |
| | OPAA-14 | AACGGGCCAA | 543 |
| | OPAA-15 | ACGGAAGCCC | 544 |
| | OPAA-16 | GGAACCCACA | 545 |
| | OPAA-17 | GAGCCCGACT | 546 |
| | OPAA-18 | TGGTCCAGCC | 547 |
| | OPAA-19 | TGAGGCGTGT | 548 |
| | OPAA-20 | TTGCCTTCGG | 549 |
| KIT AB | OPAB-01 | CCGTCGGTAG | 550 |
| | OPAB-02 | GGAAACCCCT | 551 |
| | OPAB-03 | TGGCGCACAC | 552 |
| | OPAB-04 | GGCACGCGTT | 553 |
| | OPAB-05 | CCCGAAGCGA | 554 |
| | OPAB-06 | GTGGCTTGGA | 555 |
| | OPAB-07 | GTAAACCGCC | 556 |
| | OPAB-08 | GTTACGGACC | 557 |
| | OPAB-09 | GGGCGACTAC | 558 |
| | OPAB-10 | TTCCCTCCCA | 559 |
| | OPAB-11 | GTGCGCAATG | 560 |
| | OPAB-12 | CCTGTACCGA | 561 |
| | OPAB-13 | CCTACCGTGG | 562 |
| | OPAB-14 | AAGTGCGACC | 563 |
| | OPAB-15 | CCTCCTTCTC | 564 |
| | OPAB-16 | CCCGGATGGT | 565 |
| | OPAB-17 | TCGCATCCAG | 566 |
| | OPAB-18 | CTGGCGTGTC | 567 |
| | OPAB-19 | ACACCGATGG | 568 |
| | OPAB-20 | CTTCTCGGAC | 569 |
| KIT AC | OPAC-01 | TCCCAGCAGA | 570 |
| | OPAC-02 | GTCGTCGTCT | 571 |
| | OPAC-03 | CACTGGCCCA | 572 |
| | OPAC-04 | ACGGGACCTG | 573 |
| | OPAC-05 | GTTAGTGCGG | 574 |
| | OPAC-06 | CCAGAACGGA | 575 |
| | OPAC-07 | GTGGCCGATG | 576 |
| | OPAC-08 | TTTGGGTGCC | 577 |
| | OPAC-09 | AGAGCGTACC | 578 |
| | OPAC-10 | AGCAGCGAGG | 579 |
| | OPAC-11 | CCTGGGTCAG | 580 |
| | OPAC-12 | GGCGAGTGTG | 581 |
| | OPAC-13 | GACCCGATTG | 582 |
| | OPAC-14 | GTCGGTTGTC | 583 |
| | OPAC-15 | TGCCGTGAGA | 584 |
| | OPAC-16 | CCTCCTACGG | 585 |
| | OPAC-17 | CCTGGAGCTT | 586 |
| | OPAC-18 | TTGGGGAGA | 587 |
| | OPAC-19 | AGTCCGCCTG | 588 |
| | OPAC-20 | ACGGAAGTGG | 589 |
| KIT AD | OPAD-01 | CAAAGGGCGG | 590 |
| | OPAD-02 | CTGAACCGCT | 591 |
| | OPAD-03 | TCTCGCCTAC | 592 |
| | OPAD-04 | GTAGGCCTCA | 593 |
| | OPAD-05 | ACCGCATGGG | 594 |
| | OPAD-06 | AAGTGCACGG | 595 |
| | OPAD-07 | CCCTACTGGT | 596 |
| | OPAD-08 | GGCAGGCAAG | 597 |
| | OPAD-09 | TCGCTTCTCC | 598 |
| | OPAD-10 | AAGAGGCCAG | 599 |
| | OPAD-11 | CAATCGGGTC | 600 |
| | OPAD-12 | AAGAGGGCGT | 601 |
| | OPAD-13 | GGTTCCTCTG | 602 |
| | OPAD-14 | GAACGAGGGT | 603 |
| | OPAD-15 | TTTGCCCCGT | 604 |
| | OPAD-16 | AACGGGCGTC | 605 |
| | OPAD-17 | GGCAAACCCT | 606 |
| | OPAD-18 | ACGAGAGGCA | 607 |
| | OPAD-19 | CTTGGCACGA | 608 |
| | OPAD-20 | TCTTCGGAGG | 609 |
| KIT AE | OPAE-01 | TGAGGGCCGT | 610 |
| | OPAE-02 | TCGTTCACCC | 611 |
| | OPAE-03 | CATAGAGCGG | 612 |

TABLE 3-continued

Operon RAPD ® 10-mer kits A-01 to BH-20

| Kit Name | Primer Name | Sequence | SEQ ID NO: |
|---|---|---|---|
| | OPAE-04 | CCAGCACTTC | 613 |
| | OPAE-05 | CCTGTCAGTG | 614 |
| | OPAE-06 | GGGGAAGACA | 615 |
| | OPAE-07 | GTGTCAGTGG | 616 |
| | OPAE-08 | CTGGCTCAGA | 617 |
| | OPAE-09 | TGCCACGAGG | 618 |
| | OPAE-10 | CTGAAGCGCA | 619 |
| | OPAE-11 | AAGACCGGGA | 620 |
| | OPAE-12 | CCGAGCAATC | 621 |
| | OPAE-13 | TGTGGACTGG | 622 |
| | OPAE-14 | GAGAGGCTCC | 623 |
| | OPAE-15 | TGCCTGGACC | 624 |
| | OPAE-16 | TCCGTGCTGA | 625 |
| | OPAE-17 | GGCAGGTTCA | 626 |
| | OPAE-18 | CTGGTGCTGA | 627 |
| | OPAE-19 | GACAGTCCCT | 628 |
| | OPAE-20 | TTGACCCCAG | 629 |
| KIT AF | OPAF-01 | CCTACACGGT | 630 |
| | OPAF-02 | CAGCCGAGAA | 631 |
| | OPAF-03 | GAAGGAGGCA | 632 |
| | OPAF-04 | TTGCGGCTGA | 633 |
| | OPAF-05 | CCCGATCAGA | 634 |
| | OPAF-06 | CCGCAGTCTG | 635 |
| | OPAF-07 | GGAAAGCGTC | 636 |
| | OPAF-08 | CTCTGCCTGA | 637 |
| | OPAF-09 | CCCCTCAGAA | 638 |
| | OPAF-10 | GGTTGGAGAC | 639 |
| | OPAF-11 | ACTGGGCCTC | 640 |
| | OPAF-12 | GACGCAGCTT | 641 |
| | OPAF-13 | CCGAGGTGAC | 642 |
| | OPAF-14 | GGTGCGCACT | 643 |
| | OPAF-15 | CACGAACCTC | 644 |
| | OPAF-16 | TCCCGGTGAG | 645 |
| | OPAF-17 | TGAACCGAGG | 646 |
| | OPAF-18 | GTGTCCCTCT | 647 |
| | OPAF-19 | GGACAAGCAG | 648 |
| | OPAF-20 | CTCCGCACAG | 649 |
| KIT AG | OPAG-01 | CTACGGCTTC | 650 |
| | OPAG-02 | CTGAGGTCCT | 651 |
| | OPAG-03 | TGCGGGAGTG | 652 |
| | OPAG-04 | GGAGCGTACT | 653 |
| | OPAG-05 | CCCACTAGAC | 654 |
| | OPAG-06 | GGTGGCCAAG | 655 |
| | OPAG-07 | CACAGACCTG | 656 |
| | OPAG-08 | AAGAGCCCTC | 657 |
| | OPAG-09 | CCGAGGGGTT | 658 |
| | OPAG-10 | ACTGCCCGAC | 659 |
| | OPAG-11 | TTACGGTGGG | 660 |
| | OPAG-12 | CTCCCAGGGT | 661 |
| | OPAG-13 | GGCTTGGCGA | 662 |
| | OPAG-14 | CTCTCGGCGA | 663 |
| | OPAG-15 | CCCACACGCA | 664 |
| | OPAG-16 | CCTGCGACAG | 665 |
| | OPAG-17 | AGCGGAAGTG | 666 |
| | OPAG-18 | GTGGGCATAC | 667 |
| | OPAG-19 | AGCCTCGGTT | 668 |
| | OPAG-20 | TGCGCTCCTC | 669 |
| KIT AH | OPAH-01 | TCCGCAACCA | 670 |
| | OPAH-02 | CACTTCCGCT | 671 |
| | OPAH-03 | GGTTACTGCC | 672 |
| | OPAH-04 | CTCCCCAGAC | 673 |
| | OPAH-05 | TTGCAGGCAG | 674 |
| | OPAH-06 | GTAAGCCCCT | 675 |
| | OPAH-07 | CCCTACGGAG | 676 |
| | OPAH-08 | TTCCCGTGCC | 677 |
| | OPAH-09 | AGAACCGAGG | 678 |
| | OPAH-10 | GGGATGACCA | 679 |
| | OPAH-11 | TCCGCTGAGA | 680 |
| | OPAH-12 | TCCAACGGCT | 681 |
| | OPAH-13 | TGAGTCCGCA | 682 |
| | OPAH-14 | TGTGGCCGAA | 683 |
| | OPAH-15 | CTACAGCGAG | 684 |
| | OPAH-16 | CAAGGTGGGT | 685 |
| | OPAH-17 | CAGTGGGGAG | 686 |
| | OPAH-18 | GGGCTAGTCA | 687 |

TABLE 3-continued

Operon RAPD ® 10-mer kits A-01 to BH-20

| Kit Name | Primer Name | Sequence | SEQ ID NO: |
|---|---|---|---|
| | OPAH-19 | GGCAGTTCTC | 688 |
| | OPAH-20 | GGAAGGTGAG | 689 |
| KIT AI | OPAI-01 | GGCATCGGCT | 690 |
| | OPAI-02 | AGCCGTTCAG | 691 |
| | OPAI-03 | GGGTCCAAAG | 692 |
| | OPAI-04 | CTATCCTGCC | 693 |
| | OPAI-05 | GTCGTAGCGG | 694 |
| | OPAI-06 | TGCCGCACTT | 695 |
| | OPAI-07 | ACGAGCATGG | 696 |
| | OPAI-08 | AAGCCCCCCA | 697 |
| | OPAI-09 | TCGCTGGTGT | 698 |
| | OPAI-10 | TCGGGGCATC | 699 |
| | OPAI-11 | ACGGCGATGA | 700 |
| | OPAI-12 | GACGCGAACC | 701 |
| | OPAI-13 | ACGCTGCGAC | 702 |
| | OPAI-14 | TGGTGCACTC | 703 |
| | OPAI-15 | GACACAGCCC | 704 |
| | OPAI-16 | AAGGCACGAG | 705 |
| | OPAI-17 | CCTCACGTCC | 706 |
| | OPAI-18 | TCGCGGAACC | 707 |
| | OPAI-19 | GGCAAAGCTG | 708 |
| | OPAI-20 | CCTGTTCCCT | 709 |
| KIT AJ | OPAJ-01 | ACGGGTCAGA | 710 |
| | OPAJ-02 | TCGCACAGTC | 711 |
| | OPAJ-03 | AGCACCTCGT | 712 |
| | OPAJ-04 | GAATGCGACC | 713 |
| | OPAJ-05 | CAGCGTTGCC | 714 |
| | OPAJ-06 | GTCGGAGTGG | 715 |
| | OPAJ-07 | CCCTCCCTAA | 716 |
| | OPAJ-08 | GTGCTCCCTC | 717 |
| | OPAJ-09 | ACGGCACGCA | 718 |
| | OPAJ-10 | GTTACCGCGA | 719 |
| | OPAJ-11 | GAACGCTGCC | 720 |
| | OPAJ-12 | CAGTTCCCGT | 721 |
| | OPAJ-13 | CAGCCGTTCC | 722 |
| | OPAJ-14 | ACCGATGCTG | 723 |
| | OPAJ-15 | GAATCCGGCA | 724 |
| | OPAJ-16 | TCTGGACCGA | 725 |
| | OPAJ-17 | ACCCCCTATG | 726 |
| | OPAJ-18 | GGCTAGGTGG | 727 |
| | OPAJ-19 | ACAGTGGCCT | 728 |
| | OPAJ-20 | ACACGTGGTC | 729 |
| KIT AK | OPAK-01 | TCTGCTACGG | 730 |
| | OPAK-02 | CCATCGGAGG | 731 |
| | OPAK-03 | GGTCCTACCA | 732 |
| | OPAK-04 | AGGGTCGGTC | 733 |
| | OPAK-05 | GATGGCAGTC | 734 |
| | OPAK-06 | TCACGTCCCT | 735 |
| | OPAK-07 | CTTGGGGGAC | 736 |
| | OPAK-08 | CCGAAGGGTG | 737 |
| | OPAK-09 | AGGTCGGCGT | 738 |
| | OPAK-10 | CAAGCGTCAC | 739 |
| | OPAK-11 | CAGTGTGCTC | 740 |
| | OPAK-12 | AGTGTAGCCC | 741 |
| | OPAK-13 | TCCCACGAGT | 742 |
| | OPAK-14 | CTGTCATGCC | 743 |
| | OPAK-15 | ACCTGCCGTT | 744 |
| | OPAK-16 | CTGCGTGCTC | 745 |
| | OPAK-17 | CAGCGGTCAC | 746 |
| | OPAK-18 | ACCCGGAAAC | 747 |
| | OPAK-19 | TCGCAGCGAG | 748 |
| | OPAK-20 | TGATGGCGTC | 749 |
| KIT AL | OPAL-01 | TGTGACGAGG | 750 |
| | OPAL-02 | ACCCTGTGGG | 751 |
| | OPAL-03 | CCCACCCTTG | 752 |
| | OPAL-04 | ACAACGGTCC | 753 |
| | OPAL-05 | GACTGCGCCA | 754 |
| | OPAL-06 | AAGCGTCCTC | 755 |
| | OPAL-07 | CCGTCCATCC | 756 |
| | OPAL-08 | GTCGCCCTCA | 757 |
| | OPAL-09 | CAGCGAGTAG | 758 |
| | OPAL-10 | AAGGCCCCTG | 759 |
| | OPAL-11 | GTCACGTCCT | 760 |
| | OPAL-12 | CCCAGGCTAC | 761 |
| | OPAL-13 | GAATGGCACC | 762 |

TABLE 3-continued

Operon RAPD® 10-mer kits A-01 to BH-20

| Kit Name | Primer Name | Sequence | SEQ ID NO: |
|---|---|---|---|
| | OPAL-14 | TCGCTCCGTT | 763 |
| | OPAL-15 | AGGGGACACC | 764 |
| | OPAL-16 | CTTTCGAGGG | 765 |
| | OPAL-17 | CCGCAAGTGT | 766 |
| | OPAL-18 | GGAGTGGACT | 767 |
| | OPAL-19 | TCTGCCAGTG | 768 |
| | OPAL-20 | AGGAGTCGGA | 769 |
| KIT AM | OPAM-01 | TCACGTACGG | 770 |
| | OPAM-02 | ACTTGACGGG | 771 |
| | OPAM-03 | CTTCCCTGTG | 772 |
| | OPAM-04 | GAGGGACCTC | 773 |
| | OPAM-05 | GGGCTATGCC | 774 |
| | OPAM-06 | CTCGGGATGT | 775 |
| | OPAM-07 | AACCGCGGCA | 776 |
| | OPAM-08 | ACCACGAGTG | 777 |
| | OPAM-09 | TGCCGGTTCA | 778 |
| | OPAM-10 | CAGACCGACC | 779 |
| | OPAM-11 | AGATGCGCGG | 780 |
| | OPAM-12 | TCTCACCGTC | 781 |
| | OPAM-13 | CACGGCACAA | 782 |
| | OPAM-14 | TGGTTGCGGA | 783 |
| | OPAM-15 | GATGCGATGG | 784 |
| | OPAM-16 | TGGCGGTTTG | 785 |
| | OPAM-17 | CCTAACGTCC | 786 |
| | OPAM-18 | ACGGGACTCT | 787 |
| | OPAM-19 | CCAGGTCTTC | 788 |
| | OPAM-20 | ACCAACCAGG | 789 |
| KIT AN | OPAN-01 | ACTCCACGTC | 790 |
| | OPAN-02 | CACCGCAGTT | 791 |
| | OPAN-03 | AGCCAGGCTG | 792 |
| | OPAN-04 | GGCGTAAGTC | 793 |
| | OPAN-05 | GGGTGCAGTT | 794 |
| | OPAN-06 | GGGAACCCGT | 795 |
| | OPAN-07 | TCGCTGCGGA | 796 |
| | OPAN-08 | AAGGCTGCTG | 797 |
| | OPAN-09 | GGGGGAGATG | 798 |
| | OPAN-10 | CTGTGTGCTC | 799 |
| | OPAN-11 | GTCCATGCAG | 800 |
| | OPAN-12 | AACGGCGGTC | 801 |
| | OPAN-13 | CTTCCAGGAC | 802 |
| | OPAN-14 | AGCCGGGTAA | 803 |
| | OPAN-15 | TGATGCCGCT | 804 |
| | OPAN-16 | GTGTCGAGTC | 805 |
| | OPAN-17 | TCAGCACAGG | 806 |
| | OPAN-18 | TGTCCTGCGT | 807 |
| | OPAN-19 | ACCACGCCTT | 808 |
| | OPAN-20 | GAGTCCTCAC | 809 |
| KIT AO | OPAO-01 | AAGACGACGG | 810 |
| | OPAO-02 | AATCCGCTGG | 811 |
| | OPAO-03 | AGTCGGCCCA | 812 |
| | OPAO-04 | AACAGGGCAG | 813 |
| | OPAO-05 | TGGAAGCACC | 814 |
| | OPAO-06 | AGGCAGCCTG | 815 |
| | OPAO-07 | GATGCGACGG | 816 |
| | OPAO-08 | ACTGGCTCTC | 817 |
| | OPAO-09 | CCAGATGGGG | 818 |
| | OPAO-10 | GACATCGTCC | 819 |
| | OPAO-11 | GGGGGCTTGA | 820 |
| | OPAO-12 | TCCCGGTCTC | 821 |
| | OPAO-13 | CCCACAGGTG | 822 |
| | OPAO-14 | CTACTGGGGT | 823 |
| | OPAO-15 | GAAGGCTCCC | 824 |
| | OPAO-16 | CACAACGGGA | 825 |
| | OPAO-17 | CCCATGTGTG | 826 |
| | OPAO-18 | GGGAGCGCTT | 827 |
| | OPAO-19 | GTTCTCGGAC | 828 |
| | OPAO-20 | GGCTTGCCTG | 829 |
| KIT AP | OPAP-01 | AACTGGCCCC | 830 |
| | OPAP-02 | TGGTCATCCC | 831 |
| | OPAP-03 | GTAAGGCGCA | 832 |
| | OPAP-04 | CTCTTGGGCT | 833 |
| | OPAP-05 | GACTTCAGGG | 834 |
| | OPAP-06 | GTCACGTCTC | 835 |
| | OPAP-07 | ACCACCCGCT | 836 |
| | OPAP-08 | ACCCCCACAC | 837 |

TABLE 3-continued

Operon RAPD ® 10-mer kits A-01 to BH-20

| Kit Name | Primer Name | Sequence | SEQ ID NO: |
|---|---|---|---|
| | OPAP-09 | GTGGTCCAGA | 838 |
| | OPAP-10 | TGGGTGATCC | 839 |
| | OPAP-11 | CTGGCTTCTG | 840 |
| | OPAP-12 | GTCTTACCCC | 841 |
| | OPAP-13 | TGAAGCCCCT | 842 |
| | OPAP-14 | TGCCATGCTG | 843 |
| | OPAP-15 | GGGTTGGAAG | 844 |
| | OPAP-16 | GGGCAGATAC | 845 |
| | OPAP-17 | ACGGCACTCC | 846 |
| | OPAP-18 | GTCGTCGACA | 847 |
| | OPAP-19 | GTGTCTGCCT | 848 |
| | OPAP-20 | CCCGGATACA | 849 |
| KIT AQ | OPAQ-01 | GGCAGGTGGA | 850 |
| | OPAQ-02 | ACCCTCGGAC | 851 |
| | OPAQ-03 | GAGGTGTCTG | 852 |
| | OPAQ-04 | GACGGCTATC | 853 |
| | OPAQ-05 | ACGGAGCTGA | 854 |
| | OPAQ-06 | ACGGATCCCC | 855 |
| | OPAQ-07 | GGAGTAACGG | 856 |
| | OPAQ-08 | TCGGTAGACC | 857 |
| | OPAQ-09 | AGTCCCCCTC | 858 |
| | OPAQ-10 | CATACCCTCC | 859 |
| | OPAQ-11 | GACGCCTCCA | 860 |
| | OPAQ-12 | CAGCTCCTGT | 861 |
| | OPAQ-13 | GAGTCGGCTG | 862 |
| | OPAQ-14 | CCCGTGTAGG | 863 |
| | OPAQ-15 | TGCGATGCGA | 864 |
| | OPAQ-16 | CCCGGAAGAG | 865 |
| | OPAQ-17 | TTCGCCTGTC | 866 |
| | OPAQ-18 | GGGAGCGAGT | 867 |
| | OPAQ-19 | AGTAGGGCCT | 868 |
| | OPAQ-20 | GTGAACGCTC | 869 |
| KIT AR | OPAR-01 | CCATTCCGAG | 870 |
| | OPAR-02 | CACCTGCTGA | 871 |
| | OPAR-03 | GTGAGGCGCA | 872 |
| | OPAR-04 | CCAGGAGAAG | 873 |
| | OPAR-05 | CATACCTGCC | 874 |
| | OPAR-06 | TGGGGCTCAA | 875 |
| | OPAR-07 | TCCTTCGGTG | 876 |
| | OPAR-08 | GTGAATGCGG | 877 |
| | OPAR-09 | GGGGTGTTCT | 878 |
| | OPAR-10 | TGGGGCTGTC | 879 |
| | OPAR-11 | GGGAAGACGG | 880 |
| | OPAR-12 | GGATCGTCGG | 881 |
| | OPAR-13 | GGGTCGGCTT | 882 |
| | OPAR-14 | CTCACAGCAC | 883 |
| | OPAR-15 | ACACTCTGCC | 884 |
| | OPAR-16 | CCTTGCGCCT | 885 |
| | OPAR-17 | CCACCACGAC | 886 |
| | OPAR-18 | CTACCGGCAC | 887 |
| | OPAR-19 | CTGATCGCGG | 888 |
| | OPAR-20 | TGCGCCATCC | 889 |
| KIT AS | OPAS-01 | CACACCGTGT | 890 |
| | OPAS-02 | GTCCTCGTGT | 891 |
| | OPAS-03 | ACGGTTCCAC | 892 |
| | OPAS-04 | GTCTTGGGCA | 893 |
| | OPAS-05 | GTCACCTGCT | 894 |
| | OPAS-06 | GGCGCGTTAG | 895 |
| | OPAS-07 | GACGAGCAGG | 896 |
| | OPAS-08 | GGCTGCCAGT | 897 |
| | OPAS-09 | TGGAGTCCCC | 898 |
| | OPAS-10 | CCCGTCTACC | 899 |
| | OPAS-11 | ACCGTGCCGT | 900 |
| | OPAS-12 | TGACCAGGCA | 901 |
| | OPAS-13 | CACGGACCGA | 902 |
| | OPAS-14 | TCGCAGCGTT | 903 |
| | OPAS-15 | CTGCAATGGG | 904 |
| | OPAS-16 | AACCCTTCCC | 905 |
| | OPAS-17 | AGTTCCGCGA | 906 |
| | OPAS-18 | GTTGCGCAGT | 907 |
| | OPAS-19 | TGACAGCCCC | 908 |
| | OPAS-20 | TCTGCCTGGA | 909 |
| KIT AT | OPAT-01 | CAGTGGTTCC | 910 |
| | OPAT-02 | CAGGTCTAGG | 911 |
| | OPAT-03 | GACTGGGAGG | 912 |

TABLE 3-continued

Operon RAPD ® 10-mer kits A-01 to BH-20

| Kit Name | Primer Name | Sequence | SEQ ID NO: |
|---|---|---|---|
| | OPAT-04 | TTGCCTCGCC | 913 |
| | OPAT-05 | ACACCTGCCA | 914 |
| | OPAT-06 | CCGTCCCTGA | 915 |
| | OPAT-07 | ACTGCGACCA | 916 |
| | OPAT-08 | TCCTCGTGGG | 917 |
| | OPAT-09 | CCGTTAGCGT | 918 |
| | OPAT-10 | ACCTCCGGTC | 919 |
| | OPAT-11 | CCAGATCTCC | 920 |
| | OPAT-12 | CTGCCTAGCC | 921 |
| | OPAT-13 | CTGGTGGAAG | 922 |
| | OPAT-14 | GTGCCGCACT | 923 |
| | OPAT-15 | TGACGCACGG | 924 |
| | OPAT-16 | CTCTCCGTAG | 925 |
| | OPAT-17 | AGCGACTGCT | 926 |
| | OPAT-18 | CCAGCTGTGA | 927 |
| | OPAT-19 | ACCAAGGCAC | 928 |
| | OPAT-20 | ACATCAGCCC | 929 |
| KIT AU | OPAU-01 | GGGATGGAAC | 930 |
| | OPAU-02 | CCAACCCGCA | 931 |
| | OPAU-03 | ACGAAACGGG | 932 |
| | OPAU-04 | GGCTTCTGTC | 933 |
| | OPAU-05 | GAGCTACCGT | 934 |
| | OPAU-06 | TCTCTAGGGG | 935 |
| | OPAU-07 | AGACCCTTGG | 936 |
| | OPAU-08 | CACCGATCCA | 937 |
| | OPAU-09 | ACGGCCAATC | 938 |
| | OPAU-10 | GGCGTATGGT | 939 |
| | OPAU-11 | CTTCTCGGTC | 940 |
| | OPAU-12 | CCACTCGTGT | 941 |
| | OPAU-13 | CCAAGCACAC | 942 |
| | OPAU-14 | CACCTCGACC | 943 |
| | OPAU-15 | TGCTGACGAC | 944 |
| | OPAU-16 | TCTTAGGCGG | 945 |
| | OPAU-17 | TTGGCATCCC | 946 |
| | OPAU-18 | CACCACTAGG | 947 |
| | OPAU-19 | AGCCTGGGA | 948 |
| | OPAU-20 | GTCGAAACCC | 949 |
| KIT AV | OPAV-01 | TGAGGGGAA | 950 |
| | OPAV-02 | TCACCGTGTC | 951 |
| | OPAV-03 | TGTAGCCGTG | 952 |
| | OPAV-04 | TCTGCCATCC | 953 |
| | OPAV-05 | GTGAGCGTGG | 954 |
| | OPAV-06 | CCCGAGATCC | 955 |
| | OPAV-07 | CTACCAGGGA | 956 |
| | OPAV-08 | TGAGAAGCGG | 957 |
| | OPAV-09 | GAGGTCCTAC | 958 |
| | OPAV-10 | ACCCCTGGCA | 959 |
| | OPAV-11 | GACCCCGACA | 960 |
| | OPAV-12 | AGCCGTCGAA | 961 |
| | OPAV-13 | CTGACTTCCC | 962 |
| | OPAV-14 | CTCCGGATCA | 963 |
| | OPAV-15 | GGCAGCAGGT | 964 |
| | OPAV-16 | GACAAGGACC | 965 |
| | OPAV-17 | CTCGAACCCC | 966 |
| | OPAV-18 | TTGCTCACGG | 967 |
| | OPAV-19 | CTCGATCACC | 968 |
| | OPAV-20 | TCATGCGCAC | 969 |
| KIT AW | OPAW-01 | ACCTAGGGGA | 970 |
| | OPAW-02 | TCGCAGGTTC | 971 |
| | OPAW-03 | CCATGCGGAG | 972 |
| | OPAW-04 | AGGAGCGACA | 973 |
| | OPAW-05 | CTGCTTCGAG | 974 |
| | OPAW-06 | TTTGGGCCCC | 975 |
| | OPAW-07 | AGCCCCCAAG | 976 |
| | OPAW-08 | CTGTCTGTGG | 977 |
| | OPAW-09 | ACTGGGTCGG | 978 |
| | OPAW-10 | GGTGTTTGCC | 979 |
| | OPAW-11 | CTGCCACGAG | 980 |
| | OPAW-12 | GAGCAAGGCA | 981 |
| | OPAW-13 | CTACGATGCC | 982 |
| | OPAW-14 | GGTTCTGCTC | 983 |
| | OPAW-15 | CCAGTCCCAA | 984 |
| | OPAW-16 | TTACCCCGCT | 985 |
| | OPAW-17 | TGCTGCTGCC | 986 |
| | OPAW-18 | GGCGCAACTG | 987 |

TABLE 3-continued

Operon RAPD ® 10-mer kits A-01 to BH-20

| Kit Name | Primer Name | Sequence | SEQ ID NO: |
|---|---|---|---|
| | OPAW-19 | GGACACAGAG | 988 |
| | OPAW-20 | TGTCCTAGCC | 989 |
| KIT AX | OPAX-01 | GTGTGCCGTT | 990 |
| | OPAX-02 | GGGAGGCAAA | 991 |
| | OPAX-03 | CCAAGAGGCT | 992 |
| | OPAX-04 | TCCCCAGGAG | 993 |
| | OPAX-05 | AGTGCACACC | 994 |
| | OPAX-06 | AGGCATCGTG | 995 |
| | OPAX-07 | ACGCGACAGA | 996 |
| | OPAX-08 | AGTATGGCGG | 997 |
| | OPAX-09 | GGAAGTCCTG | 998 |
| | OPAX-10 | CCAGGCTGAC | 999 |
| | OPAX-11 | TGATTGCGGG | 1000 |
| | OPAX-12 | GGTCGGGTCA | 1001 |
| | OPAX-13 | GAGCACTGCT | 1002 |
| | OPAX-14 | CACGGGCTTG | 1003 |
| | OPAX-15 | CAGCAATCCC | 1004 |
| | OPAX-16 | GTCTGTGCGG | 1005 |
| | OPAX-17 | TGGGCTCTGG | 1006 |
| | OPAX-18 | GTGTGCAGTG | 1007 |
| | OPAX-19 | CCCTGTCGCA | 1008 |
| | OPAX-20 | ACACTCGGCA | 1009 |
| KIT AY | OPAY-01 | GTCCACCTCT | 1010 |
| | OPAY-02 | TGCGAAGGCT | 1011 |
| | OPAY-03 | TTTCCGGGAG | 1012 |
| | OPAY-04 | AAGGCTCGAC | 1013 |
| | OPAY-05 | TCGCTGCGTT | 1014 |
| | OPAY-06 | GGCTTCGCAA | 1015 |
| | OPAY-07 | GACCGTCTGT | 1016 |
| | OPAY-08 | AGGCTTCCCT | 1017 |
| | OPAY-09 | CCGATCCAAC | 1018 |
| | OPAY-10 | CAAGGCCCCT | 1019 |
| | OPAY-11 | ACGCGCCTTC | 1020 |
| | OPAY-12 | CTGTCGGCGT | 1021 |
| | OPAY-13 | CCGCTCGTAA | 1022 |
| | OPAY-14 | GGTGGGTAGA | 1023 |
| | OPAY-15 | CCAAGAGGCA | 1024 |
| | OPAY-16 | GGTGTGGTTC | 1025 |
| | OPAY-17 | GGTGATTCGG | 1026 |
| | OPAY-18 | ACCCCAACCA | 1027 |
| | OPAY-19 | AACTTGGCCC | 1028 |
| | OPAY-20 | TCATTCGCCC | 1029 |
| KIT AZ | OPAZ-01 | TCGGATCCGT | 1030 |
| | OPAZ-02 | CCTGAACGGA | 1031 |
| | OPAZ-03 | GGCTGTGTGG | 1032 |
| | OPAZ-04 | CCAGCCTCAG | 1033 |
| | OPAZ-05 | TCCGCATACC | 1034 |
| | OPAZ-06 | CCTTCGGAGG | 1035 |
| | OPAZ-07 | CACGAGTCTC | 1036 |
| | OPAZ-08 | TCGCTCGTAG | 1037 |
| | OPAZ-09 | CCTTGACCCC | 1038 |
| | OPAZ-10 | ACTCTGGGGA | 1039 |
| | OPAZ-11 | TCCAGCGCGT | 1040 |
| | OPAZ-12 | GATGGGCCTG | 1041 |
| | OPAZ-13 | CCCGAAGCAA | 1042 |
| | OPAZ-14 | CACGGCTTCC | 1043 |
| | OPAZ-15 | TCCGCTAGTC | 1044 |
| | OPAZ-16 | AGGCGAACTG | 1045 |
| | OPAZ-17 | CACGCAGATG | 1046 |
| | OPAZ-18 | CCGACGTTGA | 1047 |
| | OPAZ-19 | ACACTCTCGG | 1048 |
| | OPAZ-20 | CATCACCCCT | 1049 |
| KIT BA | OPBA-01 | TTCCCCACCC | 1050 |
| | OPBA-02 | TGCTCGGCTC | 1051 |
| | OPBA-03 | GTGCGAGAAC | 1052 |
| | OPBA-04 | TCCTAGGCTC | 1053 |
| | OPBA-05 | TGCGTTCCAC | 1054 |
| | OPBA-06 | GGACGACCGT | 1055 |
| | OPBA-07 | GGGTCGCATC | 1056 |
| | OPBA-08 | CCACAGCCGA | 1057 |
| | OPBA-09 | GGAACTCCAC | 1058 |
| | OPBA-10 | GGACGTTGAG | 1059 |
| | OPBA-11 | CCACCTTCAG | 1060 |
| | OPBA-12 | TGTTGGGCAC | 1061 |
| | OPBA-13 | AGGGCGAATG | 1062 |

TABLE 3-continued

Operon RAPD ® 10-mer kits A-01 to BH-20

| Kit Name | Primer Name | Sequence | SEQ ID NO: |
|---|---|---|---|
| | OPBA-14 | TCGGGAGTGG | 1063 |
| | OPBA-15 | GAAGACCTGG | 1064 |
| | OPBA-16 | CCACGCATCA | 1065 |
| | OPBA-17 | TGTACCCCTG | 1066 |
| | OPBA-18 | CTCGGATGTC | 1067 |
| | OPBA-19 | CCATCCGTTG | 1068 |
| | OPBA-20 | GAGCGCTACC | 1069 |
| KIT BB | OPBB-01 | ACACTGGCTG | 1070 |
| | OPBB-02 | CCCCCGTTAG | 1071 |
| | OPBB-03 | TCACGTGGCT | 1072 |
| | OPBB-04 | ACCAGGTCAC | 1073 |
| | OPBB-05 | GGGCCGAACA | 1074 |
| | OPBB-06 | CTGAAGCTGG | 1075 |
| | OPBB-07 | GAAGGCTGGG | 1076 |
| | OPBB-08 | TCGTCGAAGG | 1077 |
| | OPBB-09 | AGGCCGGTCA | 1078 |
| | OPBB-10 | ACTTGCCTGG | 1079 |
| | OPBB-11 | TGCGGGTTCC | 1080 |
| | OPBB-12 | TTCGGCCGAC | 1081 |
| | OPBB-13 | CTTCGGTGTG | 1082 |
| | OPBB-14 | GTGGGACCTG | 1083 |
| | OPBB-15 | AAGTGCCCTG | 1084 |
| | OPBB-16 | TCGGCACCGT | 1085 |
| | OPBB-17 | ACACCGTGCC | 1086 |
| | OPBB-18 | CAACCGGTCT | 1087 |
| | OPBB-19 | TTGCGGACAG | 1088 |
| | OPBB-20 | CCAGGTGTAG | 1089 |
| KIT BC | OPBC-01 | CCTTCGGCTC | 1090 |
| | OPBC-02 | ACAGTAGCGG | 1091 |
| | OPBC-03 | GGCTTGACCT | 1092 |
| | OPBC-04 | CCACGTGCCA | 1093 |
| | OPBC-05 | GAGGCGATTG | 1094 |
| | OPBC-06 | GAAGGCGAGA | 1095 |
| | OPBC-07 | TGTGCCTGAC | 1096 |
| | OPBC-08 | GGTCTTCCCT | 1097 |
| | OPBC-09 | GTCATGCGAC | 1098 |
| | OPBC-10 | AACGTCGAGG | 1099 |
| | OPBC-11 | TTTTGCCCCC | 1100 |
| | OPBC-12 | CCTCCACCAG | 1101 |
| | OPBC-13 | CCTGGCACAG | 1102 |
| | OPBC-14 | GGTCCGACGA | 1103 |
| | OPBC-15 | CCAGACTCCA | 1104 |
| | OPBC-16 | CTGGTGCTCA | 1105 |
| | OPBC-17 | CCGTTAGTCC | 1106 |
| | OPBC-18 | GTGAAGGAGG | 1107 |
| | OPBC-19 | ACAAGCGCGA | 1108 |
| | OPBC-20 | AGCACTGGGG | 1109 |
| KIT BD | OPBD-01 | TCACTCGCTC | 1110 |
| | OPBD-02 | CCTCCCCAAG | 1111 |
| | OPBD-03 | GAGCCCCGAA | 1112 |
| | OPBD-04 | TCGGGTGTTG | 1113 |
| | OPBD-05 | GTGCGGAGAG | 1114 |
| | OPBD-06 | AAGCTGGCGT | 1115 |
| | OPBD-07 | GAGCTGGTCC | 1116 |
| | OPBD-08 | CATACGGGCT | 1117 |
| | OPBD-09 | CCACGGTCAG | 1118 |
| | OPBD-10 | GACGCTATGG | 1119 |
| | OPBD-11 | CAACCGAGTC | 1120 |
| | OPBD-12 | GGGAACCGTC | 1121 |
| | OPBD-13 | CCTGGAACGG | 1122 |
| | OPBD-14 | TCCCTGTGAG | 1123 |
| | OPBD-15 | TGTCGTGGTC | 1124 |
| | OPBD-16 | GAACTCCCAG | 1125 |
| | OPBD-17 | GTTCGCTCCC | 1126 |
| | OPBD-18 | ACGCACACTC | 1127 |
| | OPBD-19 | GGTTCCTCTC | 1128 |
| | OPBD-20 | AGGCGGCACA | 1129 |
| KIT BE | OPBE-01 | CACTCCTGGT | 1130 |
| | OPBE-02 | ACGCCTGTAG | 1131 |
| | OPBE-03 | TGGACTCGGT | 1132 |
| | OPBE-04 | CCCAAGCGAA | 1133 |
| | OPBE-05 | GGAACGCTAC | 1134 |
| | OPBE-06 | CAGCGGGTCA | 1135 |
| | OPBE-07 | CCGTCCTATG | 1136 |
| | OPBE-08 | GGGAAGCGTC | 1137 |

TABLE 3-continued

Operon RAPD ® 10-mer kits A-01 to BH-20

| Kit Name | Primer Name | Sequence | SEQ ID NO: |
|---|---|---|---|
| | OPBE-09 | CCCGCTTTCC | 1138 |
| | OPBE-10 | AAGCGGCCCT | 1139 |
| | OPBE-11 | GTCCTGCTGT | 1140 |
| | OPBE-12 | GGTTGTTCCC | 1141 |
| | OPBE-13 | TCGGTGAGTC | 1142 |
| | OPBE-14 | CTTTGCGCAC | 1143 |
| | OPBE-15 | TTCGGCGATG | 1144 |
| | OPBE-16 | CTCCACGACT | 1145 |
| | OPBE-17 | GGGAAAAGCC | 1146 |
| | OPBE-18 | CCAAGCCGTC | 1147 |
| | OPBE-19 | AGGCCAACAG | 1148 |
| | OPBE-20 | CAAAGGCGTG | 1149 |
| KIT BF | OPBF-01 | GGAGCTGACT | 1150 |
| | OPBF-02 | GACACACTCC | 1151 |
| | OPBF-03 | TCCCTTGACC | 1152 |
| | OPBF-04 | GACAGGTTGG | 1153 |
| | OPBF-05 | CACCCCGAAA | 1154 |
| | OPBF-06 | TCCACGGGCA | 1155 |
| | OPBF-07 | CACCATCGTG | 1156 |
| | OPBF-08 | CCTGGGTCCA | 1157 |
| | OPBF-09 | ACCCAGGTTG | 1158 |
| | OPBF-10 | GTGACCAGAG | 1159 |
| | OPBF-11 | GACGACCGCA | 1160 |
| | OPBF-12 | CTTCGCTGTC | 1161 |
| | OPBF-13 | CCGCCGGTAA | 1162 |
| | OPBF-14 | CCGCGTTGAG | 1163 |
| | OPBF-15 | ACGCGAACCT | 1164 |
| | OPBF-16 | AGGGTCCGTG | 1165 |
| | OPBF-17 | CAAGCTCGTG | 1166 |
| | OPBF-18 | AGCCAAGGAC | 1167 |
| | OPBF-19 | TTCCCGCACT | 1168 |
| | OPBF-20 | ACCCTGAGGA | 1169 |
| KIT BG | OPBG-01 | GTGGCTCTCC | 1170 |
| | OPBG-02 | GGAAAGCCCA | 1171 |
| | OPBG-03 | GTGCCACTTC | 1172 |
| | OPBG-04 | GTTCCCGACA | 1173 |
| | OPBG-05 | CAAGCCGTGA | 1174 |
| | OPBG-06 | GTGGATCGTC | 1175 |
| | OPBG-07 | CAGAGGTTCC | 1176 |
| | OPBG-08 | GACCAGAGGT | 1177 |
| | OPBG-09 | GGCTCTGGGT | 1178 |
| | OPBG-10 | GGGATAAGGG | 1179 |
| | OPBG-11 | ACGGCAATGG | 1180 |
| | OPBG-12 | CCCGAGAAAC | 1181 |
| | OPBG-13 | GGTTGGGCCA | 1182 |
| | OPBG-14 | GACCAGCCCA | 1183 |
| | OPBG-15 | ACGGGAGAGA | 1184 |
| | OPBG-16 | TGCTTGGGTG | 1185 |
| | OPBG-17 | TCCGGGACTC | 1186 |
| | OPBG-18 | TGGCGCTGGT | 1187 |
| | OPBG-19 | GGTCTCGCTC | 1188 |
| | OPBG-20 | TGGTACCTGG | 1189 |
| KIT BH | OPBH-01 | CCGACTCTGG | 1190 |
| | OPBH-02 | GTAAGCCGAG | 1191 |
| | OPBH-03 | GGAGCAGCAA | 1192 |
| | OPBH-04 | ACCTGCCAAC | 1193 |
| | OPBH-05 | GTAGGTCGCA | 1194 |
| | OPBH-06 | TCGTGGCACA | 1195 |
| | OPBH-07 | TGTACGGCAC | 1196 |
| | OPBH-08 | ACGGAGGCAG | 1197 |
| | OPBH-09 | GTCTTCCGTC | 1198 |
| | OPBH-10 | GTGTGCCTGG | 1199 |
| | OPBH-11 | AGCCCAAAGG | 1200 |
| | OPBH-12 | TCGCCTTGTC | 1201 |
| | OPBH-13 | AGTTGGGCAG | 1202 |
| | OPBH-14 | ACCGTGGGTG | 1203 |
| | OPBH-15 | GAGAACGCTG | 1204 |
| | OPBH-16 | CTGCGGGTTC | 1205 |
| | OPBH-17 | CTCTTACGGG | 1206 |
| | OPBH-18 | GACGCTTGTC | 1207 |
| | OPBH-19 | GTCGTGCGGA | 1208 |
| | OPBH-20 | CACCGACATC | 1209 |

DEFINITIONS

BSA—Bulked Segregant Analysis—Selection strategy wherein, in large segregating populations, individuals with the same trait (phenotype) or DNA of these individuals are bulked into "pools". After screening of these pools with DNA techniques, markers are identified which are linked to the relevant phenotype.

cM—centimorgan—Unit for the genetic distance between markers, based on the number of crossing-overs per hundred individuals.

DNA marker—A DNA fragment which is linked to a gene or another piece of DNA with a known location on the genome, which is used to monitor heritability of this gene or this location.

Dominant—Allel which masks the phenotypical expression of another allel when both are present.

Gel-electrophoresis—Method for separating molecules (DNA, RNA, protein among others), on the basis of their size, shape or charge, in a matrix (agarose or polyacrylamide) under the influence of an electric field.

Gene—The basic unit of heredity, whereby hereditary traits are transmitted from parents to progeny.

Introgression—A chromosome fragment of a line which can for instance be inserted into another line by crossing.

IRDye labels—Labels which are used for Licor imaging systems, the detection of which takes place at 700 nm or 800 nm.

iSSR-primer (inter Simple Sequence Repeat primer)—A primer designed on the 5' end of an SSR (Single Sequence Repeat), a piece of DNA consisting of a repetition of 2 or 3 nucleotides.

Monogenic—Determined by a single gene.

PCR (Polymerase Chain Reaction)—An in vitro amplification method for multiplying a specific DNA fragment. This synthesis reaction makes use of a minimum of one oligonucleotide primer which hybridizes with a piece of DNA, after which a DNA polymerase amplifies the flanking region via successive temperature cycles.

Primer—A short oligonucleotide (~20-50 bp) complementary to the sequence of a single-strand DNA molecule, which serves as starting point of a polymerase.

RAPD-primer (Random Amplified Polymorphic DNA primer)—A 10-mer with a "random" sequence, wherein the GC-content lies between 60% and 70% and wherein the primer ends are not self-complementary.

RAMPs (Random Amplified Microsatellite Polymorphisms)-DNA fingerprinting technique based on RAPD and iSSR primers with which polymorphisms between different DNA monsters are detected.

Resistance—The ability of a plant to wholly or partially prevent the effects and/or growth of a pathogen.

BC (Backcrossing)—Crossing of an individual with one of the original parents.

The invention claimed is:

1. A *Brassica oleracea* plant, comprising a single dominant resistance gene to *Albugo candida*, wherein the resistance gene comes from the *B. oleracea* plant line 9002757, the seeds of said line were deposited in the American Type Culture Collection (ATCC) under number PTA-7412, and wherein the presence of the single dominant resistance gene is demonstrated using at least one DNA marker linked to the resistance gene; wherein the at least one DNA marker is selected from the group consisting of SEQ ID NO: 1 to SEQ ID NO:9.

2. The plant as claimed in claim 1, wherein the resistance gene is present in heterozygous form.

3. The plant as claimed in claim 1, wherein the resistance gene is present in homozygous form.

4. The plant as claimed in claim 1, wherein the presence of the resistance gene is demonstrated using at least two DNA markers linked to the resistance gene.

5. The plant as claimed in claim 4, wherein the at least two DNA markers enclose the resistance gene.

6. The plant as claimed in claim 1, wherein the presence of the at least one DNA marker in the genome of the plant is demonstrated by polymerase chain reaction (PCR) using (1) a primer sequence selected from the group consisting of SEQ ID NO: 1 to SEQ ID NO: 9 and (2) a RAPD primer.

7. The plant as claimed in claim 1, wherein the plant is selected from the group consisting of *Brassica oleracea* convar. *botrytis* var. *botrytis*, *Brassica oleracea* convar. *botrytis* var. *cymosa*, *Brassica oleracea* convar. *botrytis* var. *asparagoides*, *Brassica oleracea* convar. *oleracea* var. *gemnifera*, *Brassica oleracea* convar. *capitata* var. *alba* *Brassica oleracea* convar. *capitata* var. *rubra*, *Brassica oleracea* convar. *capitata* var. *sabauda*, *Brassica oleracea* convar. *acephela* var. *sabellica*, *Brassica oleracea* convar. *acephela* var. *gongyloides* and *Brassica oleracea* var. *tronchuda* syn. *costata*.

8. A fruit or plant part from the plant as claimed in claim 1, wherein the fruit or plant part comprises the at least one DNA marker linked to the resistance gene.

9. A method for providing a *Brassica oleracea* plant with a resistance to *Albugo candida*, the method comprising
(a) crossing a first *B. oleracea* plant, which comprises a resistance gene from the *B. oleracea* plant line 9002757, the seeds of said line were deposited in the ATCC, under number PTA-7412, with a susceptible second *B. oleracea* plant to produce progeny plants;
(b) detecting in the progeny plants the presence of one or more DNA markers linked to the resistance gene, wherein the DNA marker is selected from the group consisting of SEQ ID NO: 1 to 9; and (c) selecting progeny plants in which the presence of the one or more DNA markers linked to the resistance gene has been demonstrated.

10. The method as claimed in claim 9, wherein the resistance gene is present in heterozygous form.

11. The method as claimed in claim 9, wherein the resistance gene is present in homozygous form.

12. The method as claimed in claim 9, wherein the presence of the resistance gene in the selected plants is confirmed by way of a disease test.

13. The method as claimed in claim 9, wherein the selection of the resistant B. oleracea plant in step (c) comprises selecting a B. oleracea plant which comprises at least two DNA markers linked to the resistance gene, wherein the DNA markers enclose the resistance gene.

14. The method as claimed in claim 9, wherein the susceptible B. oleracea plant is selected from the group consisting of B. oleracea convar. botrytis var. botrytis, B. oleracea convar. botrytis var. cymosa, B. oleracea convar. botrytis var. asparagoides, B. oleracea convar. oleracea var. gemnifera, B. oleracea convar. capitata var. alba, B. oleracea convar. capitata var. rubra, B. oleracea convar. capitata var. sabauda, B. oleracea convar. acephela var. sabellica, B. oleracea convar. acephela var. gongyloides, and B. oleracea var. tronchuda syn. costata.

15. A Brassica oleracea plant resistant to Albugo candida obtained with the method as claimed in claim 9, wherein the plant comprises the one or more DNA markers linked to the resistance gene.

16. A method for identifying a Brassica oleracea plant comprising a resistance gene to Albugo candida, wherein the resistance gene comes from the B. oleracea plant line 9002757, the seeds of said line were deposited in the ATCC under number PTA-7412, the method comprising:
  detecting at least one DNA marker linked to the resistance gene to A. candida, wherein the at least one DNA marker is selected from the group consisting of SEQ ID NO: 1 to SEQ ID NO:9, and wherein the presence of the at least one DNA marker is demonstrated by PCR using (1) a primer sequence selected from the group consisting of SEQ ID NO: 1 to SEQ ID NO: 9 and (2) a RAPD primer.

17. The plant as claimed in claim 2, wherein the presence of the resistance gene can be demonstrated using at least two DNA markers linked to the resistance gene.

18. The plants as claimed in claim 3, wherein the presence of the resistance gene is demonstrated using at least two DNA marker markers linked to the resistance gene.

19. The method as claimed in claim 10, wherein the presence of the resistance gene in the selected plants is confirmed by way of a disease test.

20. The method as claimed in claim 11, wherein the presence of the resistance gene in the selected plants is confirmed by way of a disease test.

21. The method as claimed in claim 9, wherein the presence of the one or more DNA markers is demonstrated by PCR using (1) a primer sequence selected from the group consisting of SEQ ID NO:1 to SEQ ID NO:9 and (2) a RAPD primer.

* * * * *

SEQUENCE LISTING

```
<160> NUMBER OF SEQ ID NOS: 1209

<210> SEQ ID NO 1
<211> LENGTH: 33
<212> TYPE: DNA
<213> ORGANISM: Brassica oleracea

<400> SEQUENCE: 1
caggaaacag ctatgacaaa aagagagaga gag                             33

<210> SEQ ID NO 2
<211> LENGTH: 33
<212> TYPE: DNA
<213> ORGANISM: Brassica oleracea

<400> SEQUENCE: 2
caggaaacag ctatgactac gacacacaca cac                             33

<210> SEQ ID NO 3
<211> LENGTH: 37
<212> TYPE: DNA
<213> ORGANISM: Brassica oleracea

<400> SEQUENCE: 3
caggaaacag ctatgacata catatatata tatatat                         37

<210> SEQ ID NO 4
<211> LENGTH: 33
<212> TYPE: DNA
<213> ORGANISM: Brassica oleracea

<400> SEQUENCE: 4
caggaaacag ctatgaccca ggtgtgtgtg tgt                             33
```

-continued

```
<210> SEQ ID NO 5
<211> LENGTH: 34
<212> TYPE: DNA
<213> ORGANISM: Brassica oleracea

<400> SEQUENCE: 5
caggaaacag ctatgacagt ggagagagag agag                              34

<210> SEQ ID NO 6
<211> LENGTH: 33
<212> TYPE: DNA
<213> ORGANISM: Brassica oleracea

<400> SEQUENCE: 6
caggaaacag ctatgacact atctctctct ctc                               33

<210> SEQ ID NO 7
<211> LENGTH: 33
<212> TYPE: DNA
<213> ORGANISM: Brassica oleracea

<400> SEQUENCE: 7
caggaaacag ctatgacatc ttcatcatca tca                               33

<210> SEQ ID NO 8
<211> LENGTH: 31
<212> TYPE: DNA
<213> ORGANISM: Brassica oleracea

<400> SEQUENCE: 8
caggaaacag ctatgacgtt tgagagagag a                                 31

<210> SEQ ID NO 9
<211> LENGTH: 33
<212> TYPE: DNA
<213> ORGANISM: Brassica oleracea

<400> SEQUENCE: 9
caggaaacag ctatgacccc acaacaacaa caa                               33

<210> SEQ ID NO 10
<211> LENGTH: 10
<212> TYPE: DNA
<213> ORGANISM: Artificial sequence
<220> FEATURE:
<223> OTHER INFORMATION: Primer OPA-01

<400> SEQUENCE: 10
caggccttc                                                          10

<210> SEQ ID NO 11
<211> LENGTH: 10
<212> TYPE: DNA
<213> ORGANISM: Artificial sequence
<220> FEATURE:
<223> OTHER INFORMATION: Primer OPA-02

<400> SEQUENCE: 11
tgccgagctg                                                         10

<210> SEQ ID NO 12
<211> LENGTH: 10
<212> TYPE: DNA
<213> ORGANISM: Artificial sequence
<220> FEATURE:
<223> OTHER INFORMATION: Primer OPA-03
```

```
<400> SEQUENCE: 12
agtcagccac                                                          10

<210> SEQ ID NO 13
<211> LENGTH: 10
<212> TYPE: DNA
<213> ORGANISM: Artificial sequence
<220> FEATURE:
<223> OTHER INFORMATION: Primer OPA-04

<400> SEQUENCE: 13
aatcgggctg                                                          10

<210> SEQ ID NO 14
<211> LENGTH: 10
<212> TYPE: DNA
<213> ORGANISM: Artificial sequence
<220> FEATURE:
<223> OTHER INFORMATION: Primer OPA-05

<400> SEQUENCE: 14
aggggtcttg                                                          10

<210> SEQ ID NO 15
<211> LENGTH: 10
<212> TYPE: DNA
<213> ORGANISM: Artificial sequence
<220> FEATURE:
<223> OTHER INFORMATION: Primer OPA-06

<400> SEQUENCE: 15
ggtccctgac                                                          10

<210> SEQ ID NO 16
<211> LENGTH: 10
<212> TYPE: DNA
<213> ORGANISM: Artificial sequence
<220> FEATURE:
<223> OTHER INFORMATION: Primer OPA-07

<400> SEQUENCE: 16
gaaacgggtg                                                          10

<210> SEQ ID NO 17
<211> LENGTH: 10
<212> TYPE: DNA
<213> ORGANISM: Artificial sequence
<220> FEATURE:
<223> OTHER INFORMATION: Primer OPA-08

<400> SEQUENCE: 17
gtgacgtagg                                                          10

<210> SEQ ID NO 18
<211> LENGTH: 10
<212> TYPE: DNA
<213> ORGANISM: Artificial sequence
<220> FEATURE:
<223> OTHER INFORMATION: Primer OPA-09

<400> SEQUENCE: 18
gggtaacgcc                                                          10

<210> SEQ ID NO 19
<211> LENGTH: 10
```

```
<212> TYPE: DNA
<213> ORGANISM: Artificial sequence
<220> FEATURE:
<223> OTHER INFORMATION: Primer OPA-10

<400> SEQUENCE: 19
gtgatcgcag                                                              10

<210> SEQ ID NO 20
<211> LENGTH: 10
<212> TYPE: DNA
<213> ORGANISM: Artificial sequence
<220> FEATURE:
<223> OTHER INFORMATION: Primer OPA-11

<400> SEQUENCE: 20
caatcgccgt                                                              10

<210> SEQ ID NO 21
<211> LENGTH: 10
<212> TYPE: DNA
<213> ORGANISM: Artificial sequence
<220> FEATURE:
<223> OTHER INFORMATION: Primer OPA-12

<400> SEQUENCE: 21
tcggcgatag                                                              10

<210> SEQ ID NO 22
<211> LENGTH: 10
<212> TYPE: DNA
<213> ORGANISM: Artificial sequence
<220> FEATURE:
<223> OTHER INFORMATION: Primer OPA-13

<400> SEQUENCE: 22
cagcacccac                                                              10

<210> SEQ ID NO 23
<211> LENGTH: 10
<212> TYPE: DNA
<213> ORGANISM: Artificial sequence
<220> FEATURE:
<223> OTHER INFORMATION: Primer OPA-14

<400> SEQUENCE: 23
tctgtgctgg                                                              10

<210> SEQ ID NO 24
<211> LENGTH: 10
<212> TYPE: DNA
<213> ORGANISM: Artificial sequence
<220> FEATURE:
<223> OTHER INFORMATION: Primer OPA-15

<400> SEQUENCE: 24
ttccgaaccc                                                              10

<210> SEQ ID NO 25
<211> LENGTH: 10
<212> TYPE: DNA
<213> ORGANISM: Artificial sequence
<220> FEATURE:
<223> OTHER INFORMATION: Primer OPA-16

<400> SEQUENCE: 25
agccagcgaa                                                              10
```

<210> SEQ ID NO 26
<211> LENGTH: 10
<212> TYPE: DNA
<213> ORGANISM: Artificial sequence
<220> FEATURE:
<223> OTHER INFORMATION: Primer OPA-17

<400> SEQUENCE: 26
gaccgcttgt                                                                 10

<210> SEQ ID NO 27
<211> LENGTH: 10
<212> TYPE: DNA
<213> ORGANISM: Artificial sequence
<220> FEATURE:
<223> OTHER INFORMATION: Primer OPA-18

<400> SEQUENCE: 27
aggtgaccgt                                                                 10

<210> SEQ ID NO 28
<211> LENGTH: 10
<212> TYPE: DNA
<213> ORGANISM: Artificial sequence
<220> FEATURE:
<223> OTHER INFORMATION: Primer OPA-19

<400> SEQUENCE: 28
caaacgtcgg                                                                 10

<210> SEQ ID NO 29
<211> LENGTH: 10
<212> TYPE: DNA
<213> ORGANISM: Artificial sequence
<220> FEATURE:
<223> OTHER INFORMATION: Primer OPA-20

<400> SEQUENCE: 29
gttgcgatcc                                                                 10

<210> SEQ ID NO 30
<211> LENGTH: 10
<212> TYPE: DNA
<213> ORGANISM: Artificial sequence
<220> FEATURE:
<223> OTHER INFORMATION: Primer OPB-01

<400> SEQUENCE: 30
gtttcgctcc                                                                 10

<210> SEQ ID NO 31
<211> LENGTH: 10
<212> TYPE: DNA
<213> ORGANISM: Artificial sequence
<220> FEATURE:
<223> OTHER INFORMATION: Primer OPB-02

<400> SEQUENCE: 31
tgatccctgg                                                                 10

<210> SEQ ID NO 32
<211> LENGTH: 10
<212> TYPE: DNA
<213> ORGANISM: Artificial sequence
<220> FEATURE:
<223> OTHER INFORMATION: Primer OPB-03

```
<400> SEQUENCE: 32
catcccctg                                                            10

<210> SEQ ID NO 33
<211> LENGTH: 10
<212> TYPE: DNA
<213> ORGANISM: Artificial sequence
<220> FEATURE:
<223> OTHER INFORMATION: Primer OPB-04

<400> SEQUENCE: 33
ggactggagt                                                           10

<210> SEQ ID NO 34
<211> LENGTH: 10
<212> TYPE: DNA
<213> ORGANISM: Artificial sequence
<220> FEATURE:
<223> OTHER INFORMATION: Primer OPB-05

<400> SEQUENCE: 34
tgcgcccttc                                                           10

<210> SEQ ID NO 35
<211> LENGTH: 10
<212> TYPE: DNA
<213> ORGANISM: Artificial sequence
<220> FEATURE:
<223> OTHER INFORMATION: Primer OPB-06

<400> SEQUENCE: 35
tgctctgccc                                                           10

<210> SEQ ID NO 36
<211> LENGTH: 10
<212> TYPE: DNA
<213> ORGANISM: Artificial sequence
<220> FEATURE:
<223> OTHER INFORMATION: Primer OPB-07

<400> SEQUENCE: 36
ggtgacgcag                                                           10

<210> SEQ ID NO 37
<211> LENGTH: 10
<212> TYPE: DNA
<213> ORGANISM: Artificial sequence
<220> FEATURE:
<223> OTHER INFORMATION: Primer OPB-08

<400> SEQUENCE: 37
gtccacacgg                                                           10

<210> SEQ ID NO 38
<211> LENGTH: 10
<212> TYPE: DNA
<213> ORGANISM: Artificial sequence
<220> FEATURE:
<223> OTHER INFORMATION: Primer OPB-09

<400> SEQUENCE: 38
tgggggactc                                                           10

<210> SEQ ID NO 39
<211> LENGTH: 10
```

```
<212> TYPE: DNA
<213> ORGANISM: Artificial sequence
<220> FEATURE:
<223> OTHER INFORMATION: Primer OPB-10

<400> SEQUENCE: 39
ctgctgggac                                                          10

<210> SEQ ID NO 40
<211> LENGTH: 10
<212> TYPE: DNA
<213> ORGANISM: Artificial sequence
<220> FEATURE:
<223> OTHER INFORMATION: Primer OPB-11

<400> SEQUENCE: 40
gtagacccgt                                                          10

<210> SEQ ID NO 41
<211> LENGTH: 10
<212> TYPE: DNA
<213> ORGANISM: Artificial sequence
<220> FEATURE:
<223> OTHER INFORMATION: Primer OPB-12

<400> SEQUENCE: 41
ccttgacgca                                                          10

<210> SEQ ID NO 42
<211> LENGTH: 10
<212> TYPE: DNA
<213> ORGANISM: Artificial sequence
<220> FEATURE:
<223> OTHER INFORMATION: Primer OPB-13

<400> SEQUENCE: 42
ttcccccgct                                                          10

<210> SEQ ID NO 43
<211> LENGTH: 10
<212> TYPE: DNA
<213> ORGANISM: Artificial sequence
<220> FEATURE:
<223> OTHER INFORMATION: Primer OPB-14

<400> SEQUENCE: 43
tccgctctgg                                                          10

<210> SEQ ID NO 44
<211> LENGTH: 10
<212> TYPE: DNA
<213> ORGANISM: Artificial sequence
<220> FEATURE:
<223> OTHER INFORMATION: Primer OPB-15

<400> SEQUENCE: 44
ggagggtgtt                                                          10

<210> SEQ ID NO 45
<211> LENGTH: 10
<212> TYPE: DNA
<213> ORGANISM: Artificial sequence
<220> FEATURE:
<223> OTHER INFORMATION: Primer OPB-16

<400> SEQUENCE: 45
tttgcccgga                                                          10
```

<210> SEQ ID NO 46
<211> LENGTH: 10
<212> TYPE: DNA
<213> ORGANISM: Artificial sequence
<220> FEATURE:
<223> OTHER INFORMATION: Primer OPB-17

<400> SEQUENCE: 46
agggaacgag                                                              10

<210> SEQ ID NO 47
<211> LENGTH: 10
<212> TYPE: DNA
<213> ORGANISM: Artificial sequence
<220> FEATURE:
<223> OTHER INFORMATION: Primer OPB-18

<400> SEQUENCE: 47
ccacagcagt                                                              10

<210> SEQ ID NO 48
<211> LENGTH: 10
<212> TYPE: DNA
<213> ORGANISM: Artificial sequence
<220> FEATURE:
<223> OTHER INFORMATION: Primer OPB-19

<400> SEQUENCE: 48
accccgaag                                                               10

<210> SEQ ID NO 49
<211> LENGTH: 10
<212> TYPE: DNA
<213> ORGANISM: Artificial sequence
<220> FEATURE:
<223> OTHER INFORMATION: Primer OPB-20

<400> SEQUENCE: 49
ggacccttac                                                              10

<210> SEQ ID NO 50
<211> LENGTH: 10
<212> TYPE: DNA
<213> ORGANISM: Artificial sequence
<220> FEATURE:
<223> OTHER INFORMATION: Primer OPC-01

<400> SEQUENCE: 50
ttcgagccag                                                              10

<210> SEQ ID NO 51
<211> LENGTH: 10
<212> TYPE: DNA
<213> ORGANISM: Artificial sequence
<220> FEATURE:
<223> OTHER INFORMATION: Primer OPC-02

<400> SEQUENCE: 51
gtgaggcgtc                                                              10

<210> SEQ ID NO 52
<211> LENGTH: 10
<212> TYPE: DNA
<213> ORGANISM: Artificial sequence
<220> FEATURE:
<223> OTHER INFORMATION: Primer OPC-03

<400> SEQUENCE: 52 ggggggtcttt                                                                10

<210> SEQ ID NO 53
<211> LENGTH: 10
<212> TYPE: DNA
<213> ORGANISM: Artificial sequence
<220> FEATURE:
<223> OTHER INFORMATION: Primer OPC-04

<400> SEQUENCE: 53
ccgcatctac                                                                 10

<210> SEQ ID NO 54
<211> LENGTH: 10
<212> TYPE: DNA
<213> ORGANISM: Artificial sequence
<220> FEATURE:
<223> OTHER INFORMATION: Primer OPC-05

<400> SEQUENCE: 54
gatgaccgcc                                                                 10

<210> SEQ ID NO 55
<211> LENGTH: 10
<212> TYPE: DNA
<213> ORGANISM: Artificial sequence
<220> FEATURE:
<223> OTHER INFORMATION: Primer OPC-06

<400> SEQUENCE: 55
gaacggactc                                                                 10

<210> SEQ ID NO 56
<211> LENGTH: 10
<212> TYPE: DNA
<213> ORGANISM: Artificial sequence
<220> FEATURE:
<223> OTHER INFORMATION: Primer OPC-07

<400> SEQUENCE: 56
gtcccgacga                                                                 10

<210> SEQ ID NO 57
<211> LENGTH: 10
<212> TYPE: DNA
<213> ORGANISM: Artificial sequence
<220> FEATURE:
<223> OTHER INFORMATION: Primer OPC-08

<400> SEQUENCE: 57
tggaccggtg                                                                 10

<210> SEQ ID NO 58
<211> LENGTH: 10
<212> TYPE: DNA
<213> ORGANISM: Artificial sequence
<220> FEATURE:
<223> OTHER INFORMATION: Primer OPC-09

<400> SEQUENCE: 58
ctcaccgtcc                                                                 10

<210> SEQ ID NO 59
<211> LENGTH: 10

```
<212> TYPE: DNA
<213> ORGANISM: Artificial sequence
<220> FEATURE:
<223> OTHER INFORMATION: Primer OPC-10

<400> SEQUENCE: 59
tgtctgggtg                                                               10

<210> SEQ ID NO 60
<211> LENGTH: 10
<212> TYPE: DNA
<213> ORGANISM: Artificial sequence
<220> FEATURE:
<223> OTHER INFORMATION: Primer OPC-11

<400> SEQUENCE: 60
aaagctgcgg                                                               10

<210> SEQ ID NO 61
<211> LENGTH: 10
<212> TYPE: DNA
<213> ORGANISM: Artificial sequence
<220> FEATURE:
<223> OTHER INFORMATION: Primer OPC-12

<400> SEQUENCE: 61
tgtcatcccc                                                               10

<210> SEQ ID NO 62
<211> LENGTH: 10
<212> TYPE: DNA
<213> ORGANISM: Artificial sequence
<220> FEATURE:
<223> OTHER INFORMATION: Primer OPC-13

<400> SEQUENCE: 62
aagcctcgtc                                                               10

<210> SEQ ID NO 63
<211> LENGTH: 10
<212> TYPE: DNA
<213> ORGANISM: Artificial sequence
<220> FEATURE:
<223> OTHER INFORMATION: Primer OPC-14

<400> SEQUENCE: 63
tgcgtgcttg                                                               10

<210> SEQ ID NO 64
<211> LENGTH: 10
<212> TYPE: DNA
<213> ORGANISM: Artificial sequence
<220> FEATURE:
<223> OTHER INFORMATION: Primer OPC-15

<400> SEQUENCE: 64
gacggatcag                                                               10

<210> SEQ ID NO 65
<211> LENGTH: 10
<212> TYPE: DNA
<213> ORGANISM: Artificial sequence
<220> FEATURE:
<223> OTHER INFORMATION: Primer OPC-16

<400> SEQUENCE: 65
cacactccag                                                               10
```

```
<210> SEQ ID NO 66
<211> LENGTH: 10
<212> TYPE: DNA
<213> ORGANISM: Artificial sequence
<220> FEATURE:
<223> OTHER INFORMATION: Primer OPC-17

<400> SEQUENCE: 66 ttcccccccag                                                              10

<210> SEQ ID NO 67
<211> LENGTH: 10
<212> TYPE: DNA
<213> ORGANISM: Artificial sequence
<220> FEATURE:
<223> OTHER INFORMATION: Primer OPC-18

<400> SEQUENCE: 67
tgagtgggtg                                                               10

<210> SEQ ID NO 68
<211> LENGTH: 10
<212> TYPE: DNA
<213> ORGANISM: Artificial sequence
<220> FEATURE:
<223> OTHER INFORMATION: Primer OPC-19

<400> SEQUENCE: 68
gttgccagcc                                                               10

<210> SEQ ID NO 69
<211> LENGTH: 10
<212> TYPE: DNA
<213> ORGANISM: Artificial sequence
<220> FEATURE:
<223> OTHER INFORMATION: Primer OPC-20

<400> SEQUENCE: 69
acttcgccac                                                               10

<210> SEQ ID NO 70
<211> LENGTH: 10
<212> TYPE: DNA
<213> ORGANISM: Artificial sequence
<220> FEATURE:
<223> OTHER INFORMATION: Primer OPD-01

<400> SEQUENCE: 70
accgcgaagg                                                               10

<210> SEQ ID NO 71
<211> LENGTH: 10
<212> TYPE: DNA
<213> ORGANISM: Artificial sequence
<220> FEATURE:
<223> OTHER INFORMATION: Primer OPD-02

<400> SEQUENCE: 71
ggacccaacc                                                               10

<210> SEQ ID NO 72
<211> LENGTH: 10
<212> TYPE: DNA
<213> ORGANISM: Artificial sequence
<220> FEATURE:
<223> OTHER INFORMATION: Primer OPD-03
```

```
<400> SEQUENCE: 72
gtcgccgtca                                                          10

<210> SEQ ID NO 73
<211> LENGTH: 10
<212> TYPE: DNA
<213> ORGANISM: Artificial sequence
<220> FEATURE:
<223> OTHER INFORMATION: Primer OPD-04

<400> SEQUENCE: 73
tctggtgagg                                                          10

<210> SEQ ID NO 74
<211> LENGTH: 10
<212> TYPE: DNA
<213> ORGANISM: Artificial sequence
<220> FEATURE:
<223> OTHER INFORMATION: Primer OPD-05

<400> SEQUENCE: 74
tgagcggaca                                                          10

<210> SEQ ID NO 75
<211> LENGTH: 10
<212> TYPE: DNA
<213> ORGANISM: Artificial sequence
<220> FEATURE:
<223> OTHER INFORMATION: Primer OPD-06

<400> SEQUENCE: 75
acctgaacgg                                                          10

<210> SEQ ID NO 76
<211> LENGTH: 10
<212> TYPE: DNA
<213> ORGANISM: Artificial sequence
<220> FEATURE:
<223> OTHER INFORMATION: Primer OPD-07

<400> SEQUENCE: 76
ttggcacggg                                                          10

<210> SEQ ID NO 77
<211> LENGTH: 10
<212> TYPE: DNA
<213> ORGANISM: Artificial sequence
<220> FEATURE:
<223> OTHER INFORMATION: Primer OPD-08

<400> SEQUENCE: 77
gtgtgcccca                                                          10

<210> SEQ ID NO 78
<211> LENGTH: 10
<212> TYPE: DNA
<213> ORGANISM: Artificial sequence
<220> FEATURE:
<223> OTHER INFORMATION: Primer OPD-09

<400> SEQUENCE: 78
ctctggagac                                                          10

<210> SEQ ID NO 79
<211> LENGTH: 10
```

```
<212> TYPE: DNA
<213> ORGANISM: Artificial sequence
<220> FEATURE:
<223> OTHER INFORMATION: Primer OPD-10

<400> SEQUENCE: 79
ggtctacacc                                                                10

<210> SEQ ID NO 80
<211> LENGTH: 10
<212> TYPE: DNA
<213> ORGANISM: Artificial sequence
<220> FEATURE:
<223> OTHER INFORMATION: Primer OPD-11

<400> SEQUENCE: 80
agcgccattg                                                                10

<210> SEQ ID NO 81
<211> LENGTH: 10
<212> TYPE: DNA
<213> ORGANISM: Artificial sequence
<220> FEATURE:
<223> OTHER INFORMATION: Primer OPD-12

<400> SEQUENCE: 81
caccgtatcc                                                                10

<210> SEQ ID NO 82
<211> LENGTH: 10
<212> TYPE: DNA
<213> ORGANISM: Artificial sequence
<220> FEATURE:
<223> OTHER INFORMATION: Primer OPD-13

<400> SEQUENCE: 82
ggggtgacga                                                                10

<210> SEQ ID NO 83
<211> LENGTH: 10
<212> TYPE: DNA
<213> ORGANISM: Artificial sequence
<220> FEATURE:
<223> OTHER INFORMATION: Primer OPD-14

<400> SEQUENCE: 83
cttccccaag                                                                10

<210> SEQ ID NO 84
<211> LENGTH: 10
<212> TYPE: DNA
<213> ORGANISM: Artificial sequence
<220> FEATURE:
<223> OTHER INFORMATION: Primer OPD-15

<400> SEQUENCE: 84
catccgtgct                                                                10

<210> SEQ ID NO 85
<211> LENGTH: 10
<212> TYPE: DNA
<213> ORGANISM: Artificial sequence
<220> FEATURE:
<223> OTHER INFORMATION: Primer OPD-16

<400> SEQUENCE: 85
agggcgtaag                                                                10
```

<210> SEQ ID NO 86
<211> LENGTH: 10
<212> TYPE: DNA
<213> ORGANISM: Artificial sequence
<220> FEATURE:
<223> OTHER INFORMATION: Primer OPD-17

<400> SEQUENCE: 86
tttcccacgg                                                          10

<210> SEQ ID NO 87
<211> LENGTH: 10
<212> TYPE: DNA
<213> ORGANISM: Artificial sequence
<220> FEATURE:
<223> OTHER INFORMATION: Primer OPD-18

<400> SEQUENCE: 87
gagagccaac                                                          10

<210> SEQ ID NO 88
<211> LENGTH: 10
<212> TYPE: DNA
<213> ORGANISM: Artificial sequence
<220> FEATURE:
<223> OTHER INFORMATION: Primer OPD-19

<400> SEQUENCE: 88
ctggggactt                                                          10

<210> SEQ ID NO 89
<211> LENGTH: 10
<212> TYPE: DNA
<213> ORGANISM: Artificial sequence
<220> FEATURE:
<223> OTHER INFORMATION: Primer OPD-20

<400> SEQUENCE: 89
acccggtcac                                                          10

<210> SEQ ID NO 90
<211> LENGTH: 10
<212> TYPE: DNA
<213> ORGANISM: Artificial sequence
<220> FEATURE:
<223> OTHER INFORMATION: Primer OPE-01

<400> SEQUENCE: 90
cccaaggtcc                                                          10

<210> SEQ ID NO 91
<211> LENGTH: 10
<212> TYPE: DNA
<213> ORGANISM: Artificial sequence
<220> FEATURE:
<223> OTHER INFORMATION: Primer OPE-02

<400> SEQUENCE: 91
ggtgcgggaa                                                          10

<210> SEQ ID NO 92
<211> LENGTH: 10
<212> TYPE: DNA
<213> ORGANISM: Artificial sequence
<220> FEATURE:
<223> OTHER INFORMATION: Primer OPE-03

```
<400> SEQUENCE: 92
ccagatgcac                                                               10

<210> SEQ ID NO 93
<211> LENGTH: 10
<212> TYPE: DNA
<213> ORGANISM: Artificial sequence
<220> FEATURE:
<223> OTHER INFORMATION: Primer OPE-04

<400> SEQUENCE: 93
gtgacatgcc                                                               10

<210> SEQ ID NO 94
<211> LENGTH: 10
<212> TYPE: DNA
<213> ORGANISM: Artificial sequence
<220> FEATURE:
<223> OTHER INFORMATION: Primer OPE-05

<400> SEQUENCE: 94
tcagggaggt                                                               10

<210> SEQ ID NO 95
<211> LENGTH: 10
<212> TYPE: DNA
<213> ORGANISM: Artificial sequence
<220> FEATURE:
<223> OTHER INFORMATION: Primer OPE-06

<400> SEQUENCE: 95
aagacccctc                                                               10

<210> SEQ ID NO 96
<211> LENGTH: 10
<212> TYPE: DNA
<213> ORGANISM: Artificial sequence
<220> FEATURE:
<223> OTHER INFORMATION: Primer OPE-07

<400> SEQUENCE: 96
agatgcagcc                                                               10

<210> SEQ ID NO 97
<211> LENGTH: 10
<212> TYPE: DNA
<213> ORGANISM: Artificial sequence
<220> FEATURE:
<223> OTHER INFORMATION: Primer OPE-08

<400> SEQUENCE: 97
tcaccacggt                                                               10

<210> SEQ ID NO 98
<211> LENGTH: 10
<212> TYPE: DNA
<213> ORGANISM: Artificial sequence
<220> FEATURE:
<223> OTHER INFORMATION: Primer OPE-09

<400> SEQUENCE: 98
cttcacccga                                                               10

<210> SEQ ID NO 99
<211> LENGTH: 10
```

```
<212> TYPE: DNA
<213> ORGANISM: Artificial sequence
<220> FEATURE:
<223> OTHER INFORMATION: Primer OPE-10

<400> SEQUENCE: 99
caccaggtga                                                              10

<210> SEQ ID NO 100
<211> LENGTH: 10
<212> TYPE: DNA
<213> ORGANISM: Artificial sequence
<220> FEATURE:
<223> OTHER INFORMATION: Primer OPE-11

<400> SEQUENCE: 100
gagtctcagg                                                              10

<210> SEQ ID NO 101
<211> LENGTH: 10
<212> TYPE: DNA
<213> ORGANISM: Artificial sequence
<220> FEATURE:
<223> OTHER INFORMATION: Primer OPE-12

<400> SEQUENCE: 101
ttatcgcccc                                                              10

<210> SEQ ID NO 102
<211> LENGTH: 10
<212> TYPE: DNA
<213> ORGANISM: Artificial sequence
<220> FEATURE:
<223> OTHER INFORMATION: Primer OPE-13

<400> SEQUENCE: 102
cccgattcgg                                                              10

<210> SEQ ID NO 103
<211> LENGTH: 10
<212> TYPE: DNA
<213> ORGANISM: Artificial sequence
<220> FEATURE:
<223> OTHER INFORMATION: Primer OPE-14

<400> SEQUENCE: 103
tgcggctgag                                                              10

<210> SEQ ID NO 104
<211> LENGTH: 10
<212> TYPE: DNA
<213> ORGANISM: Artificial sequence
<220> FEATURE:
<223> OTHER INFORMATION: Primer OPE-15

<400> SEQUENCE: 104
acgcacaacc                                                              10

<210> SEQ ID NO 105
<211> LENGTH: 10
<212> TYPE: DNA
<213> ORGANISM: Artificial sequence
<220> FEATURE:
<223> OTHER INFORMATION: Primer OPE-16

<400> SEQUENCE: 105
ggtgactgtg                                                              10
```

<210> SEQ ID NO 106
<211> LENGTH: 10
<212> TYPE: DNA
<213> ORGANISM: Artificial sequence
<220> FEATURE:
<223> OTHER INFORMATION: Primer OPE-17

<400> SEQUENCE: 106
ctactgccgt                                                              10

<210> SEQ ID NO 107
<211> LENGTH: 10
<212> TYPE: DNA
<213> ORGANISM: Artificial sequence
<220> FEATURE:
<223> OTHER INFORMATION: Primer OPE-18

<400> SEQUENCE: 107
ggactgcaga                                                              10

<210> SEQ ID NO 108
<211> LENGTH: 10
<212> TYPE: DNA
<213> ORGANISM: Artificial sequence
<220> FEATURE:
<223> OTHER INFORMATION: Primer OPE-19

<400> SEQUENCE: 108
acggcgtatg                                                              10

<210> SEQ ID NO 109
<211> LENGTH: 10
<212> TYPE: DNA
<213> ORGANISM: Artificial sequence
<220> FEATURE:
<223> OTHER INFORMATION: Primer OPE-20

<400> SEQUENCE: 109
aacggtgacc                                                              10

<210> SEQ ID NO 110
<211> LENGTH: 10
<212> TYPE: DNA
<213> ORGANISM: Artificial sequence
<220> FEATURE:
<223> OTHER INFORMATION: Primer OPF-01

<400> SEQUENCE: 110
acggatcctg                                                              10

<210> SEQ ID NO 111
<211> LENGTH: 10
<212> TYPE: DNA
<213> ORGANISM: Artificial sequence
<220> FEATURE:
<223> OTHER INFORMATION: Primer OPF-02

<400> SEQUENCE: 111
gaggatccct                                                              10

<210> SEQ ID NO 112
<211> LENGTH: 10
<212> TYPE: DNA
<213> ORGANISM: Artificial sequence
<220> FEATURE:
<223> OTHER INFORMATION: Primer OPF-03

```
<400> SEQUENCE: 112
cctgatcacc                                                          10

<210> SEQ ID NO 113
<211> LENGTH: 10
<212> TYPE: DNA
<213> ORGANISM: Artificial sequence
<220> FEATURE:
<223> OTHER INFORMATION: Primer OPF-04

<400> SEQUENCE: 113
ggtgatcagg                                                          10

<210> SEQ ID NO 114
<211> LENGTH: 10
<212> TYPE: DNA
<213> ORGANISM: Artificial sequence
<220> FEATURE:
<223> OTHER INFORMATION: Primer OPF-05

<400> SEQUENCE: 114
ccgaattccc                                                          10

<210> SEQ ID NO 115
<211> LENGTH: 10
<212> TYPE: DNA
<213> ORGANISM: Artificial sequence
<220> FEATURE:
<223> OTHER INFORMATION: Primer OPF-06

<400> SEQUENCE: 115
gggaattcgg                                                          10

<210> SEQ ID NO 116
<211> LENGTH: 10
<212> TYPE: DNA
<213> ORGANISM: Artificial sequence
<220> FEATURE:
<223> OTHER INFORMATION: Primer OPF-07

<400> SEQUENCE: 116
ccgatatccc                                                          10

<210> SEQ ID NO 117
<211> LENGTH: 10
<212> TYPE: DNA
<213> ORGANISM: Artificial sequence
<220> FEATURE:
<223> OTHER INFORMATION: Primer OPF-08

<400> SEQUENCE: 117
gggatatcgg                                                          10

<210> SEQ ID NO 118
<211> LENGTH: 10
<212> TYPE: DNA
<213> ORGANISM: Artificial sequence
<220> FEATURE:
<223> OTHER INFORMATION: Primer OPF-09

<400> SEQUENCE: 118
ccaagcttcc                                                          10

<210> SEQ ID NO 119
<211> LENGTH: 10
```

```
<212> TYPE: DNA
<213> ORGANISM: Artificial sequence
<220> FEATURE:
<223> OTHER INFORMATION: Primer OPF-10

<400> SEQUENCE: 119
ggaagcttgg                                                             10

<210> SEQ ID NO 120
<211> LENGTH: 10
<212> TYPE: DNA
<213> ORGANISM: Artificial sequence
<220> FEATURE:
<223> OTHER INFORMATION: Primer OPF-11

<400> SEQUENCE: 120
ttggtacccc                                                             10

<210> SEQ ID NO 121
<211> LENGTH: 10
<212> TYPE: DNA
<213> ORGANISM: Artificial sequence
<220> FEATURE:
<223> OTHER INFORMATION: Primer OPF-12

<400> SEQUENCE: 121
acggtaccag                                                             10

<210> SEQ ID NO 122
<211> LENGTH: 10
<212> TYPE: DNA
<213> ORGANISM: Artificial sequence
<220> FEATURE:
<223> OTHER INFORMATION: Primer OPF-13

<400> SEQUENCE: 122
ggctgcagaa                                                             10

<210> SEQ ID NO 123
<211> LENGTH: 10
<212> TYPE: DNA
<213> ORGANISM: Artificial sequence
<220> FEATURE:
<223> OTHER INFORMATION: Primer OPF-14

<400> SEQUENCE: 123
tgctgcaggt                                                             10

<210> SEQ ID NO 124
<211> LENGTH: 10
<212> TYPE: DNA
<213> ORGANISM: Artificial sequence
<220> FEATURE:
<223> OTHER INFORMATION: Primer OPF-15

<400> SEQUENCE: 124
ccagtactcc                                                             10

<210> SEQ ID NO 125
<211> LENGTH: 10
<212> TYPE: DNA
<213> ORGANISM: Artificial sequence
<220> FEATURE:
<223> OTHER INFORMATION: Primer OPF-16

<400> SEQUENCE: 125
ggagtactgg                                                             10
```

<210> SEQ ID NO 126
<211> LENGTH: 10
<212> TYPE: DNA
<213> ORGANISM: Artificial sequence
<220> FEATURE:
<223> OTHER INFORMATION: Primer OPF-17

<400> SEQUENCE: 126
aacccgggaa                                                          10

<210> SEQ ID NO 127
<211> LENGTH: 10
<212> TYPE: DNA
<213> ORGANISM: Artificial sequence
<220> FEATURE:
<223> OTHER INFORMATION: Primer OPF-18

<400> SEQUENCE: 127
ttcccgggtt                                                          10

<210> SEQ ID NO 128
<211> LENGTH: 10
<212> TYPE: DNA
<213> ORGANISM: Artificial sequence
<220> FEATURE:
<223> OTHER INFORMATION: Primer OPF-19

<400> SEQUENCE: 128
cctctagacc                                                          10

<210> SEQ ID NO 129
<211> LENGTH: 10
<212> TYPE: DNA
<213> ORGANISM: Artificial sequence
<220> FEATURE:
<223> OTHER INFORMATION: Primer OPF-20

<400> SEQUENCE: 129
ggtctagagg                                                          10

<210> SEQ ID NO 130
<211> LENGTH: 10
<212> TYPE: DNA
<213> ORGANISM: Artificial sequence
<220> FEATURE:
<223> OTHER INFORMATION: Primer OPG-01

<400> SEQUENCE: 130
ctacggagga                                                          10

<210> SEQ ID NO 131
<211> LENGTH: 10
<212> TYPE: DNA
<213> ORGANISM: Artificial sequence
<220> FEATURE:
<223> OTHER INFORMATION: Primer OPG-02

<400> SEQUENCE: 131
ggcactgagg                                                          10

<210> SEQ ID NO 132
<211> LENGTH: 10
<212> TYPE: DNA
<213> ORGANISM: Artificial sequence
<220> FEATURE:
<223> OTHER INFORMATION: Primer OPG-03

```
<400> SEQUENCE: 132
gagccctcca                                                          10

<210> SEQ ID NO 133
<211> LENGTH: 10
<212> TYPE: DNA
<213> ORGANISM: Artificial sequence
<220> FEATURE:
<223> OTHER INFORMATION: Primer OPG-04

<400> SEQUENCE: 133
agcgtgtctg                                                          10

<210> SEQ ID NO 134
<211> LENGTH: 10
<212> TYPE: DNA
<213> ORGANISM: Artificial sequence
<220> FEATURE:
<223> OTHER INFORMATION: Primer OPG-05

<400> SEQUENCE: 134
ctgagacgga                                                          10

<210> SEQ ID NO 135
<211> LENGTH: 10
<212> TYPE: DNA
<213> ORGANISM: Artificial sequence
<220> FEATURE:
<223> OTHER INFORMATION: Primer OPG-06

<400> SEQUENCE: 135
gtgcctaacc                                                          10

<210> SEQ ID NO 136
<211> LENGTH: 10
<212> TYPE: DNA
<213> ORGANISM: Artificial sequence
<220> FEATURE:
<223> OTHER INFORMATION: Primer OPG-07

<400> SEQUENCE: 136
gaacctgcgg                                                          10

<210> SEQ ID NO 137
<211> LENGTH: 10
<212> TYPE: DNA
<213> ORGANISM: Artificial sequence
<220> FEATURE:
<223> OTHER INFORMATION: Primer OPG-08

<400> SEQUENCE: 137
tcacgtccac                                                          10

<210> SEQ ID NO 138
<211> LENGTH: 10
<212> TYPE: DNA
<213> ORGANISM: Artificial sequence
<220> FEATURE:
<223> OTHER INFORMATION: Primer OPG-09

<400> SEQUENCE: 138
ctgacgtcac                                                          10

<210> SEQ ID NO 139
<211> LENGTH: 10
```

```
<212> TYPE: DNA
<213> ORGANISM: Artificial sequence
<220> FEATURE:
<223> OTHER INFORMATION: Primer OPG-10

<400> SEQUENCE: 139
agggccgtct                                                            10

<210> SEQ ID NO 140
<211> LENGTH: 10
<212> TYPE: DNA
<213> ORGANISM: Artificial sequence
<220> FEATURE:
<223> OTHER INFORMATION: Primer OPG-11

<400> SEQUENCE: 140
tgcccgtcgt                                                            10

<210> SEQ ID NO 141
<211> LENGTH: 10
<212> TYPE: DNA
<213> ORGANISM: Artificial sequence
<220> FEATURE:
<223> OTHER INFORMATION: Primer OPG-12

<400> SEQUENCE: 141
cagctcacga                                                            10

<210> SEQ ID NO 142
<211> LENGTH: 10
<212> TYPE: DNA
<213> ORGANISM: Artificial sequence
<220> FEATURE:
<223> OTHER INFORMATION: Primer OPG-13

<400> SEQUENCE: 142
ctctccgcca                                                            10

<210> SEQ ID NO 143
<211> LENGTH: 10
<212> TYPE: DNA
<213> ORGANISM: Artificial sequence
<220> FEATURE:
<223> OTHER INFORMATION: Primer OPG-14

<400> SEQUENCE: 143
ggatgagacc                                                            10

<210> SEQ ID NO 144
<211> LENGTH: 10
<212> TYPE: DNA
<213> ORGANISM: Artificial sequence
<220> FEATURE:
<223> OTHER INFORMATION: Primer OPG-15

<400> SEQUENCE: 144
actgggactc                                                            10

<210> SEQ ID NO 145
<211> LENGTH: 10
<212> TYPE: DNA
<213> ORGANISM: Artificial sequence
<220> FEATURE:
<223> OTHER INFORMATION: Primer OPG-16

<400> SEQUENCE: 145
agcgtcctcc                                                            10
```

<210> SEQ ID NO 146
<211> LENGTH: 10
<212> TYPE: DNA
<213> ORGANISM: Artificial sequence
<220> FEATURE:
<223> OTHER INFORMATION: Primer OPG-17

<400> SEQUENCE: 146
acgaccgaca                                                          10

<210> SEQ ID NO 147
<211> LENGTH: 10
<212> TYPE: DNA
<213> ORGANISM: Artificial sequence
<220> FEATURE:
<223> OTHER INFORMATION: Primer OPG-18

<400> SEQUENCE: 147
ggctcatgtg                                                          10

<210> SEQ ID NO 148
<211> LENGTH: 10
<212> TYPE: DNA
<213> ORGANISM: Artificial sequence
<220> FEATURE:
<223> OTHER INFORMATION: Primer OPG-19

<400> SEQUENCE: 148
gtcagggcaa                                                          10

<210> SEQ ID NO 149
<211> LENGTH: 10
<212> TYPE: DNA
<213> ORGANISM: Artificial sequence
<220> FEATURE:
<223> OTHER INFORMATION: Primer OPG-20

<400> SEQUENCE: 149
tctccctcag                                                          10

<210> SEQ ID NO 150
<211> LENGTH: 10
<212> TYPE: DNA
<213> ORGANISM: Artificial sequence
<220> FEATURE:
<223> OTHER INFORMATION: Primer OPH-01

<400> SEQUENCE: 150
ggtcggagaa                                                          10

<210> SEQ ID NO 151
<211> LENGTH: 10
<212> TYPE: DNA
<213> ORGANISM: Artificial sequence
<220> FEATURE:
<223> OTHER INFORMATION: Primer OPH-02

<400> SEQUENCE: 151
tcggacgtga                                                          10

<210> SEQ ID NO 152
<211> LENGTH: 10
<212> TYPE: DNA
<213> ORGANISM: Artificial sequence
<220> FEATURE:
<223> OTHER INFORMATION: Primer OPH-03

```
<400> SEQUENCE: 152
agacgtccac                                                            10

<210> SEQ ID NO 153
<211> LENGTH: 10
<212> TYPE: DNA
<213> ORGANISM: Artificial sequence
<220> FEATURE:
<223> OTHER INFORMATION: Primer OPH-04

<400> SEQUENCE: 153
ggaagtcgcc                                                            10

<210> SEQ ID NO 154
<211> LENGTH: 10
<212> TYPE: DNA
<213> ORGANISM: Artificial sequence
<220> FEATURE:
<223> OTHER INFORMATION: Primer OPH-05

<400> SEQUENCE: 154
agtcgtcccc                                                            10

<210> SEQ ID NO 155
<211> LENGTH: 10
<212> TYPE: DNA
<213> ORGANISM: Artificial sequence
<220> FEATURE:
<223> OTHER INFORMATION: Primer OPH-06

<400> SEQUENCE: 155
acgcatcgca                                                            10

<210> SEQ ID NO 156
<211> LENGTH: 10
<212> TYPE: DNA
<213> ORGANISM: Artificial sequence
<220> FEATURE:
<223> OTHER INFORMATION: Primer OPH-07

<400> SEQUENCE: 156
ctgcatcgtg                                                            10

<210> SEQ ID NO 157
<211> LENGTH: 10
<212> TYPE: DNA
<213> ORGANISM: Artificial sequence
<220> FEATURE:
<223> OTHER INFORMATION: Primer OPH-08

<400> SEQUENCE: 157
gaaacacccc                                                            10

<210> SEQ ID NO 158
<211> LENGTH: 10
<212> TYPE: DNA
<213> ORGANISM: Artificial sequence
<220> FEATURE:
<223> OTHER INFORMATION: Primer OPH-09

<400> SEQUENCE: 158
tgtagctggg                                                            10

<210> SEQ ID NO 159
<211> LENGTH: 10
```

```
<212> TYPE: DNA
<213> ORGANISM: Artificial sequence
<220> FEATURE:
<223> OTHER INFORMATION: Primer OPH-10

<400> SEQUENCE: 159
cctacgtcag                                                            10

<210> SEQ ID NO 160
<211> LENGTH: 10
<212> TYPE: DNA
<213> ORGANISM: Artificial sequence
<220> FEATURE:
<223> OTHER INFORMATION: Primer OPH-11

<400> SEQUENCE: 160
cttccgcagt                                                            10

<210> SEQ ID NO 161
<211> LENGTH: 10
<212> TYPE: DNA
<213> ORGANISM: Artificial sequence
<220> FEATURE:
<223> OTHER INFORMATION: Primer OPH-12

<400> SEQUENCE: 161
acgcgcatgt                                                            10

<210> SEQ ID NO 162
<211> LENGTH: 10
<212> TYPE: DNA
<213> ORGANISM: Artificial sequence
<220> FEATURE:
<223> OTHER INFORMATION: Primer OPH-13

<400> SEQUENCE: 162
gacgccacac                                                            10

<210> SEQ ID NO 163
<211> LENGTH: 10
<212> TYPE: DNA
<213> ORGANISM: Artificial sequence
<220> FEATURE:
<223> OTHER INFORMATION: Primer OPH-14

<400> SEQUENCE: 163
accaggttgg                                                            10

<210> SEQ ID NO 164
<211> LENGTH: 10
<212> TYPE: DNA
<213> ORGANISM: Artificial sequence
<220> FEATURE:
<223> OTHER INFORMATION: Primer OPH-15

<400> SEQUENCE: 164
aatggcgcag                                                            10

<210> SEQ ID NO 165
<211> LENGTH: 10
<212> TYPE: DNA
<213> ORGANISM: Artificial sequence
<220> FEATURE:
<223> OTHER INFORMATION: Primer OPH-16

<400> SEQUENCE: 165
tctcagctgg                                                            10
```

<210> SEQ ID NO 166
<211> LENGTH: 10
<212> TYPE: DNA
<213> ORGANISM: Artificial sequence
<220> FEATURE:
<223> OTHER INFORMATION: Primer OPH-17

<400> SEQUENCE: 166
cactctcctc                                                                10

<210> SEQ ID NO 167
<211> LENGTH: 10
<212> TYPE: DNA
<213> ORGANISM: Artificial sequence
<220> FEATURE:
<223> OTHER INFORMATION: Primer OPH-18

<400> SEQUENCE: 167
gaatcggcca                                                                10

<210> SEQ ID NO 168
<211> LENGTH: 10
<212> TYPE: DNA
<213> ORGANISM: Artificial sequence
<220> FEATURE:
<223> OTHER INFORMATION: Primer OPH-19

<400> SEQUENCE: 168
ctgaccagcc                                                                10

<210> SEQ ID NO 169
<211> LENGTH: 10
<212> TYPE: DNA
<213> ORGANISM: Artificial sequence
<220> FEATURE:
<223> OTHER INFORMATION: Primer OPH-20

<400> SEQUENCE: 169
gggagacatc                                                                10

<210> SEQ ID NO 170
<211> LENGTH: 10
<212> TYPE: DNA
<213> ORGANISM: Artificial sequence
<220> FEATURE:
<223> OTHER INFORMATION: Primer OPI-01

<400> SEQUENCE: 170
acctggacac                                                                10

<210> SEQ ID NO 171
<211> LENGTH: 10
<212> TYPE: DNA
<213> ORGANISM: Artificial sequence
<220> FEATURE:
<223> OTHER INFORMATION: Primer OPI-02

<400> SEQUENCE: 171
ggaggagagg                                                                10

<210> SEQ ID NO 172
<211> LENGTH: 10
<212> TYPE: DNA
<213> ORGANISM: Artificial sequence
<220> FEATURE:
<223> OTHER INFORMATION: Primer OPI-03

<400> SEQUENCE: 172
cagaagccca                                                                  10

<210> SEQ ID NO 173
<211> LENGTH: 10
<212> TYPE: DNA
<213> ORGANISM: Artificial sequence
<220> FEATURE:
<223> OTHER INFORMATION: Primer OPI-04

<400> SEQUENCE: 173
ccgcctagtc                                                                  10

<210> SEQ ID NO 174
<211> LENGTH: 10
<212> TYPE: DNA
<213> ORGANISM: Artificial sequence
<220> FEATURE:
<223> OTHER INFORMATION: Primer OPI-05

<400> SEQUENCE: 174
tgttccacgg                                                                  10

<210> SEQ ID NO 175
<211> LENGTH: 10
<212> TYPE: DNA
<213> ORGANISM: Artificial sequence
<220> FEATURE:
<223> OTHER INFORMATION: Primer OPI-06

<400> SEQUENCE: 175
aaggcggcag                                                                  10

<210> SEQ ID NO 176
<211> LENGTH: 10
<212> TYPE: DNA
<213> ORGANISM: Artificial sequence
<220> FEATURE:
<223> OTHER INFORMATION: Primer OPI-07

<400> SEQUENCE: 176
cagcgacaag                                                                  10

<210> SEQ ID NO 177
<211> LENGTH: 10
<212> TYPE: DNA
<213> ORGANISM: Artificial sequence
<220> FEATURE:
<223> OTHER INFORMATION: Primer OPI-08

<400> SEQUENCE: 177
tttgcccggt                                                                  10

<210> SEQ ID NO 178
<211> LENGTH: 10
<212> TYPE: DNA
<213> ORGANISM: Artificial sequence
<220> FEATURE:
<223> OTHER INFORMATION: Primer OPI-09

<400> SEQUENCE: 178
tggagagcag                                                                  10

<210> SEQ ID NO 179
<211> LENGTH: 10

<212> TYPE: DNA
<213> ORGANISM: Artificial sequence
<220> FEATURE:
<223> OTHER INFORMATION: Primer OPI-10

<400> SEQUENCE: 179
acaacgcgag                                                              10

<210> SEQ ID NO 180
<211> LENGTH: 10
<212> TYPE: DNA
<213> ORGANISM: Artificial sequence
<220> FEATURE:
<223> OTHER INFORMATION: Primer OPI-11

<400> SEQUENCE: 180
acatgccgtg                                                              10

<210> SEQ ID NO 181
<211> LENGTH: 10
<212> TYPE: DNA
<213> ORGANISM: Artificial sequence
<220> FEATURE:
<223> OTHER INFORMATION: Primer OPI-12

<400> SEQUENCE: 181
agagggcaca                                                              10

<210> SEQ ID NO 182
<211> LENGTH: 10
<212> TYPE: DNA
<213> ORGANISM: Artificial sequence
<220> FEATURE:
<223> OTHER INFORMATION: Primer OPI-13

<400> SEQUENCE: 182
ctggggctga                                                              10

<210> SEQ ID NO 183
<211> LENGTH: 10
<212> TYPE: DNA
<213> ORGANISM: Artificial sequence
<220> FEATURE:
<223> OTHER INFORMATION: Primer OPI-14

<400> SEQUENCE: 183
tgacggcggt                                                              10

<210> SEQ ID NO 184
<211> LENGTH: 10
<212> TYPE: DNA
<213> ORGANISM: Artificial sequence
<220> FEATURE:
<223> OTHER INFORMATION: Primer OPI-15

<400> SEQUENCE: 184
tcatccgagg                                                              10

<210> SEQ ID NO 185
<211> LENGTH: 10
<212> TYPE: DNA
<213> ORGANISM: Artificial sequence
<220> FEATURE:
<223> OTHER INFORMATION: Primer OPI-16

<400> SEQUENCE: 185
tctccgccct                                                              10

```
<210> SEQ ID NO 186
<211> LENGTH: 10
<212> TYPE: DNA
<213> ORGANISM: Artificial sequence
<220> FEATURE:
<223> OTHER INFORMATION: Primer OPI-17

<400> SEQUENCE: 186
ggtggtgatg                                                          10

<210> SEQ ID NO 187
<211> LENGTH: 10
<212> TYPE: DNA
<213> ORGANISM: Artificial sequence
<220> FEATURE:
<223> OTHER INFORMATION: Primer OPI-18

<400> SEQUENCE: 187
tgcccagcct                                                          10

<210> SEQ ID NO 188
<211> LENGTH: 10
<212> TYPE: DNA
<213> ORGANISM: Artificial sequence
<220> FEATURE:
<223> OTHER INFORMATION: Primer OPI-19

<400> SEQUENCE: 188
aatgcgggag                                                          10

<210> SEQ ID NO 189
<211> LENGTH: 10
<212> TYPE: DNA
<213> ORGANISM: Artificial sequence
<220> FEATURE:
<223> OTHER INFORMATION: Primer OPI-20

<400> SEQUENCE: 189
aaagtgcggg                                                          10

<210> SEQ ID NO 190
<211> LENGTH: 10
<212> TYPE: DNA
<213> ORGANISM: Artificial sequence
<220> FEATURE:
<223> OTHER INFORMATION: Primer OPJ-01

<400> SEQUENCE: 190
cccggcataa                                                          10

<210> SEQ ID NO 191
<211> LENGTH: 10
<212> TYPE: DNA
<213> ORGANISM: Artificial sequence
<220> FEATURE:
<223> OTHER INFORMATION: Primer OPJ-02

<400> SEQUENCE: 191
cccgttggga                                                          10

<210> SEQ ID NO 192
<211> LENGTH: 10
<212> TYPE: DNA
<213> ORGANISM: Artificial sequence
<220> FEATURE:
<223> OTHER INFORMATION: Primer OPJ-03
```

```
<400> SEQUENCE: 192
tctccgcttg                                                          10

<210> SEQ ID NO 193
<211> LENGTH: 10
<212> TYPE: DNA
<213> ORGANISM: Artificial sequence
<220> FEATURE:
<223> OTHER INFORMATION: Primer OPJ-04

<400> SEQUENCE: 193
ccgaacacgg                                                          10

<210> SEQ ID NO 194
<211> LENGTH: 10
<212> TYPE: DNA
<213> ORGANISM: Artificial sequence
<220> FEATURE:
<223> OTHER INFORMATION: Primer OPJ-05

<400> SEQUENCE: 194
ctccatgggg                                                          10

<210> SEQ ID NO 195
<211> LENGTH: 10
<212> TYPE: DNA
<213> ORGANISM: Artificial sequence
<220> FEATURE:
<223> OTHER INFORMATION: Primer OPJ-06

<400> SEQUENCE: 195
tcgttccgca                                                          10

<210> SEQ ID NO 196
<211> LENGTH: 10
<212> TYPE: DNA
<213> ORGANISM: Artificial sequence
<220> FEATURE:
<223> OTHER INFORMATION: Primer OPJ-07

<400> SEQUENCE: 196
cctctcgaca                                                          10

<210> SEQ ID NO 197
<211> LENGTH: 10
<212> TYPE: DNA
<213> ORGANISM: Artificial sequence
<220> FEATURE:
<223> OTHER INFORMATION: Primer OPJ-08

<400> SEQUENCE: 197
cataccgtgg                                                          10

<210> SEQ ID NO 198
<211> LENGTH: 10
<212> TYPE: DNA
<213> ORGANISM: Artificial sequence
<220> FEATURE:
<223> OTHER INFORMATION: Primer OPJ-09

<400> SEQUENCE: 198
tgagcctcac                                                          10

<210> SEQ ID NO 199
<211> LENGTH: 10
```

```
<212> TYPE: DNA
<213> ORGANISM: Artificial sequence
<220> FEATURE:
<223> OTHER INFORMATION: Primer OPJ-10

<400> SEQUENCE: 199
aagcccgagg                                                              10

<210> SEQ ID NO 200
<211> LENGTH: 10
<212> TYPE: DNA
<213> ORGANISM: Artificial sequence
<220> FEATURE:
<223> OTHER INFORMATION: Primer OPJ-11

<400> SEQUENCE: 200
actcctgcga                                                              10

<210> SEQ ID NO 201
<211> LENGTH: 10
<212> TYPE: DNA
<213> ORGANISM: Artificial sequence
<220> FEATURE:
<223> OTHER INFORMATION: Primer OPJ-12

<400> SEQUENCE: 201
gtcccgtggt                                                              10

<210> SEQ ID NO 202
<211> LENGTH: 10
<212> TYPE: DNA
<213> ORGANISM: Artificial sequence
<220> FEATURE:
<223> OTHER INFORMATION: Primer OPJ-13

<400> SEQUENCE: 202
ccacactacc                                                              10

<210> SEQ ID NO 203
<211> LENGTH: 10
<212> TYPE: DNA
<213> ORGANISM: Artificial sequence
<220> FEATURE:
<223> OTHER INFORMATION: Primer OPJ-14

<400> SEQUENCE: 203
cacccggatg                                                              10

<210> SEQ ID NO 204
<211> LENGTH: 10
<212> TYPE: DNA
<213> ORGANISM: Artificial sequence
<220> FEATURE:
<223> OTHER INFORMATION: Primer OPJ-15

<400> SEQUENCE: 204
tgtagcaggg                                                              10

<210> SEQ ID NO 205
<211> LENGTH: 10
<212> TYPE: DNA
<213> ORGANISM: Artificial sequence
<220> FEATURE:
<223> OTHER INFORMATION: Primer OPJ-16

<400> SEQUENCE: 205
ctgcttaggg                                                              10
```

```
<210> SEQ ID NO 206
<211> LENGTH: 10
<212> TYPE: DNA
<213> ORGANISM: Artificial sequence
<220> FEATURE:
<223> OTHER INFORMATION: Primer OPJ-17

<400> SEQUENCE: 206
acgccagttc                                                              10

<210> SEQ ID NO 207
<211> LENGTH: 10
<212> TYPE: DNA
<213> ORGANISM: Artificial sequence
<220> FEATURE:
<223> OTHER INFORMATION: Primer OPJ-18

<400> SEQUENCE: 207
tggtcgcaga                                                              10

<210> SEQ ID NO 208
<211> LENGTH: 10
<212> TYPE: DNA
<213> ORGANISM: Artificial sequence
<220> FEATURE:
<223> OTHER INFORMATION: Primer OPJ-19

<400> SEQUENCE: 208
ggacaccact                                                              10

<210> SEQ ID NO 209
<211> LENGTH: 10
<212> TYPE: DNA
<213> ORGANISM: Artificial sequence
<220> FEATURE:
<223> OTHER INFORMATION: Primer OPJ-20

<400> SEQUENCE: 209
aagcggcctc                                                              10

<210> SEQ ID NO 210
<211> LENGTH: 10
<212> TYPE: DNA
<213> ORGANISM: Artificial sequence
<220> FEATURE:
<223> OTHER INFORMATION: Primer OPK-01

<400> SEQUENCE: 210
cattcgagcc                                                              10

<210> SEQ ID NO 211
<211> LENGTH: 10
<212> TYPE: DNA
<213> ORGANISM: Artificial sequence
<220> FEATURE:
<223> OTHER INFORMATION: Primer OPK-02

<400> SEQUENCE: 211
gtctccgcaa                                                              10

<210> SEQ ID NO 212
<211> LENGTH: 10
<212> TYPE: DNA
<213> ORGANISM: Artificial sequence
<220> FEATURE:
<223> OTHER INFORMATION: Primer OPK-03
```

-continued

<400> SEQUENCE: 212
ccagcttagg                                                          10

<210> SEQ ID NO 213
<211> LENGTH: 10
<212> TYPE: DNA
<213> ORGANISM: Artificial sequence
<220> FEATURE:
<223> OTHER INFORMATION: Primer OPK-04

<400> SEQUENCE: 213
ccgcccaaac                                                          10

<210> SEQ ID NO 214
<211> LENGTH: 10
<212> TYPE: DNA
<213> ORGANISM: Artificial sequence
<220> FEATURE:
<223> OTHER INFORMATION: Primer OPK-05

<400> SEQUENCE: 214
tctgtcgagg                                                          10

<210> SEQ ID NO 215
<211> LENGTH: 10
<212> TYPE: DNA
<213> ORGANISM: Artificial sequence
<220> FEATURE:
<223> OTHER INFORMATION: Primer OPK-06

<400> SEQUENCE: 215
cacctttccc                                                          10

<210> SEQ ID NO 216
<211> LENGTH: 10
<212> TYPE: DNA
<213> ORGANISM: Artificial sequence
<220> FEATURE:
<223> OTHER INFORMATION: Primer OPK-07

<400> SEQUENCE: 216
agcgagcaag                                                          10

<210> SEQ ID NO 217
<211> LENGTH: 10
<212> TYPE: DNA
<213> ORGANISM: Artificial sequence
<220> FEATURE:
<223> OTHER INFORMATION: Primer OPK-08

<400> SEQUENCE: 217
gaacactggg                                                          10

<210> SEQ ID NO 218
<211> LENGTH: 10
<212> TYPE: DNA
<213> ORGANISM: Artificial sequence
<220> FEATURE:
<223> OTHER INFORMATION: Primer OPK-09

<400> SEQUENCE: 218
ccctaccgac                                                          10

<210> SEQ ID NO 219
<211> LENGTH: 10

```
<212> TYPE: DNA
<213> ORGANISM: Artificial sequence
<220> FEATURE:
<223> OTHER INFORMATION: Primer OPK-10

<400> SEQUENCE: 219
gtgcaacgtg                                                              10

<210> SEQ ID NO 220
<211> LENGTH: 10
<212> TYPE: DNA
<213> ORGANISM: Artificial sequence
<220> FEATURE:
<223> OTHER INFORMATION: Primer OPK-11

<400> SEQUENCE: 220
aatgccccag                                                              10

<210> SEQ ID NO 221
<211> LENGTH: 10
<212> TYPE: DNA
<213> ORGANISM: Artificial sequence
<220> FEATURE:
<223> OTHER INFORMATION: Primer OPK-12

<400> SEQUENCE: 221
tggccctcac                                                              10

<210> SEQ ID NO 222
<211> LENGTH: 10
<212> TYPE: DNA
<213> ORGANISM: Artificial sequence
<220> FEATURE:
<223> OTHER INFORMATION: Primer OPK-13

<400> SEQUENCE: 222
ggttgtaccc                                                              10

<210> SEQ ID NO 223
<211> LENGTH: 10
<212> TYPE: DNA
<213> ORGANISM: Artificial sequence
<220> FEATURE:
<223> OTHER INFORMATION: Primer OPK-14

<400> SEQUENCE: 223
cccgctacac                                                              10

<210> SEQ ID NO 224
<211> LENGTH: 10
<212> TYPE: DNA
<213> ORGANISM: Artificial sequence
<220> FEATURE:
<223> OTHER INFORMATION: Primer OPK-15

<400> SEQUENCE: 224
ctcctgccaa                                                              10

<210> SEQ ID NO 225
<211> LENGTH: 10
<212> TYPE: DNA
<213> ORGANISM: Artificial sequence
<220> FEATURE:
<223> OTHER INFORMATION: Primer OPK-16

<400> SEQUENCE: 225
gagcgtcgaa                                                              10
```

<210> SEQ ID NO 226
<211> LENGTH: 10
<212> TYPE: DNA
<213> ORGANISM: Artificial sequence
<220> FEATURE:
<223> OTHER INFORMATION: Primer OPK-17

<400> SEQUENCE: 226
cccagctgtg                                                                10

<210> SEQ ID NO 227
<211> LENGTH: 10
<212> TYPE: DNA
<213> ORGANISM: Artificial sequence
<220> FEATURE:
<223> OTHER INFORMATION: Primer OPK-18

<400> SEQUENCE: 227
cctagtcgag                                                                10

<210> SEQ ID NO 228
<211> LENGTH: 10
<212> TYPE: DNA
<213> ORGANISM: Artificial sequence
<220> FEATURE:
<223> OTHER INFORMATION: Primer OPK-19

<400> SEQUENCE: 228
cacaggcgga                                                                10

<210> SEQ ID NO 229
<211> LENGTH: 10
<212> TYPE: DNA
<213> ORGANISM: Artificial sequence
<220> FEATURE:
<223> OTHER INFORMATION: Primer OPK-20

<400> SEQUENCE: 229
gtgtcgcgag                                                                10

<210> SEQ ID NO 230
<211> LENGTH: 10
<212> TYPE: DNA
<213> ORGANISM: Artificial sequence
<220> FEATURE:
<223> OTHER INFORMATION: Primer OPL-01

<400> SEQUENCE: 230
ggcatgacct                                                                10

<210> SEQ ID NO 231
<211> LENGTH: 10
<212> TYPE: DNA
<213> ORGANISM: Artificial sequence
<220> FEATURE:
<223> OTHER INFORMATION: Primer OPL-02

<400> SEQUENCE: 231
tgggcgtcaa                                                                10

<210> SEQ ID NO 232
<211> LENGTH: 10
<212> TYPE: DNA
<213> ORGANISM: Artificial sequence
<220> FEATURE:
<223> OTHER INFORMATION: Primer OPL-03

```
<400> SEQUENCE: 232
ccagcagctt                                                              10

<210> SEQ ID NO 233
<211> LENGTH: 10
<212> TYPE: DNA
<213> ORGANISM: Artificial sequence
<220> FEATURE:
<223> OTHER INFORMATION: Primer OPL-04

<400> SEQUENCE: 233
gactgcacac                                                              10

<210> SEQ ID NO 234
<211> LENGTH: 10
<212> TYPE: DNA
<213> ORGANISM: Artificial sequence
<220> FEATURE:
<223> OTHER INFORMATION: Primer OPL-05

<400> SEQUENCE: 234
acgcaggcac                                                              10

<210> SEQ ID NO 235
<211> LENGTH: 10
<212> TYPE: DNA
<213> ORGANISM: Artificial sequence
<220> FEATURE:
<223> OTHER INFORMATION: Primer OPL-06

<400> SEQUENCE: 235
gagggaagag                                                              10

<210> SEQ ID NO 236
<211> LENGTH: 10
<212> TYPE: DNA
<213> ORGANISM: Artificial sequence
<220> FEATURE:
<223> OTHER INFORMATION: Primer OPL-07

<400> SEQUENCE: 236
aggcgggaac                                                              10

<210> SEQ ID NO 237
<211> LENGTH: 10
<212> TYPE: DNA
<213> ORGANISM: Artificial sequence
<220> FEATURE:
<223> OTHER INFORMATION: Primer OPL-08

<400> SEQUENCE: 237
agcaggtgga                                                              10

<210> SEQ ID NO 238
<211> LENGTH: 10
<212> TYPE: DNA
<213> ORGANISM: Artificial sequence
<220> FEATURE:
<223> OTHER INFORMATION: Primer OPL-09

<400> SEQUENCE: 238
tgcgagagtc                                                              10

<210> SEQ ID NO 239
<211> LENGTH: 10
```

```
<212> TYPE: DNA
<213> ORGANISM: Artificial sequence
<220> FEATURE:
<223> OTHER INFORMATION: Primer OPL-10

<400> SEQUENCE: 239
tgggagatgg                                                           10

<210> SEQ ID NO 240
<211> LENGTH: 10
<212> TYPE: DNA
<213> ORGANISM: Artificial sequence
<220> FEATURE:
<223> OTHER INFORMATION: Primer OPL-11

<400> SEQUENCE: 240
acgatgagcc                                                           10

<210> SEQ ID NO 241
<211> LENGTH: 10
<212> TYPE: DNA
<213> ORGANISM: Artificial sequence
<220> FEATURE:
<223> OTHER INFORMATION: Primer OPL-12

<400> SEQUENCE: 241
gggcggtact                                                           10

<210> SEQ ID NO 242
<211> LENGTH: 10
<212> TYPE: DNA
<213> ORGANISM: Artificial sequence
<220> FEATURE:
<223> OTHER INFORMATION: Primer OPL-13

<400> SEQUENCE: 242
accgcctgct                                                           10

<210> SEQ ID NO 243
<211> LENGTH: 10
<212> TYPE: DNA
<213> ORGANISM: Artificial sequence
<220> FEATURE:
<223> OTHER INFORMATION: Primer OPL-14

<400> SEQUENCE: 243
gtgacaggct                                                           10

<210> SEQ ID NO 244
<211> LENGTH: 10
<212> TYPE: DNA
<213> ORGANISM: Artificial sequence
<220> FEATURE:
<223> OTHER INFORMATION: Primer OPL-15

<400> SEQUENCE: 244
aagagagggg                                                           10

<210> SEQ ID NO 245
<211> LENGTH: 10
<212> TYPE: DNA
<213> ORGANISM: Artificial sequence
<220> FEATURE:
<223> OTHER INFORMATION: Primer OPL-16

<400> SEQUENCE: 245
aggttgcagg                                                           10
```

<210> SEQ ID NO 246
<211> LENGTH: 10
<212> TYPE: DNA
<213> ORGANISM: Artificial sequence
<220> FEATURE:
<223> OTHER INFORMATION: Primer OPL-17

<400> SEQUENCE: 246
agcctgagcc                                                          10

<210> SEQ ID NO 247
<211> LENGTH: 10
<212> TYPE: DNA
<213> ORGANISM: Artificial sequence
<220> FEATURE:
<223> OTHER INFORMATION: Primer OPL-18

<400> SEQUENCE: 247
accacccacc                                                          10

<210> SEQ ID NO 248
<211> LENGTH: 10
<212> TYPE: DNA
<213> ORGANISM: Artificial sequence
<220> FEATURE:
<223> OTHER INFORMATION: Primer OPL-19

<400> SEQUENCE: 248
gagtggtgac                                                          10

<210> SEQ ID NO 249
<211> LENGTH: 10
<212> TYPE: DNA
<213> ORGANISM: Artificial sequence
<220> FEATURE:
<223> OTHER INFORMATION: Primer OPL-20

<400> SEQUENCE: 249
tggtggacca                                                          10

<210> SEQ ID NO 250
<211> LENGTH: 10
<212> TYPE: DNA
<213> ORGANISM: Artificial sequence
<220> FEATURE:
<223> OTHER INFORMATION: Primer OPM-01

<400> SEQUENCE: 250
gttggtggct                                                          10

<210> SEQ ID NO 251
<211> LENGTH: 10
<212> TYPE: DNA
<213> ORGANISM: Artificial sequence
<220> FEATURE:
<223> OTHER INFORMATION: Primer OPM-02

<400> SEQUENCE: 251
acaacgcctc                                                          10

<210> SEQ ID NO 252
<211> LENGTH: 10
<212> TYPE: DNA
<213> ORGANISM: Artificial sequence
<220> FEATURE:
<223> OTHER INFORMATION: Primer OPM-03

<400> SEQUENCE: 252
ggggatgag                                                          10

<210> SEQ ID NO 253
<211> LENGTH: 10
<212> TYPE: DNA
<213> ORGANISM: Artificial sequence
<220> FEATURE:
<223> OTHER INFORMATION: Primer OPM-04

<400> SEQUENCE: 253
ggcggttgtc                                                         10

<210> SEQ ID NO 254
<211> LENGTH: 10
<212> TYPE: DNA
<213> ORGANISM: Artificial sequence
<220> FEATURE:
<223> OTHER INFORMATION: Primer OPM-05

<400> SEQUENCE: 254
gggaacgtgt                                                         10

<210> SEQ ID NO 255
<211> LENGTH: 10
<212> TYPE: DNA
<213> ORGANISM: Artificial sequence
<220> FEATURE:
<223> OTHER INFORMATION: Primer OPM-06

<400> SEQUENCE: 255
ctgggcaact                                                         10

<210> SEQ ID NO 256
<211> LENGTH: 10
<212> TYPE: DNA
<213> ORGANISM: Artificial sequence
<220> FEATURE:
<223> OTHER INFORMATION: Primer OPM-07

<400> SEQUENCE: 256
ccgtgactca                                                         10

<210> SEQ ID NO 257
<211> LENGTH: 10
<212> TYPE: DNA
<213> ORGANISM: Artificial sequence
<220> FEATURE:
<223> OTHER INFORMATION: Primer OPM-08

<400> SEQUENCE: 257
tctgttcccc                                                         10

<210> SEQ ID NO 258
<211> LENGTH: 10
<212> TYPE: DNA
<213> ORGANISM: Artificial sequence
<220> FEATURE:
<223> OTHER INFORMATION: Primer OPM-09

<400> SEQUENCE: 258
gtcttgcgga                                                         10

<210> SEQ ID NO 259
<211> LENGTH: 10

```
<212> TYPE: DNA
<213> ORGANISM: Artificial sequence
<220> FEATURE:
<223> OTHER INFORMATION: Primer OPM-10

<400> SEQUENCE: 259
tctggcgcac                                                          10

<210> SEQ ID NO 260
<211> LENGTH: 10
<212> TYPE: DNA
<213> ORGANISM: Artificial sequence
<220> FEATURE:
<223> OTHER INFORMATION: Primer OPM-11

<400> SEQUENCE: 260
gtccactgtg                                                          10

<210> SEQ ID NO 261
<211> LENGTH: 10
<212> TYPE: DNA
<213> ORGANISM: Artificial sequence
<220> FEATURE:
<223> OTHER INFORMATION: Primer OPM-12

<400> SEQUENCE: 261
gggacgttgg                                                          10

<210> SEQ ID NO 262
<211> LENGTH: 10
<212> TYPE: DNA
<213> ORGANISM: Artificial sequence
<220> FEATURE:
<223> OTHER INFORMATION: Primer OPM-13

<400> SEQUENCE: 262
ggtggtcaag                                                          10

<210> SEQ ID NO 263
<211> LENGTH: 10
<212> TYPE: DNA
<213> ORGANISM: Artificial sequence
<220> FEATURE:
<223> OTHER INFORMATION: Primer OPM-14

<400> SEQUENCE: 263
agggtcgttc                                                          10

<210> SEQ ID NO 264
<211> LENGTH: 10
<212> TYPE: DNA
<213> ORGANISM: Artificial sequence
<220> FEATURE:
<223> OTHER INFORMATION: Primer OPM-15

<400> SEQUENCE: 264
gacctaccac                                                          10

<210> SEQ ID NO 265
<211> LENGTH: 10
<212> TYPE: DNA
<213> ORGANISM: Artificial sequence
<220> FEATURE:
<223> OTHER INFORMATION: Primer OPM-16

<400> SEQUENCE: 265
gtaaccagcc                                                          10
```

-continued

<210> SEQ ID NO 266
<211> LENGTH: 10
<212> TYPE: DNA
<213> ORGANISM: Artificial sequence
<220> FEATURE:
<223> OTHER INFORMATION: Primer OPM-17

<400> SEQUENCE: 266 tcagtccggg								10

<210> SEQ ID NO 267
<211> LENGTH: 10
<212> TYPE: DNA
<213> ORGANISM: Artificial sequence
<220> FEATURE:
<223> OTHER INFORMATION: Primer OPM-18

<400> SEQUENCE: 267 caccatccgt								10

<210> SEQ ID NO 268
<211> LENGTH: 10
<212> TYPE: DNA
<213> ORGANISM: Artificial sequence
<220> FEATURE:
<223> OTHER INFORMATION: Primer OPM-19

<400> SEQUENCE: 268 ccttcaggca								10

<210> SEQ ID NO 269
<211> LENGTH: 10
<212> TYPE: DNA
<213> ORGANISM: Artificial sequence
<220> FEATURE:
<223> OTHER INFORMATION: Primer OPM-20

<400> SEQUENCE: 269 aggtcttggg								10

<210> SEQ ID NO 270
<211> LENGTH: 10
<212> TYPE: DNA
<213> ORGANISM: Artificial sequence
<220> FEATURE:
<223> OTHER INFORMATION: Primer OPN-01

<400> SEQUENCE: 270 ctcacgttgg								10

<210> SEQ ID NO 271
<211> LENGTH: 10
<212> TYPE: DNA
<213> ORGANISM: Artificial sequence
<220> FEATURE:
<223> OTHER INFORMATION: Primer OPN-02

<400> SEQUENCE: 271 accaggggca								10

<210> SEQ ID NO 272
<211> LENGTH: 10
<212> TYPE: DNA
<213> ORGANISM: Artificial sequence
<220> FEATURE:
<223> OTHER INFORMATION: Primer OPN-03

```
<400> SEQUENCE: 272
ggtactcccc                                                            10

<210> SEQ ID NO 273
<211> LENGTH: 10
<212> TYPE: DNA
<213> ORGANISM: Artificial sequence
<220> FEATURE:
<223> OTHER INFORMATION: Primer OPN-04

<400> SEQUENCE: 273
gaccgaccca                                                            10

<210> SEQ ID NO 274
<211> LENGTH: 10
<212> TYPE: DNA
<213> ORGANISM: Artificial sequence
<220> FEATURE:
<223> OTHER INFORMATION: Primer OPN-05

<400> SEQUENCE: 274
actgaacgcc                                                            10

<210> SEQ ID NO 275
<211> LENGTH: 10
<212> TYPE: DNA
<213> ORGANISM: Artificial sequence
<220> FEATURE:
<223> OTHER INFORMATION: Primer OPN-06

<400> SEQUENCE: 275
gagacgcaca                                                            10

<210> SEQ ID NO 276
<211> LENGTH: 10
<212> TYPE: DNA
<213> ORGANISM: Artificial sequence
<220> FEATURE:
<223> OTHER INFORMATION: Primer OPN-07

<400> SEQUENCE: 276
cagcccagag                                                            10

<210> SEQ ID NO 277
<211> LENGTH: 10
<212> TYPE: DNA
<213> ORGANISM: Artificial sequence
<220> FEATURE:
<223> OTHER INFORMATION: Primer OPN-08

<400> SEQUENCE: 277
acctcagctc                                                            10

<210> SEQ ID NO 278
<211> LENGTH: 10
<212> TYPE: DNA
<213> ORGANISM: Artificial sequence
<220> FEATURE:
<223> OTHER INFORMATION: Primer OPN-09

<400> SEQUENCE: 278
tgccggcttg                                                            10

<210> SEQ ID NO 279
<211> LENGTH: 10
```

```
<212> TYPE: DNA
<213> ORGANISM: Artificial sequence
<220> FEATURE:
<223> OTHER INFORMATION: Primer OPN-10

<400> SEQUENCE: 279
acaactgggg                                                          10

<210> SEQ ID NO 280
<211> LENGTH: 10
<212> TYPE: DNA
<213> ORGANISM: Artificial sequence
<220> FEATURE:
<223> OTHER INFORMATION: Primer OPN-11

<400> SEQUENCE: 280
tcgccgcaaa                                                          10

<210> SEQ ID NO 281
<211> LENGTH: 10
<212> TYPE: DNA
<213> ORGANISM: Artificial sequence
<220> FEATURE:
<223> OTHER INFORMATION: Primer OPN-12

<400> SEQUENCE: 281
cacagacacc                                                          10

<210> SEQ ID NO 282
<211> LENGTH: 10
<212> TYPE: DNA
<213> ORGANISM: Artificial sequence
<220> FEATURE:
<223> OTHER INFORMATION: Primer OPN-13

<400> SEQUENCE: 282
agcgtcactc                                                          10

<210> SEQ ID NO 283
<211> LENGTH: 10
<212> TYPE: DNA
<213> ORGANISM: Artificial sequence
<220> FEATURE:
<223> OTHER INFORMATION: Primer OPN-14

<400> SEQUENCE: 283
tcgtgcgggt                                                          10

<210> SEQ ID NO 284
<211> LENGTH: 10
<212> TYPE: DNA
<213> ORGANISM: Artificial sequence
<220> FEATURE:
<223> OTHER INFORMATION: Primer OPN-15

<400> SEQUENCE: 284
cagcgactgt                                                          10

<210> SEQ ID NO 285
<211> LENGTH: 10
<212> TYPE: DNA
<213> ORGANISM: Artificial sequence
<220> FEATURE:
<223> OTHER INFORMATION: Primer OPN-16

<400> SEQUENCE: 285
aagcgacctg                                                          10
```

```
<210> SEQ ID NO 286
<211> LENGTH: 10
<212> TYPE: DNA
<213> ORGANISM: Artificial sequence
<220> FEATURE:
<223> OTHER INFORMATION: Primer OPN-17

<400> SEQUENCE: 286
cattggggag                                                          10

<210> SEQ ID NO 287
<211> LENGTH: 10
<212> TYPE: DNA
<213> ORGANISM: Artificial sequence
<220> FEATURE:
<223> OTHER INFORMATION: Primer OPN-18

<400> SEQUENCE: 287
ggtgaggtca                                                          10

<210> SEQ ID NO 288
<211> LENGTH: 10
<212> TYPE: DNA
<213> ORGANISM: Artificial sequence
<220> FEATURE:
<223> OTHER INFORMATION: Primer OPN-19

<400> SEQUENCE: 288
gtccgtactg                                                          10

<210> SEQ ID NO 289
<211> LENGTH: 10
<212> TYPE: DNA
<213> ORGANISM: Artificial sequence
<220> FEATURE:
<223> OTHER INFORMATION: Primer OPN-20

<400> SEQUENCE: 289
ggtgctccgt                                                          10

<210> SEQ ID NO 290
<211> LENGTH: 10
<212> TYPE: DNA
<213> ORGANISM: Artificial sequence
<220> FEATURE:
<223> OTHER INFORMATION: Primer OPO-01

<400> SEQUENCE: 290
ggcacgtaag                                                          10

<210> SEQ ID NO 291
<211> LENGTH: 10
<212> TYPE: DNA
<213> ORGANISM: Artificial sequence
<220> FEATURE:
<223> OTHER INFORMATION: Primer OPO-02

<400> SEQUENCE: 291
acgtagcgtc                                                          10

<210> SEQ ID NO 292
<211> LENGTH: 10
<212> TYPE: DNA
<213> ORGANISM: Artificial sequence
<220> FEATURE:
<223> OTHER INFORMATION: Primer OPO-03
```

```
<400> SEQUENCE: 292
ctgttgctac                                                            10

<210> SEQ ID NO 293
<211> LENGTH: 10
<212> TYPE: DNA
<213> ORGANISM: Artificial sequence
<220> FEATURE:
<223> OTHER INFORMATION: Primer OPO-04

<400> SEQUENCE: 293
aagtccgctc                                                            10

<210> SEQ ID NO 294
<211> LENGTH: 10
<212> TYPE: DNA
<213> ORGANISM: Artificial sequence
<220> FEATURE:
<223> OTHER INFORMATION: Primer OPO-05

<400> SEQUENCE: 294
cccagtcact                                                            10

<210> SEQ ID NO 295
<211> LENGTH: 10
<212> TYPE: DNA
<213> ORGANISM: Artificial sequence
<220> FEATURE:
<223> OTHER INFORMATION: Primer OPO-06

<400> SEQUENCE: 295
ccacgggaag                                                            10

<210> SEQ ID NO 296
<211> LENGTH: 10
<212> TYPE: DNA
<213> ORGANISM: Artificial sequence
<220> FEATURE:
<223> OTHER INFORMATION: Primer OPO-07

<400> SEQUENCE: 296
cagcactgac                                                            10

<210> SEQ ID NO 297
<211> LENGTH: 10
<212> TYPE: DNA
<213> ORGANISM: Artificial sequence
<220> FEATURE:
<223> OTHER INFORMATION: Primer OPO-08

<400> SEQUENCE: 297
cctccagtgt                                                            10

<210> SEQ ID NO 298
<211> LENGTH: 10
<212> TYPE: DNA
<213> ORGANISM: Artificial sequence
<220> FEATURE:
<223> OTHER INFORMATION: Primer OPO-09

<400> SEQUENCE: 298
tcccacgcaa                                                            10

<210> SEQ ID NO 299
<211> LENGTH: 10
```

```
<212> TYPE: DNA
<213> ORGANISM: Artificial sequence
<220> FEATURE:
<223> OTHER INFORMATION: Primer OPO-10

<400> SEQUENCE: 299
tcagagcgcc                                                              10

<210> SEQ ID NO 300
<211> LENGTH: 10
<212> TYPE: DNA
<213> ORGANISM: Artificial sequence
<220> FEATURE:
<223> OTHER INFORMATION: Primer OPO-11

<400> SEQUENCE: 300
gacaggaggt                                                              10

<210> SEQ ID NO 301
<211> LENGTH: 10
<212> TYPE: DNA
<213> ORGANISM: Artificial sequence
<220> FEATURE:
<223> OTHER INFORMATION: Primer OPO-12

<400> SEQUENCE: 301
cagtgctgtg                                                              10

<210> SEQ ID NO 302
<211> LENGTH: 10
<212> TYPE: DNA
<213> ORGANISM: Artificial sequence
<220> FEATURE:
<223> OTHER INFORMATION: Primer OPO-13

<400> SEQUENCE: 302
gtcagagtcc                                                              10

<210> SEQ ID NO 303
<211> LENGTH: 10
<212> TYPE: DNA
<213> ORGANISM: Artificial sequence
<220> FEATURE:
<223> OTHER INFORMATION: Primer OPO-14

<400> SEQUENCE: 303
agcatggctc                                                              10

<210> SEQ ID NO 304
<211> LENGTH: 10
<212> TYPE: DNA
<213> ORGANISM: Artificial sequence
<220> FEATURE:
<223> OTHER INFORMATION: Primer OPO-15

<400> SEQUENCE: 304
tggcgtcctt                                                              10

<210> SEQ ID NO 305
<211> LENGTH: 10
<212> TYPE: DNA
<213> ORGANISM: Artificial sequence
<220> FEATURE:
<223> OTHER INFORMATION: Primer OPO-16

<400> SEQUENCE: 305
tcggcggttc                                                              10
```

<210> SEQ ID NO 306
<211> LENGTH: 10
<212> TYPE: DNA
<213> ORGANISM: Artificial sequence
<220> FEATURE:
<223> OTHER INFORMATION: Primer OPO-17

<400> SEQUENCE: 306
ggcttatgcc                                                                10

<210> SEQ ID NO 307
<211> LENGTH: 10
<212> TYPE: DNA
<213> ORGANISM: Artificial sequence
<220> FEATURE:
<223> OTHER INFORMATION: Primer OPO-18

<400> SEQUENCE: 307
ctcgctatcc                                                                10

<210> SEQ ID NO 308
<211> LENGTH: 10
<212> TYPE: DNA
<213> ORGANISM: Artificial sequence
<220> FEATURE:
<223> OTHER INFORMATION: Primer OPO-19

<400> SEQUENCE: 308
ggtgcacgtt                                                                10

<210> SEQ ID NO 309
<211> LENGTH: 10
<212> TYPE: DNA
<213> ORGANISM: Artificial sequence
<220> FEATURE:
<223> OTHER INFORMATION: Primer OPO-20

<400> SEQUENCE: 309
acacacgctg                                                                10

<210> SEQ ID NO 310
<211> LENGTH: 10
<212> TYPE: DNA
<213> ORGANISM: Artificial sequence
<220> FEATURE:
<223> OTHER INFORMATION: Primer OPP-01

<400> SEQUENCE: 310
gtagcactcc                                                                10

<210> SEQ ID NO 311
<211> LENGTH: 10
<212> TYPE: DNA
<213> ORGANISM: Artificial sequence
<220> FEATURE:
<223> OTHER INFORMATION: Primer OPP-02

<400> SEQUENCE: 311
tcggcacgca                                                                10

<210> SEQ ID NO 312
<211> LENGTH: 10
<212> TYPE: DNA
<213> ORGANISM: Artificial sequence
<220> FEATURE:
<223> OTHER INFORMATION: Primer OPP-03

<400> SEQUENCE: 312
ctgatacgcc                                                              10

<210> SEQ ID NO 313
<211> LENGTH: 10
<212> TYPE: DNA
<213> ORGANISM: Artificial sequence
<220> FEATURE:
<223> OTHER INFORMATION: Primer OPP-04

<400> SEQUENCE: 313
gtgtctcagg                                                              10

<210> SEQ ID NO 314
<211> LENGTH: 10
<212> TYPE: DNA
<213> ORGANISM: Artificial sequence
<220> FEATURE:
<223> OTHER INFORMATION: Primer OPP-05

<400> SEQUENCE: 314
ccccggtaac                                                              10

<210> SEQ ID NO 315
<211> LENGTH: 10
<212> TYPE: DNA
<213> ORGANISM: Artificial sequence
<220> FEATURE:
<223> OTHER INFORMATION: Primer OPP-06

<400> SEQUENCE: 315
gtgggctgac                                                              10

<210> SEQ ID NO 316
<211> LENGTH: 10
<212> TYPE: DNA
<213> ORGANISM: Artificial sequence
<220> FEATURE:
<223> OTHER INFORMATION: Primer OPP-07

<400> SEQUENCE: 316
gtccatgcca                                                              10

<210> SEQ ID NO 317
<211> LENGTH: 10
<212> TYPE: DNA
<213> ORGANISM: Artificial sequence
<220> FEATURE:
<223> OTHER INFORMATION: Primer OPP-08

<400> SEQUENCE: 317
acatcgccca                                                              10

<210> SEQ ID NO 318
<211> LENGTH: 10
<212> TYPE: DNA
<213> ORGANISM: Artificial sequence
<220> FEATURE:
<223> OTHER INFORMATION: Primer OPP-09

<400> SEQUENCE: 318
gtggtccgca                                                              10

<210> SEQ ID NO 319
<211> LENGTH: 10

```
<212> TYPE: DNA
<213> ORGANISM: Artificial sequence
<220> FEATURE:
<223> OTHER INFORMATION: Primer OPP-10

<400> SEQUENCE: 319
tcccgcctac                                                          10

<210> SEQ ID NO 320
<211> LENGTH: 10
<212> TYPE: DNA
<213> ORGANISM: Artificial sequence
<220> FEATURE:
<223> OTHER INFORMATION: Primer OPP-11

<400> SEQUENCE: 320
aacgcgtcgg                                                          10

<210> SEQ ID NO 321
<211> LENGTH: 10
<212> TYPE: DNA
<213> ORGANISM: Artificial sequence
<220> FEATURE:
<223> OTHER INFORMATION: Primer OPP-12

<400> SEQUENCE: 321
aagggcgagt                                                          10

<210> SEQ ID NO 322
<211> LENGTH: 10
<212> TYPE: DNA
<213> ORGANISM: Artificial sequence
<220> FEATURE:
<223> OTHER INFORMATION: Primer OPP-13

<400> SEQUENCE: 322
ggagtgcctc                                                          10

<210> SEQ ID NO 323
<211> LENGTH: 10
<212> TYPE: DNA
<213> ORGANISM: Artificial sequence
<220> FEATURE:
<223> OTHER INFORMATION: Primer OPP-14

<400> SEQUENCE: 323
ccagccgaac                                                          10

<210> SEQ ID NO 324
<211> LENGTH: 10
<212> TYPE: DNA
<213> ORGANISM: Artificial sequence
<220> FEATURE:
<223> OTHER INFORMATION: Primer OPP-15

<400> SEQUENCE: 324
ggaagccaac                                                          10

<210> SEQ ID NO 325
<211> LENGTH: 10
<212> TYPE: DNA
<213> ORGANISM: Artificial sequence
<220> FEATURE:
<223> OTHER INFORMATION: Primer OPP-16

<400> SEQUENCE: 325
ccaagctgcc                                                          10
```

<210> SEQ ID NO 326
<211> LENGTH: 10
<212> TYPE: DNA
<213> ORGANISM: Artificial sequence
<220> FEATURE:
<223> OTHER INFORMATION: Primer OPP-17

<400> SEQUENCE: 326
tgacccgcct                                                                10

<210> SEQ ID NO 327
<211> LENGTH: 10
<212> TYPE: DNA
<213> ORGANISM: Artificial sequence
<220> FEATURE:
<223> OTHER INFORMATION: Primer OPP-18

<400> SEQUENCE: 327
ggcttggcct                                                                10

<210> SEQ ID NO 328
<211> LENGTH: 10
<212> TYPE: DNA
<213> ORGANISM: Artificial sequence
<220> FEATURE:
<223> OTHER INFORMATION: Primer OPP-19

<400> SEQUENCE: 328
gggaaggaca                                                                10

<210> SEQ ID NO 329
<211> LENGTH: 10
<212> TYPE: DNA
<213> ORGANISM: Artificial sequence
<220> FEATURE:
<223> OTHER INFORMATION: Primer OPP-20

<400> SEQUENCE: 329
gaccctagtc                                                                10

<210> SEQ ID NO 330
<211> LENGTH: 10
<212> TYPE: DNA
<213> ORGANISM: Artificial sequence
<220> FEATURE:
<223> OTHER INFORMATION: Primer OPQ-01

<400> SEQUENCE: 330
gggacgatgg                                                                10

<210> SEQ ID NO 331
<211> LENGTH: 10
<212> TYPE: DNA
<213> ORGANISM: Artificial sequence
<220> FEATURE:
<223> OTHER INFORMATION: Primer OPQ-02

<400> SEQUENCE: 331
tctgtcggtc                                                                10

<210> SEQ ID NO 332
<211> LENGTH: 10
<212> TYPE: DNA
<213> ORGANISM: Artificial sequence
<220> FEATURE:
<223> OTHER INFORMATION: Primer OPQ-03

```
<400> SEQUENCE: 332
ggtcacctca                                                          10

<210> SEQ ID NO 333
<211> LENGTH: 10
<212> TYPE: DNA
<213> ORGANISM: Artificial sequence
<220> FEATURE:
<223> OTHER INFORMATION: Primer OPQ-04

<400> SEQUENCE: 333
agtgcgctga                                                          10

<210> SEQ ID NO 334
<211> LENGTH: 10
<212> TYPE: DNA
<213> ORGANISM: Artificial sequence
<220> FEATURE:
<223> OTHER INFORMATION: Primer OPQ-05

<400> SEQUENCE: 334
ccgcgtcttg                                                          10

<210> SEQ ID NO 335
<211> LENGTH: 10
<212> TYPE: DNA
<213> ORGANISM: Artificial sequence
<220> FEATURE:
<223> OTHER INFORMATION: Primer OPQ-06

<400> SEQUENCE: 335
gagcgccttg                                                          10

<210> SEQ ID NO 336
<211> LENGTH: 10
<212> TYPE: DNA
<213> ORGANISM: Artificial sequence
<220> FEATURE:
<223> OTHER INFORMATION: Primer OPQ-07

<400> SEQUENCE: 336
ccccgatggt                                                          10

<210> SEQ ID NO 337
<211> LENGTH: 10
<212> TYPE: DNA
<213> ORGANISM: Artificial sequence
<220> FEATURE:
<223> OTHER INFORMATION: Primer OPQ-08

<400> SEQUENCE: 337
ctccagcgga                                                          10

<210> SEQ ID NO 338
<211> LENGTH: 10
<212> TYPE: DNA
<213> ORGANISM: Artificial sequence
<220> FEATURE:
<223> OTHER INFORMATION: Primer OPQ-09

<400> SEQUENCE: 338
ggctaaccga                                                          10

<210> SEQ ID NO 339
<211> LENGTH: 10
```

<212> TYPE: DNA
<213> ORGANISM: Artificial sequence
<220> FEATURE:
<223> OTHER INFORMATION: Primer OPQ-10

<400> SEQUENCE: 339
tgtgcccgaa                                                              10

<210> SEQ ID NO 340
<211> LENGTH: 10
<212> TYPE: DNA
<213> ORGANISM: Artificial sequence
<220> FEATURE:
<223> OTHER INFORMATION: Primer OPQ-11

<400> SEQUENCE: 340
tctccgcaac                                                              10

<210> SEQ ID NO 341
<211> LENGTH: 10
<212> TYPE: DNA
<213> ORGANISM: Artificial sequence
<220> FEATURE:
<223> OTHER INFORMATION: Primer OPQ-12

<400> SEQUENCE: 341
agtagggcac                                                              10

<210> SEQ ID NO 342
<211> LENGTH: 10
<212> TYPE: DNA
<213> ORGANISM: Artificial sequence
<220> FEATURE:
<223> OTHER INFORMATION: Primer OPQ-13

<400> SEQUENCE: 342
ggagtggaca                                                              10

<210> SEQ ID NO 343
<211> LENGTH: 10
<212> TYPE: DNA
<213> ORGANISM: Artificial sequence
<220> FEATURE:
<223> OTHER INFORMATION: Primer OPQ-14

<400> SEQUENCE: 343
ggacgcttca                                                              10

<210> SEQ ID NO 344
<211> LENGTH: 10
<212> TYPE: DNA
<213> ORGANISM: Artificial sequence
<220> FEATURE:
<223> OTHER INFORMATION: Primer OPQ-15

<400> SEQUENCE: 344
gggtaacgtg                                                              10

<210> SEQ ID NO 345
<211> LENGTH: 10
<212> TYPE: DNA
<213> ORGANISM: Artificial sequence
<220> FEATURE:
<223> OTHER INFORMATION: Primer OPQ-16

<400> SEQUENCE: 345
agtgcagcca                                                              10

<210> SEQ ID NO 346
<211> LENGTH: 10
<212> TYPE: DNA
<213> ORGANISM: Artificial sequence
<220> FEATURE:
<223> OTHER INFORMATION: Primer OPQ-17

<400> SEQUENCE: 346 gaagcccttg					10

<210> SEQ ID NO 347
<211> LENGTH: 10
<212> TYPE: DNA
<213> ORGANISM: Artificial sequence
<220> FEATURE:
<223> OTHER INFORMATION: Primer OPQ-18

<400> SEQUENCE: 347 aggctgggtg					10

<210> SEQ ID NO 348
<211> LENGTH: 10
<212> TYPE: DNA
<213> ORGANISM: Artificial sequence
<220> FEATURE:
<223> OTHER INFORMATION: Primer OPQ-19

<400> SEQUENCE: 348 cccctatca					10

<210> SEQ ID NO 349
<211> LENGTH: 10
<212> TYPE: DNA
<213> ORGANISM: Artificial sequence
<220> FEATURE:
<223> OTHER INFORMATION: Primer OPQ-20

<400> SEQUENCE: 349 tcgcccagtc					10

<210> SEQ ID NO 350
<211> LENGTH: 10
<212> TYPE: DNA
<213> ORGANISM: Artificial sequence
<220> FEATURE:
<223> OTHER INFORMATION: Primer OPR-01

<400> SEQUENCE: 350 tgcgggtcct					10

<210> SEQ ID NO 351
<211> LENGTH: 10
<212> TYPE: DNA
<213> ORGANISM: Artificial sequence
<220> FEATURE:
<223> OTHER INFORMATION: Primer OPR-02

<400> SEQUENCE: 351 cacagctgcc					10

<210> SEQ ID NO 352
<211> LENGTH: 10
<212> TYPE: DNA
<213> ORGANISM: Artificial sequence
<220> FEATURE:
<223> OTHER INFORMATION: Primer OPR-03

```
<400> SEQUENCE: 352
acacagaggg                                                            10

<210> SEQ ID NO 353
<211> LENGTH: 10
<212> TYPE: DNA
<213> ORGANISM: Artificial sequence
<220> FEATURE:
<223> OTHER INFORMATION: Primer OPR-04

<400> SEQUENCE: 353
cccgtagcac                                                            10

<210> SEQ ID NO 354
<211> LENGTH: 10
<212> TYPE: DNA
<213> ORGANISM: Artificial sequence
<220> FEATURE:
<223> OTHER INFORMATION: Primer OPR-05

<400> SEQUENCE: 354
gacctagtgg                                                            10

<210> SEQ ID NO 355
<211> LENGTH: 10
<212> TYPE: DNA
<213> ORGANISM: Artificial sequence
<220> FEATURE:
<223> OTHER INFORMATION: Primer OPR-06

<400> SEQUENCE: 355
gtctacggca                                                            10

<210> SEQ ID NO 356
<211> LENGTH: 10
<212> TYPE: DNA
<213> ORGANISM: Artificial sequence
<220> FEATURE:
<223> OTHER INFORMATION: Primer OPR-07

<400> SEQUENCE: 356
actggcctga                                                            10

<210> SEQ ID NO 357
<211> LENGTH: 10
<212> TYPE: DNA
<213> ORGANISM: Artificial sequence
<220> FEATURE:
<223> OTHER INFORMATION: Primer OPR-08

<400> SEQUENCE: 357
cccgttgcct                                                            10

<210> SEQ ID NO 358
<211> LENGTH: 10
<212> TYPE: DNA
<213> ORGANISM: Artificial sequence
<220> FEATURE:
<223> OTHER INFORMATION: Primer OPR-09

<400> SEQUENCE: 358
tgagcacgag                                                            10

<210> SEQ ID NO 359
<211> LENGTH: 10
```

```
<212> TYPE: DNA
<213> ORGANISM: Artificial sequence
<220> FEATURE:
<223> OTHER INFORMATION: Primer OPR-10

<400> SEQUENCE: 359
ccattcccca                                                            10

<210> SEQ ID NO 360
<211> LENGTH: 10
<212> TYPE: DNA
<213> ORGANISM: Artificial sequence
<220> FEATURE:
<223> OTHER INFORMATION: Primer OPR-11

<400> SEQUENCE: 360
gtagccgtct                                                            10

<210> SEQ ID NO 361
<211> LENGTH: 10
<212> TYPE: DNA
<213> ORGANISM: Artificial sequence
<220> FEATURE:
<223> OTHER INFORMATION: Primer OPR-12

<400> SEQUENCE: 361
acaggtgcgt                                                            10

<210> SEQ ID NO 362
<211> LENGTH: 10
<212> TYPE: DNA
<213> ORGANISM: Artificial sequence
<220> FEATURE:
<223> OTHER INFORMATION: Primer OPR-13

<400> SEQUENCE: 362
ggacgacaag                                                            10

<210> SEQ ID NO 363
<211> LENGTH: 10
<212> TYPE: DNA
<213> ORGANISM: Artificial sequence
<220> FEATURE:
<223> OTHER INFORMATION: Primer OPR-14

<400> SEQUENCE: 363
caggattccc                                                            10

<210> SEQ ID NO 364
<211> LENGTH: 10
<212> TYPE: DNA
<213> ORGANISM: Artificial sequence
<220> FEATURE:
<223> OTHER INFORMATION: Primer OPR-15

<400> SEQUENCE: 364
ggacaacgag                                                            10

<210> SEQ ID NO 365
<211> LENGTH: 10
<212> TYPE: DNA
<213> ORGANISM: Artificial sequence
<220> FEATURE:
<223> OTHER INFORMATION: Primer OPR-16

<400> SEQUENCE: 365
ctctgcgcgt                                                            10
```

<210> SEQ ID NO 366
<211> LENGTH: 10
<212> TYPE: DNA
<213> ORGANISM: Artificial sequence
<220> FEATURE:
<223> OTHER INFORMATION: Primer OPR-17

<400> SEQUENCE: 366
ccgtacgtag                                                          10

<210> SEQ ID NO 367
<211> LENGTH: 10
<212> TYPE: DNA
<213> ORGANISM: Artificial sequence
<220> FEATURE:
<223> OTHER INFORMATION: Primer OPR-18

<400> SEQUENCE: 367
ggctttgcca                                                          10

<210> SEQ ID NO 368
<211> LENGTH: 10
<212> TYPE: DNA
<213> ORGANISM: Artificial sequence
<220> FEATURE:
<223> OTHER INFORMATION: Primer OPR-19

<400> SEQUENCE: 368
cctcctcatc                                                          10

<210> SEQ ID NO 369
<211> LENGTH: 10
<212> TYPE: DNA
<213> ORGANISM: Artificial sequence
<220> FEATURE:
<223> OTHER INFORMATION: Primer OPR-20

<400> SEQUENCE: 369
acggcaagga                                                          10

<210> SEQ ID NO 370
<211> LENGTH: 10
<212> TYPE: DNA
<213> ORGANISM: Artificial sequence
<220> FEATURE:
<223> OTHER INFORMATION: Primer OPS-01

<400> SEQUENCE: 370
ctactgcgct                                                          10

<210> SEQ ID NO 371
<211> LENGTH: 10
<212> TYPE: DNA
<213> ORGANISM: Artificial sequence
<220> FEATURE:
<223> OTHER INFORMATION: Primer OPS-02

<400> SEQUENCE: 371
cctctgactg                                                          10

<210> SEQ ID NO 372
<211> LENGTH: 10
<212> TYPE: DNA
<213> ORGANISM: Artificial sequence
<220> FEATURE:
<223> OTHER INFORMATION: Primer OPS-03

<400> SEQUENCE: 372
cagaggtccc                                                          10

<210> SEQ ID NO 373
<211> LENGTH: 10
<212> TYPE: DNA
<213> ORGANISM: Artificial sequence
<220> FEATURE:
<223> OTHER INFORMATION: Primer OPS-04

<400> SEQUENCE: 373
cacccccttg                                                          10

<210> SEQ ID NO 374
<211> LENGTH: 10
<212> TYPE: DNA
<213> ORGANISM: Artificial sequence
<220> FEATURE:
<223> OTHER INFORMATION: Primer OPS-05

<400> SEQUENCE: 374
tttggggcct                                                          10

<210> SEQ ID NO 375
<211> LENGTH: 10
<212> TYPE: DNA
<213> ORGANISM: Artificial sequence
<220> FEATURE:
<223> OTHER INFORMATION: Primer OPS-06

<400> SEQUENCE: 375
gatacctcgg                                                          10

<210> SEQ ID NO 376
<211> LENGTH: 10
<212> TYPE: DNA
<213> ORGANISM: Artificial sequence
<220> FEATURE:
<223> OTHER INFORMATION: Primer OPS-07

<400> SEQUENCE: 376
tccgatgctg                                                          10

<210> SEQ ID NO 377
<211> LENGTH: 10
<212> TYPE: DNA
<213> ORGANISM: Artificial sequence
<220> FEATURE:
<223> OTHER INFORMATION: Primer OPS-08

<400> SEQUENCE: 377
ttcagggtgg                                                          10

<210> SEQ ID NO 378
<211> LENGTH: 10
<212> TYPE: DNA
<213> ORGANISM: Artificial sequence
<220> FEATURE:
<223> OTHER INFORMATION: Primer OPS-09

<400> SEQUENCE: 378
tcctggtccc                                                          10

<210> SEQ ID NO 379
<211> LENGTH: 10

```
<212> TYPE: DNA
<213> ORGANISM: Artificial sequence
<220> FEATURE:
<223> OTHER INFORMATION: Primer OPS-10

<400> SEQUENCE: 379
accgttccag                                                              10

<210> SEQ ID NO 380
<211> LENGTH: 10
<212> TYPE: DNA
<213> ORGANISM: Artificial sequence
<220> FEATURE:
<223> OTHER INFORMATION: Primer OPS-11

<400> SEQUENCE: 380
agtcgggtgg                                                              10

<210> SEQ ID NO 381
<211> LENGTH: 10
<212> TYPE: DNA
<213> ORGANISM: Artificial sequence
<220> FEATURE:
<223> OTHER INFORMATION: Primer OPS-12

<400> SEQUENCE: 381
ctgggtgagt                                                              10

<210> SEQ ID NO 382
<211> LENGTH: 10
<212> TYPE: DNA
<213> ORGANISM: Artificial sequence
<220> FEATURE:
<223> OTHER INFORMATION: Primer OPS-13

<400> SEQUENCE: 382
gtcgttcctg                                                              10

<210> SEQ ID NO 383
<211> LENGTH: 10
<212> TYPE: DNA
<213> ORGANISM: Artificial sequence
<220> FEATURE:
<223> OTHER INFORMATION: Primer OPS-14

<400> SEQUENCE: 383
aaaggggtcc                                                              10

<210> SEQ ID NO 384
<211> LENGTH: 10
<212> TYPE: DNA
<213> ORGANISM: Artificial sequence
<220> FEATURE:
<223> OTHER INFORMATION: Primer OPS-15

<400> SEQUENCE: 384
cagttcacgg                                                              10

<210> SEQ ID NO 385
<211> LENGTH: 10
<212> TYPE: DNA
<213> ORGANISM: Artificial sequence
<220> FEATURE:
<223> OTHER INFORMATION: Primer OPS-16

<400> SEQUENCE: 385 aggggggttcc                                                             10
```

<210> SEQ ID NO 386
<211> LENGTH: 10
<212> TYPE: DNA
<213> ORGANISM: Artificial sequence
<220> FEATURE:
<223> OTHER INFORMATION: Primer OPS-17

<400> SEQUENCE: 386
tggggaccac                                                           10

<210> SEQ ID NO 387
<211> LENGTH: 10
<212> TYPE: DNA
<213> ORGANISM: Artificial sequence
<220> FEATURE:
<223> OTHER INFORMATION: Primer OPS-18

<400> SEQUENCE: 387
ctggcgaact                                                           10

<210> SEQ ID NO 388
<211> LENGTH: 10
<212> TYPE: DNA
<213> ORGANISM: Artificial sequence
<220> FEATURE:
<223> OTHER INFORMATION: Primer OPS-19

<400> SEQUENCE: 388
gagtcagcag                                                           10

<210> SEQ ID NO 389
<211> LENGTH: 10
<212> TYPE: DNA
<213> ORGANISM: Artificial sequence
<220> FEATURE:
<223> OTHER INFORMATION: Primer OPS-20

<400> SEQUENCE: 389
tctggacgga                                                           10

<210> SEQ ID NO 390
<211> LENGTH: 10
<212> TYPE: DNA
<213> ORGANISM: Artificial sequence
<220> FEATURE:
<223> OTHER INFORMATION: Primer OPT-01

<400> SEQUENCE: 390
gggccactca                                                           10

<210> SEQ ID NO 391
<211> LENGTH: 10
<212> TYPE: DNA
<213> ORGANISM: Artificial sequence
<220> FEATURE:
<223> OTHER INFORMATION: Primer OPT-02

<400> SEQUENCE: 391
ggagagactc                                                           10

<210> SEQ ID NO 392
<211> LENGTH: 10
<212> TYPE: DNA
<213> ORGANISM: Artificial sequence
<220> FEATURE:
<223> OTHER INFORMATION: Primer OPT-03

<400> SEQUENCE: 392
tccactcctg                                                          10

<210> SEQ ID NO 393
<211> LENGTH: 10
<212> TYPE: DNA
<213> ORGANISM: Artificial sequence
<220> FEATURE:
<223> OTHER INFORMATION: Primer OPT-04

<400> SEQUENCE: 393
cacagaggga                                                          10

<210> SEQ ID NO 394
<211> LENGTH: 10
<212> TYPE: DNA
<213> ORGANISM: Artificial sequence
<220> FEATURE:
<223> OTHER INFORMATION: Primer OPT-05

<400> SEQUENCE: 394
gggtttggca                                                          10

<210> SEQ ID NO 395
<211> LENGTH: 10
<212> TYPE: DNA
<213> ORGANISM: Artificial sequence
<220> FEATURE:
<223> OTHER INFORMATION: Primer OPT-06

<400> SEQUENCE: 395
caagggcaga                                                          10

<210> SEQ ID NO 396
<211> LENGTH: 10
<212> TYPE: DNA
<213> ORGANISM: Artificial sequence
<220> FEATURE:
<223> OTHER INFORMATION: Primer OPT-07

<400> SEQUENCE: 396
ggcaggctgt                                                          10

<210> SEQ ID NO 397
<211> LENGTH: 10
<212> TYPE: DNA
<213> ORGANISM: Artificial sequence
<220> FEATURE:
<223> OTHER INFORMATION: Primer OPT-08

<400> SEQUENCE: 397
aacggcgaca                                                          10

<210> SEQ ID NO 398
<211> LENGTH: 10
<212> TYPE: DNA
<213> ORGANISM: Artificial sequence
<220> FEATURE:
<223> OTHER INFORMATION: Primer OPT-09

<400> SEQUENCE: 398
cacccctgag                                                          10

<210> SEQ ID NO 399
<211> LENGTH: 10

<210> SEQ ID NO 399
<211> LENGTH: 10
<212> TYPE: DNA
<213> ORGANISM: Artificial sequence
<220> FEATURE:
<223> OTHER INFORMATION: Primer OPT-10

<400> SEQUENCE: 399
ccttcggaag                                                                 10

<210> SEQ ID NO 400
<211> LENGTH: 10
<212> TYPE: DNA
<213> ORGANISM: Artificial sequence
<220> FEATURE:
<223> OTHER INFORMATION: Primer OPT-11

<400> SEQUENCE: 400
ttccccgcga                                                                 10

<210> SEQ ID NO 401
<211> LENGTH: 10
<212> TYPE: DNA
<213> ORGANISM: Artificial sequence
<220> FEATURE:
<223> OTHER INFORMATION: Primer OPT-12

<400> SEQUENCE: 401
gggtgtgtag                                                                 10

<210> SEQ ID NO 402
<211> LENGTH: 10
<212> TYPE: DNA
<213> ORGANISM: Artificial sequence
<220> FEATURE:
<223> OTHER INFORMATION: Primer OPT-13

<400> SEQUENCE: 402
aggactgcca                                                                 10

<210> SEQ ID NO 403
<211> LENGTH: 10
<212> TYPE: DNA
<213> ORGANISM: Artificial sequence
<220> FEATURE:
<223> OTHER INFORMATION: Primer OPT-14

<400> SEQUENCE: 403
aatgccgcag                                                                 10

<210> SEQ ID NO 404
<211> LENGTH: 10
<212> TYPE: DNA
<213> ORGANISM: Artificial sequence
<220> FEATURE:
<223> OTHER INFORMATION: Primer OPT-15

<400> SEQUENCE: 404
ggatgccact                                                                 10

<210> SEQ ID NO 405
<211> LENGTH: 10
<212> TYPE: DNA
<213> ORGANISM: Artificial sequence
<220> FEATURE:
<223> OTHER INFORMATION: Primer OPT-16

<400> SEQUENCE: 405
ggtgaacgct                                                                 10

<210> SEQ ID NO 406
<211> LENGTH: 10
<212> TYPE: DNA
<213> ORGANISM: Artificial sequence
<220> FEATURE:
<223> OTHER INFORMATION: Primer OPT-17

<400> SEQUENCE: 406
ccaacgtcgt                                                              10

<210> SEQ ID NO 407
<211> LENGTH: 10
<212> TYPE: DNA
<213> ORGANISM: Artificial sequence
<220> FEATURE:
<223> OTHER INFORMATION: Primer OPT-18

<400> SEQUENCE: 407
gatgccagac                                                              10

<210> SEQ ID NO 408
<211> LENGTH: 10
<212> TYPE: DNA
<213> ORGANISM: Artificial sequence
<220> FEATURE:
<223> OTHER INFORMATION: Primer OPT-19

<400> SEQUENCE: 408
gtccgtatgg                                                              10

<210> SEQ ID NO 409
<211> LENGTH: 10
<212> TYPE: DNA
<213> ORGANISM: Artificial sequence
<220> FEATURE:
<223> OTHER INFORMATION: Primer OPT-20

<400> SEQUENCE: 409
gaccaatgcc                                                              10

<210> SEQ ID NO 410
<211> LENGTH: 10
<212> TYPE: DNA
<213> ORGANISM: Artificial sequence
<220> FEATURE:
<223> OTHER INFORMATION: Primer OPU-01

<400> SEQUENCE: 410
acggacgtca                                                              10

<210> SEQ ID NO 411
<211> LENGTH: 10
<212> TYPE: DNA
<213> ORGANISM: Artificial sequence
<220> FEATURE:
<223> OTHER INFORMATION: Primer OPU-02

<400> SEQUENCE: 411
ctgaggtctc                                                              10

<210> SEQ ID NO 412
<211> LENGTH: 10
<212> TYPE: DNA
<213> ORGANISM: Artificial sequence
<220> FEATURE:
<223> OTHER INFORMATION: Primer OPU-03

```
<400> SEQUENCE: 412
ctatgccgac                                                              10

<210> SEQ ID NO 413
<211> LENGTH: 10
<212> TYPE: DNA
<213> ORGANISM: Artificial sequence
<220> FEATURE:
<223> OTHER INFORMATION: Primer OPU-04

<400> SEQUENCE: 413
accttcggac                                                              10

<210> SEQ ID NO 414
<211> LENGTH: 10
<212> TYPE: DNA
<213> ORGANISM: Artificial sequence
<220> FEATURE:
<223> OTHER INFORMATION: Primer OPU-05

<400> SEQUENCE: 414
ttggcggcct                                                              10

<210> SEQ ID NO 415
<211> LENGTH: 10
<212> TYPE: DNA
<213> ORGANISM: Artificial sequence
<220> FEATURE:
<223> OTHER INFORMATION: Primer OPU-06

<400> SEQUENCE: 415
acctttgcgg                                                              10

<210> SEQ ID NO 416
<211> LENGTH: 10
<212> TYPE: DNA
<213> ORGANISM: Artificial sequence
<220> FEATURE:
<223> OTHER INFORMATION: Primer OPU-07

<400> SEQUENCE: 416
cctgctcatc                                                              10

<210> SEQ ID NO 417
<211> LENGTH: 10
<212> TYPE: DNA
<213> ORGANISM: Artificial sequence
<220> FEATURE:
<223> OTHER INFORMATION: Primer OPU-08

<400> SEQUENCE: 417
ggcgaaggtt                                                              10

<210> SEQ ID NO 418
<211> LENGTH: 10
<212> TYPE: DNA
<213> ORGANISM: Artificial sequence
<220> FEATURE:
<223> OTHER INFORMATION: Primer OPU-09

<400> SEQUENCE: 418
ccacatcggt                                                              10

<210> SEQ ID NO 419
<211> LENGTH: 10
```

```
<212> TYPE: DNA
<213> ORGANISM: Artificial sequence
<220> FEATURE:
<223> OTHER INFORMATION: Primer OPU-10

<400> SEQUENCE: 419
acctcggcac                                                          10

<210> SEQ ID NO 420
<211> LENGTH: 10
<212> TYPE: DNA
<213> ORGANISM: Artificial sequence
<220> FEATURE:
<223> OTHER INFORMATION: Primer OPU-11

<400> SEQUENCE: 420
agacccagag                                                          10

<210> SEQ ID NO 421
<211> LENGTH: 10
<212> TYPE: DNA
<213> ORGANISM: Artificial sequence
<220> FEATURE:
<223> OTHER INFORMATION: Primer OPU-12

<400> SEQUENCE: 421
tcaccagcca                                                          10

<210> SEQ ID NO 422
<211> LENGTH: 10
<212> TYPE: DNA
<213> ORGANISM: Artificial sequence
<220> FEATURE:
<223> OTHER INFORMATION: Primer OPU-13

<400> SEQUENCE: 422
ggctggttcc                                                          10

<210> SEQ ID NO 423
<211> LENGTH: 10
<212> TYPE: DNA
<213> ORGANISM: Artificial sequence
<220> FEATURE:
<223> OTHER INFORMATION: Primer OPU-14

<400> SEQUENCE: 423
tgggtccctc                                                          10

<210> SEQ ID NO 424
<211> LENGTH: 10
<212> TYPE: DNA
<213> ORGANISM: Artificial sequence
<220> FEATURE:
<223> OTHER INFORMATION: Primer OPU-15

<400> SEQUENCE: 424
acgggccagt                                                          10

<210> SEQ ID NO 425
<211> LENGTH: 10
<212> TYPE: DNA
<213> ORGANISM: Artificial sequence
<220> FEATURE:
<223> OTHER INFORMATION: Primer OPU-16

<400> SEQUENCE: 425
ctgcgctgga                                                          10
```

<210> SEQ ID NO 426
<211> LENGTH: 10
<212> TYPE: DNA
<213> ORGANISM: Artificial sequence
<220> FEATURE:
<223> OTHER INFORMATION: Primer OPU-17

<400> SEQUENCE: 426
acctggggag                                                          10

<210> SEQ ID NO 427
<211> LENGTH: 10
<212> TYPE: DNA
<213> ORGANISM: Artificial sequence
<220> FEATURE:
<223> OTHER INFORMATION: Primer OPU-18

<400> SEQUENCE: 427
gaggtccaca                                                          10

<210> SEQ ID NO 428
<211> LENGTH: 10
<212> TYPE: DNA
<213> ORGANISM: Artificial sequence
<220> FEATURE:
<223> OTHER INFORMATION: Primer OPU-19

<400> SEQUENCE: 428
gtcagtgcgg                                                          10

<210> SEQ ID NO 429
<211> LENGTH: 10
<212> TYPE: DNA
<213> ORGANISM: Artificial sequence
<220> FEATURE:
<223> OTHER INFORMATION: Primer OPU-20

<400> SEQUENCE: 429
acagccccca                                                          10

<210> SEQ ID NO 430
<211> LENGTH: 10
<212> TYPE: DNA
<213> ORGANISM: Artificial sequence
<220> FEATURE:
<223> OTHER INFORMATION: Primer OPV-01

<400> SEQUENCE: 430
tgacgcatgg                                                          10

<210> SEQ ID NO 431
<211> LENGTH: 10
<212> TYPE: DNA
<213> ORGANISM: Artificial sequence
<220> FEATURE:
<223> OTHER INFORMATION: Primer OPV-02

<400> SEQUENCE: 431
agtcactccc                                                          10

<210> SEQ ID NO 432
<211> LENGTH: 10
<212> TYPE: DNA
<213> ORGANISM: Artificial sequence
<220> FEATURE:
<223> OTHER INFORMATION: Primer OPV-03

```
<400> SEQUENCE: 432
ctccctgcaa                                                              10

<210> SEQ ID NO 433
<211> LENGTH: 10
<212> TYPE: DNA
<213> ORGANISM: Artificial sequence
<220> FEATURE:
<223> OTHER INFORMATION: Primer OPV-04

<400> SEQUENCE: 433
cccctcacga                                                              10

<210> SEQ ID NO 434
<211> LENGTH: 10
<212> TYPE: DNA
<213> ORGANISM: Artificial sequence
<220> FEATURE:
<223> OTHER INFORMATION: Primer OPV-05

<400> SEQUENCE: 434
tccgagaggg                                                              10

<210> SEQ ID NO 435
<211> LENGTH: 10
<212> TYPE: DNA
<213> ORGANISM: Artificial sequence
<220> FEATURE:
<223> OTHER INFORMATION: Primer OPV-06

<400> SEQUENCE: 435
acgcccaggt                                                              10

<210> SEQ ID NO 436
<211> LENGTH: 10
<212> TYPE: DNA
<213> ORGANISM: Artificial sequence
<220> FEATURE:
<223> OTHER INFORMATION: Primer OPV-07

<400> SEQUENCE: 436
gaagccagcc                                                              10

<210> SEQ ID NO 437
<211> LENGTH: 10
<212> TYPE: DNA
<213> ORGANISM: Artificial sequence
<220> FEATURE:
<223> OTHER INFORMATION: Primer OPV-08

<400> SEQUENCE: 437
ggacggcgtt                                                              10

<210> SEQ ID NO 438
<211> LENGTH: 10
<212> TYPE: DNA
<213> ORGANISM: Artificial sequence
<220> FEATURE:
<223> OTHER INFORMATION: Primer OPV-09

<400> SEQUENCE: 438
tgtacccgtc                                                              10

<210> SEQ ID NO 439
<211> LENGTH: 10
```

<212> TYPE: DNA
<213> ORGANISM: Artificial sequence
<220> FEATURE:
<223> OTHER INFORMATION: Primer OPV-10

<400> SEQUENCE: 439
ggacctgctg                                                              10

<210> SEQ ID NO 440
<211> LENGTH: 10
<212> TYPE: DNA
<213> ORGANISM: Artificial sequence
<220> FEATURE:
<223> OTHER INFORMATION: Primer OPV-11

<400> SEQUENCE: 440
ctcgacagag                                                              10

<210> SEQ ID NO 441
<211> LENGTH: 10
<212> TYPE: DNA
<213> ORGANISM: Artificial sequence
<220> FEATURE:
<223> OTHER INFORMATION: Primer OPV-12

<400> SEQUENCE: 441
acccccact                                                               10

<210> SEQ ID NO 442
<211> LENGTH: 10
<212> TYPE: DNA
<213> ORGANISM: Artificial sequence
<220> FEATURE:
<223> OTHER INFORMATION: Primer OPV-13

<400> SEQUENCE: 442
accccctgaa                                                              10

<210> SEQ ID NO 443
<211> LENGTH: 10
<212> TYPE: DNA
<213> ORGANISM: Artificial sequence
<220> FEATURE:
<223> OTHER INFORMATION: Primer OPV-14

<400> SEQUENCE: 443
agatcccgcc                                                              10

<210> SEQ ID NO 444
<211> LENGTH: 10
<212> TYPE: DNA
<213> ORGANISM: Artificial sequence
<220> FEATURE:
<223> OTHER INFORMATION: Primer OPV-15

<400> SEQUENCE: 444
cagtgccggt                                                              10

<210> SEQ ID NO 445
<211> LENGTH: 10
<212> TYPE: DNA
<213> ORGANISM: Artificial sequence
<220> FEATURE:
<223> OTHER INFORMATION: Primer OPV-16

<400> SEQUENCE: 445
acaccccaca                                                              10

<210> SEQ ID NO 446
<211> LENGTH: 10
<212> TYPE: DNA
<213> ORGANISM: Artificial sequence
<220> FEATURE:
<223> OTHER INFORMATION: Primer OPV-17

<400> SEQUENCE: 446
accggcttgt                                                          10

<210> SEQ ID NO 447
<211> LENGTH: 10
<212> TYPE: DNA
<213> ORGANISM: Artificial sequence
<220> FEATURE:
<223> OTHER INFORMATION: Primer OPV-18

<400> SEQUENCE: 447
tggtggcgtt                                                          10

<210> SEQ ID NO 448
<211> LENGTH: 10
<212> TYPE: DNA
<213> ORGANISM: Artificial sequence
<220> FEATURE:
<223> OTHER INFORMATION: Primer OPV-19

<400> SEQUENCE: 448
gggtgtgcag                                                          10

<210> SEQ ID NO 449
<211> LENGTH: 10
<212> TYPE: DNA
<213> ORGANISM: Artificial sequence
<220> FEATURE:
<223> OTHER INFORMATION: Primer OPV-20

<400> SEQUENCE: 449
cagcatggtc                                                          10

<210> SEQ ID NO 450
<211> LENGTH: 10
<212> TYPE: DNA
<213> ORGANISM: Artificial sequence
<220> FEATURE:
<223> OTHER INFORMATION: Primer OPW-01

<400> SEQUENCE: 450
ctcagtgtcc                                                          10

<210> SEQ ID NO 451
<211> LENGTH: 10
<212> TYPE: DNA
<213> ORGANISM: Artificial sequence
<220> FEATURE:
<223> OTHER INFORMATION: Primer OPW-02

<400> SEQUENCE: 451
accccgccaa                                                          10

<210> SEQ ID NO 452
<211> LENGTH: 10
<212> TYPE: DNA
<213> ORGANISM: Artificial sequence
<220> FEATURE:
<223> OTHER INFORMATION: Primer OPW-03

```
<400> SEQUENCE: 452
gtccggagtg                                                          10

<210> SEQ ID NO 453
<211> LENGTH: 10
<212> TYPE: DNA
<213> ORGANISM: Artificial sequence
<220> FEATURE:
<223> OTHER INFORMATION: Primer OPW-04

<400> SEQUENCE: 453
cagaagcgga                                                          10

<210> SEQ ID NO 454
<211> LENGTH: 10
<212> TYPE: DNA
<213> ORGANISM: Artificial sequence
<220> FEATURE:
<223> OTHER INFORMATION: Primer OPW-05

<400> SEQUENCE: 454
ggcggataag                                                          10

<210> SEQ ID NO 455
<211> LENGTH: 10
<212> TYPE: DNA
<213> ORGANISM: Artificial sequence
<220> FEATURE:
<223> OTHER INFORMATION: Primer OPW-06

<400> SEQUENCE: 455
aggcccgatg                                                          10

<210> SEQ ID NO 456
<211> LENGTH: 10
<212> TYPE: DNA
<213> ORGANISM: Artificial sequence
<220> FEATURE:
<223> OTHER INFORMATION: Primer OPW-07

<400> SEQUENCE: 456
ctggacgtca                                                          10

<210> SEQ ID NO 457
<211> LENGTH: 10
<212> TYPE: DNA
<213> ORGANISM: Artificial sequence
<220> FEATURE:
<223> OTHER INFORMATION: Primer OPW-08

<400> SEQUENCE: 457
gactgcctct                                                          10

<210> SEQ ID NO 458
<211> LENGTH: 10
<212> TYPE: DNA
<213> ORGANISM: Artificial sequence
<220> FEATURE:
<223> OTHER INFORMATION: Primer OPW-09

<400> SEQUENCE: 458
gtgaccgagt                                                          10

<210> SEQ ID NO 459
<211> LENGTH: 10
```

```
<212> TYPE: DNA
<213> ORGANISM: Artificial sequence
<220> FEATURE:
<223> OTHER INFORMATION: Primer OPW-10

<400> SEQUENCE: 459
tcgcatccct                                                              10

<210> SEQ ID NO 460
<211> LENGTH: 10
<212> TYPE: DNA
<213> ORGANISM: Artificial sequence
<220> FEATURE:
<223> OTHER INFORMATION: Primer OPW-11

<400> SEQUENCE: 460
ctgatgcgtg                                                              10

<210> SEQ ID NO 461
<211> LENGTH: 10
<212> TYPE: DNA
<213> ORGANISM: Artificial sequence
<220> FEATURE:
<223> OTHER INFORMATION: Primer OPW-12

<400> SEQUENCE: 461
tgggcagaag                                                              10

<210> SEQ ID NO 462
<211> LENGTH: 10
<212> TYPE: DNA
<213> ORGANISM: Artificial sequence
<220> FEATURE:
<223> OTHER INFORMATION: Primer OPW-13

<400> SEQUENCE: 462
cacagcgaca                                                              10

<210> SEQ ID NO 463
<211> LENGTH: 10
<212> TYPE: DNA
<213> ORGANISM: Artificial sequence
<220> FEATURE:
<223> OTHER INFORMATION: Primer OPW-14

<400> SEQUENCE: 463
ctgctgagca                                                              10

<210> SEQ ID NO 464
<211> LENGTH: 10
<212> TYPE: DNA
<213> ORGANISM: Artificial sequence
<220> FEATURE:
<223> OTHER INFORMATION: Primer OPW-15

<400> SEQUENCE: 464
acaccggaac                                                              10

<210> SEQ ID NO 465
<211> LENGTH: 10
<212> TYPE: DNA
<213> ORGANISM: Artificial sequence
<220> FEATURE:
<223> OTHER INFORMATION: Primer OPW-16

<400> SEQUENCE: 465
cagcctacca                                                              10
```

<210> SEQ ID NO 466
<211> LENGTH: 10
<212> TYPE: DNA
<213> ORGANISM: Artificial sequence
<220> FEATURE:
<223> OTHER INFORMATION: Primer OPW-17

<400> SEQUENCE: 466
gtcctgggtt                                                                10

<210> SEQ ID NO 467
<211> LENGTH: 10
<212> TYPE: DNA
<213> ORGANISM: Artificial sequence
<220> FEATURE:
<223> OTHER INFORMATION: Primer OPW-18

<400> SEQUENCE: 467
ttcagggcac                                                                10

<210> SEQ ID NO 468
<211> LENGTH: 10
<212> TYPE: DNA
<213> ORGANISM: Artificial sequence
<220> FEATURE:
<223> OTHER INFORMATION: Primer OPW-19

<400> SEQUENCE: 468
caaagcgctc                                                                10

<210> SEQ ID NO 469
<211> LENGTH: 10
<212> TYPE: DNA
<213> ORGANISM: Artificial sequence
<220> FEATURE:
<223> OTHER INFORMATION: Primer OPW-20

<400> SEQUENCE: 469
tgtggcagca                                                                10

<210> SEQ ID NO 470
<211> LENGTH: 10
<212> TYPE: DNA
<213> ORGANISM: Artificial sequence
<220> FEATURE:
<223> OTHER INFORMATION: Primer OPX-01

<400> SEQUENCE: 470
ctgggcacga                                                                10

<210> SEQ ID NO 471
<211> LENGTH: 10
<212> TYPE: DNA
<213> ORGANISM: Artificial sequence
<220> FEATURE:
<223> OTHER INFORMATION: Primer OPX-02

<400> SEQUENCE: 471
ttccgccacc                                                                10

<210> SEQ ID NO 472
<211> LENGTH: 10
<212> TYPE: DNA
<213> ORGANISM: Artificial sequence
<220> FEATURE:
<223> OTHER INFORMATION: Primer OPX-03

<400> SEQUENCE: 472
tggcgcagtg                                                          10

<210> SEQ ID NO 473
<211> LENGTH: 10
<212> TYPE: DNA
<213> ORGANISM: Artificial sequence
<220> FEATURE:
<223> OTHER INFORMATION: Primer OPX-04

<400> SEQUENCE: 473
ccgctaccga                                                          10

<210> SEQ ID NO 474
<211> LENGTH: 10
<212> TYPE: DNA
<213> ORGANISM: Artificial sequence
<220> FEATURE:
<223> OTHER INFORMATION: Primer OPX-05

<400> SEQUENCE: 474
cctttccctc                                                          10

<210> SEQ ID NO 475
<211> LENGTH: 10
<212> TYPE: DNA
<213> ORGANISM: Artificial sequence
<220> FEATURE:
<223> OTHER INFORMATION: Primer OPX-06

<400> SEQUENCE: 475
acgccagagg                                                          10

<210> SEQ ID NO 476
<211> LENGTH: 10
<212> TYPE: DNA
<213> ORGANISM: Artificial sequence
<220> FEATURE:
<223> OTHER INFORMATION: Primer OPX-07

<400> SEQUENCE: 476
gagcgaggct                                                          10

<210> SEQ ID NO 477
<211> LENGTH: 10
<212> TYPE: DNA
<213> ORGANISM: Artificial sequence
<220> FEATURE:
<223> OTHER INFORMATION: Primer OPX-08

<400> SEQUENCE: 477
caggggtgga                                                          10

<210> SEQ ID NO 478
<211> LENGTH: 10
<212> TYPE: DNA
<213> ORGANISM: Artificial sequence
<220> FEATURE:
<223> OTHER INFORMATION: Primer OPX-09

<400> SEQUENCE: 478
ggtctggttg                                                          10

<210> SEQ ID NO 479
<211> LENGTH: 10

```
<212> TYPE: DNA
<213> ORGANISM: Artificial sequence
<220> FEATURE:
<223> OTHER INFORMATION: Primer OPX-10

<400> SEQUENCE: 479
ccctagactg                                                          10

<210> SEQ ID NO 480
<211> LENGTH: 10
<212> TYPE: DNA
<213> ORGANISM: Artificial sequence
<220> FEATURE:
<223> OTHER INFORMATION: Primer OPX-11

<400> SEQUENCE: 480
ggagcctcag                                                          10

<210> SEQ ID NO 481
<211> LENGTH: 10
<212> TYPE: DNA
<213> ORGANISM: Artificial sequence
<220> FEATURE:
<223> OTHER INFORMATION: Primer OPX-12

<400> SEQUENCE: 481
tcgccagcca                                                          10

<210> SEQ ID NO 482
<211> LENGTH: 10
<212> TYPE: DNA
<213> ORGANISM: Artificial sequence
<220> FEATURE:
<223> OTHER INFORMATION: Primer OPX-13

<400> SEQUENCE: 482
acgggagcaa                                                          10

<210> SEQ ID NO 483
<211> LENGTH: 10
<212> TYPE: DNA
<213> ORGANISM: Artificial sequence
<220> FEATURE:
<223> OTHER INFORMATION: Primer OPX-14

<400> SEQUENCE: 483
acaggtgctg                                                          10

<210> SEQ ID NO 484
<211> LENGTH: 10
<212> TYPE: DNA
<213> ORGANISM: Artificial sequence
<220> FEATURE:
<223> OTHER INFORMATION: Primer OPX-15

<400> SEQUENCE: 484
cagacaagcc                                                          10

<210> SEQ ID NO 485
<211> LENGTH: 10
<212> TYPE: DNA
<213> ORGANISM: Artificial sequence
<220> FEATURE:
<223> OTHER INFORMATION: Primer OPX-16

<400> SEQUENCE: 485
ctctgttcgg                                                          10
```

```
<210> SEQ ID NO 486
<211> LENGTH: 10
<212> TYPE: DNA
<213> ORGANISM: Artificial sequence
<220> FEATURE:
<223> OTHER INFORMATION: Primer OPX-17

<400> SEQUENCE: 486
gacacggacc                                                              10

<210> SEQ ID NO 487
<211> LENGTH: 10
<212> TYPE: DNA
<213> ORGANISM: Artificial sequence
<220> FEATURE:
<223> OTHER INFORMATION: Primer OPX-18

<400> SEQUENCE: 487
gactaggtgg                                                              10

<210> SEQ ID NO 488
<211> LENGTH: 10
<212> TYPE: DNA
<213> ORGANISM: Artificial sequence
<220> FEATURE:
<223> OTHER INFORMATION: Primer OPX-19

<400> SEQUENCE: 488
tggcaaggca                                                              10

<210> SEQ ID NO 489
<211> LENGTH: 10
<212> TYPE: DNA
<213> ORGANISM: Artificial sequence
<220> FEATURE:
<223> OTHER INFORMATION: Primer OPX-20

<400> SEQUENCE: 489
cccagctaga                                                              10

<210> SEQ ID NO 490
<211> LENGTH: 10
<212> TYPE: DNA
<213> ORGANISM: Artificial sequence
<220> FEATURE:
<223> OTHER INFORMATION: Primer OPY-01

<400> SEQUENCE: 490
gtggcatctc                                                              10

<210> SEQ ID NO 491
<211> LENGTH: 10
<212> TYPE: DNA
<213> ORGANISM: Artificial sequence
<220> FEATURE:
<223> OTHER INFORMATION: Primer OPY-02

<400> SEQUENCE: 491
catcgccgca                                                              10

<210> SEQ ID NO 492
<211> LENGTH: 10
<212> TYPE: DNA
<213> ORGANISM: Artificial sequence
<220> FEATURE:
<223> OTHER INFORMATION: Primer OPY-03
```

```
<400> SEQUENCE: 492
acagcctgct                                                          10

<210> SEQ ID NO 493
<211> LENGTH: 10
<212> TYPE: DNA
<213> ORGANISM: Artificial sequence
<220> FEATURE:
<223> OTHER INFORMATION: Primer OPY-04

<400> SEQUENCE: 493
ggctgcaatg                                                          10

<210> SEQ ID NO 494
<211> LENGTH: 10
<212> TYPE: DNA
<213> ORGANISM: Artificial sequence
<220> FEATURE:
<223> OTHER INFORMATION: Primer OPY-05

<400> SEQUENCE: 494
ggctgcgaca                                                          10

<210> SEQ ID NO 495
<211> LENGTH: 10
<212> TYPE: DNA
<213> ORGANISM: Artificial sequence
<220> FEATURE:
<223> OTHER INFORMATION: Primer OPY-06

<400> SEQUENCE: 495
aaggctcacc                                                          10

<210> SEQ ID NO 496
<211> LENGTH: 10
<212> TYPE: DNA
<213> ORGANISM: Artificial sequence
<220> FEATURE:
<223> OTHER INFORMATION: Primer OPY-07

<400> SEQUENCE: 496
agagccgtca                                                          10

<210> SEQ ID NO 497
<211> LENGTH: 10
<212> TYPE: DNA
<213> ORGANISM: Artificial sequence
<220> FEATURE:
<223> OTHER INFORMATION: Primer OPY-08

<400> SEQUENCE: 497
aggcagagca                                                          10

<210> SEQ ID NO 498
<211> LENGTH: 10
<212> TYPE: DNA
<213> ORGANISM: Artificial sequence
<220> FEATURE:
<223> OTHER INFORMATION: Primer OPY-09

<400> SEQUENCE: 498
agcagcgcac                                                          10

<210> SEQ ID NO 499
<211> LENGTH: 10
```

```
<212> TYPE: DNA
<213> ORGANISM: Artificial sequence
<220> FEATURE:
<223> OTHER INFORMATION: Primer OPY-10

<400> SEQUENCE: 499
caaacgtggg                                                              10

<210> SEQ ID NO 500
<211> LENGTH: 10
<212> TYPE: DNA
<213> ORGANISM: Artificial sequence
<220> FEATURE:
<223> OTHER INFORMATION: Primer OPY-11

<400> SEQUENCE: 500
agacgatggg                                                              10

<210> SEQ ID NO 501
<211> LENGTH: 10
<212> TYPE: DNA
<213> ORGANISM: Artificial sequence
<220> FEATURE:
<223> OTHER INFORMATION: Primer OPY-12

<400> SEQUENCE: 501
aagcctgcga                                                              10

<210> SEQ ID NO 502
<211> LENGTH: 10
<212> TYPE: DNA
<213> ORGANISM: Artificial sequence
<220> FEATURE:
<223> OTHER INFORMATION: Primer OPY-13

<400> SEQUENCE: 502
gggtctcggt                                                              10

<210> SEQ ID NO 503
<211> LENGTH: 10
<212> TYPE: DNA
<213> ORGANISM: Artificial sequence
<220> FEATURE:
<223> OTHER INFORMATION: Primer OPY-14

<400> SEQUENCE: 503
ggtcgatctg                                                              10

<210> SEQ ID NO 504
<211> LENGTH: 10
<212> TYPE: DNA
<213> ORGANISM: Artificial sequence
<220> FEATURE:
<223> OTHER INFORMATION: Primer OPY-15

<400> SEQUENCE: 504
agtcgcccTT                                                              10

<210> SEQ ID NO 505
<211> LENGTH: 10
<212> TYPE: DNA
<213> ORGANISM: Artificial sequence
<220> FEATURE:
<223> OTHER INFORMATION: Primer OPY-16

<400> SEQUENCE: 505
gggccaatgt                                                              10
```

<210> SEQ ID NO 506
<211> LENGTH: 10
<212> TYPE: DNA
<213> ORGANISM: Artificial sequence
<220> FEATURE:
<223> OTHER INFORMATION: Primer OPY-17

<400> SEQUENCE: 506
gacgtggtga                                                          10

<210> SEQ ID NO 507
<211> LENGTH: 10
<212> TYPE: DNA
<213> ORGANISM: Artificial sequence
<220> FEATURE:
<223> OTHER INFORMATION: Primer OPY-18

<400> SEQUENCE: 507
gtggagtcag                                                          10

<210> SEQ ID NO 508
<211> LENGTH: 10
<212> TYPE: DNA
<213> ORGANISM: Artificial sequence
<220> FEATURE:
<223> OTHER INFORMATION: Primer OPY-19

<400> SEQUENCE: 508
tgagggtccc                                                          10

<210> SEQ ID NO 509
<211> LENGTH: 10
<212> TYPE: DNA
<213> ORGANISM: Artificial sequence
<220> FEATURE:
<223> OTHER INFORMATION: Primer OPY-20

<400> SEQUENCE: 509
agccgtggaa                                                          10

<210> SEQ ID NO 510
<211> LENGTH: 10
<212> TYPE: DNA
<213> ORGANISM: Artificial sequence
<220> FEATURE:
<223> OTHER INFORMATION: Primer OPZ-01

<400> SEQUENCE: 510
tctgtgccac                                                          10

<210> SEQ ID NO 511
<211> LENGTH: 10
<212> TYPE: DNA
<213> ORGANISM: Artificial sequence
<220> FEATURE:
<223> OTHER INFORMATION: Primer OPZ-02

<400> SEQUENCE: 511
cctacgggga                                                          10

<210> SEQ ID NO 512
<211> LENGTH: 10
<212> TYPE: DNA
<213> ORGANISM: Artificial sequence
<220> FEATURE:
<223> OTHER INFORMATION: Primer OPZ-03

-continued

```
<400> SEQUENCE: 512
cagcaccgca                                                          10

<210> SEQ ID NO 513
<211> LENGTH: 10
<212> TYPE: DNA
<213> ORGANISM: Artificial sequence
<220> FEATURE:
<223> OTHER INFORMATION: Primer OPZ-04

<400> SEQUENCE: 513
aggctgtgct                                                          10

<210> SEQ ID NO 514
<211> LENGTH: 10
<212> TYPE: DNA
<213> ORGANISM: Artificial sequence
<220> FEATURE:
<223> OTHER INFORMATION: Primer OPZ-05

<400> SEQUENCE: 514
tcccatgctg                                                          10

<210> SEQ ID NO 515
<211> LENGTH: 10
<212> TYPE: DNA
<213> ORGANISM: Artificial sequence
<220> FEATURE:
<223> OTHER INFORMATION: Primer OPZ-06

<400> SEQUENCE: 515
gtgccgttca                                                          10

<210> SEQ ID NO 516
<211> LENGTH: 10
<212> TYPE: DNA
<213> ORGANISM: Artificial sequence
<220> FEATURE:
<223> OTHER INFORMATION: Primer OPZ-07

<400> SEQUENCE: 516
ccaggaggac                                                          10

<210> SEQ ID NO 517
<211> LENGTH: 10
<212> TYPE: DNA
<213> ORGANISM: Artificial sequence
<220> FEATURE:
<223> OTHER INFORMATION: Primer OPZ-08

<400> SEQUENCE: 517
gggtgggtaa                                                          10

<210> SEQ ID NO 518
<211> LENGTH: 10
<212> TYPE: DNA
<213> ORGANISM: Artificial sequence
<220> FEATURE:
<223> OTHER INFORMATION: Primer OPZ-09

<400> SEQUENCE: 518
caccccagtc                                                          10

<210> SEQ ID NO 519
<211> LENGTH: 10
```

```
<212> TYPE: DNA
<213> ORGANISM: Artificial sequence
<220> FEATURE:
<223> OTHER INFORMATION: Primer OPZ-10

<400> SEQUENCE: 519
ccgacaaacc                                                           10

<210> SEQ ID NO 520
<211> LENGTH: 10
<212> TYPE: DNA
<213> ORGANISM: Artificial sequence
<220> FEATURE:
<223> OTHER INFORMATION: Primer OPZ-11

<400> SEQUENCE: 520
ctcagtcgca                                                           10

<210> SEQ ID NO 521
<211> LENGTH: 10
<212> TYPE: DNA
<213> ORGANISM: Artificial sequence
<220> FEATURE:
<223> OTHER INFORMATION: Primer OPZ-12

<400> SEQUENCE: 521
tcaacgggac                                                           10

<210> SEQ ID NO 522
<211> LENGTH: 10
<212> TYPE: DNA
<213> ORGANISM: Artificial sequence
<220> FEATURE:
<223> OTHER INFORMATION: Primer OPZ-13

<400> SEQUENCE: 522
gactaagccc                                                           10

<210> SEQ ID NO 523
<211> LENGTH: 10
<212> TYPE: DNA
<213> ORGANISM: Artificial sequence
<220> FEATURE:
<223> OTHER INFORMATION: Primer OPZ-14

<400> SEQUENCE: 523
tcggaggttc                                                           10

<210> SEQ ID NO 524
<211> LENGTH: 10
<212> TYPE: DNA
<213> ORGANISM: Artificial sequence
<220> FEATURE:
<223> OTHER INFORMATION: Primer OPZ-15

<400> SEQUENCE: 524
cagggctttc                                                           10

<210> SEQ ID NO 525
<211> LENGTH: 10
<212> TYPE: DNA
<213> ORGANISM: Artificial sequence
<220> FEATURE:
<223> OTHER INFORMATION: Primer OPZ-16

<400> SEQUENCE: 525
tccccatcac                                                           10
```

<210> SEQ ID NO 526
<211> LENGTH: 10
<212> TYPE: DNA
<213> ORGANISM: Artificial sequence
<220> FEATURE:
<223> OTHER INFORMATION: Primer OPZ-17

<400> SEQUENCE: 526
ccttcccact                                                          10

<210> SEQ ID NO 527
<211> LENGTH: 10
<212> TYPE: DNA
<213> ORGANISM: Artificial sequence
<220> FEATURE:
<223> OTHER INFORMATION: Primer OPZ-18

<400> SEQUENCE: 527
agggtctgtg                                                          10

<210> SEQ ID NO 528
<211> LENGTH: 10
<212> TYPE: DNA
<213> ORGANISM: Artificial sequence
<220> FEATURE:
<223> OTHER INFORMATION: Primer OPZ-19

<400> SEQUENCE: 528
gtgcgagcaa                                                          10

<210> SEQ ID NO 529
<211> LENGTH: 10
<212> TYPE: DNA
<213> ORGANISM: Artificial sequence
<220> FEATURE:
<223> OTHER INFORMATION: Primer OPZ-20

<400> SEQUENCE: 529
actttggcgg                                                          10

<210> SEQ ID NO 530
<211> LENGTH: 10
<212> TYPE: DNA
<213> ORGANISM: Artificial sequence
<220> FEATURE:
<223> OTHER INFORMATION: Primer OPAA-01

<400> SEQUENCE: 530
agacggctcc                                                          10

<210> SEQ ID NO 531
<211> LENGTH: 10
<212> TYPE: DNA
<213> ORGANISM: Artificial sequence
<220> FEATURE:
<223> OTHER INFORMATION: Primer OPAA-02

<400> SEQUENCE: 531
gagaccagac                                                          10

<210> SEQ ID NO 532
<211> LENGTH: 10
<212> TYPE: DNA
<213> ORGANISM: Artificial sequence
<220> FEATURE:
<223> OTHER INFORMATION: Primer OPAA-03

```
<400> SEQUENCE: 532
ttagcgcccc                                                              10

<210> SEQ ID NO 533
<211> LENGTH: 10
<212> TYPE: DNA
<213> ORGANISM: Artificial sequence
<220> FEATURE:
<223> OTHER INFORMATION: Primer OPAA-04

<400> SEQUENCE: 533
aggactgctc                                                              10

<210> SEQ ID NO 534
<211> LENGTH: 10
<212> TYPE: DNA
<213> ORGANISM: Artificial sequence
<220> FEATURE:
<223> OTHER INFORMATION: Primer OPAA-05

<400> SEQUENCE: 534
ggctttagcc                                                              10

<210> SEQ ID NO 535
<211> LENGTH: 10
<212> TYPE: DNA
<213> ORGANISM: Artificial sequence
<220> FEATURE:
<223> OTHER INFORMATION: Primer OPAA-06

<400> SEQUENCE: 535
gtgggtgcca                                                              10

<210> SEQ ID NO 536
<211> LENGTH: 10
<212> TYPE: DNA
<213> ORGANISM: Artificial sequence
<220> FEATURE:
<223> OTHER INFORMATION: Primer OPAA-07

<400> SEQUENCE: 536
ctacgctcac                                                              10

<210> SEQ ID NO 537
<211> LENGTH: 10
<212> TYPE: DNA
<213> ORGANISM: Artificial sequence
<220> FEATURE:
<223> OTHER INFORMATION: Primer OPAA-08

<400> SEQUENCE: 537
tccgcagtag                                                              10

<210> SEQ ID NO 538
<211> LENGTH: 10
<212> TYPE: DNA
<213> ORGANISM: Artificial sequence
<220> FEATURE:
<223> OTHER INFORMATION: Primer OPAA-09

<400> SEQUENCE: 538
agatgggcag                                                              10

<210> SEQ ID NO 539
<211> LENGTH: 10
```

<212> TYPE: DNA
<213> ORGANISM: Artificial sequence
<220> FEATURE:
<223> OTHER INFORMATION: Primer OPAA-10

<400> SEQUENCE: 539
tggtcgggtg                                                          10

<210> SEQ ID NO 540
<211> LENGTH: 10
<212> TYPE: DNA
<213> ORGANISM: Artificial sequence
<220> FEATURE:
<223> OTHER INFORMATION: Primer OPAA-11

<400> SEQUENCE: 540
acccgacctg                                                          10

<210> SEQ ID NO 541
<211> LENGTH: 10
<212> TYPE: DNA
<213> ORGANISM: Artificial sequence
<220> FEATURE:
<223> OTHER INFORMATION: Primer OPAA-12

<400> SEQUENCE: 541
ggacctcttg                                                          10

<210> SEQ ID NO 542
<211> LENGTH: 10
<212> TYPE: DNA
<213> ORGANISM: Artificial sequence
<220> FEATURE:
<223> OTHER INFORMATION: Primer OPAA-13

<400> SEQUENCE: 542
gagcgtcgct                                                          10

<210> SEQ ID NO 543
<211> LENGTH: 10
<212> TYPE: DNA
<213> ORGANISM: Artificial sequence
<220> FEATURE:
<223> OTHER INFORMATION: Primer OPAA-14

<400> SEQUENCE: 543
aacgggccaa                                                          10

<210> SEQ ID NO 544
<211> LENGTH: 10
<212> TYPE: DNA
<213> ORGANISM: Artificial sequence
<220> FEATURE:
<223> OTHER INFORMATION: Primer OPAA-15

<400> SEQUENCE: 544
acggaagccc                                                          10

<210> SEQ ID NO 545
<211> LENGTH: 10
<212> TYPE: DNA
<213> ORGANISM: Artificial sequence
<220> FEATURE:
<223> OTHER INFORMATION: Primer OPAA-16

<400> SEQUENCE: 545
ggaacccaca                                                          10

<210> SEQ ID NO 546
<211> LENGTH: 10
<212> TYPE: DNA
<213> ORGANISM: Artificial sequence
<220> FEATURE:
<223> OTHER INFORMATION: Primer OPAA-17

<400> SEQUENCE: 546
gagcccgact                                                                10

<210> SEQ ID NO 547
<211> LENGTH: 10
<212> TYPE: DNA
<213> ORGANISM: Artificial sequence
<220> FEATURE:
<223> OTHER INFORMATION: Primer OPAA-18

<400> SEQUENCE: 547
tggtccagcc                                                                10

<210> SEQ ID NO 548
<211> LENGTH: 10
<212> TYPE: DNA
<213> ORGANISM: Artificial sequence
<220> FEATURE:
<223> OTHER INFORMATION: Primer OPAA-19

<400> SEQUENCE: 548
tgaggcgtgt                                                                10

<210> SEQ ID NO 549
<211> LENGTH: 10
<212> TYPE: DNA
<213> ORGANISM: Artificial sequence
<220> FEATURE:
<223> OTHER INFORMATION: Primer OPAA-20

<400> SEQUENCE: 549
ttgccttcgg                                                                10

<210> SEQ ID NO 550
<211> LENGTH: 10
<212> TYPE: DNA
<213> ORGANISM: Artificial sequence
<220> FEATURE:
<223> OTHER INFORMATION: Primer OPAB-01

<400> SEQUENCE: 550
ccgtcggtag                                                                10

<210> SEQ ID NO 551
<211> LENGTH: 10
<212> TYPE: DNA
<213> ORGANISM: Artificial sequence
<220> FEATURE:
<223> OTHER INFORMATION: Primer OPAB-02

<400> SEQUENCE: 551
ggaaacccct                                                                10

<210> SEQ ID NO 552
<211> LENGTH: 10
<212> TYPE: DNA
<213> ORGANISM: Artificial sequence
<220> FEATURE:
<223> OTHER INFORMATION: Primer OPAB-03

```
<400> SEQUENCE: 552
tggcgcacac                                                          10

<210> SEQ ID NO 553
<211> LENGTH: 10
<212> TYPE: DNA
<213> ORGANISM: Artificial sequence
<220> FEATURE:
<223> OTHER INFORMATION: Primer OPAB-04

<400> SEQUENCE: 553
ggcacgcgtt                                                          10

<210> SEQ ID NO 554
<211> LENGTH: 10
<212> TYPE: DNA
<213> ORGANISM: Artificial sequence
<220> FEATURE:
<223> OTHER INFORMATION: Primer OPAB-05

<400> SEQUENCE: 554
cccgaagcga                                                          10

<210> SEQ ID NO 555
<211> LENGTH: 10
<212> TYPE: DNA
<213> ORGANISM: Artificial sequence
<220> FEATURE:
<223> OTHER INFORMATION: Primer OPAB-06

<400> SEQUENCE: 555
gtggcttgga                                                          10

<210> SEQ ID NO 556
<211> LENGTH: 10
<212> TYPE: DNA
<213> ORGANISM: Artificial sequence
<220> FEATURE:
<223> OTHER INFORMATION: Primer OPAB-07

<400> SEQUENCE: 556
gtaaaccgcc                                                          10

<210> SEQ ID NO 557
<211> LENGTH: 10
<212> TYPE: DNA
<213> ORGANISM: Artificial sequence
<220> FEATURE:
<223> OTHER INFORMATION: Primer OPAB-08

<400> SEQUENCE: 557
gttacggacc                                                          10

<210> SEQ ID NO 558
<211> LENGTH: 10
<212> TYPE: DNA
<213> ORGANISM: Artificial sequence
<220> FEATURE:
<223> OTHER INFORMATION: Primer OPAB-09

<400> SEQUENCE: 558
gggcgactac                                                          10

<210> SEQ ID NO 559
<211> LENGTH: 10
```

```
<212> TYPE: DNA
<213> ORGANISM: Artificial sequence
<220> FEATURE:
<223> OTHER INFORMATION: Primer OPAB-10

<400> SEQUENCE: 559
ttccctccca                                                          10

<210> SEQ ID NO 560
<211> LENGTH: 10
<212> TYPE: DNA
<213> ORGANISM: Artificial sequence
<220> FEATURE:
<223> OTHER INFORMATION: Primer OPAB-11

<400> SEQUENCE: 560
gtgcgcaatg                                                          10

<210> SEQ ID NO 561
<211> LENGTH: 10
<212> TYPE: DNA
<213> ORGANISM: Artificial sequence
<220> FEATURE:
<223> OTHER INFORMATION: Primer OPAB-12

<400> SEQUENCE: 561
cctgtaccga                                                          10

<210> SEQ ID NO 562
<211> LENGTH: 10
<212> TYPE: DNA
<213> ORGANISM: Artificial sequence
<220> FEATURE:
<223> OTHER INFORMATION: Primer OPAB-13

<400> SEQUENCE: 562
cctaccgtgg                                                          10

<210> SEQ ID NO 563
<211> LENGTH: 10
<212> TYPE: DNA
<213> ORGANISM: Artificial sequence
<220> FEATURE:
<223> OTHER INFORMATION: Primer OPAB-14

<400> SEQUENCE: 563
aagtgcgacc                                                          10

<210> SEQ ID NO 564
<211> LENGTH: 10
<212> TYPE: DNA
<213> ORGANISM: Artificial sequence
<220> FEATURE:
<223> OTHER INFORMATION: Primer OPAB-15

<400> SEQUENCE: 564
cctccttctc                                                          10

<210> SEQ ID NO 565
<211> LENGTH: 10
<212> TYPE: DNA
<213> ORGANISM: Artificial sequence
<220> FEATURE:
<223> OTHER INFORMATION: Primer OPAB-16

<400> SEQUENCE: 565
cccggatggt                                                          10
```

<210> SEQ ID NO 566
<211> LENGTH: 10
<212> TYPE: DNA
<213> ORGANISM: Artificial sequence
<220> FEATURE:
<223> OTHER INFORMATION: Primer OPAB-17

<400> SEQUENCE: 566
tcgcatccag                                                            10

<210> SEQ ID NO 567
<211> LENGTH: 10
<212> TYPE: DNA
<213> ORGANISM: Artificial sequence
<220> FEATURE:
<223> OTHER INFORMATION: Primer OPAB-18

<400> SEQUENCE: 567
ctggcgtgtc                                                            10

<210> SEQ ID NO 568
<211> LENGTH: 10
<212> TYPE: DNA
<213> ORGANISM: Artificial sequence
<220> FEATURE:
<223> OTHER INFORMATION: Primer OPAB-19

<400> SEQUENCE: 568
acaccgatgg                                                            10

<210> SEQ ID NO 569
<211> LENGTH: 10
<212> TYPE: DNA
<213> ORGANISM: Artificial sequence
<220> FEATURE:
<223> OTHER INFORMATION: Primer OPAB-20

<400> SEQUENCE: 569
cttctcggac                                                            10

<210> SEQ ID NO 570
<211> LENGTH: 10
<212> TYPE: DNA
<213> ORGANISM: Artificial sequence
<220> FEATURE:
<223> OTHER INFORMATION: Primer OPAC-01

<400> SEQUENCE: 570
tcccagcaga                                                            10

<210> SEQ ID NO 571
<211> LENGTH: 10
<212> TYPE: DNA
<213> ORGANISM: Artificial sequence
<220> FEATURE:
<223> OTHER INFORMATION: Primer OPAC-02

<400> SEQUENCE: 571
gtcgtcgtct                                                            10

<210> SEQ ID NO 572
<211> LENGTH: 10
<212> TYPE: DNA
<213> ORGANISM: Artificial sequence
<220> FEATURE:
<223> OTHER INFORMATION: Primer OPAC-03

```
<400> SEQUENCE: 572
cactggccca                                                          10

<210> SEQ ID NO 573
<211> LENGTH: 10
<212> TYPE: DNA
<213> ORGANISM: Artificial sequence
<220> FEATURE:
<223> OTHER INFORMATION: Primer OPAC-04

<400> SEQUENCE: 573
acgggacctg                                                          10

<210> SEQ ID NO 574
<211> LENGTH: 10
<212> TYPE: DNA
<213> ORGANISM: Artificial sequence
<220> FEATURE:
<223> OTHER INFORMATION: Primer OPAC-05

<400> SEQUENCE: 574
gttagtgcgg                                                          10

<210> SEQ ID NO 575
<211> LENGTH: 10
<212> TYPE: DNA
<213> ORGANISM: Artificial sequence
<220> FEATURE:
<223> OTHER INFORMATION: Primer OPAC-06

<400> SEQUENCE: 575
ccagaacgga                                                          10

<210> SEQ ID NO 576
<211> LENGTH: 10
<212> TYPE: DNA
<213> ORGANISM: Artificial sequence
<220> FEATURE:
<223> OTHER INFORMATION: Primer OPAC-07

<400> SEQUENCE: 576
gtggccgatg                                                          10

<210> SEQ ID NO 577
<211> LENGTH: 10
<212> TYPE: DNA
<213> ORGANISM: Artificial sequence
<220> FEATURE:
<223> OTHER INFORMATION: Primer OPAC-08

<400> SEQUENCE: 577
tttgggtgcc                                                          10

<210> SEQ ID NO 578
<211> LENGTH: 10
<212> TYPE: DNA
<213> ORGANISM: Artificial sequence
<220> FEATURE:
<223> OTHER INFORMATION: Primer OPAC-09

<400> SEQUENCE: 578
agagcgtacc                                                          10

<210> SEQ ID NO 579
<211> LENGTH: 10
```

```
<212> TYPE: DNA
<213> ORGANISM: Artificial sequence
<220> FEATURE:
<223> OTHER INFORMATION: Primer OPAC-10

<400> SEQUENCE: 579
agcagcgagg                                                          10

<210> SEQ ID NO 580
<211> LENGTH: 10
<212> TYPE: DNA
<213> ORGANISM: Artificial sequence
<220> FEATURE:
<223> OTHER INFORMATION: Primer OPAC-11

<400> SEQUENCE: 580
cctgggtcag                                                          10

<210> SEQ ID NO 581
<211> LENGTH: 10
<212> TYPE: DNA
<213> ORGANISM: Artificial sequence
<220> FEATURE:
<223> OTHER INFORMATION: Primer OPAC-12

<400> SEQUENCE: 581
ggcgagtgtg                                                          10

<210> SEQ ID NO 582
<211> LENGTH: 10
<212> TYPE: DNA
<213> ORGANISM: Artificial sequence
<220> FEATURE:
<223> OTHER INFORMATION: Primer OPAC-13

<400> SEQUENCE: 582
gacccgattg                                                          10

<210> SEQ ID NO 583
<211> LENGTH: 10
<212> TYPE: DNA
<213> ORGANISM: Artificial sequence
<220> FEATURE:
<223> OTHER INFORMATION: Primer OPAC-14

<400> SEQUENCE: 583
gtcggttgtc                                                          10

<210> SEQ ID NO 584
<211> LENGTH: 10
<212> TYPE: DNA
<213> ORGANISM: Artificial sequence
<220> FEATURE:
<223> OTHER INFORMATION: Primer OPAC-15

<400> SEQUENCE: 584
tgccgtgaga                                                          10

<210> SEQ ID NO 585
<211> LENGTH: 10
<212> TYPE: DNA
<213> ORGANISM: Artificial sequence
<220> FEATURE:
<223> OTHER INFORMATION: Primer OPAC-16

<400> SEQUENCE: 585
cctcctacgg                                                          10
```

```
<210> SEQ ID NO 586
<211> LENGTH: 10
<212> TYPE: DNA
<213> ORGANISM: Artificial sequence
<220> FEATURE:
<223> OTHER INFORMATION: Primer OPAC-17

<400> SEQUENCE: 586
cctggagctt                                                           10

<210> SEQ ID NO 587
<211> LENGTH: 10
<212> TYPE: DNA
<213> ORGANISM: Artificial sequence
<220> FEATURE:
<223> OTHER INFORMATION: Primer OPAC-18

<400> SEQUENCE: 587
ttgggggaga                                                           10

<210> SEQ ID NO 588
<211> LENGTH: 10
<212> TYPE: DNA
<213> ORGANISM: Artificial sequence
<220> FEATURE:
<223> OTHER INFORMATION: Primer OPAC-19

<400> SEQUENCE: 588
agtccgcctg                                                           10

<210> SEQ ID NO 589
<211> LENGTH: 10
<212> TYPE: DNA
<213> ORGANISM: Artificial sequence
<220> FEATURE:
<223> OTHER INFORMATION: Primer OPAC-20

<400> SEQUENCE: 589
acggaagtgg                                                           10

<210> SEQ ID NO 590
<211> LENGTH: 10
<212> TYPE: DNA
<213> ORGANISM: Artificial sequence
<220> FEATURE:
<223> OTHER INFORMATION: Primer OPAD-01

<400> SEQUENCE: 590
caaagggcgg                                                           10

<210> SEQ ID NO 591
<211> LENGTH: 10
<212> TYPE: DNA
<213> ORGANISM: Artificial sequence
<220> FEATURE:
<223> OTHER INFORMATION: Primer OPAD-02

<400> SEQUENCE: 591
ctgaaccgct                                                           10

<210> SEQ ID NO 592
<211> LENGTH: 10
<212> TYPE: DNA
<213> ORGANISM: Artificial sequence
<220> FEATURE:
<223> OTHER INFORMATION: Primer OPAD-03
```

```
<400> SEQUENCE: 592
tctcgcctac                                                         10

<210> SEQ ID NO 593
<211> LENGTH: 10
<212> TYPE: DNA
<213> ORGANISM: Artificial sequence
<220> FEATURE:
<223> OTHER INFORMATION: Primer OPAD-04

<400> SEQUENCE: 593
gtaggcctca                                                         10

<210> SEQ ID NO 594
<211> LENGTH: 10
<212> TYPE: DNA
<213> ORGANISM: Artificial sequence
<220> FEATURE:
<223> OTHER INFORMATION: Primer OPAD-05

<400> SEQUENCE: 594
accgcatggg                                                         10

<210> SEQ ID NO 595
<211> LENGTH: 10
<212> TYPE: DNA
<213> ORGANISM: Artificial sequence
<220> FEATURE:
<223> OTHER INFORMATION: Primer OPAD-06

<400> SEQUENCE: 595
aagtgcacgg                                                         10

<210> SEQ ID NO 596
<211> LENGTH: 10
<212> TYPE: DNA
<213> ORGANISM: Artificial sequence
<220> FEATURE:
<223> OTHER INFORMATION: Primer OPAD-07

<400> SEQUENCE: 596
ccctactggt                                                         10

<210> SEQ ID NO 597
<211> LENGTH: 10
<212> TYPE: DNA
<213> ORGANISM: Artificial sequence
<220> FEATURE:
<223> OTHER INFORMATION: Primer OPAD-08

<400> SEQUENCE: 597
ggcaggcaag                                                         10

<210> SEQ ID NO 598
<211> LENGTH: 10
<212> TYPE: DNA
<213> ORGANISM: Artificial sequence
<220> FEATURE:
<223> OTHER INFORMATION: Primer OPAD-09

<400> SEQUENCE: 598
tcgcttctcc                                                         10

<210> SEQ ID NO 599
<211> LENGTH: 10
```

```
<212> TYPE: DNA
<213> ORGANISM: Artificial sequence
<220> FEATURE:
<223> OTHER INFORMATION: Primer OPAD-10

<400> SEQUENCE: 599
aagaggccag                                                          10

<210> SEQ ID NO 600
<211> LENGTH: 10
<212> TYPE: DNA
<213> ORGANISM: Artificial sequence
<220> FEATURE:
<223> OTHER INFORMATION: Primer OPAD-11

<400> SEQUENCE: 600
caatcgggtc                                                          10

<210> SEQ ID NO 601
<211> LENGTH: 10
<212> TYPE: DNA
<213> ORGANISM: Artificial sequence
<220> FEATURE:
<223> OTHER INFORMATION: Primer OPAD-12

<400> SEQUENCE: 601
aagagggcgt                                                          10

<210> SEQ ID NO 602
<211> LENGTH: 10
<212> TYPE: DNA
<213> ORGANISM: Artificial sequence
<220> FEATURE:
<223> OTHER INFORMATION: Primer OPAD-13

<400> SEQUENCE: 602
ggttcctctg                                                          10

<210> SEQ ID NO 603
<211> LENGTH: 10
<212> TYPE: DNA
<213> ORGANISM: Artificial sequence
<220> FEATURE:
<223> OTHER INFORMATION: Primer OPAD-14

<400> SEQUENCE: 603
gaacgagggt                                                          10

<210> SEQ ID NO 604
<211> LENGTH: 10
<212> TYPE: DNA
<213> ORGANISM: Artificial sequence
<220> FEATURE:
<223> OTHER INFORMATION: Primer OPAD-15

<400> SEQUENCE: 604
tttgccccgt                                                          10

<210> SEQ ID NO 605
<211> LENGTH: 10
<212> TYPE: DNA
<213> ORGANISM: Artificial sequence
<220> FEATURE:
<223> OTHER INFORMATION: Primer OPAD-16

<400> SEQUENCE: 605
aacgggcgtc                                                          10
```

<210> SEQ ID NO 606
<211> LENGTH: 10
<212> TYPE: DNA
<213> ORGANISM: Artificial sequence
<220> FEATURE:
<223> OTHER INFORMATION: Primer OPAD-17

<400> SEQUENCE: 606
ggcaaaccct                                                              10

<210> SEQ ID NO 607
<211> LENGTH: 10
<212> TYPE: DNA
<213> ORGANISM: Artificial sequence
<220> FEATURE:
<223> OTHER INFORMATION: Primer OPAD-18

<400> SEQUENCE: 607
acgagaggca                                                              10

<210> SEQ ID NO 608
<211> LENGTH: 10
<212> TYPE: DNA
<213> ORGANISM: Artificial sequence
<220> FEATURE:
<223> OTHER INFORMATION: Primer OPAD-19

<400> SEQUENCE: 608
cttggcacga                                                              10

<210> SEQ ID NO 609
<211> LENGTH: 10
<212> TYPE: DNA
<213> ORGANISM: Artificial sequence
<220> FEATURE:
<223> OTHER INFORMATION: Primer OPAD-20

<400> SEQUENCE: 609
tcttcggagg                                                              10

<210> SEQ ID NO 610
<211> LENGTH: 10
<212> TYPE: DNA
<213> ORGANISM: Artificial sequence
<220> FEATURE:
<223> OTHER INFORMATION: Primer OPAE-01

<400> SEQUENCE: 610
tgagggccgt                                                              10

<210> SEQ ID NO 611
<211> LENGTH: 10
<212> TYPE: DNA
<213> ORGANISM: Artificial sequence
<220> FEATURE:
<223> OTHER INFORMATION: Primer OPAE-02

<400> SEQUENCE: 611
tcgttcaccc                                                              10

<210> SEQ ID NO 612
<211> LENGTH: 10
<212> TYPE: DNA
<213> ORGANISM: Artificial sequence
<220> FEATURE:
<223> OTHER INFORMATION: Primer OPAE-03

<400> SEQUENCE: 612
catagagcgg                                                          10

<210> SEQ ID NO 613
<211> LENGTH: 10
<212> TYPE: DNA
<213> ORGANISM: Artificial sequence
<220> FEATURE:
<223> OTHER INFORMATION: Primer OPAE-04

<400> SEQUENCE: 613
ccagcacttc                                                          10

<210> SEQ ID NO 614
<211> LENGTH: 10
<212> TYPE: DNA
<213> ORGANISM: Artificial sequence
<220> FEATURE:
<223> OTHER INFORMATION: Primer OPAE-05

<400> SEQUENCE: 614
cctgtcagtg                                                          10

<210> SEQ ID NO 615
<211> LENGTH: 10
<212> TYPE: DNA
<213> ORGANISM: Artificial sequence
<220> FEATURE:
<223> OTHER INFORMATION: Primer OPAE-06

<400> SEQUENCE: 615
ggggaagaca                                                          10

<210> SEQ ID NO 616
<211> LENGTH: 10
<212> TYPE: DNA
<213> ORGANISM: Artificial sequence
<220> FEATURE:
<223> OTHER INFORMATION: Primer OPAE-07

<400> SEQUENCE: 616
gtgtcagtgg                                                          10

<210> SEQ ID NO 617
<211> LENGTH: 10
<212> TYPE: DNA
<213> ORGANISM: Artificial sequence
<220> FEATURE:
<223> OTHER INFORMATION: Primer OPAE-08

<400> SEQUENCE: 617
ctggctcaga                                                          10

<210> SEQ ID NO 618
<211> LENGTH: 10
<212> TYPE: DNA
<213> ORGANISM: Artificial sequence
<220> FEATURE:
<223> OTHER INFORMATION: Primer OPAE-09

<400> SEQUENCE: 618
tgccacgagg                                                          10

<210> SEQ ID NO 619
<211> LENGTH: 10

```
<212> TYPE: DNA
<213> ORGANISM: Artificial sequence
<220> FEATURE:
<223> OTHER INFORMATION: Primer OPAE-10

<400> SEQUENCE: 619
ctgaagcgca                                                          10

<210> SEQ ID NO 620
<211> LENGTH: 10
<212> TYPE: DNA
<213> ORGANISM: Artificial sequence
<220> FEATURE:
<223> OTHER INFORMATION: Primer OPAE-11

<400> SEQUENCE: 620
aagaccggga                                                          10

<210> SEQ ID NO 621
<211> LENGTH: 10
<212> TYPE: DNA
<213> ORGANISM: Artificial sequence
<220> FEATURE:
<223> OTHER INFORMATION: Primer OPAE-12

<400> SEQUENCE: 621
ccgagcaatc                                                          10

<210> SEQ ID NO 622
<211> LENGTH: 10
<212> TYPE: DNA
<213> ORGANISM: Artificial sequence
<220> FEATURE:
<223> OTHER INFORMATION: Primer OPAE-13

<400> SEQUENCE: 622
tgtggactgg                                                          10

<210> SEQ ID NO 623
<211> LENGTH: 10
<212> TYPE: DNA
<213> ORGANISM: Artificial sequence
<220> FEATURE:
<223> OTHER INFORMATION: Primer OPAE-14

<400> SEQUENCE: 623
gagaggctcc                                                          10

<210> SEQ ID NO 624
<211> LENGTH: 10
<212> TYPE: DNA
<213> ORGANISM: Artificial sequence
<220> FEATURE:
<223> OTHER INFORMATION: Primer OPAE-15

<400> SEQUENCE: 624
tgcctggacc                                                          10

<210> SEQ ID NO 625
<211> LENGTH: 10
<212> TYPE: DNA
<213> ORGANISM: Artificial sequence
<220> FEATURE:
<223> OTHER INFORMATION: Primer OPAE-16

<400> SEQUENCE: 625
tccgtgctga                                                          10
```

<210> SEQ ID NO 626
<211> LENGTH: 10
<212> TYPE: DNA
<213> ORGANISM: Artificial sequence
<220> FEATURE:
<223> OTHER INFORMATION: Primer OPAE-17

<400> SEQUENCE: 626
ggcaggttca                                                                10

<210> SEQ ID NO 627
<211> LENGTH: 10
<212> TYPE: DNA
<213> ORGANISM: Artificial sequence
<220> FEATURE:
<223> OTHER INFORMATION: Primer OPAE-18

<400> SEQUENCE: 627
ctggtgctga                                                                10

<210> SEQ ID NO 628
<211> LENGTH: 10
<212> TYPE: DNA
<213> ORGANISM: Artificial sequence
<220> FEATURE:
<223> OTHER INFORMATION: Primer OPAE-19

<400> SEQUENCE: 628
gacagtccct                                                                10

<210> SEQ ID NO 629
<211> LENGTH: 10
<212> TYPE: DNA
<213> ORGANISM: Artificial sequence
<220> FEATURE:
<223> OTHER INFORMATION: Primer OPAE-20

<400> SEQUENCE: 629
ttgaccccag                                                                10

<210> SEQ ID NO 630
<211> LENGTH: 10
<212> TYPE: DNA
<213> ORGANISM: Artificial sequence
<220> FEATURE:
<223> OTHER INFORMATION: Primer OPAF-01

<400> SEQUENCE: 630
cctacacggt                                                                10

<210> SEQ ID NO 631
<211> LENGTH: 10
<212> TYPE: DNA
<213> ORGANISM: Artificial sequence
<220> FEATURE:
<223> OTHER INFORMATION: Primer OPAF-02

<400> SEQUENCE: 631
cagccgagaa                                                                10

<210> SEQ ID NO 632
<211> LENGTH: 10
<212> TYPE: DNA
<213> ORGANISM: Artificial sequence
<220> FEATURE:
<223> OTHER INFORMATION: Primer OPAF-03

```
<400> SEQUENCE: 632
gaaggaggca                                                              10

<210> SEQ ID NO 633
<211> LENGTH: 10
<212> TYPE: DNA
<213> ORGANISM: Artificial sequence
<220> FEATURE:
<223> OTHER INFORMATION: Primer OPAF-04

<400> SEQUENCE: 633
ttgcggctga                                                              10

<210> SEQ ID NO 634
<211> LENGTH: 10
<212> TYPE: DNA
<213> ORGANISM: Artificial sequence
<220> FEATURE:
<223> OTHER INFORMATION: Primer OPAF-05

<400> SEQUENCE: 634
cccgatcaga                                                              10

<210> SEQ ID NO 635
<211> LENGTH: 10
<212> TYPE: DNA
<213> ORGANISM: Artificial sequence
<220> FEATURE:
<223> OTHER INFORMATION: Primer OPAF-06

<400> SEQUENCE: 635
ccgcagtctg                                                              10

<210> SEQ ID NO 636
<211> LENGTH: 10
<212> TYPE: DNA
<213> ORGANISM: Artificial sequence
<220> FEATURE:
<223> OTHER INFORMATION: Primer OPAF-07

<400> SEQUENCE: 636
ggaaagcgtc                                                              10

<210> SEQ ID NO 637
<211> LENGTH: 10
<212> TYPE: DNA
<213> ORGANISM: Artificial sequence
<220> FEATURE:
<223> OTHER INFORMATION: Primer OPAF-08

<400> SEQUENCE: 637
ctctgcctga                                                              10

<210> SEQ ID NO 638
<211> LENGTH: 10
<212> TYPE: DNA
<213> ORGANISM: Artificial sequence
<220> FEATURE:
<223> OTHER INFORMATION: Primer OPAF-09

<400> SEQUENCE: 638
cccctcagaa                                                              10

<210> SEQ ID NO 639
<211> LENGTH: 10
```

```
<212> TYPE: DNA
<213> ORGANISM: Artificial sequence
<220> FEATURE:
<223> OTHER INFORMATION: Primer OPAF-10

<400> SEQUENCE: 639
ggttggagac                                                          10

<210> SEQ ID NO 640
<211> LENGTH: 10
<212> TYPE: DNA
<213> ORGANISM: Artificial sequence
<220> FEATURE:
<223> OTHER INFORMATION: Primer OPAF-11

<400> SEQUENCE: 640
actgggcctc                                                          10

<210> SEQ ID NO 641
<211> LENGTH: 10
<212> TYPE: DNA
<213> ORGANISM: Artificial sequence
<220> FEATURE:
<223> OTHER INFORMATION: Primer OPAF-12

<400> SEQUENCE: 641
gacgcagctt                                                          10

<210> SEQ ID NO 642
<211> LENGTH: 10
<212> TYPE: DNA
<213> ORGANISM: Artificial sequence
<220> FEATURE:
<223> OTHER INFORMATION: Primer OPAF-13

<400> SEQUENCE: 642
ccgaggtgac                                                          10

<210> SEQ ID NO 643
<211> LENGTH: 10
<212> TYPE: DNA
<213> ORGANISM: Artificial sequence
<220> FEATURE:
<223> OTHER INFORMATION: Primer OPAF-14

<400> SEQUENCE: 643
ggtgcgcact                                                          10

<210> SEQ ID NO 644
<211> LENGTH: 10
<212> TYPE: DNA
<213> ORGANISM: Artificial sequence
<220> FEATURE:
<223> OTHER INFORMATION: Primer OPAF-15

<400> SEQUENCE: 644
cacgaacctc                                                          10

<210> SEQ ID NO 645
<211> LENGTH: 10
<212> TYPE: DNA
<213> ORGANISM: Artificial sequence
<220> FEATURE:
<223> OTHER INFORMATION: Primer OPAF-16

<400> SEQUENCE: 645
tcccggtgag                                                          10
```

<210> SEQ ID NO 646
<211> LENGTH: 10
<212> TYPE: DNA
<213> ORGANISM: Artificial sequence
<220> FEATURE:
<223> OTHER INFORMATION: Primer OPAF-17

<400> SEQUENCE: 646
tgaaccgagg                                                           10

<210> SEQ ID NO 647
<211> LENGTH: 10
<212> TYPE: DNA
<213> ORGANISM: Artificial sequence
<220> FEATURE:
<223> OTHER INFORMATION: Primer OPAF-18

<400> SEQUENCE: 647
gtgtccctct                                                           10

<210> SEQ ID NO 648
<211> LENGTH: 10
<212> TYPE: DNA
<213> ORGANISM: Artificial sequence
<220> FEATURE:
<223> OTHER INFORMATION: Primer OPAF-19

<400> SEQUENCE: 648
ggacaagcag                                                           10

<210> SEQ ID NO 649
<211> LENGTH: 10
<212> TYPE: DNA
<213> ORGANISM: Artificial sequence
<220> FEATURE:
<223> OTHER INFORMATION: Primer OPAF-20

<400> SEQUENCE: 649
ctccgcacag                                                           10

<210> SEQ ID NO 650
<211> LENGTH: 10
<212> TYPE: DNA
<213> ORGANISM: Artificial sequence
<220> FEATURE:
<223> OTHER INFORMATION: Primer OPAG-01

<400> SEQUENCE: 650
ctacggcttc                                                           10

<210> SEQ ID NO 651
<211> LENGTH: 10
<212> TYPE: DNA
<213> ORGANISM: Artificial sequence
<220> FEATURE:
<223> OTHER INFORMATION: Primer OPAG-02

<400> SEQUENCE: 651
ctgaggtcct                                                           10

<210> SEQ ID NO 652
<211> LENGTH: 10
<212> TYPE: DNA
<213> ORGANISM: Artificial sequence
<220> FEATURE:
<223> OTHER INFORMATION: Primer OPAG-03

```
<400> SEQUENCE: 652
tgcgggagtg                                                          10

<210> SEQ ID NO 653
<211> LENGTH: 10
<212> TYPE: DNA
<213> ORGANISM: Artificial sequence
<220> FEATURE:
<223> OTHER INFORMATION: Primer OPAG-04

<400> SEQUENCE: 653
ggagcgtact                                                          10

<210> SEQ ID NO 654
<211> LENGTH: 10
<212> TYPE: DNA
<213> ORGANISM: Artificial sequence
<220> FEATURE:
<223> OTHER INFORMATION: Primer OPAG-05

<400> SEQUENCE: 654
cccactagac                                                          10

<210> SEQ ID NO 655
<211> LENGTH: 10
<212> TYPE: DNA
<213> ORGANISM: Artificial sequence
<220> FEATURE:
<223> OTHER INFORMATION: Primer OPAG-06

<400> SEQUENCE: 655
ggtggccaag                                                          10

<210> SEQ ID NO 656
<211> LENGTH: 10
<212> TYPE: DNA
<213> ORGANISM: Artificial sequence
<220> FEATURE:
<223> OTHER INFORMATION: Primer OPAG-07

<400> SEQUENCE: 656
cacagacctg                                                          10

<210> SEQ ID NO 657
<211> LENGTH: 10
<212> TYPE: DNA
<213> ORGANISM: Artificial sequence
<220> FEATURE:
<223> OTHER INFORMATION: Primer OPAG-08

<400> SEQUENCE: 657
aagagccctc                                                          10

<210> SEQ ID NO 658
<211> LENGTH: 10
<212> TYPE: DNA
<213> ORGANISM: Artificial sequence
<220> FEATURE:
<223> OTHER INFORMATION: Primer OPAG-09

<400> SEQUENCE: 658
ccgaggggtt                                                          10

<210> SEQ ID NO 659
<211> LENGTH: 10
```

-continued

<212> TYPE: DNA
<213> ORGANISM: Artificial sequence
<220> FEATURE:
<223> OTHER INFORMATION: Primer OPAG-10

<400> SEQUENCE: 659
actgcccgac                                                              10

<210> SEQ ID NO 660
<211> LENGTH: 10
<212> TYPE: DNA
<213> ORGANISM: Artificial sequence
<220> FEATURE:
<223> OTHER INFORMATION: Primer OPAG-11

<400> SEQUENCE: 660
ttacggtggg                                                              10

<210> SEQ ID NO 661
<211> LENGTH: 10
<212> TYPE: DNA
<213> ORGANISM: Artificial sequence
<220> FEATURE:
<223> OTHER INFORMATION: Primer OPAG-12

<400> SEQUENCE: 661
ctcccagggt                                                              10

<210> SEQ ID NO 662
<211> LENGTH: 10
<212> TYPE: DNA
<213> ORGANISM: Artificial sequence
<220> FEATURE:
<223> OTHER INFORMATION: Primer OPAG-13

<400> SEQUENCE: 662
ggcttggcga                                                              10

<210> SEQ ID NO 663
<211> LENGTH: 10
<212> TYPE: DNA
<213> ORGANISM: Artificial sequence
<220> FEATURE:
<223> OTHER INFORMATION: Primer OPAG-14

<400> SEQUENCE: 663
ctctcggcga                                                              10

<210> SEQ ID NO 664
<211> LENGTH: 10
<212> TYPE: DNA
<213> ORGANISM: Artificial sequence
<220> FEATURE:
<223> OTHER INFORMATION: Primer OPAG-15

<400> SEQUENCE: 664
cccacacgca                                                              10

<210> SEQ ID NO 665
<211> LENGTH: 10
<212> TYPE: DNA
<213> ORGANISM: Artificial sequence
<220> FEATURE:
<223> OTHER INFORMATION: Primer OPAG-16

<400> SEQUENCE: 665
cctgcgacag                                                              10

<210> SEQ ID NO 666
<211> LENGTH: 10
<212> TYPE: DNA
<213> ORGANISM: Artificial sequence
<220> FEATURE:
<223> OTHER INFORMATION: Primer OPAG-17

<400> SEQUENCE: 666
agcggaagtg                                                          10

<210> SEQ ID NO 667
<211> LENGTH: 10
<212> TYPE: DNA
<213> ORGANISM: Artificial sequence
<220> FEATURE:
<223> OTHER INFORMATION: Primer OPAG-18

<400> SEQUENCE: 667
gtgggcatac                                                          10

<210> SEQ ID NO 668
<211> LENGTH: 10
<212> TYPE: DNA
<213> ORGANISM: Artificial sequence
<220> FEATURE:
<223> OTHER INFORMATION: Primer OPAG-19

<400> SEQUENCE: 668
agcctcggtt                                                          10

<210> SEQ ID NO 669
<211> LENGTH: 10
<212> TYPE: DNA
<213> ORGANISM: Artificial sequence
<220> FEATURE:
<223> OTHER INFORMATION: Primer OPAG-20

<400> SEQUENCE: 669
tgcgctcctc                                                          10

<210> SEQ ID NO 670
<211> LENGTH: 10
<212> TYPE: DNA
<213> ORGANISM: Artificial sequence
<220> FEATURE:
<223> OTHER INFORMATION: Primer OPAH-01

<400> SEQUENCE: 670
tccgcaacca                                                          10

<210> SEQ ID NO 671
<211> LENGTH: 10
<212> TYPE: DNA
<213> ORGANISM: Artificial sequence
<220> FEATURE:
<223> OTHER INFORMATION: Primer OPAH-02

<400> SEQUENCE: 671
cacttccgct                                                          10

<210> SEQ ID NO 672
<211> LENGTH: 10
<212> TYPE: DNA
<213> ORGANISM: Artificial sequence
<220> FEATURE:
<223> OTHER INFORMATION: Primer OPAH-03

```
<400> SEQUENCE: 672
ggttactgcc                                                          10

<210> SEQ ID NO 673
<211> LENGTH: 10
<212> TYPE: DNA
<213> ORGANISM: Artificial sequence
<220> FEATURE:
<223> OTHER INFORMATION: Primer OPAH-04

<400> SEQUENCE: 673
ctccccagac                                                          10

<210> SEQ ID NO 674
<211> LENGTH: 10
<212> TYPE: DNA
<213> ORGANISM: Artificial sequence
<220> FEATURE:
<223> OTHER INFORMATION: Primer OPAH-05

<400> SEQUENCE: 674
ttgcaggcag                                                          10

<210> SEQ ID NO 675
<211> LENGTH: 10
<212> TYPE: DNA
<213> ORGANISM: Artificial sequence
<220> FEATURE:
<223> OTHER INFORMATION: Primer OPAH-06

<400> SEQUENCE: 675
gtaagcccct                                                          10

<210> SEQ ID NO 676
<211> LENGTH: 10
<212> TYPE: DNA
<213> ORGANISM: Artificial sequence
<220> FEATURE:
<223> OTHER INFORMATION: Primer OPAH-07

<400> SEQUENCE: 676
ccctacggag                                                          10

<210> SEQ ID NO 677
<211> LENGTH: 10
<212> TYPE: DNA
<213> ORGANISM: Artificial sequence
<220> FEATURE:
<223> OTHER INFORMATION: Primer OPAH-08

<400> SEQUENCE: 677
ttcccgtgcc                                                          10

<210> SEQ ID NO 678
<211> LENGTH: 10
<212> TYPE: DNA
<213> ORGANISM: Artificial sequence
<220> FEATURE:
<223> OTHER INFORMATION: Primer OPAH-09

<400> SEQUENCE: 678
agaaccgagg                                                          10

<210> SEQ ID NO 679
<211> LENGTH: 10
```

```
<212> TYPE: DNA
<213> ORGANISM: Artificial sequence
<220> FEATURE:
<223> OTHER INFORMATION: Primer OPAH-10

<400> SEQUENCE: 679
gggatgacca                                                          10

<210> SEQ ID NO 680
<211> LENGTH: 10
<212> TYPE: DNA
<213> ORGANISM: Artificial sequence
<220> FEATURE:
<223> OTHER INFORMATION: Primer OPAH-11

<400> SEQUENCE: 680
tccgctgaga                                                          10

<210> SEQ ID NO 681
<211> LENGTH: 10
<212> TYPE: DNA
<213> ORGANISM: Artificial sequence
<220> FEATURE:
<223> OTHER INFORMATION: Primer OPAH-12

<400> SEQUENCE: 681
tccaacggct                                                          10

<210> SEQ ID NO 682
<211> LENGTH: 10
<212> TYPE: DNA
<213> ORGANISM: Artificial sequence
<220> FEATURE:
<223> OTHER INFORMATION: Primer OPAH-13

<400> SEQUENCE: 682
tgagtccgca                                                          10

<210> SEQ ID NO 683
<211> LENGTH: 10
<212> TYPE: DNA
<213> ORGANISM: Artificial sequence
<220> FEATURE:
<223> OTHER INFORMATION: Primer OPAH-14

<400> SEQUENCE: 683
tgtggccgaa                                                          10

<210> SEQ ID NO 684
<211> LENGTH: 10
<212> TYPE: DNA
<213> ORGANISM: Artificial sequence
<220> FEATURE:
<223> OTHER INFORMATION: Primer OPAH-15

<400> SEQUENCE: 684
ctacagcgag                                                          10

<210> SEQ ID NO 685
<211> LENGTH: 10
<212> TYPE: DNA
<213> ORGANISM: Artificial sequence
<220> FEATURE:
<223> OTHER INFORMATION: Primer OPAH-16

<400> SEQUENCE: 685
caaggtgggt                                                          10
```

<210> SEQ ID NO 686
<211> LENGTH: 10
<212> TYPE: DNA
<213> ORGANISM: Artificial sequence
<220> FEATURE:
<223> OTHER INFORMATION: Primer OPAH-17

<400> SEQUENCE: 686
cagtggggag                                                          10

<210> SEQ ID NO 687
<211> LENGTH: 10
<212> TYPE: DNA
<213> ORGANISM: Artificial sequence
<220> FEATURE:
<223> OTHER INFORMATION: Primer OPAH-18

<400> SEQUENCE: 687
gggctagtca                                                          10

<210> SEQ ID NO 688
<211> LENGTH: 10
<212> TYPE: DNA
<213> ORGANISM: Artificial sequence
<220> FEATURE:
<223> OTHER INFORMATION: Primer OPAH-19

<400> SEQUENCE: 688
ggcagttctc                                                          10

<210> SEQ ID NO 689
<211> LENGTH: 10
<212> TYPE: DNA
<213> ORGANISM: Artificial sequence
<220> FEATURE:
<223> OTHER INFORMATION: Primer OPAH-20

<400> SEQUENCE: 689
ggaaggtgag                                                          10

<210> SEQ ID NO 690
<211> LENGTH: 10
<212> TYPE: DNA
<213> ORGANISM: Artificial sequence
<220> FEATURE:
<223> OTHER INFORMATION: Primer OPAI-01

<400> SEQUENCE: 690
ggcatcggct                                                          10

<210> SEQ ID NO 691
<211> LENGTH: 10
<212> TYPE: DNA
<213> ORGANISM: Artificial sequence
<220> FEATURE:
<223> OTHER INFORMATION: Primer OPAI-02

<400> SEQUENCE: 691
agccgttcag                                                          10

<210> SEQ ID NO 692
<211> LENGTH: 10
<212> TYPE: DNA
<213> ORGANISM: Artificial sequence
<220> FEATURE:
<223> OTHER INFORMATION: Primer OPAI-03

```
<400> SEQUENCE: 692
gggtccaaag                                                          10

<210> SEQ ID NO 693
<211> LENGTH: 10
<212> TYPE: DNA
<213> ORGANISM: Artificial sequence
<220> FEATURE:
<223> OTHER INFORMATION: Primer OPAI-04

<400> SEQUENCE: 693
ctatcctgcc                                                          10

<210> SEQ ID NO 694
<211> LENGTH: 10
<212> TYPE: DNA
<213> ORGANISM: Artificial sequence
<220> FEATURE:
<223> OTHER INFORMATION: Primer OPAI-05

<400> SEQUENCE: 694
gtcgtagcgg                                                          10

<210> SEQ ID NO 695
<211> LENGTH: 10
<212> TYPE: DNA
<213> ORGANISM: Artificial sequence
<220> FEATURE:
<223> OTHER INFORMATION: Primer OPAI-06

<400> SEQUENCE: 695
tgccgcactt                                                          10

<210> SEQ ID NO 696
<211> LENGTH: 10
<212> TYPE: DNA
<213> ORGANISM: Artificial sequence
<220> FEATURE:
<223> OTHER INFORMATION: Primer OPAI-07

<400> SEQUENCE: 696
acgagcatgg                                                          10

<210> SEQ ID NO 697
<211> LENGTH: 10
<212> TYPE: DNA
<213> ORGANISM: Artificial sequence
<220> FEATURE:
<223> OTHER INFORMATION: Primer OPAI-08

<400> SEQUENCE: 697
aagcccccca                                                          10

<210> SEQ ID NO 698
<211> LENGTH: 10
<212> TYPE: DNA
<213> ORGANISM: Artificial sequence
<220> FEATURE:
<223> OTHER INFORMATION: Primer OPAI-09

<400> SEQUENCE: 698
tcgctggtgt                                                          10

<210> SEQ ID NO 699
<211> LENGTH: 10
```

```
<212> TYPE: DNA
<213> ORGANISM: Artificial sequence
<220> FEATURE:
<223> OTHER INFORMATION: Primer OPAI-10

<400> SEQUENCE: 699
tcggggcatc                                                              10

<210> SEQ ID NO 700
<211> LENGTH: 10
<212> TYPE: DNA
<213> ORGANISM: Artificial sequence
<220> FEATURE:
<223> OTHER INFORMATION: Primer OPAI-11

<400> SEQUENCE: 700
acggcgatga                                                              10

<210> SEQ ID NO 701
<211> LENGTH: 10
<212> TYPE: DNA
<213> ORGANISM: Artificial sequence
<220> FEATURE:
<223> OTHER INFORMATION: Primer OPAI-12

<400> SEQUENCE: 701
gacgcgaacc                                                              10

<210> SEQ ID NO 702
<211> LENGTH: 10
<212> TYPE: DNA
<213> ORGANISM: Artificial sequence
<220> FEATURE:
<223> OTHER INFORMATION: Primer OPAI-13

<400> SEQUENCE: 702
acgctgcgac                                                              10

<210> SEQ ID NO 703
<211> LENGTH: 10
<212> TYPE: DNA
<213> ORGANISM: Artificial sequence
<220> FEATURE:
<223> OTHER INFORMATION: Primer OPAI-14

<400> SEQUENCE: 703
tggtgcactc                                                              10

<210> SEQ ID NO 704
<211> LENGTH: 10
<212> TYPE: DNA
<213> ORGANISM: Artificial sequence
<220> FEATURE:
<223> OTHER INFORMATION: Primer OPAI-15

<400> SEQUENCE: 704
gacacagccc                                                              10

<210> SEQ ID NO 705
<211> LENGTH: 10
<212> TYPE: DNA
<213> ORGANISM: Artificial sequence
<220> FEATURE:
<223> OTHER INFORMATION: Primer OPAI-16

<400> SEQUENCE: 705
aaggcacgag                                                              10
```

<210> SEQ ID NO 706
<211> LENGTH: 10
<212> TYPE: DNA
<213> ORGANISM: Artificial sequence
<220> FEATURE:
<223> OTHER INFORMATION: Primer OPAI-17

<400> SEQUENCE: 706
cctcacgtcc                                                              10

<210> SEQ ID NO 707
<211> LENGTH: 10
<212> TYPE: DNA
<213> ORGANISM: Artificial sequence
<220> FEATURE:
<223> OTHER INFORMATION: Primer OPAI-18

<400> SEQUENCE: 707
tcgcggaacc                                                              10

<210> SEQ ID NO 708
<211> LENGTH: 10
<212> TYPE: DNA
<213> ORGANISM: Artificial sequence
<220> FEATURE:
<223> OTHER INFORMATION: Primer OPAI-19

<400> SEQUENCE: 708
ggcaaagctg                                                              10

<210> SEQ ID NO 709
<211> LENGTH: 10
<212> TYPE: DNA
<213> ORGANISM: Artificial sequence
<220> FEATURE:
<223> OTHER INFORMATION: Primer OPAI-20

<400> SEQUENCE: 709
cctgttccct                                                              10

<210> SEQ ID NO 710
<211> LENGTH: 10
<212> TYPE: DNA
<213> ORGANISM: Artificial sequence
<220> FEATURE:
<223> OTHER INFORMATION: Primer OPAJ-01

<400> SEQUENCE: 710
acgggtcaga                                                              10

<210> SEQ ID NO 711
<211> LENGTH: 10
<212> TYPE: DNA
<213> ORGANISM: Artificial sequence
<220> FEATURE:
<223> OTHER INFORMATION: Primer OPAJ-02

<400> SEQUENCE: 711
tcgcacagtc                                                              10

<210> SEQ ID NO 712
<211> LENGTH: 10
<212> TYPE: DNA
<213> ORGANISM: Artificial sequence
<220> FEATURE:
<223> OTHER INFORMATION: Primer OPAJ-03

```
<400> SEQUENCE: 712
agcacctcgt                                                           10

<210> SEQ ID NO 713
<211> LENGTH: 10
<212> TYPE: DNA
<213> ORGANISM: Artificial sequence
<220> FEATURE:
<223> OTHER INFORMATION: Primer OPAJ-04

<400> SEQUENCE: 713
gaatgcgacc                                                           10

<210> SEQ ID NO 714
<211> LENGTH: 10
<212> TYPE: DNA
<213> ORGANISM: Artificial sequence
<220> FEATURE:
<223> OTHER INFORMATION: Primer OPAJ-05

<400> SEQUENCE: 714
cagcgttgcc                                                           10

<210> SEQ ID NO 715
<211> LENGTH: 10
<212> TYPE: DNA
<213> ORGANISM: Artificial sequence
<220> FEATURE:
<223> OTHER INFORMATION: Primer OPAJ-06

<400> SEQUENCE: 715
gtcggagtgg                                                           10

<210> SEQ ID NO 716
<211> LENGTH: 10
<212> TYPE: DNA
<213> ORGANISM: Artificial sequence
<220> FEATURE:
<223> OTHER INFORMATION: Primer OPAJ-07

<400> SEQUENCE: 716
ccctccctaa                                                           10

<210> SEQ ID NO 717
<211> LENGTH: 10
<212> TYPE: DNA
<213> ORGANISM: Artificial sequence
<220> FEATURE:
<223> OTHER INFORMATION: Primer OPAJ-08

<400> SEQUENCE: 717
gtgctccctc                                                           10

<210> SEQ ID NO 718
<211> LENGTH: 10
<212> TYPE: DNA
<213> ORGANISM: Artificial sequence
<220> FEATURE:
<223> OTHER INFORMATION: Primer OPAJ-09

<400> SEQUENCE: 718
acggcacgca                                                           10

<210> SEQ ID NO 719
<211> LENGTH: 10
```

```
<212> TYPE: DNA
<213> ORGANISM: Artificial sequence
<220> FEATURE:
<223> OTHER INFORMATION: Primer OPAJ-10

<400> SEQUENCE: 719
gttaccgcga                                                            10

<210> SEQ ID NO 720
<211> LENGTH: 10
<212> TYPE: DNA
<213> ORGANISM: Artificial sequence
<220> FEATURE:
<223> OTHER INFORMATION: Primer OPAJ-11

<400> SEQUENCE: 720
gaacgctgcc                                                            10

<210> SEQ ID NO 721
<211> LENGTH: 10
<212> TYPE: DNA
<213> ORGANISM: Artificial sequence
<220> FEATURE:
<223> OTHER INFORMATION: Primer OPAJ-12

<400> SEQUENCE: 721
cagttcccgt                                                            10

<210> SEQ ID NO 722
<211> LENGTH: 10
<212> TYPE: DNA
<213> ORGANISM: Artificial sequence
<220> FEATURE:
<223> OTHER INFORMATION: Primer OPAJ-13

<400> SEQUENCE: 722
cagccgttcc                                                            10

<210> SEQ ID NO 723
<211> LENGTH: 10
<212> TYPE: DNA
<213> ORGANISM: Artificial sequence
<220> FEATURE:
<223> OTHER INFORMATION: Primer OPAJ-14

<400> SEQUENCE: 723
accgatgctg                                                            10

<210> SEQ ID NO 724
<211> LENGTH: 10
<212> TYPE: DNA
<213> ORGANISM: Artificial sequence
<220> FEATURE:
<223> OTHER INFORMATION: Primer OPAJ-15

<400> SEQUENCE: 724
gaatccggca                                                            10

<210> SEQ ID NO 725
<211> LENGTH: 10
<212> TYPE: DNA
<213> ORGANISM: Artificial sequence
<220> FEATURE:
<223> OTHER INFORMATION: Primer OPAJ-16

<400> SEQUENCE: 725
tctggaccga                                                            10
```

<210> SEQ ID NO 726
<211> LENGTH: 10
<212> TYPE: DNA
<213> ORGANISM: Artificial sequence
<220> FEATURE:
<223> OTHER INFORMATION: Primer OPAJ-17

<400> SEQUENCE: 726
accccctatg                                                              10

<210> SEQ ID NO 727
<211> LENGTH: 10
<212> TYPE: DNA
<213> ORGANISM: Artificial sequence
<220> FEATURE:
<223> OTHER INFORMATION: Primer OPAJ-18

<400> SEQUENCE: 727
ggctaggtgg                                                              10

<210> SEQ ID NO 728
<211> LENGTH: 10
<212> TYPE: DNA
<213> ORGANISM: Artificial sequence
<220> FEATURE:
<223> OTHER INFORMATION: Primer OPAJ-19

<400> SEQUENCE: 728
acagtggcct                                                              10

<210> SEQ ID NO 729
<211> LENGTH: 10
<212> TYPE: DNA
<213> ORGANISM: Artificial sequence
<220> FEATURE:
<223> OTHER INFORMATION: Primer OPAJ-20

<400> SEQUENCE: 729
acacgtggtc                                                              10

<210> SEQ ID NO 730
<211> LENGTH: 10
<212> TYPE: DNA
<213> ORGANISM: Artificial sequence
<220> FEATURE:
<223> OTHER INFORMATION: Primer OPAK-01

<400> SEQUENCE: 730
tctgctacgg                                                              10

<210> SEQ ID NO 731
<211> LENGTH: 10
<212> TYPE: DNA
<213> ORGANISM: Artificial sequence
<220> FEATURE:
<223> OTHER INFORMATION: Primer OPAK-02

<400> SEQUENCE: 731
ccatcggagg                                                              10

<210> SEQ ID NO 732
<211> LENGTH: 10
<212> TYPE: DNA
<213> ORGANISM: Artificial sequence
<220> FEATURE:
<223> OTHER INFORMATION: Primer OPAK-03

```
<400> SEQUENCE: 732
ggtcctacca                                                              10

<210> SEQ ID NO 733
<211> LENGTH: 10
<212> TYPE: DNA
<213> ORGANISM: Artificial sequence
<220> FEATURE:
<223> OTHER INFORMATION: Primer OPAK-04

<400> SEQUENCE: 733
agggtcggtc                                                              10

<210> SEQ ID NO 734
<211> LENGTH: 10
<212> TYPE: DNA
<213> ORGANISM: Artificial sequence
<220> FEATURE:
<223> OTHER INFORMATION: Primer OPAK-05

<400> SEQUENCE: 734
gatggcagtc                                                              10

<210> SEQ ID NO 735
<211> LENGTH: 10
<212> TYPE: DNA
<213> ORGANISM: Artificial sequence
<220> FEATURE:
<223> OTHER INFORMATION: Primer OPAK-06

<400> SEQUENCE: 735
tcacgtccct                                                              10

<210> SEQ ID NO 736
<211> LENGTH: 10
<212> TYPE: DNA
<213> ORGANISM: Artificial sequence
<220> FEATURE:
<223> OTHER INFORMATION: Primer OPAK-07

<400> SEQUENCE: 736
cttgggggac                                                              10

<210> SEQ ID NO 737
<211> LENGTH: 10
<212> TYPE: DNA
<213> ORGANISM: Artificial sequence
<220> FEATURE:
<223> OTHER INFORMATION: Primer OPAK-08

<400> SEQUENCE: 737
ccgaagggtg                                                              10

<210> SEQ ID NO 738
<211> LENGTH: 10
<212> TYPE: DNA
<213> ORGANISM: Artificial sequence
<220> FEATURE:
<223> OTHER INFORMATION: Primer OPAK-09

<400> SEQUENCE: 738
aggtcggcgt                                                              10

<210> SEQ ID NO 739
<211> LENGTH: 10
```

```
<212> TYPE: DNA
<213> ORGANISM: Artificial sequence
<220> FEATURE:
<223> OTHER INFORMATION: Primer OPAK-10

<400> SEQUENCE: 739
caagcgtcac                                                              10

<210> SEQ ID NO 740
<211> LENGTH: 10
<212> TYPE: DNA
<213> ORGANISM: Artificial sequence
<220> FEATURE:
<223> OTHER INFORMATION: Primer OPAK-11

<400> SEQUENCE: 740
cagtgtgctc                                                              10

<210> SEQ ID NO 741
<211> LENGTH: 10
<212> TYPE: DNA
<213> ORGANISM: Artificial sequence
<220> FEATURE:
<223> OTHER INFORMATION: Primer OPAK-12

<400> SEQUENCE: 741
agtgtagccc                                                              10

<210> SEQ ID NO 742
<211> LENGTH: 10
<212> TYPE: DNA
<213> ORGANISM: Artificial sequence
<220> FEATURE:
<223> OTHER INFORMATION: Primer OPAK-13

<400> SEQUENCE: 742
tcccacgagt                                                              10

<210> SEQ ID NO 743
<211> LENGTH: 10
<212> TYPE: DNA
<213> ORGANISM: Artificial sequence
<220> FEATURE:
<223> OTHER INFORMATION: Primer OPAK-14

<400> SEQUENCE: 743
ctgtcatgcc                                                              10

<210> SEQ ID NO 744
<211> LENGTH: 10
<212> TYPE: DNA
<213> ORGANISM: Artificial sequence
<220> FEATURE:
<223> OTHER INFORMATION: Primer OPAK-15

<400> SEQUENCE: 744
acctgccgtt                                                              10

<210> SEQ ID NO 745
<211> LENGTH: 10
<212> TYPE: DNA
<213> ORGANISM: Artificial sequence
<220> FEATURE:
<223> OTHER INFORMATION: Primer OPAK-16

<400> SEQUENCE: 745
ctgcgtgctc                                                              10
```

<210> SEQ ID NO 746
<211> LENGTH: 10
<212> TYPE: DNA
<213> ORGANISM: Artificial sequence
<220> FEATURE:
<223> OTHER INFORMATION: Primer OPAK-17

<400> SEQUENCE: 746
cagcggtcac                                                          10

<210> SEQ ID NO 747
<211> LENGTH: 10
<212> TYPE: DNA
<213> ORGANISM: Artificial sequence
<220> FEATURE:
<223> OTHER INFORMATION: Primer OPAK-18

<400> SEQUENCE: 747
acccggaaac                                                          10

<210> SEQ ID NO 748
<211> LENGTH: 10
<212> TYPE: DNA
<213> ORGANISM: Artificial sequence
<220> FEATURE:
<223> OTHER INFORMATION: Primer OPAK-19

<400> SEQUENCE: 748
tcgcagcgag                                                          10

<210> SEQ ID NO 749
<211> LENGTH: 10
<212> TYPE: DNA
<213> ORGANISM: Artificial sequence
<220> FEATURE:
<223> OTHER INFORMATION: Primer OPAK-20

<400> SEQUENCE: 749
tgatggcgtc                                                          10

<210> SEQ ID NO 750
<211> LENGTH: 10
<212> TYPE: DNA
<213> ORGANISM: Artificial sequence
<220> FEATURE:
<223> OTHER INFORMATION: Primer OPAL-01

<400> SEQUENCE: 750
tgtgacgagg                                                          10

<210> SEQ ID NO 751
<211> LENGTH: 10
<212> TYPE: DNA
<213> ORGANISM: Artificial sequence
<220> FEATURE:
<223> OTHER INFORMATION: Primer OPAL-02

<400> SEQUENCE: 751
accctgtggg                                                          10

<210> SEQ ID NO 752
<211> LENGTH: 10
<212> TYPE: DNA
<213> ORGANISM: Artificial sequence
<220> FEATURE:
<223> OTHER INFORMATION: Primer OPAL-03

```
<400> SEQUENCE: 752
cccacccttg                                                          10

<210> SEQ ID NO 753
<211> LENGTH: 10
<212> TYPE: DNA
<213> ORGANISM: Artificial sequence
<220> FEATURE:
<223> OTHER INFORMATION: Primer OPAL-04

<400> SEQUENCE: 753
acaacggtcc                                                          10

<210> SEQ ID NO 754
<211> LENGTH: 10
<212> TYPE: DNA
<213> ORGANISM: Artificial sequence
<220> FEATURE:
<223> OTHER INFORMATION: Primer OPAL-05

<400> SEQUENCE: 754
gactgcgcca                                                          10

<210> SEQ ID NO 755
<211> LENGTH: 10
<212> TYPE: DNA
<213> ORGANISM: Artificial sequence
<220> FEATURE:
<223> OTHER INFORMATION: Primer OPAL-06

<400> SEQUENCE: 755
aagcgtcctc                                                          10

<210> SEQ ID NO 756
<211> LENGTH: 10
<212> TYPE: DNA
<213> ORGANISM: Artificial sequence
<220> FEATURE:
<223> OTHER INFORMATION: Primer OPAL-07

<400> SEQUENCE: 756
ccgtccatcc                                                          10

<210> SEQ ID NO 757
<211> LENGTH: 10
<212> TYPE: DNA
<213> ORGANISM: Artificial sequence
<220> FEATURE:
<223> OTHER INFORMATION: Primer OPAL-08

<400> SEQUENCE: 757
gtcgccctca                                                          10

<210> SEQ ID NO 758
<211> LENGTH: 10
<212> TYPE: DNA
<213> ORGANISM: Artificial sequence
<220> FEATURE:
<223> OTHER INFORMATION: Primer OPAL-09

<400> SEQUENCE: 758
cagcgagtag                                                          10

<210> SEQ ID NO 759
<211> LENGTH: 10
```

<212> TYPE: DNA
<213> ORGANISM: Artificial sequence
<220> FEATURE:
<223> OTHER INFORMATION: Primer OPAL-10

<400> SEQUENCE: 759
aaggcccctg                                                          10

<210> SEQ ID NO 760
<211> LENGTH: 10
<212> TYPE: DNA
<213> ORGANISM: Artificial sequence
<220> FEATURE:
<223> OTHER INFORMATION: Primer OPAL-11

<400> SEQUENCE: 760
gtcacgtcct                                                          10

<210> SEQ ID NO 761
<211> LENGTH: 10
<212> TYPE: DNA
<213> ORGANISM: Artificial sequence
<220> FEATURE:
<223> OTHER INFORMATION: Primer OPAL-12

<400> SEQUENCE: 761
cccaggctac                                                          10

<210> SEQ ID NO 762
<211> LENGTH: 10
<212> TYPE: DNA
<213> ORGANISM: Artificial sequence
<220> FEATURE:
<223> OTHER INFORMATION: Primer OPAL-13

<400> SEQUENCE: 762
gaatggcacc                                                          10

<210> SEQ ID NO 763
<211> LENGTH: 10
<212> TYPE: DNA
<213> ORGANISM: Artificial sequence
<220> FEATURE:
<223> OTHER INFORMATION: Primer OPAL-14

<400> SEQUENCE: 763
tcgctccgtt                                                          10

<210> SEQ ID NO 764
<211> LENGTH: 10
<212> TYPE: DNA
<213> ORGANISM: Artificial sequence
<220> FEATURE:
<223> OTHER INFORMATION: Primer OPAL-15

<400> SEQUENCE: 764
aggggacacc                                                          10

<210> SEQ ID NO 765
<211> LENGTH: 10
<212> TYPE: DNA
<213> ORGANISM: Artificial sequence
<220> FEATURE:
<223> OTHER INFORMATION: Primer OPAL-16

<400> SEQUENCE: 765
ctttcgaggg                                                          10

<210> SEQ ID NO 766
<211> LENGTH: 10
<212> TYPE: DNA
<213> ORGANISM: Artificial sequence
<220> FEATURE:
<223> OTHER INFORMATION: Primer OPAL-17

<400> SEQUENCE: 766
ccgcaagtgt                                                              10

<210> SEQ ID NO 767
<211> LENGTH: 10
<212> TYPE: DNA
<213> ORGANISM: Artificial sequence
<220> FEATURE:
<223> OTHER INFORMATION: Primer OPAL-18

<400> SEQUENCE: 767
ggagtggact                                                              10

<210> SEQ ID NO 768
<211> LENGTH: 10
<212> TYPE: DNA
<213> ORGANISM: Artificial sequence
<220> FEATURE:
<223> OTHER INFORMATION: Primer OPAL-19

<400> SEQUENCE: 768
tctgccagtg                                                              10

<210> SEQ ID NO 769
<211> LENGTH: 10
<212> TYPE: DNA
<213> ORGANISM: Artificial sequence
<220> FEATURE:
<223> OTHER INFORMATION: Primer OPAL-20

<400> SEQUENCE: 769
aggagtcgga                                                              10

<210> SEQ ID NO 770
<211> LENGTH: 10
<212> TYPE: DNA
<213> ORGANISM: Artificial sequence
<220> FEATURE:
<223> OTHER INFORMATION: Primer OPAM-01

<400> SEQUENCE: 770
tcacgtacgg                                                              10

<210> SEQ ID NO 771
<211> LENGTH: 10
<212> TYPE: DNA
<213> ORGANISM: Artificial sequence
<220> FEATURE:
<223> OTHER INFORMATION: Primer OPAM-02

<400> SEQUENCE: 771
acttgacggg                                                              10

<210> SEQ ID NO 772
<211> LENGTH: 10
<212> TYPE: DNA
<213> ORGANISM: Artificial sequence
<220> FEATURE:
<223> OTHER INFORMATION: Primer OPAM-03

<400> SEQUENCE: 772
cttccctgtg                                                              10

<210> SEQ ID NO 773
<211> LENGTH: 10
<212> TYPE: DNA
<213> ORGANISM: Artificial sequence
<220> FEATURE:
<223> OTHER INFORMATION: Primer OPAM-04

<400> SEQUENCE: 773
gagggacctc                                                              10

<210> SEQ ID NO 774
<211> LENGTH: 10
<212> TYPE: DNA
<213> ORGANISM: Artificial sequence
<220> FEATURE:
<223> OTHER INFORMATION: Primer OPAM-05

<400> SEQUENCE: 774
gggctatgcc                                                              10

<210> SEQ ID NO 775
<211> LENGTH: 10
<212> TYPE: DNA
<213> ORGANISM: Artificial sequence
<220> FEATURE:
<223> OTHER INFORMATION: Primer OPAM-06

<400> SEQUENCE: 775
ctcgggatgt                                                              10

<210> SEQ ID NO 776
<211> LENGTH: 10
<212> TYPE: DNA
<213> ORGANISM: Artificial sequence
<220> FEATURE:
<223> OTHER INFORMATION: Primer OPAM-07

<400> SEQUENCE: 776
aaccgcggca                                                              10

<210> SEQ ID NO 777
<211> LENGTH: 10
<212> TYPE: DNA
<213> ORGANISM: Artificial sequence
<220> FEATURE:
<223> OTHER INFORMATION: Primer OPAM-08

<400> SEQUENCE: 777
accacgagtg                                                              10

<210> SEQ ID NO 778
<211> LENGTH: 10
<212> TYPE: DNA
<213> ORGANISM: Artificial sequence
<220> FEATURE:
<223> OTHER INFORMATION: Primer OPAM-09

<400> SEQUENCE: 778
tgccggttca                                                              10

<210> SEQ ID NO 779
<211> LENGTH: 10

```
<212> TYPE: DNA
<213> ORGANISM: Artificial sequence
<220> FEATURE:
<223> OTHER INFORMATION: Primer OPAM-10

<400> SEQUENCE: 779
cagaccgacc                                                          10

<210> SEQ ID NO 780
<211> LENGTH: 10
<212> TYPE: DNA
<213> ORGANISM: Artificial sequence
<220> FEATURE:
<223> OTHER INFORMATION: Primer OPAM-11

<400> SEQUENCE: 780
agatgcgcgg                                                          10

<210> SEQ ID NO 781
<211> LENGTH: 10
<212> TYPE: DNA
<213> ORGANISM: Artificial sequence
<220> FEATURE:
<223> OTHER INFORMATION: Primer OPAM-12

<400> SEQUENCE: 781
tctcaccgtc                                                          10

<210> SEQ ID NO 782
<211> LENGTH: 10
<212> TYPE: DNA
<213> ORGANISM: Artificial sequence
<220> FEATURE:
<223> OTHER INFORMATION: Primer OPAM-13

<400> SEQUENCE: 782
cacggcacaa                                                          10

<210> SEQ ID NO 783
<211> LENGTH: 10
<212> TYPE: DNA
<213> ORGANISM: Artificial sequence
<220> FEATURE:
<223> OTHER INFORMATION: Primer OPAM-14

<400> SEQUENCE: 783
tggttgcgga                                                          10

<210> SEQ ID NO 784
<211> LENGTH: 10
<212> TYPE: DNA
<213> ORGANISM: Artificial sequence
<220> FEATURE:
<223> OTHER INFORMATION: Primer OPAM-15

<400> SEQUENCE: 784
gatgcgatgg                                                          10

<210> SEQ ID NO 785
<211> LENGTH: 10
<212> TYPE: DNA
<213> ORGANISM: Artificial sequence
<220> FEATURE:
<223> OTHER INFORMATION: Primer OPAM-16

<400> SEQUENCE: 785
tggcggtttg                                                          10
```

<210> SEQ ID NO 786
<211> LENGTH: 10
<212> TYPE: DNA
<213> ORGANISM: Artificial sequence
<220> FEATURE:
<223> OTHER INFORMATION: Primer OPAM-17

<400> SEQUENCE: 786
cctaacgtcc                                                                10

<210> SEQ ID NO 787
<211> LENGTH: 10
<212> TYPE: DNA
<213> ORGANISM: Artificial sequence
<220> FEATURE:
<223> OTHER INFORMATION: Primer OPAM-18

<400> SEQUENCE: 787
acgggactct                                                                10

<210> SEQ ID NO 788
<211> LENGTH: 10
<212> TYPE: DNA
<213> ORGANISM: Artificial sequence
<220> FEATURE:
<223> OTHER INFORMATION: Primer OPAM-19

<400> SEQUENCE: 788
ccaggtcttc                                                                10

<210> SEQ ID NO 789
<211> LENGTH: 10
<212> TYPE: DNA
<213> ORGANISM: Artificial sequence
<220> FEATURE:
<223> OTHER INFORMATION: Primer OPAM-20

<400> SEQUENCE: 789
accaaccagg                                                                10

<210> SEQ ID NO 790
<211> LENGTH: 10
<212> TYPE: DNA
<213> ORGANISM: Artificial sequence
<220> FEATURE:
<223> OTHER INFORMATION: Primer OPAN-01

<400> SEQUENCE: 790
actccacgtc                                                                10

<210> SEQ ID NO 791
<211> LENGTH: 10
<212> TYPE: DNA
<213> ORGANISM: Artificial sequence
<220> FEATURE:
<223> OTHER INFORMATION: Primer OPAN-02

<400> SEQUENCE: 791
caccgcagtt                                                                10

<210> SEQ ID NO 792
<211> LENGTH: 10
<212> TYPE: DNA
<213> ORGANISM: Artificial sequence
<220> FEATURE:
<223> OTHER INFORMATION: Primer OPAN-03

<400> SEQUENCE: 792
agccaggctg                                                              10

<210> SEQ ID NO 793
<211> LENGTH: 10
<212> TYPE: DNA
<213> ORGANISM: Artificial sequence
<220> FEATURE:
<223> OTHER INFORMATION: Primer OPAN-04

<400> SEQUENCE: 793
ggcgtaagtc                                                              10

<210> SEQ ID NO 794
<211> LENGTH: 10
<212> TYPE: DNA
<213> ORGANISM: Artificial sequence
<220> FEATURE:
<223> OTHER INFORMATION: Primer OPAN-05

<400> SEQUENCE: 794
gggtgcagtt                                                              10

<210> SEQ ID NO 795
<211> LENGTH: 10
<212> TYPE: DNA
<213> ORGANISM: Artificial sequence
<220> FEATURE:
<223> OTHER INFORMATION: Primer OPAN-06

<400> SEQUENCE: 795
gggaacccgt                                                              10

<210> SEQ ID NO 796
<211> LENGTH: 10
<212> TYPE: DNA
<213> ORGANISM: Artificial sequence
<220> FEATURE:
<223> OTHER INFORMATION: Primer OPAN-07

<400> SEQUENCE: 796
tcgctgcgga                                                              10

<210> SEQ ID NO 797
<211> LENGTH: 10
<212> TYPE: DNA
<213> ORGANISM: Artificial sequence
<220> FEATURE:
<223> OTHER INFORMATION: Primer OPAN-08

<400> SEQUENCE: 797
aaggctgctg                                                              10

<210> SEQ ID NO 798
<211> LENGTH: 10
<212> TYPE: DNA
<213> ORGANISM: Artificial sequence
<220> FEATURE:
<223> OTHER INFORMATION: Primer OPAN-09

<400> SEQUENCE: 798
gggggagatg                                                              10

<210> SEQ ID NO 799
<211> LENGTH: 10

```
<212> TYPE: DNA
<213> ORGANISM: Artificial sequence
<220> FEATURE:
<223> OTHER INFORMATION: Primer OPAN-10

<400> SEQUENCE: 799
ctgtgtgctc                                                          10

<210> SEQ ID NO 800
<211> LENGTH: 10
<212> TYPE: DNA
<213> ORGANISM: Artificial sequence
<220> FEATURE:
<223> OTHER INFORMATION: Primer OPAN-11

<400> SEQUENCE: 800
gtccatgcag                                                          10

<210> SEQ ID NO 801
<211> LENGTH: 10
<212> TYPE: DNA
<213> ORGANISM: Artificial sequence
<220> FEATURE:
<223> OTHER INFORMATION: Primer OPAN-12

<400> SEQUENCE: 801
aacggcggtc                                                          10

<210> SEQ ID NO 802
<211> LENGTH: 10
<212> TYPE: DNA
<213> ORGANISM: Artificial sequence
<220> FEATURE:
<223> OTHER INFORMATION: Primer OPAN-13

<400> SEQUENCE: 802
cttccaggac                                                          10

<210> SEQ ID NO 803
<211> LENGTH: 10
<212> TYPE: DNA
<213> ORGANISM: Artificial sequence
<220> FEATURE:
<223> OTHER INFORMATION: Primer OPAN-14

<400> SEQUENCE: 803
agccgggtaa                                                          10

<210> SEQ ID NO 804
<211> LENGTH: 10
<212> TYPE: DNA
<213> ORGANISM: Artificial sequence
<220> FEATURE:
<223> OTHER INFORMATION: Primer OPAN-15

<400> SEQUENCE: 804
tgatgccgct                                                          10

<210> SEQ ID NO 805
<211> LENGTH: 10
<212> TYPE: DNA
<213> ORGANISM: Artificial sequence
<220> FEATURE:
<223> OTHER INFORMATION: Primer OPAN-16

<400> SEQUENCE: 805
gtgtcgagtc                                                          10
```

<210> SEQ ID NO 806
<211> LENGTH: 10
<212> TYPE: DNA
<213> ORGANISM: Artificial sequence
<220> FEATURE:
<223> OTHER INFORMATION: Primer OPAN-17

<400> SEQUENCE: 806
tcagcacagg                                                          10

<210> SEQ ID NO 807
<211> LENGTH: 10
<212> TYPE: DNA
<213> ORGANISM: Artificial sequence
<220> FEATURE:
<223> OTHER INFORMATION: Primer OPAN-18

<400> SEQUENCE: 807
tgtcctgcgt                                                          10

<210> SEQ ID NO 808
<211> LENGTH: 10
<212> TYPE: DNA
<213> ORGANISM: Artificial sequence
<220> FEATURE:
<223> OTHER INFORMATION: Primer OPAN-19

<400> SEQUENCE: 808
accacgcctt                                                          10

<210> SEQ ID NO 809
<211> LENGTH: 10
<212> TYPE: DNA
<213> ORGANISM: Artificial sequence
<220> FEATURE:
<223> OTHER INFORMATION: Primer OPAN-20

<400> SEQUENCE: 809
gagtcctcac                                                          10

<210> SEQ ID NO 810
<211> LENGTH: 10
<212> TYPE: DNA
<213> ORGANISM: Artificial sequence
<220> FEATURE:
<223> OTHER INFORMATION: Primer OPAO-01

<400> SEQUENCE: 810
aagacgacgg                                                          10

<210> SEQ ID NO 811
<211> LENGTH: 10
<212> TYPE: DNA
<213> ORGANISM: Artificial sequence
<220> FEATURE:
<223> OTHER INFORMATION: Primer OPAO-02

<400> SEQUENCE: 811
aatccgctgg                                                          10

<210> SEQ ID NO 812
<211> LENGTH: 10
<212> TYPE: DNA
<213> ORGANISM: Artificial sequence
<220> FEATURE:
<223> OTHER INFORMATION: Primer OPAO-03

```
<400> SEQUENCE: 812
agtcggccca                                                          10

<210> SEQ ID NO 813
<211> LENGTH: 10
<212> TYPE: DNA
<213> ORGANISM: Artificial sequence
<220> FEATURE:
<223> OTHER INFORMATION: Primer OPAO-04

<400> SEQUENCE: 813
aacagggcag                                                          10

<210> SEQ ID NO 814
<211> LENGTH: 10
<212> TYPE: DNA
<213> ORGANISM: Artificial sequence
<220> FEATURE:
<223> OTHER INFORMATION: Primer OPAO-05

<400> SEQUENCE: 814
tggaagcacc                                                          10

<210> SEQ ID NO 815
<211> LENGTH: 10
<212> TYPE: DNA
<213> ORGANISM: Artificial sequence
<220> FEATURE:
<223> OTHER INFORMATION: Primer OPAO-06

<400> SEQUENCE: 815
aggcagcctg                                                          10

<210> SEQ ID NO 816
<211> LENGTH: 10
<212> TYPE: DNA
<213> ORGANISM: Artificial sequence
<220> FEATURE:
<223> OTHER INFORMATION: Primer OPAO-07

<400> SEQUENCE: 816
gatgcgacgg                                                          10

<210> SEQ ID NO 817
<211> LENGTH: 10
<212> TYPE: DNA
<213> ORGANISM: Artificial sequence
<220> FEATURE:
<223> OTHER INFORMATION: Primer OPAO-08

<400> SEQUENCE: 817
actggctctc                                                          10

<210> SEQ ID NO 818
<211> LENGTH: 10
<212> TYPE: DNA
<213> ORGANISM: Artificial sequence
<220> FEATURE:
<223> OTHER INFORMATION: Primer OPAO-09

<400> SEQUENCE: 818
ccagatgggg                                                          10

<210> SEQ ID NO 819
<211> LENGTH: 10
```

```
<212> TYPE: DNA
<213> ORGANISM: Artificial sequence
<220> FEATURE:
<223> OTHER INFORMATION: Primer OPAO-10

<400> SEQUENCE: 819
gacatcgtcc                                                          10

<210> SEQ ID NO 820
<211> LENGTH: 10
<212> TYPE: DNA
<213> ORGANISM: Artificial sequence
<220> FEATURE:
<223> OTHER INFORMATION: Primer OPAO-11

<400> SEQUENCE: 820
gggggcttga                                                          10

<210> SEQ ID NO 821
<211> LENGTH: 10
<212> TYPE: DNA
<213> ORGANISM: Artificial sequence
<220> FEATURE:
<223> OTHER INFORMATION: Primer OPAO-12

<400> SEQUENCE: 821
tcccggtctc                                                          10

<210> SEQ ID NO 822
<211> LENGTH: 10
<212> TYPE: DNA
<213> ORGANISM: Artificial sequence
<220> FEATURE:
<223> OTHER INFORMATION: Primer OPAO-13

<400> SEQUENCE: 822
cccacaggtg                                                          10

<210> SEQ ID NO 823
<211> LENGTH: 10
<212> TYPE: DNA
<213> ORGANISM: Artificial sequence
<220> FEATURE:
<223> OTHER INFORMATION: Primer OPAO-14

<400> SEQUENCE: 823
ctactggggt                                                          10

<210> SEQ ID NO 824
<211> LENGTH: 10
<212> TYPE: DNA
<213> ORGANISM: Artificial sequence
<220> FEATURE:
<223> OTHER INFORMATION: Primer OPAO-15

<400> SEQUENCE: 824
gaaggctccc                                                          10

<210> SEQ ID NO 825
<211> LENGTH: 10
<212> TYPE: DNA
<213> ORGANISM: Artificial sequence
<220> FEATURE:
<223> OTHER INFORMATION: Primer OPAO-16

<400> SEQUENCE: 825
cacaacggga                                                          10
```

<210> SEQ ID NO 826
<211> LENGTH: 10
<212> TYPE: DNA
<213> ORGANISM: Artificial sequence
<220> FEATURE:
<223> OTHER INFORMATION: Primer OPAO-17

<400> SEQUENCE: 826
cccatgtgtg                                                              10

<210> SEQ ID NO 827
<211> LENGTH: 10
<212> TYPE: DNA
<213> ORGANISM: Artificial sequence
<220> FEATURE:
<223> OTHER INFORMATION: Primer OPAO-18

<400> SEQUENCE: 827
gggagcgctt                                                              10

<210> SEQ ID NO 828
<211> LENGTH: 10
<212> TYPE: DNA
<213> ORGANISM: Artificial sequence
<220> FEATURE:
<223> OTHER INFORMATION: Primer OPAO-19

<400> SEQUENCE: 828
gttctcggac                                                              10

<210> SEQ ID NO 829
<211> LENGTH: 10
<212> TYPE: DNA
<213> ORGANISM: Artificial sequence
<220> FEATURE:
<223> OTHER INFORMATION: Primer OPAO-20

<400> SEQUENCE: 829
ggcttgcctg                                                              10

<210> SEQ ID NO 830
<211> LENGTH: 10
<212> TYPE: DNA
<213> ORGANISM: Artificial sequence
<220> FEATURE:
<223> OTHER INFORMATION: Primer OPAP-01

<400> SEQUENCE: 830
aactggcccc                                                              10

<210> SEQ ID NO 831
<211> LENGTH: 10
<212> TYPE: DNA
<213> ORGANISM: Artificial sequence
<220> FEATURE:
<223> OTHER INFORMATION: Primer OPAP-02

<400> SEQUENCE: 831
tggtcatccc                                                              10

<210> SEQ ID NO 832
<211> LENGTH: 10
<212> TYPE: DNA
<213> ORGANISM: Artificial sequence
<220> FEATURE:
<223> OTHER INFORMATION: Primer OPAP-03

```
<400> SEQUENCE: 832
gtaaggcgca                                                          10

<210> SEQ ID NO 833
<211> LENGTH: 10
<212> TYPE: DNA
<213> ORGANISM: Artificial sequence
<220> FEATURE:
<223> OTHER INFORMATION: Primer OPAP-04

<400> SEQUENCE: 833
ctcttgggct                                                          10

<210> SEQ ID NO 834
<211> LENGTH: 10
<212> TYPE: DNA
<213> ORGANISM: Artificial sequence
<220> FEATURE:
<223> OTHER INFORMATION: Primer OPAP-05

<400> SEQUENCE: 834
gacttcaggg                                                          10

<210> SEQ ID NO 835
<211> LENGTH: 10
<212> TYPE: DNA
<213> ORGANISM: Artificial sequence
<220> FEATURE:
<223> OTHER INFORMATION: Primer OPAP-06

<400> SEQUENCE: 835
gtcacgtctc                                                          10

<210> SEQ ID NO 836
<211> LENGTH: 10
<212> TYPE: DNA
<213> ORGANISM: Artificial sequence
<220> FEATURE:
<223> OTHER INFORMATION: Primer OPAP-07

<400> SEQUENCE: 836
accacccgct                                                          10

<210> SEQ ID NO 837
<211> LENGTH: 10
<212> TYPE: DNA
<213> ORGANISM: Artificial sequence
<220> FEATURE:
<223> OTHER INFORMATION: Primer OPAP-08

<400> SEQUENCE: 837
acccccacac                                                          10

<210> SEQ ID NO 838
<211> LENGTH: 10
<212> TYPE: DNA
<213> ORGANISM: Artificial sequence
<220> FEATURE:
<223> OTHER INFORMATION: Primer OPAP-09

<400> SEQUENCE: 838
gtggtccaga                                                          10

<210> SEQ ID NO 839
<211> LENGTH: 10
```

```
<212> TYPE: DNA
<213> ORGANISM: Artificial sequence
<220> FEATURE:
<223> OTHER INFORMATION: Primer OPAP-10

<400> SEQUENCE: 839
tgggtgatcc                                                          10

<210> SEQ ID NO 840
<211> LENGTH: 10
<212> TYPE: DNA
<213> ORGANISM: Artificial sequence
<220> FEATURE:
<223> OTHER INFORMATION: Primer OPAP-11

<400> SEQUENCE: 840
ctggcttctg                                                          10

<210> SEQ ID NO 841
<211> LENGTH: 10
<212> TYPE: DNA
<213> ORGANISM: Artificial sequence
<220> FEATURE:
<223> OTHER INFORMATION: Primer OPAP-12

<400> SEQUENCE: 841
gtcttacccc                                                          10

<210> SEQ ID NO 842
<211> LENGTH: 10
<212> TYPE: DNA
<213> ORGANISM: Artificial sequence
<220> FEATURE:
<223> OTHER INFORMATION: Primer OPAP-13

<400> SEQUENCE: 842
tgaagcccct                                                          10

<210> SEQ ID NO 843
<211> LENGTH: 10
<212> TYPE: DNA
<213> ORGANISM: Artificial sequence
<220> FEATURE:
<223> OTHER INFORMATION: Primer OPAP-14

<400> SEQUENCE: 843
tgccatgctg                                                          10

<210> SEQ ID NO 844
<211> LENGTH: 10
<212> TYPE: DNA
<213> ORGANISM: Artificial sequence
<220> FEATURE:
<223> OTHER INFORMATION: Primer OPAP-15

<400> SEQUENCE: 844
gggttggaag                                                          10

<210> SEQ ID NO 845
<211> LENGTH: 10
<212> TYPE: DNA
<213> ORGANISM: Artificial sequence
<220> FEATURE:
<223> OTHER INFORMATION: Primer OPAP-16

<400> SEQUENCE: 845
gggcagatac                                                          10
```

<210> SEQ ID NO 846
<211> LENGTH: 10
<212> TYPE: DNA
<213> ORGANISM: Artificial sequence
<220> FEATURE:
<223> OTHER INFORMATION: Primer OPAP-17

<400> SEQUENCE: 846
acggcactcc                                                                10

<210> SEQ ID NO 847
<211> LENGTH: 10
<212> TYPE: DNA
<213> ORGANISM: Artificial sequence
<220> FEATURE:
<223> OTHER INFORMATION: Primer OPAP-18

<400> SEQUENCE: 847
gtcgtcgaca                                                                10

<210> SEQ ID NO 848
<211> LENGTH: 10
<212> TYPE: DNA
<213> ORGANISM: Artificial sequence
<220> FEATURE:
<223> OTHER INFORMATION: Primer OPAP-19

<400> SEQUENCE: 848
gtgtctgcct                                                                10

<210> SEQ ID NO 849
<211> LENGTH: 10
<212> TYPE: DNA
<213> ORGANISM: Artificial sequence
<220> FEATURE:
<223> OTHER INFORMATION: Primer OPAP-20

<400> SEQUENCE: 849
cccggataca                                                                10

<210> SEQ ID NO 850
<211> LENGTH: 10
<212> TYPE: DNA
<213> ORGANISM: Artificial sequence
<220> FEATURE:
<223> OTHER INFORMATION: Primer OPAQ-01

<400> SEQUENCE: 850
ggcaggtgga                                                                10

<210> SEQ ID NO 851
<211> LENGTH: 10
<212> TYPE: DNA
<213> ORGANISM: Artificial sequence
<220> FEATURE:
<223> OTHER INFORMATION: Primer OPAQ-02

<400> SEQUENCE: 851
accctcggac                                                                10

<210> SEQ ID NO 852
<211> LENGTH: 10
<212> TYPE: DNA
<213> ORGANISM: Artificial sequence
<220> FEATURE:
<223> OTHER INFORMATION: Primer OPAQ-03

<400> SEQUENCE: 852
gaggtgtctg                                                              10

<210> SEQ ID NO 853
<211> LENGTH: 10
<212> TYPE: DNA
<213> ORGANISM: Artificial sequence
<220> FEATURE:
<223> OTHER INFORMATION: Primer OPAQ-04

<400> SEQUENCE: 853
gacggctatc                                                              10

<210> SEQ ID NO 854
<211> LENGTH: 10
<212> TYPE: DNA
<213> ORGANISM: Artificial sequence
<220> FEATURE:
<223> OTHER INFORMATION: Primer OPAQ-05

<400> SEQUENCE: 854
acggagctga                                                              10

<210> SEQ ID NO 855
<211> LENGTH: 10
<212> TYPE: DNA
<213> ORGANISM: Artificial sequence
<220> FEATURE:
<223> OTHER INFORMATION: Primer OPAQ-06

<400> SEQUENCE: 855
acggatcccc                                                              10

<210> SEQ ID NO 856
<211> LENGTH: 10
<212> TYPE: DNA
<213> ORGANISM: Artificial sequence
<220> FEATURE:
<223> OTHER INFORMATION: Primer OPAQ-07

<400> SEQUENCE: 856
ggagtaacgg                                                              10

<210> SEQ ID NO 857
<211> LENGTH: 10
<212> TYPE: DNA
<213> ORGANISM: Artificial sequence
<220> FEATURE:
<223> OTHER INFORMATION: Primer OPAQ-08

<400> SEQUENCE: 857
tcggtagacc                                                              10

<210> SEQ ID NO 858
<211> LENGTH: 10
<212> TYPE: DNA
<213> ORGANISM: Artificial sequence
<220> FEATURE:
<223> OTHER INFORMATION: Primer OPAQ-09

<400> SEQUENCE: 858
agtcccctc                                                               10

<210> SEQ ID NO 859
<211> LENGTH: 10

<212> TYPE: DNA
<213> ORGANISM: Artificial sequence
<220> FEATURE:
<223> OTHER INFORMATION: Primer OPAQ-10

<400> SEQUENCE: 859
cataccctcc                                                              10

<210> SEQ ID NO 860
<211> LENGTH: 10
<212> TYPE: DNA
<213> ORGANISM: Artificial sequence
<220> FEATURE:
<223> OTHER INFORMATION: Primer OPAQ-11

<400> SEQUENCE: 860
gacgcctcca                                                              10

<210> SEQ ID NO 861
<211> LENGTH: 10
<212> TYPE: DNA
<213> ORGANISM: Artificial sequence
<220> FEATURE:
<223> OTHER INFORMATION: Primer OPAQ-12

<400> SEQUENCE: 861
cagctcctgt                                                              10

<210> SEQ ID NO 862
<211> LENGTH: 10
<212> TYPE: DNA
<213> ORGANISM: Artificial sequence
<220> FEATURE:
<223> OTHER INFORMATION: Primer OPAQ-13

<400> SEQUENCE: 862
gagtcggctg                                                              10

<210> SEQ ID NO 863
<211> LENGTH: 10
<212> TYPE: DNA
<213> ORGANISM: Artificial sequence
<220> FEATURE:
<223> OTHER INFORMATION: Primer OPAQ-14

<400> SEQUENCE: 863
cccgtgtagg                                                              10

<210> SEQ ID NO 864
<211> LENGTH: 10
<212> TYPE: DNA
<213> ORGANISM: Artificial sequence
<220> FEATURE:
<223> OTHER INFORMATION: Primer OPAQ-15

<400> SEQUENCE: 864
tgcgatgcga                                                              10

<210> SEQ ID NO 865
<211> LENGTH: 10
<212> TYPE: DNA
<213> ORGANISM: Artificial sequence
<220> FEATURE:
<223> OTHER INFORMATION: Primer OPAQ-16

<400> SEQUENCE: 865
cccggaagag                                                              10

<210> SEQ ID NO 866
<211> LENGTH: 10
<212> TYPE: DNA
<213> ORGANISM: Artificial sequence
<220> FEATURE:
<223> OTHER INFORMATION: Primer OPAQ-17

<400> SEQUENCE: 866
ttcgcctgtc                                                              10

<210> SEQ ID NO 867
<211> LENGTH: 10
<212> TYPE: DNA
<213> ORGANISM: Artificial sequence
<220> FEATURE:
<223> OTHER INFORMATION: Primer OPAQ-18

<400> SEQUENCE: 867
gggagcgagt                                                              10

<210> SEQ ID NO 868
<211> LENGTH: 10
<212> TYPE: DNA
<213> ORGANISM: Artificial sequence
<220> FEATURE:
<223> OTHER INFORMATION: Primer OPAQ-19

<400> SEQUENCE: 868
agtagggcct                                                              10

<210> SEQ ID NO 869
<211> LENGTH: 10
<212> TYPE: DNA
<213> ORGANISM: Artificial sequence
<220> FEATURE:
<223> OTHER INFORMATION: Primer OPAQ-20

<400> SEQUENCE: 869
gtgaacgctc                                                              10

<210> SEQ ID NO 870
<211> LENGTH: 10
<212> TYPE: DNA
<213> ORGANISM: Artificial sequence
<220> FEATURE:
<223> OTHER INFORMATION: Primer OPAR-01

<400> SEQUENCE: 870
ccattccgag                                                              10

<210> SEQ ID NO 871
<211> LENGTH: 10
<212> TYPE: DNA
<213> ORGANISM: Artificial sequence
<220> FEATURE:
<223> OTHER INFORMATION: Primer OPAR-02

<400> SEQUENCE: 871
cacctgctga                                                              10

<210> SEQ ID NO 872
<211> LENGTH: 10
<212> TYPE: DNA
<213> ORGANISM: Artificial sequence
<220> FEATURE:
<223> OTHER INFORMATION: Primer OPAR-03

```
<400> SEQUENCE: 872
gtgaggcgca                                                        10

<210> SEQ ID NO 873
<211> LENGTH: 10
<212> TYPE: DNA
<213> ORGANISM: Artificial sequence
<220> FEATURE:
<223> OTHER INFORMATION: Primer OPAR-04

<400> SEQUENCE: 873
ccaggagaag                                                        10

<210> SEQ ID NO 874
<211> LENGTH: 10
<212> TYPE: DNA
<213> ORGANISM: Artificial sequence
<220> FEATURE:
<223> OTHER INFORMATION: Primer OPAR-05

<400> SEQUENCE: 874
catacctgcc                                                        10

<210> SEQ ID NO 875
<211> LENGTH: 10
<212> TYPE: DNA
<213> ORGANISM: Artificial sequence
<220> FEATURE:
<223> OTHER INFORMATION: Primer OPAR-06

<400> SEQUENCE: 875
tggggctcaa                                                        10

<210> SEQ ID NO 876
<211> LENGTH: 10
<212> TYPE: DNA
<213> ORGANISM: Artificial sequence
<220> FEATURE:
<223> OTHER INFORMATION: Primer OPAR-07

<400> SEQUENCE: 876
tccttcggtg                                                        10

<210> SEQ ID NO 877
<211> LENGTH: 10
<212> TYPE: DNA
<213> ORGANISM: Artificial sequence
<220> FEATURE:
<223> OTHER INFORMATION: Primer OPAR-08

<400> SEQUENCE: 877
gtgaatgcgg                                                        10

<210> SEQ ID NO 878
<211> LENGTH: 10
<212> TYPE: DNA
<213> ORGANISM: Artificial sequence
<220> FEATURE:
<223> OTHER INFORMATION: Primer OPAR-09

<400> SEQUENCE: 878
ggggtgttct                                                        10

<210> SEQ ID NO 879
<211> LENGTH: 10
```

<210> SEQ ID NO 879
<211> LENGTH: 10
<212> TYPE: DNA
<213> ORGANISM: Artificial sequence
<220> FEATURE:
<223> OTHER INFORMATION: Primer OPAR-10

<400> SEQUENCE: 879
tggggctgtc                                                                10

<210> SEQ ID NO 880
<211> LENGTH: 10
<212> TYPE: DNA
<213> ORGANISM: Artificial sequence
<220> FEATURE:
<223> OTHER INFORMATION: Primer OPAR-11

<400> SEQUENCE: 880
gggaagacgg                                                                10

<210> SEQ ID NO 881
<211> LENGTH: 10
<212> TYPE: DNA
<213> ORGANISM: Artificial sequence
<220> FEATURE:
<223> OTHER INFORMATION: Primer OPAR-12

<400> SEQUENCE: 881
ggatcgtcgg                                                                10

<210> SEQ ID NO 882
<211> LENGTH: 10
<212> TYPE: DNA
<213> ORGANISM: Artificial sequence
<220> FEATURE:
<223> OTHER INFORMATION: Primer OPAR-13

<400> SEQUENCE: 882
gggtcggctt                                                                10

<210> SEQ ID NO 883
<211> LENGTH: 10
<212> TYPE: DNA
<213> ORGANISM: Artificial sequence
<220> FEATURE:
<223> OTHER INFORMATION: Primer OPAR-14

<400> SEQUENCE: 883
ctcacagcac                                                                10

<210> SEQ ID NO 884
<211> LENGTH: 10
<212> TYPE: DNA
<213> ORGANISM: Artificial sequence
<220> FEATURE:
<223> OTHER INFORMATION: Primer OPAR-15

<400> SEQUENCE: 884
acactctgcc                                                                10

<210> SEQ ID NO 885
<211> LENGTH: 10
<212> TYPE: DNA
<213> ORGANISM: Artificial sequence
<220> FEATURE:
<223> OTHER INFORMATION: Primer OPAR-16

<400> SEQUENCE: 885
ccttgcgcct                                                                10

<210> SEQ ID NO 886
<211> LENGTH: 10
<212> TYPE: DNA
<213> ORGANISM: Artificial sequence
<220> FEATURE:
<223> OTHER INFORMATION: Primer OPAR-17

<400> SEQUENCE: 886 ccaccacgac								10

<210> SEQ ID NO 887
<211> LENGTH: 10
<212> TYPE: DNA
<213> ORGANISM: Artificial sequence
<220> FEATURE:
<223> OTHER INFORMATION: Primer OPAR-18

<400> SEQUENCE: 887 ctaccggcac								10

<210> SEQ ID NO 888
<211> LENGTH: 10
<212> TYPE: DNA
<213> ORGANISM: Artificial sequence
<220> FEATURE:
<223> OTHER INFORMATION: Primer OPAR-19

<400> SEQUENCE: 888 ctgatcgcgg								10

<210> SEQ ID NO 889
<211> LENGTH: 10
<212> TYPE: DNA
<213> ORGANISM: Artificial sequence
<220> FEATURE:
<223> OTHER INFORMATION: Primer OPAR-20

<400> SEQUENCE: 889 tgcgccatcc								10

<210> SEQ ID NO 890
<211> LENGTH: 10
<212> TYPE: DNA
<213> ORGANISM: Artificial sequence
<220> FEATURE:
<223> OTHER INFORMATION: Primer OPAS-01

<400> SEQUENCE: 890 cacaccgtgt								10

<210> SEQ ID NO 891
<211> LENGTH: 10
<212> TYPE: DNA
<213> ORGANISM: Artificial sequence
<220> FEATURE:
<223> OTHER INFORMATION: Primer OPAS-02

<400> SEQUENCE: 891 gtcctcgtgt								10

<210> SEQ ID NO 892
<211> LENGTH: 10
<212> TYPE: DNA
<213> ORGANISM: Artificial sequence
<220> FEATURE:
<223> OTHER INFORMATION: Primer OPAS-03

<400> SEQUENCE: 892
acggttccac                                                              10

<210> SEQ ID NO 893
<211> LENGTH: 10
<212> TYPE: DNA
<213> ORGANISM: Artificial sequence
<220> FEATURE:
<223> OTHER INFORMATION: Primer OPAS-04

<400> SEQUENCE: 893
gtcttgggca                                                              10

<210> SEQ ID NO 894
<211> LENGTH: 10
<212> TYPE: DNA
<213> ORGANISM: Artificial sequence
<220> FEATURE:
<223> OTHER INFORMATION: Primer OPAS-05

<400> SEQUENCE: 894
gtcacctgct                                                              10

<210> SEQ ID NO 895
<211> LENGTH: 10
<212> TYPE: DNA
<213> ORGANISM: Artificial sequence
<220> FEATURE:
<223> OTHER INFORMATION: Primer OPAS-06

<400> SEQUENCE: 895
ggcgcgttag                                                              10

<210> SEQ ID NO 896
<211> LENGTH: 10
<212> TYPE: DNA
<213> ORGANISM: Artificial sequence
<220> FEATURE:
<223> OTHER INFORMATION: Primer OPAS-07

<400> SEQUENCE: 896
gacgagcagg                                                              10

<210> SEQ ID NO 897
<211> LENGTH: 10
<212> TYPE: DNA
<213> ORGANISM: Artificial sequence
<220> FEATURE:
<223> OTHER INFORMATION: Primer OPAS-08

<400> SEQUENCE: 897
ggctgccagt                                                              10

<210> SEQ ID NO 898
<211> LENGTH: 10
<212> TYPE: DNA
<213> ORGANISM: Artificial sequence
<220> FEATURE:
<223> OTHER INFORMATION: Primer OPAS-09

<400> SEQUENCE: 898
tggagtcccc                                                              10

<210> SEQ ID NO 899
<211> LENGTH: 10

-continued

<212> TYPE: DNA
<213> ORGANISM: Artificial sequence
<220> FEATURE:
<223> OTHER INFORMATION: Primer OPAS-10

<400> SEQUENCE: 899
cccgtctacc                                                            10

<210> SEQ ID NO 900
<211> LENGTH: 10
<212> TYPE: DNA
<213> ORGANISM: Artificial sequence
<220> FEATURE:
<223> OTHER INFORMATION: Primer OPAS-11

<400> SEQUENCE: 900
accgtgccgt                                                            10

<210> SEQ ID NO 901
<211> LENGTH: 10
<212> TYPE: DNA
<213> ORGANISM: Artificial sequence
<220> FEATURE:
<223> OTHER INFORMATION: Primer OPAS-12

<400> SEQUENCE: 901
tgaccaggca                                                            10

<210> SEQ ID NO 902
<211> LENGTH: 10
<212> TYPE: DNA
<213> ORGANISM: Artificial sequence
<220> FEATURE:
<223> OTHER INFORMATION: Primer OPAS-13

<400> SEQUENCE: 902
cacggaccga                                                            10

<210> SEQ ID NO 903
<211> LENGTH: 10
<212> TYPE: DNA
<213> ORGANISM: Artificial sequence
<220> FEATURE:
<223> OTHER INFORMATION: Primer OPAS-14

<400> SEQUENCE: 903
tcgcagcgtt                                                            10

<210> SEQ ID NO 904
<211> LENGTH: 10
<212> TYPE: DNA
<213> ORGANISM: Artificial sequence
<220> FEATURE:
<223> OTHER INFORMATION: Primer OPAS-15

<400> SEQUENCE: 904
ctgcaatggg                                                            10

<210> SEQ ID NO 905
<211> LENGTH: 10
<212> TYPE: DNA
<213> ORGANISM: Artificial sequence
<220> FEATURE:
<223> OTHER INFORMATION: Primer OPAS-16

<400> SEQUENCE: 905 aaccctteee                                                            10

<210> SEQ ID NO 906
<211> LENGTH: 10
<212> TYPE: DNA
<213> ORGANISM: Artificial sequence
<220> FEATURE:
<223> OTHER INFORMATION: Primer OPAS-17

<400> SEQUENCE: 906
agttccgcga                                                                 10

<210> SEQ ID NO 907
<211> LENGTH: 10
<212> TYPE: DNA
<213> ORGANISM: Artificial sequence
<220> FEATURE:
<223> OTHER INFORMATION: Primer OPAS-18

<400> SEQUENCE: 907
gttgcgcagt                                                                 10

<210> SEQ ID NO 908
<211> LENGTH: 10
<212> TYPE: DNA
<213> ORGANISM: Artificial sequence
<220> FEATURE:
<223> OTHER INFORMATION: Primer OPAS-19

<400> SEQUENCE: 908
tgacagcccc                                                                 10

<210> SEQ ID NO 909
<211> LENGTH: 10
<212> TYPE: DNA
<213> ORGANISM: Artificial sequence
<220> FEATURE:
<223> OTHER INFORMATION: Primer OPAS-20

<400> SEQUENCE: 909
tctgcctgga                                                                 10

<210> SEQ ID NO 910
<211> LENGTH: 10
<212> TYPE: DNA
<213> ORGANISM: Artificial sequence
<220> FEATURE:
<223> OTHER INFORMATION: Primer OPAT-01

<400> SEQUENCE: 910
cagtggttcc                                                                 10

<210> SEQ ID NO 911
<211> LENGTH: 10
<212> TYPE: DNA
<213> ORGANISM: Artificial sequence
<220> FEATURE:
<223> OTHER INFORMATION: Primer OPAT-02

<400> SEQUENCE: 911
caggtctagg                                                                 10

<210> SEQ ID NO 912
<211> LENGTH: 10
<212> TYPE: DNA
<213> ORGANISM: Artificial sequence
<220> FEATURE:
<223> OTHER INFORMATION: Primer OPAT-03

```
<400> SEQUENCE: 912
gactgggagg                                                              10

<210> SEQ ID NO 913
<211> LENGTH: 10
<212> TYPE: DNA
<213> ORGANISM: Artificial sequence
<220> FEATURE:
<223> OTHER INFORMATION: Primer OPAT-04

<400> SEQUENCE: 913
ttgcctcgcc                                                              10

<210> SEQ ID NO 914
<211> LENGTH: 10
<212> TYPE: DNA
<213> ORGANISM: Artificial sequence
<220> FEATURE:
<223> OTHER INFORMATION: Primer OPAT-05

<400> SEQUENCE: 914
acacctgcca                                                              10

<210> SEQ ID NO 915
<211> LENGTH: 10
<212> TYPE: DNA
<213> ORGANISM: Artificial sequence
<220> FEATURE:
<223> OTHER INFORMATION: Primer OPAT-06

<400> SEQUENCE: 915
ccgtccctga                                                              10

<210> SEQ ID NO 916
<211> LENGTH: 10
<212> TYPE: DNA
<213> ORGANISM: Artificial sequence
<220> FEATURE:
<223> OTHER INFORMATION: Primer OPAT-07

<400> SEQUENCE: 916
actgcgacca                                                              10

<210> SEQ ID NO 917
<211> LENGTH: 10
<212> TYPE: DNA
<213> ORGANISM: Artificial sequence
<220> FEATURE:
<223> OTHER INFORMATION: Primer OPAT-08

<400> SEQUENCE: 917
tcctcgtggg                                                              10

<210> SEQ ID NO 918
<211> LENGTH: 10
<212> TYPE: DNA
<213> ORGANISM: Artificial sequence
<220> FEATURE:
<223> OTHER INFORMATION: Primer OPAT-09

<400> SEQUENCE: 918
ccgttagcgt                                                              10

<210> SEQ ID NO 919
<211> LENGTH: 10
```

<212> TYPE: DNA
<213> ORGANISM: Artificial sequence
<220> FEATURE:
<223> OTHER INFORMATION: Primer OPAT-10

<400> SEQUENCE: 919
acctccggtc                                                          10

<210> SEQ ID NO 920
<211> LENGTH: 10
<212> TYPE: DNA
<213> ORGANISM: Artificial sequence
<220> FEATURE:
<223> OTHER INFORMATION: Primer OPAT-11

<400> SEQUENCE: 920
ccagatctcc                                                          10

<210> SEQ ID NO 921
<211> LENGTH: 10
<212> TYPE: DNA
<213> ORGANISM: Artificial sequence
<220> FEATURE:
<223> OTHER INFORMATION: Primer OPAT-12

<400> SEQUENCE: 921
ctgcctagcc                                                          10

<210> SEQ ID NO 922
<211> LENGTH: 10
<212> TYPE: DNA
<213> ORGANISM: Artificial sequence
<220> FEATURE:
<223> OTHER INFORMATION: Primer OPAT-13

<400> SEQUENCE: 922
ctggtggaag                                                          10

<210> SEQ ID NO 923
<211> LENGTH: 10
<212> TYPE: DNA
<213> ORGANISM: Artificial sequence
<220> FEATURE:
<223> OTHER INFORMATION: Primer OPAT-14

<400> SEQUENCE: 923
gtgccgcact                                                          10

<210> SEQ ID NO 924
<211> LENGTH: 10
<212> TYPE: DNA
<213> ORGANISM: Artificial sequence
<220> FEATURE:
<223> OTHER INFORMATION: Primer OPAT-15

<400> SEQUENCE: 924
tgacgcacgg                                                          10

<210> SEQ ID NO 925
<211> LENGTH: 10
<212> TYPE: DNA
<213> ORGANISM: Artificial sequence
<220> FEATURE:
<223> OTHER INFORMATION: Primer OPAT-16

<400> SEQUENCE: 925
ctctccgtag                                                          10

<210> SEQ ID NO 926
<211> LENGTH: 10
<212> TYPE: DNA
<213> ORGANISM: Artificial sequence
<220> FEATURE:
<223> OTHER INFORMATION: Primer OPAT-17

<400> SEQUENCE: 926 agcgactgct					10

<210> SEQ ID NO 927
<211> LENGTH: 10
<212> TYPE: DNA
<213> ORGANISM: Artificial sequence
<220> FEATURE:
<223> OTHER INFORMATION: Primer OPAT-18

<400> SEQUENCE: 927 ccagctgtga					10

<210> SEQ ID NO 928
<211> LENGTH: 10
<212> TYPE: DNA
<213> ORGANISM: Artificial sequence
<220> FEATURE:
<223> OTHER INFORMATION: Primer OPAT-19

<400> SEQUENCE: 928 accaaggcac					10

<210> SEQ ID NO 929
<211> LENGTH: 10
<212> TYPE: DNA
<213> ORGANISM: Artificial sequence
<220> FEATURE:
<223> OTHER INFORMATION: Primer OPAT-20

<400> SEQUENCE: 929 acatcagccc					10

<210> SEQ ID NO 930
<211> LENGTH: 10
<212> TYPE: DNA
<213> ORGANISM: Artificial sequence
<220> FEATURE:
<223> OTHER INFORMATION: Primer OPAU-01

<400> SEQUENCE: 930 gggatggaac					10

<210> SEQ ID NO 931
<211> LENGTH: 10
<212> TYPE: DNA
<213> ORGANISM: Artificial sequence
<220> FEATURE:
<223> OTHER INFORMATION: Primer OPAU-02

<400> SEQUENCE: 931 ccaacccgca					10

<210> SEQ ID NO 932
<211> LENGTH: 10
<212> TYPE: DNA
<213> ORGANISM: Artificial sequence
<220> FEATURE:
<223> OTHER INFORMATION: Primer OPAU-03

```
<400> SEQUENCE: 932
acgaaacggg                                                         10

<210> SEQ ID NO 933
<211> LENGTH: 10
<212> TYPE: DNA
<213> ORGANISM: Artificial sequence
<220> FEATURE:
<223> OTHER INFORMATION: Primer OPAU-04

<400> SEQUENCE: 933
ggcttctgtc                                                         10

<210> SEQ ID NO 934
<211> LENGTH: 10
<212> TYPE: DNA
<213> ORGANISM: Artificial sequence
<220> FEATURE:
<223> OTHER INFORMATION: Primer OPAU-05

<400> SEQUENCE: 934
gagctaccgt                                                         10

<210> SEQ ID NO 935
<211> LENGTH: 10
<212> TYPE: DNA
<213> ORGANISM: Artificial sequence
<220> FEATURE:
<223> OTHER INFORMATION: Primer OPAU-06

<400> SEQUENCE: 935
tctctagggg                                                         10

<210> SEQ ID NO 936
<211> LENGTH: 10
<212> TYPE: DNA
<213> ORGANISM: Artificial sequence
<220> FEATURE:
<223> OTHER INFORMATION: Primer OPAU-07

<400> SEQUENCE: 936
agacccttgg                                                         10

<210> SEQ ID NO 937
<211> LENGTH: 10
<212> TYPE: DNA
<213> ORGANISM: Artificial sequence
<220> FEATURE:
<223> OTHER INFORMATION: Primer OPAU-08

<400> SEQUENCE: 937
caccgatcca                                                         10

<210> SEQ ID NO 938
<211> LENGTH: 10
<212> TYPE: DNA
<213> ORGANISM: Artificial sequence
<220> FEATURE:
<223> OTHER INFORMATION: Primer OPAU-09

<400> SEQUENCE: 938
acggccaatc                                                         10

<210> SEQ ID NO 939
<211> LENGTH: 10
```

<212> TYPE: DNA
<213> ORGANISM: Artificial sequence
<220> FEATURE:
<223> OTHER INFORMATION: Primer OPAU-10

<400> SEQUENCE: 939
ggcgtatggt                                                          10

<210> SEQ ID NO 940
<211> LENGTH: 10
<212> TYPE: DNA
<213> ORGANISM: Artificial sequence
<220> FEATURE:
<223> OTHER INFORMATION: Primer OPAU-11

<400> SEQUENCE: 940
cttctcggtc                                                          10

<210> SEQ ID NO 941
<211> LENGTH: 10
<212> TYPE: DNA
<213> ORGANISM: Artificial sequence
<220> FEATURE:
<223> OTHER INFORMATION: Primer OPAU-12

<400> SEQUENCE: 941
ccactcgtgt                                                          10

<210> SEQ ID NO 942
<211> LENGTH: 10
<212> TYPE: DNA
<213> ORGANISM: Artificial sequence
<220> FEATURE:
<223> OTHER INFORMATION: Primer OPAU-13

<400> SEQUENCE: 942
ccaagcacac                                                          10

<210> SEQ ID NO 943
<211> LENGTH: 10
<212> TYPE: DNA
<213> ORGANISM: Artificial sequence
<220> FEATURE:
<223> OTHER INFORMATION: Primer OPAU-14

<400> SEQUENCE: 943
cacctcgacc                                                          10

<210> SEQ ID NO 944
<211> LENGTH: 10
<212> TYPE: DNA
<213> ORGANISM: Artificial sequence
<220> FEATURE:
<223> OTHER INFORMATION: Primer OPAU-15

<400> SEQUENCE: 944
tgctgacgac                                                          10

<210> SEQ ID NO 945
<211> LENGTH: 10
<212> TYPE: DNA
<213> ORGANISM: Artificial sequence
<220> FEATURE:
<223> OTHER INFORMATION: Primer OPAU-16

<400> SEQUENCE: 945
tcttaggcgg                                                          10

<210> SEQ ID NO 946
<211> LENGTH: 10
<212> TYPE: DNA
<213> ORGANISM: Artificial sequence
<220> FEATURE:
<223> OTHER INFORMATION: Primer OPAU-17

<400> SEQUENCE: 946
ttggcatccc                                                          10

<210> SEQ ID NO 947
<211> LENGTH: 10
<212> TYPE: DNA
<213> ORGANISM: Artificial sequence
<220> FEATURE:
<223> OTHER INFORMATION: Primer OPAU-18

<400> SEQUENCE: 947
caccactagg                                                          10

<210> SEQ ID NO 948
<211> LENGTH: 10
<212> TYPE: DNA
<213> ORGANISM: Artificial sequence
<220> FEATURE:
<223> OTHER INFORMATION: Primer OPAU-19

<400> SEQUENCE: 948
agcctgggga                                                          10

<210> SEQ ID NO 949
<211> LENGTH: 10
<212> TYPE: DNA
<213> ORGANISM: Artificial sequence
<220> FEATURE:
<223> OTHER INFORMATION: Primer OPAU-20

<400> SEQUENCE: 949
gtcgaaaccc                                                          10

<210> SEQ ID NO 950
<211> LENGTH: 10
<212> TYPE: DNA
<213> ORGANISM: Artificial sequence
<220> FEATURE:
<223> OTHER INFORMATION: Primer OPAV-01

<400> SEQUENCE: 950
tgaggggaa                                                           10

<210> SEQ ID NO 951
<211> LENGTH: 10
<212> TYPE: DNA
<213> ORGANISM: Artificial sequence
<220> FEATURE:
<223> OTHER INFORMATION: Primer OPAV-02

<400> SEQUENCE: 951
tcaccgtgtc                                                          10

<210> SEQ ID NO 952
<211> LENGTH: 10
<212> TYPE: DNA
<213> ORGANISM: Artificial sequence
<220> FEATURE:
<223> OTHER INFORMATION: Primer OPAV-03

```
<400> SEQUENCE: 952
tgtagccgtg                                                              10

<210> SEQ ID NO 953
<211> LENGTH: 10
<212> TYPE: DNA
<213> ORGANISM: Artificial sequence
<220> FEATURE:
<223> OTHER INFORMATION: Primer OPAV-04

<400> SEQUENCE: 953
tctgccatcc                                                              10

<210> SEQ ID NO 954
<211> LENGTH: 10
<212> TYPE: DNA
<213> ORGANISM: Artificial sequence
<220> FEATURE:
<223> OTHER INFORMATION: Primer OPAV-05

<400> SEQUENCE: 954
gtgagcgtgg                                                              10

<210> SEQ ID NO 955
<211> LENGTH: 10
<212> TYPE: DNA
<213> ORGANISM: Artificial sequence
<220> FEATURE:
<223> OTHER INFORMATION: Primer OPAV-06

<400> SEQUENCE: 955
cccgagatcc                                                              10

<210> SEQ ID NO 956
<211> LENGTH: 10
<212> TYPE: DNA
<213> ORGANISM: Artificial sequence
<220> FEATURE:
<223> OTHER INFORMATION: Primer OPAV-07

<400> SEQUENCE: 956
ctaccaggga                                                              10

<210> SEQ ID NO 957
<211> LENGTH: 10
<212> TYPE: DNA
<213> ORGANISM: Artificial sequence
<220> FEATURE:
<223> OTHER INFORMATION: Primer OPAV-08

<400> SEQUENCE: 957
tgagaagcgg                                                              10

<210> SEQ ID NO 958
<211> LENGTH: 10
<212> TYPE: DNA
<213> ORGANISM: Artificial sequence
<220> FEATURE:
<223> OTHER INFORMATION: Primer OPAV-09

<400> SEQUENCE: 958
gaggtcctac                                                              10

<210> SEQ ID NO 959
<211> LENGTH: 10
```

<212> TYPE: DNA
<213> ORGANISM: Artificial sequence
<220> FEATURE:
<223> OTHER INFORMATION: Primer OPAV-10

<400> SEQUENCE: 959 accccctggca                                                           10

<210> SEQ ID NO 960
<211> LENGTH: 10
<212> TYPE: DNA
<213> ORGANISM: Artificial sequence
<220> FEATURE:
<223> OTHER INFORMATION: Primer OPAV-11

<400> SEQUENCE: 960
gaccccgaca                                                            10

<210> SEQ ID NO 961
<211> LENGTH: 10
<212> TYPE: DNA
<213> ORGANISM: Artificial sequence
<220> FEATURE:
<223> OTHER INFORMATION: Primer OPAV-12

<400> SEQUENCE: 961
agccgtcgaa                                                            10

<210> SEQ ID NO 962
<211> LENGTH: 10
<212> TYPE: DNA
<213> ORGANISM: Artificial sequence
<220> FEATURE:
<223> OTHER INFORMATION: Primer OPAV-13

<400> SEQUENCE: 962
ctgacttccc                                                            10

<210> SEQ ID NO 963
<211> LENGTH: 10
<212> TYPE: DNA
<213> ORGANISM: Artificial sequence
<220> FEATURE:
<223> OTHER INFORMATION: Primer OPAV-14

<400> SEQUENCE: 963
ctccggatca                                                            10

<210> SEQ ID NO 964
<211> LENGTH: 10
<212> TYPE: DNA
<213> ORGANISM: Artificial sequence
<220> FEATURE:
<223> OTHER INFORMATION: Primer OPAV-15

<400> SEQUENCE: 964
ggcagcaggt                                                            10

<210> SEQ ID NO 965
<211> LENGTH: 10
<212> TYPE: DNA
<213> ORGANISM: Artificial sequence
<220> FEATURE:
<223> OTHER INFORMATION: Primer OPAV-16

<400> SEQUENCE: 965
gacaaggacc                                                            10

<210> SEQ ID NO 966
<211> LENGTH: 10
<212> TYPE: DNA
<213> ORGANISM: Artificial sequence
<220> FEATURE:
<223> OTHER INFORMATION: Primer OPAV-17

<400> SEQUENCE: 966
ctcgaacccc                                                            10

<210> SEQ ID NO 967
<211> LENGTH: 10
<212> TYPE: DNA
<213> ORGANISM: Artificial sequence
<220> FEATURE:
<223> OTHER INFORMATION: Primer OPAV-18

<400> SEQUENCE: 967
ttgctcacgg                                                            10

<210> SEQ ID NO 968
<211> LENGTH: 10
<212> TYPE: DNA
<213> ORGANISM: Artificial sequence
<220> FEATURE:
<223> OTHER INFORMATION: Primer OPAV-19

<400> SEQUENCE: 968
ctcgatcacc                                                            10

<210> SEQ ID NO 969
<211> LENGTH: 10
<212> TYPE: DNA
<213> ORGANISM: Artificial sequence
<220> FEATURE:
<223> OTHER INFORMATION: Primer OPAV-20

<400> SEQUENCE: 969
tcatgcgcac                                                            10

<210> SEQ ID NO 970
<211> LENGTH: 10
<212> TYPE: DNA
<213> ORGANISM: Artificial sequence
<220> FEATURE:
<223> OTHER INFORMATION: Primer OPAW-01

<400> SEQUENCE: 970
acctagggga                                                            10

<210> SEQ ID NO 971
<211> LENGTH: 10
<212> TYPE: DNA
<213> ORGANISM: Artificial sequence
<220> FEATURE:
<223> OTHER INFORMATION: Primer OPAW-02

<400> SEQUENCE: 971
tcgcaggttc                                                            10

<210> SEQ ID NO 972
<211> LENGTH: 10
<212> TYPE: DNA
<213> ORGANISM: Artificial sequence
<220> FEATURE:
<223> OTHER INFORMATION: Primer OPAW-03

```
<400> SEQUENCE: 972
ccatgcggag                                                              10

<210> SEQ ID NO 973
<211> LENGTH: 10
<212> TYPE: DNA
<213> ORGANISM: Artificial sequence
<220> FEATURE:
<223> OTHER INFORMATION: Primer OPAW-04

<400> SEQUENCE: 973
aggagcgaca                                                              10

<210> SEQ ID NO 974
<211> LENGTH: 10
<212> TYPE: DNA
<213> ORGANISM: Artificial sequence
<220> FEATURE:
<223> OTHER INFORMATION: Primer OPAW-05

<400> SEQUENCE: 974
ctgcttcgag                                                              10

<210> SEQ ID NO 975
<211> LENGTH: 10
<212> TYPE: DNA
<213> ORGANISM: Artificial sequence
<220> FEATURE:
<223> OTHER INFORMATION: Primer OPAW-06

<400> SEQUENCE: 975
tttgggcccc                                                              10

<210> SEQ ID NO 976
<211> LENGTH: 10
<212> TYPE: DNA
<213> ORGANISM: Artificial sequence
<220> FEATURE:
<223> OTHER INFORMATION: Primer OPAW-07

<400> SEQUENCE: 976
agcccccaag                                                              10

<210> SEQ ID NO 977
<211> LENGTH: 10
<212> TYPE: DNA
<213> ORGANISM: Artificial sequence
<220> FEATURE:
<223> OTHER INFORMATION: Primer OPAW-08

<400> SEQUENCE: 977
ctgtctgtgg                                                              10

<210> SEQ ID NO 978
<211> LENGTH: 10
<212> TYPE: DNA
<213> ORGANISM: Artificial sequence
<220> FEATURE:
<223> OTHER INFORMATION: Primer OPAW-09

<400> SEQUENCE: 978
actgggtcgg                                                              10

<210> SEQ ID NO 979
<211> LENGTH: 10
```

```
<212> TYPE: DNA
<213> ORGANISM: Artificial sequence
<220> FEATURE:
<223> OTHER INFORMATION: Primer OPAW-10

<400> SEQUENCE: 979
ggtgtttgcc                                                          10

<210> SEQ ID NO 980
<211> LENGTH: 10
<212> TYPE: DNA
<213> ORGANISM: Artificial sequence
<220> FEATURE:
<223> OTHER INFORMATION: Primer OPAW-11

<400> SEQUENCE: 980
ctgccacgag                                                          10

<210> SEQ ID NO 981
<211> LENGTH: 10
<212> TYPE: DNA
<213> ORGANISM: Artificial sequence
<220> FEATURE:
<223> OTHER INFORMATION: Primer OPAW-12

<400> SEQUENCE: 981
gagcaaggca                                                          10

<210> SEQ ID NO 982
<211> LENGTH: 10
<212> TYPE: DNA
<213> ORGANISM: Artificial sequence
<220> FEATURE:
<223> OTHER INFORMATION: Primer OPAW-13

<400> SEQUENCE: 982
ctacgatgcc                                                          10

<210> SEQ ID NO 983
<211> LENGTH: 10
<212> TYPE: DNA
<213> ORGANISM: Artificial sequence
<220> FEATURE:
<223> OTHER INFORMATION: Primer OPAW-14

<400> SEQUENCE: 983
ggttctgctc                                                          10

<210> SEQ ID NO 984
<211> LENGTH: 10
<212> TYPE: DNA
<213> ORGANISM: Artificial sequence
<220> FEATURE:
<223> OTHER INFORMATION: Primer OPAW-15

<400> SEQUENCE: 984
ccagtcccaa                                                          10

<210> SEQ ID NO 985
<211> LENGTH: 10
<212> TYPE: DNA
<213> ORGANISM: Artificial sequence
<220> FEATURE:
<223> OTHER INFORMATION: Primer OPAW-16

<400> SEQUENCE: 985
ttaccccgct                                                          10
```

<210> SEQ ID NO 986
<211> LENGTH: 10
<212> TYPE: DNA
<213> ORGANISM: Artificial sequence
<220> FEATURE:
<223> OTHER INFORMATION: Primer OPAW-17

<400> SEQUENCE: 986
tgctgctgcc                                                          10

<210> SEQ ID NO 987
<211> LENGTH: 10
<212> TYPE: DNA
<213> ORGANISM: Artificial sequence
<220> FEATURE:
<223> OTHER INFORMATION: Primer OPAW-18

<400> SEQUENCE: 987
ggcgcaactg                                                          10

<210> SEQ ID NO 988
<211> LENGTH: 10
<212> TYPE: DNA
<213> ORGANISM: Artificial sequence
<220> FEATURE:
<223> OTHER INFORMATION: Primer OPAW-19

<400> SEQUENCE: 988
ggacacagag                                                          10

<210> SEQ ID NO 989
<211> LENGTH: 10
<212> TYPE: DNA
<213> ORGANISM: Artificial sequence
<220> FEATURE:
<223> OTHER INFORMATION: Primer OPAW-20

<400> SEQUENCE: 989
tgtcctagcc                                                          10

<210> SEQ ID NO 990
<211> LENGTH: 10
<212> TYPE: DNA
<213> ORGANISM: Artificial sequence
<220> FEATURE:
<223> OTHER INFORMATION: Primer OPAX-01

<400> SEQUENCE: 990
gtgtgccgtt                                                          10

<210> SEQ ID NO 991
<211> LENGTH: 10
<212> TYPE: DNA
<213> ORGANISM: Artificial sequence
<220> FEATURE:
<223> OTHER INFORMATION: Primer OPAX-02

<400> SEQUENCE: 991
gggaggcaaa                                                          10

<210> SEQ ID NO 992
<211> LENGTH: 10
<212> TYPE: DNA
<213> ORGANISM: Artificial sequence
<220> FEATURE:
<223> OTHER INFORMATION: Primer OPAX-03

```
<400> SEQUENCE: 992
ccaagaggct                                                          10

<210> SEQ ID NO 993
<211> LENGTH: 10
<212> TYPE: DNA
<213> ORGANISM: Artificial sequence
<220> FEATURE:
<223> OTHER INFORMATION: Primer OPAX-04

<400> SEQUENCE: 993
tccccaggag                                                          10

<210> SEQ ID NO 994
<211> LENGTH: 10
<212> TYPE: DNA
<213> ORGANISM: Artificial sequence
<220> FEATURE:
<223> OTHER INFORMATION: Primer OPAX-05

<400> SEQUENCE: 994
agtgcacacc                                                          10

<210> SEQ ID NO 995
<211> LENGTH: 10
<212> TYPE: DNA
<213> ORGANISM: Artificial sequence
<220> FEATURE:
<223> OTHER INFORMATION: Primer OPAX-06

<400> SEQUENCE: 995
aggcatcgtg                                                          10

<210> SEQ ID NO 996
<211> LENGTH: 10
<212> TYPE: DNA
<213> ORGANISM: Artificial sequence
<220> FEATURE:
<223> OTHER INFORMATION: Primer OPAX-07

<400> SEQUENCE: 996
acgcgacaga                                                          10

<210> SEQ ID NO 997
<211> LENGTH: 10
<212> TYPE: DNA
<213> ORGANISM: Artificial sequence
<220> FEATURE:
<223> OTHER INFORMATION: Primer OPAX-08

<400> SEQUENCE: 997
agtatggcgg                                                          10

<210> SEQ ID NO 998
<211> LENGTH: 10
<212> TYPE: DNA
<213> ORGANISM: Artificial sequence
<220> FEATURE:
<223> OTHER INFORMATION: Primer OPAX-09

<400> SEQUENCE: 998
ggaagtcctg                                                          10

<210> SEQ ID NO 999
<211> LENGTH: 10
```

-continued

<212> TYPE: DNA
<213> ORGANISM: Artificial sequence
<220> FEATURE:
<223> OTHER INFORMATION: Primer OPAX-10

<400> SEQUENCE: 999 ccaggctgac					10

<210> SEQ ID NO 1000
<211> LENGTH: 10
<212> TYPE: DNA
<213> ORGANISM: Artificial sequence
<220> FEATURE:
<223> OTHER INFORMATION: Primer OPAX-11

<400> SEQUENCE: 1000 tgattgcggg					10

<210> SEQ ID NO 1001
<211> LENGTH: 10
<212> TYPE: DNA
<213> ORGANISM: Artificial sequence
<220> FEATURE:
<223> OTHER INFORMATION: Primer OPAX-12

<400> SEQUENCE: 1001 ggtcgggtca					10

<210> SEQ ID NO 1002
<211> LENGTH: 10
<212> TYPE: DNA
<213> ORGANISM: Artificial sequence
<220> FEATURE:
<223> OTHER INFORMATION: Primer OPAX-13

<400> SEQUENCE: 1002 gagcactgct					10

<210> SEQ ID NO 1003
<211> LENGTH: 10
<212> TYPE: DNA
<213> ORGANISM: Artificial sequence
<220> FEATURE:
<223> OTHER INFORMATION: Primer OPAX-14

<400> SEQUENCE: 1003 cacgggcttg					10

<210> SEQ ID NO 1004
<211> LENGTH: 10
<212> TYPE: DNA
<213> ORGANISM: Artificial sequence
<220> FEATURE:
<223> OTHER INFORMATION: Primer OPAX-15

<400> SEQUENCE: 1004 cagcaatccc					10

<210> SEQ ID NO 1005
<211> LENGTH: 10
<212> TYPE: DNA
<213> ORGANISM: Artificial sequence
<220> FEATURE:
<223> OTHER INFORMATION: Primer OPAX-16

<400> SEQUENCE: 1005 gtctgtgcgg					10

<210> SEQ ID NO 1006
<211> LENGTH: 10
<212> TYPE: DNA
<213> ORGANISM: Artificial sequence
<220> FEATURE:
<223> OTHER INFORMATION: Primer OPAX-17

<400> SEQUENCE: 1006
tgggctctgg                                                                10

<210> SEQ ID NO 1007
<211> LENGTH: 10
<212> TYPE: DNA
<213> ORGANISM: Artificial sequence
<220> FEATURE:
<223> OTHER INFORMATION: Primer OPAX-18

<400> SEQUENCE: 1007
gtgtgcagtg                                                                10

<210> SEQ ID NO 1008
<211> LENGTH: 10
<212> TYPE: DNA
<213> ORGANISM: Artificial sequence
<220> FEATURE:
<223> OTHER INFORMATION: Primer OPAX-19

<400> SEQUENCE: 1008
ccctgtcgca                                                                10

<210> SEQ ID NO 1009
<211> LENGTH: 10
<212> TYPE: DNA
<213> ORGANISM: Artificial sequence
<220> FEATURE:
<223> OTHER INFORMATION: Primer OPAX-20

<400> SEQUENCE: 1009
acactcggca                                                                10

<210> SEQ ID NO 1010
<211> LENGTH: 10
<212> TYPE: DNA
<213> ORGANISM: Artificial sequence
<220> FEATURE:
<223> OTHER INFORMATION: Primer OPAY-01

<400> SEQUENCE: 1010
gtccacctct                                                                10

<210> SEQ ID NO 1011
<211> LENGTH: 10
<212> TYPE: DNA
<213> ORGANISM: Artificial sequence
<220> FEATURE:
<223> OTHER INFORMATION: Primer OPAY-02

<400> SEQUENCE: 1011
tgcgaaggct                                                                10

<210> SEQ ID NO 1012
<211> LENGTH: 10
<212> TYPE: DNA
<213> ORGANISM: Artificial sequence
<220> FEATURE:
<223> OTHER INFORMATION: Primer OPAY-03

```
<400> SEQUENCE: 1012
tttccgggag                                                            10

<210> SEQ ID NO 1013
<211> LENGTH: 10
<212> TYPE: DNA
<213> ORGANISM: Artificial sequence
<220> FEATURE:
<223> OTHER INFORMATION: Primer OPAY-04

<400> SEQUENCE: 1013
aaggctcgac                                                            10

<210> SEQ ID NO 1014
<211> LENGTH: 10
<212> TYPE: DNA
<213> ORGANISM: Artificial sequence
<220> FEATURE:
<223> OTHER INFORMATION: Primer OPAY-05

<400> SEQUENCE: 1014
tcgctgcgtt                                                            10

<210> SEQ ID NO 1015
<211> LENGTH: 10
<212> TYPE: DNA
<213> ORGANISM: Artificial sequence
<220> FEATURE:
<223> OTHER INFORMATION: Primer OPAY-06

<400> SEQUENCE: 1015
ggcttcgcaa                                                            10

<210> SEQ ID NO 1016
<211> LENGTH: 10
<212> TYPE: DNA
<213> ORGANISM: Artificial sequence
<220> FEATURE:
<223> OTHER INFORMATION: Primer OPAY-07

<400> SEQUENCE: 1016
gaccgtctgt                                                            10

<210> SEQ ID NO 1017
<211> LENGTH: 10
<212> TYPE: DNA
<213> ORGANISM: Artificial sequence
<220> FEATURE:
<223> OTHER INFORMATION: Primer OPAY-08

<400> SEQUENCE: 1017
aggcttccct                                                            10

<210> SEQ ID NO 1018
<211> LENGTH: 10
<212> TYPE: DNA
<213> ORGANISM: Artificial sequence
<220> FEATURE:
<223> OTHER INFORMATION: Primer OPAY-09

<400> SEQUENCE: 1018
ccgatccaac                                                            10

<210> SEQ ID NO 1019
<211> LENGTH: 10
```

```
<212> TYPE: DNA
<213> ORGANISM: Artificial sequence
<220> FEATURE:
<223> OTHER INFORMATION: Primer OPAY-10

<400> SEQUENCE: 1019
caaggcccct                                                            10

<210> SEQ ID NO 1020
<211> LENGTH: 10
<212> TYPE: DNA
<213> ORGANISM: Artificial sequence
<220> FEATURE:
<223> OTHER INFORMATION: Primer OPAY-11

<400> SEQUENCE: 1020
acgcgccttc                                                            10

<210> SEQ ID NO 1021
<211> LENGTH: 10
<212> TYPE: DNA
<213> ORGANISM: Artificial sequence
<220> FEATURE:
<223> OTHER INFORMATION: Primer OPAY-12

<400> SEQUENCE: 1021
ctgtcggcgt                                                            10

<210> SEQ ID NO 1022
<211> LENGTH: 10
<212> TYPE: DNA
<213> ORGANISM: Artificial sequence
<220> FEATURE:
<223> OTHER INFORMATION: Primer OPAY-13

<400> SEQUENCE: 1022
ccgctcgtaa                                                            10

<210> SEQ ID NO 1023
<211> LENGTH: 10
<212> TYPE: DNA
<213> ORGANISM: Artificial sequence
<220> FEATURE:
<223> OTHER INFORMATION: Primer OPAY-14

<400> SEQUENCE: 1023
ggtgggtaga                                                            10

<210> SEQ ID NO 1024
<211> LENGTH: 10
<212> TYPE: DNA
<213> ORGANISM: Artificial sequence
<220> FEATURE:
<223> OTHER INFORMATION: Primer OPAY-15

<400> SEQUENCE: 1024
ccaagaggca                                                            10

<210> SEQ ID NO 1025
<211> LENGTH: 10
<212> TYPE: DNA
<213> ORGANISM: Artificial sequence
<220> FEATURE:
<223> OTHER INFORMATION: Primer OPAY-16

<400> SEQUENCE: 1025
ggtgtggttc                                                            10
```

<210> SEQ ID NO 1026
<211> LENGTH: 10
<212> TYPE: DNA
<213> ORGANISM: Artificial sequence
<220> FEATURE:
<223> OTHER INFORMATION: Primer OPAY-17

<400> SEQUENCE: 1026
ggtgattcgg                                                          10

<210> SEQ ID NO 1027
<211> LENGTH: 10
<212> TYPE: DNA
<213> ORGANISM: Artificial sequence
<220> FEATURE:
<223> OTHER INFORMATION: Primer OPAY-18

<400> SEQUENCE: 1027
accccaacca                                                          10

<210> SEQ ID NO 1028
<211> LENGTH: 10
<212> TYPE: DNA
<213> ORGANISM: Artificial sequence
<220> FEATURE:
<223> OTHER INFORMATION: Primer OPAY-19

<400> SEQUENCE: 1028
aacttggccc                                                          10

<210> SEQ ID NO 1029
<211> LENGTH: 10
<212> TYPE: DNA
<213> ORGANISM: Artificial sequence
<220> FEATURE:
<223> OTHER INFORMATION: Primer OPAY-20

<400> SEQUENCE: 1029
tcattcgccc                                                          10

<210> SEQ ID NO 1030
<211> LENGTH: 10
<212> TYPE: DNA
<213> ORGANISM: Artificial sequence
<220> FEATURE:
<223> OTHER INFORMATION: Primer OPAZ-01

<400> SEQUENCE: 1030
tcggatccgt                                                          10

<210> SEQ ID NO 1031
<211> LENGTH: 10
<212> TYPE: DNA
<213> ORGANISM: Artificial sequence
<220> FEATURE:
<223> OTHER INFORMATION: Primer OPAZ-02

<400> SEQUENCE: 1031
cctgaacgga                                                          10

<210> SEQ ID NO 1032
<211> LENGTH: 10
<212> TYPE: DNA
<213> ORGANISM: Artificial sequence
<220> FEATURE:
<223> OTHER INFORMATION: Primer OPAZ-03

```
<400> SEQUENCE: 1032
ggctgtgtgg                                                          10

<210> SEQ ID NO 1033
<211> LENGTH: 10
<212> TYPE: DNA
<213> ORGANISM: Artificial sequence
<220> FEATURE:
<223> OTHER INFORMATION: Primer OPAZ-04

<400> SEQUENCE: 1033
ccagcctcag                                                          10

<210> SEQ ID NO 1034
<211> LENGTH: 10
<212> TYPE: DNA
<213> ORGANISM: Artificial sequence
<220> FEATURE:
<223> OTHER INFORMATION: Primer OPAZ-05

<400> SEQUENCE: 1034
tccgcatacc                                                          10

<210> SEQ ID NO 1035
<211> LENGTH: 10
<212> TYPE: DNA
<213> ORGANISM: Artificial sequence
<220> FEATURE:
<223> OTHER INFORMATION: Primer OPAZ-06

<400> SEQUENCE: 1035
ccttcggagg                                                          10

<210> SEQ ID NO 1036
<211> LENGTH: 10
<212> TYPE: DNA
<213> ORGANISM: Artificial sequence
<220> FEATURE:
<223> OTHER INFORMATION: Primer OPAZ-07

<400> SEQUENCE: 1036
cacgagtctc                                                          10

<210> SEQ ID NO 1037
<211> LENGTH: 10
<212> TYPE: DNA
<213> ORGANISM: Artificial sequence
<220> FEATURE:
<223> OTHER INFORMATION: Primer OPAZ-08

<400> SEQUENCE: 1037
tcgctcgtag                                                          10

<210> SEQ ID NO 1038
<211> LENGTH: 10
<212> TYPE: DNA
<213> ORGANISM: Artificial sequence
<220> FEATURE:
<223> OTHER INFORMATION: Primer OPAZ-09

<400> SEQUENCE: 1038
ccttgacccc                                                          10

<210> SEQ ID NO 1039
<211> LENGTH: 10
```

```
<212> TYPE: DNA
<213> ORGANISM: Artificial sequence
<220> FEATURE:
<223> OTHER INFORMATION: Primer OPAZ-10

<400> SEQUENCE: 1039
actctgggga                                                              10

<210> SEQ ID NO 1040
<211> LENGTH: 10
<212> TYPE: DNA
<213> ORGANISM: Artificial sequence
<220> FEATURE:
<223> OTHER INFORMATION: Primer OPAZ-11

<400> SEQUENCE: 1040
tccagcgcgt                                                              10

<210> SEQ ID NO 1041
<211> LENGTH: 10
<212> TYPE: DNA
<213> ORGANISM: Artificial sequence
<220> FEATURE:
<223> OTHER INFORMATION: Primer OPAZ-12

<400> SEQUENCE: 1041
gatgggcctg                                                              10

<210> SEQ ID NO 1042
<211> LENGTH: 10
<212> TYPE: DNA
<213> ORGANISM: Artificial sequence
<220> FEATURE:
<223> OTHER INFORMATION: Primer OPAZ-13

<400> SEQUENCE: 1042
cccgaagcaa                                                              10

<210> SEQ ID NO 1043
<211> LENGTH: 10
<212> TYPE: DNA
<213> ORGANISM: Artificial sequence
<220> FEATURE:
<223> OTHER INFORMATION: Primer OPAZ-14

<400> SEQUENCE: 1043
cacggcttcc                                                              10

<210> SEQ ID NO 1044
<211> LENGTH: 10
<212> TYPE: DNA
<213> ORGANISM: Artificial sequence
<220> FEATURE:
<223> OTHER INFORMATION: Primer OPAZ-15

<400> SEQUENCE: 1044
tccgctagtc                                                              10

<210> SEQ ID NO 1045
<211> LENGTH: 10
<212> TYPE: DNA
<213> ORGANISM: Artificial sequence
<220> FEATURE:
<223> OTHER INFORMATION: Primer OPAZ-16

<400> SEQUENCE: 1045
aggcgaactg                                                              10
```

<210> SEQ ID NO 1046
<211> LENGTH: 10
<212> TYPE: DNA
<213> ORGANISM: Artificial sequence
<220> FEATURE:
<223> OTHER INFORMATION: Primer OPAZ-17

<400> SEQUENCE: 1046
cacgcagatg                                                          10

<210> SEQ ID NO 1047
<211> LENGTH: 10
<212> TYPE: DNA
<213> ORGANISM: Artificial sequence
<220> FEATURE:
<223> OTHER INFORMATION: Primer OPAZ-18

<400> SEQUENCE: 1047
ccgacgttga                                                          10

<210> SEQ ID NO 1048
<211> LENGTH: 10
<212> TYPE: DNA
<213> ORGANISM: Artificial sequence
<220> FEATURE:
<223> OTHER INFORMATION: Primer OPAZ-19

<400> SEQUENCE: 1048
acactctcgg                                                          10

<210> SEQ ID NO 1049
<211> LENGTH: 10
<212> TYPE: DNA
<213> ORGANISM: Artificial sequence
<220> FEATURE:
<223> OTHER INFORMATION: Primer OPAZ-20

<400> SEQUENCE: 1049
catcacccct                                                          10

<210> SEQ ID NO 1050
<211> LENGTH: 10
<212> TYPE: DNA
<213> ORGANISM: Artificial sequence
<220> FEATURE:
<223> OTHER INFORMATION: Primer OPBA-01

<400> SEQUENCE: 1050
ttccccaccc                                                          10

<210> SEQ ID NO 1051
<211> LENGTH: 10
<212> TYPE: DNA
<213> ORGANISM: Artificial sequence
<220> FEATURE:
<223> OTHER INFORMATION: Primer OPBA-02

<400> SEQUENCE: 1051
tgctcggctc                                                          10

<210> SEQ ID NO 1052
<211> LENGTH: 10
<212> TYPE: DNA
<213> ORGANISM: Artificial sequence
<220> FEATURE:
<223> OTHER INFORMATION: Primer OPBA-03

<400> SEQUENCE: 1052
gtgcgagaac                                                            10

<210> SEQ ID NO 1053
<211> LENGTH: 10
<212> TYPE: DNA
<213> ORGANISM: Artificial sequence
<220> FEATURE:
<223> OTHER INFORMATION: Primer OPBA-04

<400> SEQUENCE: 1053
tcctaggctc                                                            10

<210> SEQ ID NO 1054
<211> LENGTH: 10
<212> TYPE: DNA
<213> ORGANISM: Artificial sequence
<220> FEATURE:
<223> OTHER INFORMATION: Primer OPBA-05

<400> SEQUENCE: 1054
tgcgttccac                                                            10

<210> SEQ ID NO 1055
<211> LENGTH: 10
<212> TYPE: DNA
<213> ORGANISM: Artificial sequence
<220> FEATURE:
<223> OTHER INFORMATION: Primer OPBA-06

<400> SEQUENCE: 1055
ggacgaccgt                                                            10

<210> SEQ ID NO 1056
<211> LENGTH: 10
<212> TYPE: DNA
<213> ORGANISM: Artificial sequence
<220> FEATURE:
<223> OTHER INFORMATION: Primer OPBA-07

<400> SEQUENCE: 1056
gggtcgcatc                                                            10

<210> SEQ ID NO 1057
<211> LENGTH: 10
<212> TYPE: DNA
<213> ORGANISM: Artificial sequence
<220> FEATURE:
<223> OTHER INFORMATION: Primer OPBA-08

<400> SEQUENCE: 1057
ccacagccga                                                            10

<210> SEQ ID NO 1058
<211> LENGTH: 10
<212> TYPE: DNA
<213> ORGANISM: Artificial sequence
<220> FEATURE:
<223> OTHER INFORMATION: Primer OPBA-09

<400> SEQUENCE: 1058
ggaactccac                                                            10

<210> SEQ ID NO 1059
<211> LENGTH: 10

```
<212> TYPE: DNA
<213> ORGANISM: Artificial sequence
<220> FEATURE:
<223> OTHER INFORMATION: Primer OPBA-10

<400> SEQUENCE: 1059
ggacgttgag                                                            10

<210> SEQ ID NO 1060
<211> LENGTH: 10
<212> TYPE: DNA
<213> ORGANISM: Artificial sequence
<220> FEATURE:
<223> OTHER INFORMATION: Primer OPBA-11

<400> SEQUENCE: 1060
ccaccttcag                                                            10

<210> SEQ ID NO 1061
<211> LENGTH: 10
<212> TYPE: DNA
<213> ORGANISM: Artificial sequence
<220> FEATURE:
<223> OTHER INFORMATION: Primer OPBA-12

<400> SEQUENCE: 1061
tgttgggcac                                                            10

<210> SEQ ID NO 1062
<211> LENGTH: 10
<212> TYPE: DNA
<213> ORGANISM: Artificial sequence
<220> FEATURE:
<223> OTHER INFORMATION: Primer OPBA-13

<400> SEQUENCE: 1062
agggcgaatg                                                            10

<210> SEQ ID NO 1063
<211> LENGTH: 10
<212> TYPE: DNA
<213> ORGANISM: Artificial sequence
<220> FEATURE:
<223> OTHER INFORMATION: Primer OPBA-14

<400> SEQUENCE: 1063
tcgggagtgg                                                            10

<210> SEQ ID NO 1064
<211> LENGTH: 10
<212> TYPE: DNA
<213> ORGANISM: Artificial sequence
<220> FEATURE:
<223> OTHER INFORMATION: Primer OPBA-15

<400> SEQUENCE: 1064
gaagacctgg                                                            10

<210> SEQ ID NO 1065
<211> LENGTH: 10
<212> TYPE: DNA
<213> ORGANISM: Artificial sequence
<220> FEATURE:
<223> OTHER INFORMATION: Primer OPBA-16

<400> SEQUENCE: 1065
ccacgcatca                                                            10
```

<210> SEQ ID NO 1066
<211> LENGTH: 10
<212> TYPE: DNA
<213> ORGANISM: Artificial sequence
<220> FEATURE:
<223> OTHER INFORMATION: Primer OPBA-17

<400> SEQUENCE: 1066
tgtacccctg                                                          10

<210> SEQ ID NO 1067
<211> LENGTH: 10
<212> TYPE: DNA
<213> ORGANISM: Artificial sequence
<220> FEATURE:
<223> OTHER INFORMATION: Primer OPBA-18

<400> SEQUENCE: 1067
ctcggatgtc                                                          10

<210> SEQ ID NO 1068
<211> LENGTH: 10
<212> TYPE: DNA
<213> ORGANISM: Artificial sequence
<220> FEATURE:
<223> OTHER INFORMATION: Primer OPBA-19

<400> SEQUENCE: 1068
ccatccgttg                                                          10

<210> SEQ ID NO 1069
<211> LENGTH: 10
<212> TYPE: DNA
<213> ORGANISM: Artificial sequence
<220> FEATURE:
<223> OTHER INFORMATION: Primer OPBA-20

<400> SEQUENCE: 1069
gagcgctacc                                                          10

<210> SEQ ID NO 1070
<211> LENGTH: 10
<212> TYPE: DNA
<213> ORGANISM: Artificial sequence
<220> FEATURE:
<223> OTHER INFORMATION: Primer OPBB-01

<400> SEQUENCE: 1070
acactggctg                                                          10

<210> SEQ ID NO 1071
<211> LENGTH: 10
<212> TYPE: DNA
<213> ORGANISM: Artificial sequence
<220> FEATURE:
<223> OTHER INFORMATION: Primer OPBB-02

<400> SEQUENCE: 1071
cccccgttag                                                          10

<210> SEQ ID NO 1072
<211> LENGTH: 10
<212> TYPE: DNA
<213> ORGANISM: Artificial sequence
<220> FEATURE:
<223> OTHER INFORMATION: Primer OPBB-03

<400> SEQUENCE: 1072
tcacgtggct                                                              10

<210> SEQ ID NO 1073
<211> LENGTH: 10
<212> TYPE: DNA
<213> ORGANISM: Artificial sequence
<220> FEATURE:
<223> OTHER INFORMATION: Primer OPBB-04

<400> SEQUENCE: 1073
accaggtcac                                                              10

<210> SEQ ID NO 1074
<211> LENGTH: 10
<212> TYPE: DNA
<213> ORGANISM: Artificial sequence
<220> FEATURE:
<223> OTHER INFORMATION: Primer OPBB-05

<400> SEQUENCE: 1074
gggccgaaca                                                              10

<210> SEQ ID NO 1075
<211> LENGTH: 10
<212> TYPE: DNA
<213> ORGANISM: Artificial sequence
<220> FEATURE:
<223> OTHER INFORMATION: Primer OPBB-06

<400> SEQUENCE: 1075
ctgaagctgg                                                              10

<210> SEQ ID NO 1076
<211> LENGTH: 10
<212> TYPE: DNA
<213> ORGANISM: Artificial sequence
<220> FEATURE:
<223> OTHER INFORMATION: Primer OPBB-07

<400> SEQUENCE: 1076
gaaggctggg                                                              10

<210> SEQ ID NO 1077
<211> LENGTH: 10
<212> TYPE: DNA
<213> ORGANISM: Artificial sequence
<220> FEATURE:
<223> OTHER INFORMATION: Primer OPBB-08

<400> SEQUENCE: 1077
tcgtcgaagg                                                              10

<210> SEQ ID NO 1078
<211> LENGTH: 10
<212> TYPE: DNA
<213> ORGANISM: Artificial sequence
<220> FEATURE:
<223> OTHER INFORMATION: Primer OPBB-09

<400> SEQUENCE: 1078
aggccggtca                                                              10

<210> SEQ ID NO 1079
<211> LENGTH: 10

```
<212> TYPE: DNA
<213> ORGANISM: Artificial sequence
<220> FEATURE:
<223> OTHER INFORMATION: Primer OPBB-10

<400> SEQUENCE: 1079
acttgcctgg                                                              10

<210> SEQ ID NO 1080
<211> LENGTH: 10
<212> TYPE: DNA
<213> ORGANISM: Artificial sequence
<220> FEATURE:
<223> OTHER INFORMATION: Primer OPBB-11

<400> SEQUENCE: 1080
tgcgggttcc                                                              10

<210> SEQ ID NO 1081
<211> LENGTH: 10
<212> TYPE: DNA
<213> ORGANISM: Artificial sequence
<220> FEATURE:
<223> OTHER INFORMATION: Primer OPBB-12

<400> SEQUENCE: 1081
ttcggccgac                                                              10

<210> SEQ ID NO 1082
<211> LENGTH: 10
<212> TYPE: DNA
<213> ORGANISM: Artificial sequence
<220> FEATURE:
<223> OTHER INFORMATION: Primer OPBB-13

<400> SEQUENCE: 1082
cttcggtgtg                                                              10

<210> SEQ ID NO 1083
<211> LENGTH: 10
<212> TYPE: DNA
<213> ORGANISM: Artificial sequence
<220> FEATURE:
<223> OTHER INFORMATION: Primer OPBB-14

<400> SEQUENCE: 1083
gtgggacctg                                                              10

<210> SEQ ID NO 1084
<211> LENGTH: 10
<212> TYPE: DNA
<213> ORGANISM: Artificial sequence
<220> FEATURE:
<223> OTHER INFORMATION: Primer OPBB-15

<400> SEQUENCE: 1084
aagtgccctg                                                              10

<210> SEQ ID NO 1085
<211> LENGTH: 10
<212> TYPE: DNA
<213> ORGANISM: Artificial sequence
<220> FEATURE:
<223> OTHER INFORMATION: Primer OPBB-16

<400> SEQUENCE: 1085
tcggcaccgt                                                              10
```

<210> SEQ ID NO 1086
<211> LENGTH: 10
<212> TYPE: DNA
<213> ORGANISM: Artificial sequence
<220> FEATURE:
<223> OTHER INFORMATION: Primer OPBB-17

<400> SEQUENCE: 1086
acaccgtgcc                                                                10

<210> SEQ ID NO 1087
<211> LENGTH: 10
<212> TYPE: DNA
<213> ORGANISM: Artificial sequence
<220> FEATURE:
<223> OTHER INFORMATION: Primer OPBB-18

<400> SEQUENCE: 1087
caaccggtct                                                                10

<210> SEQ ID NO 1088
<211> LENGTH: 10
<212> TYPE: DNA
<213> ORGANISM: Artificial sequence
<220> FEATURE:
<223> OTHER INFORMATION: Primer OPBB-19

<400> SEQUENCE: 1088
ttgcggacag                                                                10

<210> SEQ ID NO 1089
<211> LENGTH: 10
<212> TYPE: DNA
<213> ORGANISM: Artificial sequence
<220> FEATURE:
<223> OTHER INFORMATION: Primer OPBB-20

<400> SEQUENCE: 1089
ccaggtgtag                                                                10

<210> SEQ ID NO 1090
<211> LENGTH: 10
<212> TYPE: DNA
<213> ORGANISM: Artificial sequence
<220> FEATURE:
<223> OTHER INFORMATION: Primer OPBC-01

<400> SEQUENCE: 1090
ccttcggctc                                                                10

<210> SEQ ID NO 1091
<211> LENGTH: 10
<212> TYPE: DNA
<213> ORGANISM: Artificial sequence
<220> FEATURE:
<223> OTHER INFORMATION: Primer OPBC-02

<400> SEQUENCE: 1091
acagtagcgg                                                                10

<210> SEQ ID NO 1092
<211> LENGTH: 10
<212> TYPE: DNA
<213> ORGANISM: Artificial sequence
<220> FEATURE:
<223> OTHER INFORMATION: Primer OPBC-03

```
<400> SEQUENCE: 1092
ggcttgacct                                                          10

<210> SEQ ID NO 1093
<211> LENGTH: 10
<212> TYPE: DNA
<213> ORGANISM: Artificial sequence
<220> FEATURE:
<223> OTHER INFORMATION: Primer OPBC-04

<400> SEQUENCE: 1093
ccacgtgcca                                                          10

<210> SEQ ID NO 1094
<211> LENGTH: 10
<212> TYPE: DNA
<213> ORGANISM: Artificial sequence
<220> FEATURE:
<223> OTHER INFORMATION: Primer OPBC-05

<400> SEQUENCE: 1094
gaggcgattg                                                          10

<210> SEQ ID NO 1095
<211> LENGTH: 10
<212> TYPE: DNA
<213> ORGANISM: Artificial sequence
<220> FEATURE:
<223> OTHER INFORMATION: Primer OPBC-06

<400> SEQUENCE: 1095
gaaggcgaga                                                          10

<210> SEQ ID NO 1096
<211> LENGTH: 10
<212> TYPE: DNA
<213> ORGANISM: Artificial sequence
<220> FEATURE:
<223> OTHER INFORMATION: Primer OPBC-07

<400> SEQUENCE: 1096
tgtgcctgac                                                          10

<210> SEQ ID NO 1097
<211> LENGTH: 10
<212> TYPE: DNA
<213> ORGANISM: Artificial sequence
<220> FEATURE:
<223> OTHER INFORMATION: Primer OPBC-08

<400> SEQUENCE: 1097
ggtcttccct                                                          10

<210> SEQ ID NO 1098
<211> LENGTH: 10
<212> TYPE: DNA
<213> ORGANISM: Artificial sequence
<220> FEATURE:
<223> OTHER INFORMATION: Primer OPBC-09

<400> SEQUENCE: 1098
gtcatgcgac                                                          10

<210> SEQ ID NO 1099
<211> LENGTH: 10
```

<212> TYPE: DNA
<213> ORGANISM: Artificial sequence
<220> FEATURE:
<223> OTHER INFORMATION: Primer OPBC-10

<400> SEQUENCE: 1099
aacgtcgagg                                                           10

<210> SEQ ID NO 1100
<211> LENGTH: 10
<212> TYPE: DNA
<213> ORGANISM: Artificial sequence
<220> FEATURE:
<223> OTHER INFORMATION: Primer OPBC-11

<400> SEQUENCE: 1100
ttttgccccc                                                           10

<210> SEQ ID NO 1101
<211> LENGTH: 10
<212> TYPE: DNA
<213> ORGANISM: Artificial sequence
<220> FEATURE:
<223> OTHER INFORMATION: Primer OPBC-12

<400> SEQUENCE: 1101
cctccaccag                                                           10

<210> SEQ ID NO 1102
<211> LENGTH: 10
<212> TYPE: DNA
<213> ORGANISM: Artificial sequence
<220> FEATURE:
<223> OTHER INFORMATION: Primer OPBC-13

<400> SEQUENCE: 1102
cctggcacag                                                           10

<210> SEQ ID NO 1103
<211> LENGTH: 10
<212> TYPE: DNA
<213> ORGANISM: Artificial sequence
<220> FEATURE:
<223> OTHER INFORMATION: Primer OPBC-14

<400> SEQUENCE: 1103
ggtccgacga                                                           10

<210> SEQ ID NO 1104
<211> LENGTH: 10
<212> TYPE: DNA
<213> ORGANISM: Artificial sequence
<220> FEATURE:
<223> OTHER INFORMATION: Primer OPBC-15

<400> SEQUENCE: 1104
ccagactcca                                                           10

<210> SEQ ID NO 1105
<211> LENGTH: 10
<212> TYPE: DNA
<213> ORGANISM: Artificial sequence
<220> FEATURE:
<223> OTHER INFORMATION: Primer OPBC-16

<400> SEQUENCE: 1105
ctggtgctca                                                           10

<210> SEQ ID NO 1106
<211> LENGTH: 10
<212> TYPE: DNA
<213> ORGANISM: Artificial sequence
<220> FEATURE:
<223> OTHER INFORMATION: Primer OPBC-17

<400> SEQUENCE: 1106
ccgttagtcc                                                          10

<210> SEQ ID NO 1107
<211> LENGTH: 10
<212> TYPE: DNA
<213> ORGANISM: Artificial sequence
<220> FEATURE:
<223> OTHER INFORMATION: Primer OPBC-18

<400> SEQUENCE: 1107
gtgaaggagg                                                          10

<210> SEQ ID NO 1108
<211> LENGTH: 10
<212> TYPE: DNA
<213> ORGANISM: Artificial sequence
<220> FEATURE:
<223> OTHER INFORMATION: Primer OPBC-19

<400> SEQUENCE: 1108
acaagcgcga                                                          10

<210> SEQ ID NO 1109
<211> LENGTH: 10
<212> TYPE: DNA
<213> ORGANISM: Artificial sequence
<220> FEATURE:
<223> OTHER INFORMATION: Primer OPBC-20

<400> SEQUENCE: 1109
agcactgggg                                                          10

<210> SEQ ID NO 1110
<211> LENGTH: 10
<212> TYPE: DNA
<213> ORGANISM: Artificial sequence
<220> FEATURE:
<223> OTHER INFORMATION: Primer OPBD-01

<400> SEQUENCE: 1110
tcactcgctc                                                          10

<210> SEQ ID NO 1111
<211> LENGTH: 10
<212> TYPE: DNA
<213> ORGANISM: Artificial sequence
<220> FEATURE:
<223> OTHER INFORMATION: Primer OPBD-02

<400> SEQUENCE: 1111
cctccccaag                                                          10

<210> SEQ ID NO 1112
<211> LENGTH: 10
<212> TYPE: DNA
<213> ORGANISM: Artificial sequence
<220> FEATURE:
<223> OTHER INFORMATION: Primer OPBD-03

```
<400> SEQUENCE: 1112
gagccccgaa                                                              10

<210> SEQ ID NO 1113
<211> LENGTH: 10
<212> TYPE: DNA
<213> ORGANISM: Artificial sequence
<220> FEATURE:
<223> OTHER INFORMATION: Primer OPBD-04

<400> SEQUENCE: 1113
tcgggtgttg                                                              10

<210> SEQ ID NO 1114
<211> LENGTH: 10
<212> TYPE: DNA
<213> ORGANISM: Artificial sequence
<220> FEATURE:
<223> OTHER INFORMATION: Primer OPBD-05

<400> SEQUENCE: 1114
gtgcggagag                                                              10

<210> SEQ ID NO 1115
<211> LENGTH: 10
<212> TYPE: DNA
<213> ORGANISM: Artificial sequence
<220> FEATURE:
<223> OTHER INFORMATION: Primer OPBD-06

<400> SEQUENCE: 1115
aagctggcgt                                                              10

<210> SEQ ID NO 1116
<211> LENGTH: 10
<212> TYPE: DNA
<213> ORGANISM: Artificial sequence
<220> FEATURE:
<223> OTHER INFORMATION: Primer OPBD-07

<400> SEQUENCE: 1116
gagctggtcc                                                              10

<210> SEQ ID NO 1117
<211> LENGTH: 10
<212> TYPE: DNA
<213> ORGANISM: Artificial sequence
<220> FEATURE:
<223> OTHER INFORMATION: Primer OPBD-08

<400> SEQUENCE: 1117
catacgggct                                                              10

<210> SEQ ID NO 1118
<211> LENGTH: 10
<212> TYPE: DNA
<213> ORGANISM: Artificial sequence
<220> FEATURE:
<223> OTHER INFORMATION: Primer OPBD-09

<400> SEQUENCE: 1118
ccacggtcag                                                              10

<210> SEQ ID NO 1119
<211> LENGTH: 10
```

```
<212> TYPE: DNA
<213> ORGANISM: Artificial sequence
<220> FEATURE:
<223> OTHER INFORMATION: Primer OPBD-10

<400> SEQUENCE: 1119
gacgctatgg                                                          10

<210> SEQ ID NO 1120
<211> LENGTH: 10
<212> TYPE: DNA
<213> ORGANISM: Artificial sequence
<220> FEATURE:
<223> OTHER INFORMATION: Primer OPBD-11

<400> SEQUENCE: 1120
caaccgagtc                                                          10

<210> SEQ ID NO 1121
<211> LENGTH: 10
<212> TYPE: DNA
<213> ORGANISM: Artificial sequence
<220> FEATURE:
<223> OTHER INFORMATION: Primer OPBD-12

<400> SEQUENCE: 1121
gggaaccgtc                                                          10

<210> SEQ ID NO 1122
<211> LENGTH: 10
<212> TYPE: DNA
<213> ORGANISM: Artificial sequence
<220> FEATURE:
<223> OTHER INFORMATION: Primer OPBD-13

<400> SEQUENCE: 1122
cctggaacgg                                                          10

<210> SEQ ID NO 1123
<211> LENGTH: 10
<212> TYPE: DNA
<213> ORGANISM: Artificial sequence
<220> FEATURE:
<223> OTHER INFORMATION: Primer OPBD-14

<400> SEQUENCE: 1123
tccctgtgag                                                          10

<210> SEQ ID NO 1124
<211> LENGTH: 10
<212> TYPE: DNA
<213> ORGANISM: Artificial sequence
<220> FEATURE:
<223> OTHER INFORMATION: Primer OPBD-15

<400> SEQUENCE: 1124
tgtcgtggtc                                                          10

<210> SEQ ID NO 1125
<211> LENGTH: 10
<212> TYPE: DNA
<213> ORGANISM: Artificial sequence
<220> FEATURE:
<223> OTHER INFORMATION: Primer OPBD-16

<400> SEQUENCE: 1125
gaactcccag                                                          10
```

<210> SEQ ID NO 1126
<211> LENGTH: 10
<212> TYPE: DNA
<213> ORGANISM: Artificial sequence
<220> FEATURE:
<223> OTHER INFORMATION: Primer OPBD-17

<400> SEQUENCE: 1126
gttcgctccc                                                              10

<210> SEQ ID NO 1127
<211> LENGTH: 10
<212> TYPE: DNA
<213> ORGANISM: Artificial sequence
<220> FEATURE:
<223> OTHER INFORMATION: Primer OPBD-18

<400> SEQUENCE: 1127
acgcacactc                                                              10

<210> SEQ ID NO 1128
<211> LENGTH: 10
<212> TYPE: DNA
<213> ORGANISM: Artificial sequence
<220> FEATURE:
<223> OTHER INFORMATION: Primer OPBD-19

<400> SEQUENCE: 1128
ggttcctctc                                                              10

<210> SEQ ID NO 1129
<211> LENGTH: 10
<212> TYPE: DNA
<213> ORGANISM: Artificial sequence
<220> FEATURE:
<223> OTHER INFORMATION: Primer OPBD-20

<400> SEQUENCE: 1129
aggcggcaca                                                              10

<210> SEQ ID NO 1130
<211> LENGTH: 10
<212> TYPE: DNA
<213> ORGANISM: Artificial sequence
<220> FEATURE:
<223> OTHER INFORMATION: Primer OPBE-01

<400> SEQUENCE: 1130
cactcctggt                                                              10

<210> SEQ ID NO 1131
<211> LENGTH: 10
<212> TYPE: DNA
<213> ORGANISM: Artificial sequence
<220> FEATURE:
<223> OTHER INFORMATION: Primer OPBE-02

<400> SEQUENCE: 1131
acgcctgtag                                                              10

<210> SEQ ID NO 1132
<211> LENGTH: 10
<212> TYPE: DNA
<213> ORGANISM: Artificial sequence
<220> FEATURE:
<223> OTHER INFORMATION: Primer OPBE-03

```
<400> SEQUENCE: 1132
tggactcggt                                                          10

<210> SEQ ID NO 1133
<211> LENGTH: 10
<212> TYPE: DNA
<213> ORGANISM: Artificial sequence
<220> FEATURE:
<223> OTHER INFORMATION: Primer OPBE-04

<400> SEQUENCE: 1133
cccaagcgaa                                                          10

<210> SEQ ID NO 1134
<211> LENGTH: 10
<212> TYPE: DNA
<213> ORGANISM: Artificial sequence
<220> FEATURE:
<223> OTHER INFORMATION: Primer OPBE-05

<400> SEQUENCE: 1134
ggaacgctac                                                          10

<210> SEQ ID NO 1135
<211> LENGTH: 10
<212> TYPE: DNA
<213> ORGANISM: Artificial sequence
<220> FEATURE:
<223> OTHER INFORMATION: Primer OPBE-06

<400> SEQUENCE: 1135
cagcgggtca                                                          10

<210> SEQ ID NO 1136
<211> LENGTH: 10
<212> TYPE: DNA
<213> ORGANISM: Artificial sequence
<220> FEATURE:
<223> OTHER INFORMATION: Primer OPBE-07

<400> SEQUENCE: 1136
ccgtcctatg                                                          10

<210> SEQ ID NO 1137
<211> LENGTH: 10
<212> TYPE: DNA
<213> ORGANISM: Artificial sequence
<220> FEATURE:
<223> OTHER INFORMATION: Primer OPBE-08

<400> SEQUENCE: 1137
gggaagcgtc                                                          10

<210> SEQ ID NO 1138
<211> LENGTH: 10
<212> TYPE: DNA
<213> ORGANISM: Artificial sequence
<220> FEATURE:
<223> OTHER INFORMATION: Primer OPBE-09

<400> SEQUENCE: 1138
cccgctttcc                                                          10

<210> SEQ ID NO 1139
<211> LENGTH: 10
```

```
<212> TYPE: DNA
<213> ORGANISM: Artificial sequence
<220> FEATURE:
<223> OTHER INFORMATION: Primer OPBE-10

<400> SEQUENCE: 1139
aagcggccct                                                              10

<210> SEQ ID NO 1140
<211> LENGTH: 10
<212> TYPE: DNA
<213> ORGANISM: Artificial sequence
<220> FEATURE:
<223> OTHER INFORMATION: Primer OPBE-11

<400> SEQUENCE: 1140
gtcctgctgt                                                              10

<210> SEQ ID NO 1141
<211> LENGTH: 10
<212> TYPE: DNA
<213> ORGANISM: Artificial sequence
<220> FEATURE:
<223> OTHER INFORMATION: Primer OPBE-12

<400> SEQUENCE: 1141
ggttgttccc                                                              10

<210> SEQ ID NO 1142
<211> LENGTH: 10
<212> TYPE: DNA
<213> ORGANISM: Artificial sequence
<220> FEATURE:
<223> OTHER INFORMATION: Primer OPBE-13

<400> SEQUENCE: 1142
tcggtgagtc                                                              10

<210> SEQ ID NO 1143
<211> LENGTH: 10
<212> TYPE: DNA
<213> ORGANISM: Artificial sequence
<220> FEATURE:
<223> OTHER INFORMATION: Primer OPBE-14

<400> SEQUENCE: 1143
ctttgcgcac                                                              10

<210> SEQ ID NO 1144
<211> LENGTH: 10
<212> TYPE: DNA
<213> ORGANISM: Artificial sequence
<220> FEATURE:
<223> OTHER INFORMATION: Primer OPBE-15

<400> SEQUENCE: 1144
ttcggcgatg                                                              10

<210> SEQ ID NO 1145
<211> LENGTH: 10
<212> TYPE: DNA
<213> ORGANISM: Artificial sequence
<220> FEATURE:
<223> OTHER INFORMATION: Primer OPBE-16

<400> SEQUENCE: 1145
ctccacgact                                                              10
```

<210> SEQ ID NO 1146
<211> LENGTH: 10
<212> TYPE: DNA
<213> ORGANISM: Artificial sequence
<220> FEATURE:
<223> OTHER INFORMATION: Primer OPBE-17

<400> SEQUENCE: 1146
gggaaaagcc                                                              10

<210> SEQ ID NO 1147
<211> LENGTH: 10
<212> TYPE: DNA
<213> ORGANISM: Artificial sequence
<220> FEATURE:
<223> OTHER INFORMATION: Primer OPBE-18

<400> SEQUENCE: 1147
ccaagccgtc                                                              10

<210> SEQ ID NO 1148
<211> LENGTH: 10
<212> TYPE: DNA
<213> ORGANISM: Artificial sequence
<220> FEATURE:
<223> OTHER INFORMATION: Primer OPBE-19

<400> SEQUENCE: 1148
aggccaacag                                                              10

<210> SEQ ID NO 1149
<211> LENGTH: 10
<212> TYPE: DNA
<213> ORGANISM: Artificial sequence
<220> FEATURE:
<223> OTHER INFORMATION: Primer OPBE-20

<400> SEQUENCE: 1149
caaaggcgtg                                                              10

<210> SEQ ID NO 1150
<211> LENGTH: 10
<212> TYPE: DNA
<213> ORGANISM: Artificial sequence
<220> FEATURE:
<223> OTHER INFORMATION: Primer OPBF-01

<400> SEQUENCE: 1150
ggagctgact                                                              10

<210> SEQ ID NO 1151
<211> LENGTH: 10
<212> TYPE: DNA
<213> ORGANISM: Artificial sequence
<220> FEATURE:
<223> OTHER INFORMATION: Primer OPBF-02

<400> SEQUENCE: 1151
gacacactcc                                                              10

<210> SEQ ID NO 1152
<211> LENGTH: 10
<212> TYPE: DNA
<213> ORGANISM: Artificial sequence
<220> FEATURE:
<223> OTHER INFORMATION: Primer OPBF-03

```
<400> SEQUENCE: 1152
tcccttgacc                                                                 10

<210> SEQ ID NO 1153
<211> LENGTH: 10
<212> TYPE: DNA
<213> ORGANISM: Artificial sequence
<220> FEATURE:
<223> OTHER INFORMATION: Primer OPBF-04

<400> SEQUENCE: 1153
gacaggttgg                                                                 10

<210> SEQ ID NO 1154
<211> LENGTH: 10
<212> TYPE: DNA
<213> ORGANISM: Artificial sequence
<220> FEATURE:
<223> OTHER INFORMATION: Primer OPBF-05

<400> SEQUENCE: 1154 cacccccgaaa                                                                10

<210> SEQ ID NO 1155
<211> LENGTH: 10
<212> TYPE: DNA
<213> ORGANISM: Artificial sequence
<220> FEATURE:
<223> OTHER INFORMATION: Primer OPBF-06

<400> SEQUENCE: 1155
tccacgggca                                                                 10

<210> SEQ ID NO 1156
<211> LENGTH: 10
<212> TYPE: DNA
<213> ORGANISM: Artificial sequence
<220> FEATURE:
<223> OTHER INFORMATION: Primer OPBF-07

<400> SEQUENCE: 1156
caccatcgtg                                                                 10

<210> SEQ ID NO 1157
<211> LENGTH: 10
<212> TYPE: DNA
<213> ORGANISM: Artificial sequence
<220> FEATURE:
<223> OTHER INFORMATION: Primer OPBF-08

<400> SEQUENCE: 1157
cctgggtcca                                                                 10

<210> SEQ ID NO 1158
<211> LENGTH: 10
<212> TYPE: DNA
<213> ORGANISM: Artificial sequence
<220> FEATURE:
<223> OTHER INFORMATION: Primer OPBF-09

<400> SEQUENCE: 1158
acccaggttg                                                                 10

<210> SEQ ID NO 1159
<211> LENGTH: 10
```

```
<212> TYPE: DNA
<213> ORGANISM: Artificial sequence
<220> FEATURE:
<223> OTHER INFORMATION: Primer OPBF-10

<400> SEQUENCE: 1159
gtgaccagag                                                              10

<210> SEQ ID NO 1160
<211> LENGTH: 10
<212> TYPE: DNA
<213> ORGANISM: Artificial sequence
<220> FEATURE:
<223> OTHER INFORMATION: Primer OPBF-11

<400> SEQUENCE: 1160
gacgaccgca                                                              10

<210> SEQ ID NO 1161
<211> LENGTH: 10
<212> TYPE: DNA
<213> ORGANISM: Artificial sequence
<220> FEATURE:
<223> OTHER INFORMATION: Primer OPBF-12

<400> SEQUENCE: 1161
cttcgctgtc                                                              10

<210> SEQ ID NO 1162
<211> LENGTH: 10
<212> TYPE: DNA
<213> ORGANISM: Artificial sequence
<220> FEATURE:
<223> OTHER INFORMATION: Primer OPBF-13

<400> SEQUENCE: 1162
ccgccggtaa                                                              10

<210> SEQ ID NO 1163
<211> LENGTH: 10
<212> TYPE: DNA
<213> ORGANISM: Artificial sequence
<220> FEATURE:
<223> OTHER INFORMATION: Primer OPBF-14

<400> SEQUENCE: 1163
ccgcgttgag                                                              10

<210> SEQ ID NO 1164
<211> LENGTH: 10
<212> TYPE: DNA
<213> ORGANISM: Artificial sequence
<220> FEATURE:
<223> OTHER INFORMATION: Primer OPBF-15

<400> SEQUENCE: 1164
acgcgaacct                                                              10

<210> SEQ ID NO 1165
<211> LENGTH: 10
<212> TYPE: DNA
<213> ORGANISM: Artificial sequence
<220> FEATURE:
<223> OTHER INFORMATION: Primer OPBF-16

<400> SEQUENCE: 1165
agggtccgtg                                                              10
```

<210> SEQ ID NO 1166
<211> LENGTH: 10
<212> TYPE: DNA
<213> ORGANISM: Artificial sequence
<220> FEATURE:
<223> OTHER INFORMATION: Primer OPBF-17

<400> SEQUENCE: 1166
caagctcgtg                                                          10

<210> SEQ ID NO 1167
<211> LENGTH: 10
<212> TYPE: DNA
<213> ORGANISM: Artificial sequence
<220> FEATURE:
<223> OTHER INFORMATION: Primer OPBF-18

<400> SEQUENCE: 1167
agccaaggac                                                          10

<210> SEQ ID NO 1168
<211> LENGTH: 10
<212> TYPE: DNA
<213> ORGANISM: Artificial sequence
<220> FEATURE:
<223> OTHER INFORMATION: Primer OPBF-19

<400> SEQUENCE: 1168
ttcccgcact                                                          10

<210> SEQ ID NO 1169
<211> LENGTH: 10
<212> TYPE: DNA
<213> ORGANISM: Artificial sequence
<220> FEATURE:
<223> OTHER INFORMATION: Primer OPBF-20

<400> SEQUENCE: 1169
accctgagga                                                          10

<210> SEQ ID NO 1170
<211> LENGTH: 10
<212> TYPE: DNA
<213> ORGANISM: Artificial sequence
<220> FEATURE:
<223> OTHER INFORMATION: Primer OPBG-01

<400> SEQUENCE: 1170
gtggctctcc                                                          10

<210> SEQ ID NO 1171
<211> LENGTH: 10
<212> TYPE: DNA
<213> ORGANISM: Artificial sequence
<220> FEATURE:
<223> OTHER INFORMATION: Primer OPBG-02

<400> SEQUENCE: 1171
ggaaagccca                                                          10

<210> SEQ ID NO 1172
<211> LENGTH: 10
<212> TYPE: DNA
<213> ORGANISM: Artificial sequence
<220> FEATURE:
<223> OTHER INFORMATION: Primer OPBG-03

-continued

<400> SEQUENCE: 1172
gtgccacttc                                                          10

<210> SEQ ID NO 1173
<211> LENGTH: 10
<212> TYPE: DNA
<213> ORGANISM: Artificial sequence
<220> FEATURE:
<223> OTHER INFORMATION: Primer OPBG-04

<400> SEQUENCE: 1173
gttcccgaca                                                          10

<210> SEQ ID NO 1174
<211> LENGTH: 10
<212> TYPE: DNA
<213> ORGANISM: Artificial sequence
<220> FEATURE:
<223> OTHER INFORMATION: Primer OPBG-05

<400> SEQUENCE: 1174
caagccgtga                                                          10

<210> SEQ ID NO 1175
<211> LENGTH: 10
<212> TYPE: DNA
<213> ORGANISM: Artificial sequence
<220> FEATURE:
<223> OTHER INFORMATION: Primer OPBG-06

<400> SEQUENCE: 1175
gtggatcgtc                                                          10

<210> SEQ ID NO 1176
<211> LENGTH: 10
<212> TYPE: DNA
<213> ORGANISM: Artificial sequence
<220> FEATURE:
<223> OTHER INFORMATION: Primer OPBG-07

<400> SEQUENCE: 1176
cagaggttcc                                                          10

<210> SEQ ID NO 1177
<211> LENGTH: 10
<212> TYPE: DNA
<213> ORGANISM: Artificial sequence
<220> FEATURE:
<223> OTHER INFORMATION: Primer OPBG-08

<400> SEQUENCE: 1177
gaccagaggt                                                          10

<210> SEQ ID NO 1178
<211> LENGTH: 10
<212> TYPE: DNA
<213> ORGANISM: Artificial sequence
<220> FEATURE:
<223> OTHER INFORMATION: Primer OPBG-09

<400> SEQUENCE: 1178
ggctctgggt                                                          10

<210> SEQ ID NO 1179
<211> LENGTH: 10

```
<212> TYPE: DNA
<213> ORGANISM: Artificial sequence
<220> FEATURE:
<223> OTHER INFORMATION: Primer OPBG-10

<400> SEQUENCE: 1179
gggataaggg                                                              10

<210> SEQ ID NO 1180
<211> LENGTH: 10
<212> TYPE: DNA
<213> ORGANISM: Artificial sequence
<220> FEATURE:
<223> OTHER INFORMATION: Primer OPBG-11

<400> SEQUENCE: 1180
acggcaatgg                                                              10

<210> SEQ ID NO 1181
<211> LENGTH: 10
<212> TYPE: DNA
<213> ORGANISM: Artificial sequence
<220> FEATURE:
<223> OTHER INFORMATION: Primer OPBG-12

<400> SEQUENCE: 1181
cccgagaaac                                                              10

<210> SEQ ID NO 1182
<211> LENGTH: 10
<212> TYPE: DNA
<213> ORGANISM: Artificial sequence
<220> FEATURE:
<223> OTHER INFORMATION: Primer OPBG-13

<400> SEQUENCE: 1182
ggttgggcca                                                              10

<210> SEQ ID NO 1183
<211> LENGTH: 10
<212> TYPE: DNA
<213> ORGANISM: Artificial sequence
<220> FEATURE:
<223> OTHER INFORMATION: Primer OPBG-14

<400> SEQUENCE: 1183
gaccagccca                                                              10

<210> SEQ ID NO 1184
<211> LENGTH: 10
<212> TYPE: DNA
<213> ORGANISM: Artificial sequence
<220> FEATURE:
<223> OTHER INFORMATION: Primer OPBG-15

<400> SEQUENCE: 1184
acgggagaga                                                              10

<210> SEQ ID NO 1185
<211> LENGTH: 10
<212> TYPE: DNA
<213> ORGANISM: Artificial sequence
<220> FEATURE:
<223> OTHER INFORMATION: Primer OPBG-16

<400> SEQUENCE: 1185
tgcttgggtg                                                              10
```

<210> SEQ ID NO 1186
<211> LENGTH: 10
<212> TYPE: DNA
<213> ORGANISM: Artificial sequence
<220> FEATURE:
<223> OTHER INFORMATION: Primer OPBG-17

<400> SEQUENCE: 1186
tccgggactc                                                              10

<210> SEQ ID NO 1187
<211> LENGTH: 10
<212> TYPE: DNA
<213> ORGANISM: Artificial sequence
<220> FEATURE:
<223> OTHER INFORMATION: Primer OPBG-18

<400> SEQUENCE: 1187
tggcgctggt                                                              10

<210> SEQ ID NO 1188
<211> LENGTH: 10
<212> TYPE: DNA
<213> ORGANISM: Artificial sequence
<220> FEATURE:
<223> OTHER INFORMATION: Primer OPBG-19

<400> SEQUENCE: 1188
ggtctcgctc                                                              10

<210> SEQ ID NO 1189
<211> LENGTH: 10
<212> TYPE: DNA
<213> ORGANISM: Artificial sequence
<220> FEATURE:
<223> OTHER INFORMATION: Primer OPBG-20

<400> SEQUENCE: 1189
tggtacctgg                                                              10

<210> SEQ ID NO 1190
<211> LENGTH: 10
<212> TYPE: DNA
<213> ORGANISM: Artificial sequence
<220> FEATURE:
<223> OTHER INFORMATION: Primer OPBH-01

<400> SEQUENCE: 1190
ccgactctgg                                                              10

<210> SEQ ID NO 1191
<211> LENGTH: 10
<212> TYPE: DNA
<213> ORGANISM: Artificial sequence
<220> FEATURE:
<223> OTHER INFORMATION: Primer OPBH-02

<400> SEQUENCE: 1191
gtaagccgag                                                              10

<210> SEQ ID NO 1192
<211> LENGTH: 10
<212> TYPE: DNA
<213> ORGANISM: Artificial sequence
<220> FEATURE:
<223> OTHER INFORMATION: Primer OPBH-03

```
<400> SEQUENCE: 1192
ggagcagcaa                                                              10

<210> SEQ ID NO 1193
<211> LENGTH: 10
<212> TYPE: DNA
<213> ORGANISM: Artificial sequence
<220> FEATURE:
<223> OTHER INFORMATION: Primer OPBH-04

<400> SEQUENCE: 1193
acctgccaac                                                              10

<210> SEQ ID NO 1194
<211> LENGTH: 10
<212> TYPE: DNA
<213> ORGANISM: Artificial sequence
<220> FEATURE:
<223> OTHER INFORMATION: Primer OPBH-05

<400> SEQUENCE: 1194
gtaggtcgca                                                              10

<210> SEQ ID NO 1195
<211> LENGTH: 10
<212> TYPE: DNA
<213> ORGANISM: Artificial sequence
<220> FEATURE:
<223> OTHER INFORMATION: Primer OPBH-06

<400> SEQUENCE: 1195
tcgtggcaca                                                              10

<210> SEQ ID NO 1196
<211> LENGTH: 10
<212> TYPE: DNA
<213> ORGANISM: Artificial sequence
<220> FEATURE:
<223> OTHER INFORMATION: Primer OPBH-07

<400> SEQUENCE: 1196
tgtacggcac                                                              10

<210> SEQ ID NO 1197
<211> LENGTH: 10
<212> TYPE: DNA
<213> ORGANISM: Artificial sequence
<220> FEATURE:
<223> OTHER INFORMATION: Primer OPBH-08

<400> SEQUENCE: 1197
acggaggcag                                                              10

<210> SEQ ID NO 1198
<211> LENGTH: 10
<212> TYPE: DNA
<213> ORGANISM: Artificial sequence
<220> FEATURE:
<223> OTHER INFORMATION: Primer OPBH-09

<400> SEQUENCE: 1198
gtcttccgtc                                                              10

<210> SEQ ID NO 1199
<211> LENGTH: 10
```

```
<212> TYPE: DNA
<213> ORGANISM: Artificial sequence
<220> FEATURE:
<223> OTHER INFORMATION: Primer OPBH-10

<400> SEQUENCE: 1199
gtgtgcctgg                                                              10

<210> SEQ ID NO 1200
<211> LENGTH: 10
<212> TYPE: DNA
<213> ORGANISM: Artificial sequence
<220> FEATURE:
<223> OTHER INFORMATION: Primer OPBH-11

<400> SEQUENCE: 1200
agcccaaagg                                                              10

<210> SEQ ID NO 1201
<211> LENGTH: 10
<212> TYPE: DNA
<213> ORGANISM: Artificial sequence
<220> FEATURE:
<223> OTHER INFORMATION: Primer OPBH-12

<400> SEQUENCE: 1201
tcgccttgtc                                                              10

<210> SEQ ID NO 1202
<211> LENGTH: 10
<212> TYPE: DNA
<213> ORGANISM: Artificial sequence
<220> FEATURE:
<223> OTHER INFORMATION: Primer OPBH-13

<400> SEQUENCE: 1202
agttgggcag                                                              10

<210> SEQ ID NO 1203
<211> LENGTH: 10
<212> TYPE: DNA
<213> ORGANISM: Artificial sequence
<220> FEATURE:
<223> OTHER INFORMATION: Primer OPBH-14

<400> SEQUENCE: 1203
accgtgggtg                                                              10

<210> SEQ ID NO 1204
<211> LENGTH: 10
<212> TYPE: DNA
<213> ORGANISM: Artificial sequence
<220> FEATURE:
<223> OTHER INFORMATION: Primer OPBH-15

<400> SEQUENCE: 1204
gagaacgctg                                                              10

<210> SEQ ID NO 1205
<211> LENGTH: 10
<212> TYPE: DNA
<213> ORGANISM: Artificial sequence
<220> FEATURE:
<223> OTHER INFORMATION: Primer OPBH-16

<400> SEQUENCE: 1205
ctgcgggttc                                                              10
```

```
<210> SEQ ID NO 1206
<211> LENGTH: 10
<212> TYPE: DNA
<213> ORGANISM: Artificial sequence
<220> FEATURE:
<223> OTHER INFORMATION: Primer OPBH-17

<400> SEQUENCE: 1206
ctcttacggg                                                              10

<210> SEQ ID NO 1207
<211> LENGTH: 10
<212> TYPE: DNA
<213> ORGANISM: Artificial sequence
<220> FEATURE:
<223> OTHER INFORMATION: Primer OPBH-18

<400> SEQUENCE: 1207
gacgcttgtc                                                              10

<210> SEQ ID NO 1208
<211> LENGTH: 10
<212> TYPE: DNA
<213> ORGANISM: Artificial sequence
<220> FEATURE:
<223> OTHER INFORMATION: Primer OPBH-19

<400> SEQUENCE: 1208
gtcgtgcgga                                                              10

<210> SEQ ID NO 1209
<211> LENGTH: 10
<212> TYPE: DNA
<213> ORGANISM: Artificial sequence
<220> FEATURE:
<223> OTHER INFORMATION: Primer OPBH-20

<400> SEQUENCE: 1209
caccgacatc                                                              10
```